(12) United States Patent
Svendsen et al.

(10) Patent No.: US 7,879,587 B2
(45) Date of Patent: Feb. 1, 2011

(54) LIPOLYTIC ENZYME VARIANTS

(75) Inventors: Allan Svendsen, Hoersholm (DK); Jesper Vind, Vaerloese (DK); Shamkant Anant Patkar, Lyngby (DK); Kim Borch, Birkeroed (DK)

(73) Assignee: Novozymes A/S, Bagsvaerd (DK)

( * ) Notice: Subject to any disclaimer, the term of this patent is extended or adjusted under 35 U.S.C. 154(b) by 41 days.

(21) Appl. No.: 12/443,625

(22) PCT Filed: Oct. 2, 2007

(86) PCT No.: PCT/EP2007/060473

§ 371 (c)(1),
(2), (4) Date: Apr. 8, 2009

(87) PCT Pub. No.: WO2008/040739

PCT Pub. Date: Apr. 10, 2008

(65) Prior Publication Data

US 2010/0105092 A1    Apr. 29, 2010

Related U.S. Application Data

(60) Provisional application No. 60/849,072, filed on Oct. 3, 2006.

(30) Foreign Application Priority Data

Oct. 3, 2006    (EP)    ................... 06121678

(51) Int. Cl.
*C12N 9/14*    (2006.01)
*A23D 9/013*    (2006.01)
(52) U.S. Cl. ................. 435/195; 435/197; 435/198; 426/531
(58) Field of Classification Search ............... None
See application file for complete search history.

(56) References Cited

FOREIGN PATENT DOCUMENTS

| WO | WO 88/02775 | 4/1988 |
| WO | WO 94/01541 | 1/1994 |
| WO | WO 2004/064537 | 8/2004 |
| WO | WO 2005/066347 | 7/2005 |

OTHER PUBLICATIONS

Akoh et al, Lipids, vol. 39, No. 6, pp. 513-526 (2004).
Kasrayan et al, Chemical Biochemistry, vol. 8, pp. 1409-1415 (2007).
Manetti et al, Biochimica et Biophysica Acta, vol. 1543, No. 1, pp. 146-158 (2000).
Neugnot et al, European Journal of Biochemistry, vol. 269, No. 6, pp. 1734-1475 (2002).

*Primary Examiner*—Nashaat T Nashed
(74) *Attorney, Agent, or Firm*—Kristin J. McNamara

(57) ABSTRACT

Variants with increased acyl transferase activity can be designed on the basis of a three-dimensional model by making amino acid alterations near the active Ser of lipolytic enzymes such as *C. antarctica* lipase A or the lipase/acyl transferase from *C. parapsilosis*.

15 Claims, 70 Drawing Sheets

Fig. 1
Three-dimensional model of SEQ ID NO: 1 with myristic acid

```
REMARK    4 CALA COMPLIES WITH FORMAT V. 2.0, 13-JUL-2006
ATOM      1  N   ALA A   1      -1.503 -23.618   8.339  1.00 18.67           N
ATOM      2  CA  ALA A   1      -2.771 -23.273   7.628  1.00 19.42           C
ATOM      3  CB  ALA A   1      -2.718 -21.813   7.072  1.00 19.28           C
ATOM      4  C   ALA A   1      -2.985 -24.276   6.494  1.00 19.63           C
ATOM      5  O   ALA A   1      -2.214 -25.235   6.369  1.00 20.08           O
ATOM      6  N   ALA A   2      -4.003 -24.046   5.661  1.00 19.55           N
ATOM      7  CA  ALA A   2      -4.393 -25.010   4.610  1.00 19.64           C
ATOM      8  CB  ALA A   2      -5.709 -24.642   4.020  1.00 19.60           C
ATOM      9  C   ALA A   2      -3.387 -25.183   3.491  1.00 20.02           C
ATOM     10  O   ALA A   2      -3.479 -26.141   2.724  1.00 19.67           O
ATOM     11  N   LEU A   3      -2.438 -24.253   3.391  1.00 19.82           N
ATOM     12  CA  LEU A   3      -1.356 -24.352   2.430  1.00 19.73           C
ATOM     13  CB  LEU A   3      -1.583 -23.359   1.286  1.00 20.12           C
ATOM     14  CG  LEU A   3      -2.626 -23.743   0.245  1.00 19.94           C
ATOM     15  CD1 LEU A   3      -2.918 -22.549  -0.662  1.00 19.37           C
ATOM     16  CD2 LEU A   3      -2.166 -24.984  -0.564  1.00 20.43           C
ATOM     17  C   LEU A   3      -0.051 -24.042   3.110  1.00 19.49           C
ATOM     18  O   LEU A   3      -0.040 -23.442   4.190  1.00 19.44           O
ATOM     19  N   PRO A   4       1.066 -24.405   2.482  1.00 19.30           N
ATOM     20  CA  PRO A   4       2.374 -24.030   3.026  1.00 18.36           C
ATOM     21  CB  PRO A   4       3.338 -24.553   1.975  1.00 18.62           C
ATOM     22  CG  PRO A   4       2.509 -24.557   0.692  1.00 19.21           C
ATOM     23  CD  PRO A   4       1.199 -25.120   1.192  1.00 19.59           C
ATOM     24  C   PRO A   4       2.505 -22.512   3.119  1.00 17.64           C
ATOM     25  O   PRO A   4       1.772 -21.759   2.449  1.00 17.25           O
ATOM     26  N   ASN A   5       3.443 -22.077   3.944  1.00 17.48           N
ATOM     27  CA  ASN A   5       3.869 -20.691   3.985  1.00 17.70           C
ATOM     28  CB  ASN A   5       5.076 -20.559   4.927  1.00 17.58           C
ATOM     29  CG  ASN A   5       5.454 -19.108   5.223  1.00 18.24           C
ATOM     30  OD1 ASN A   5       6.027 -18.427   4.384  1.00 16.48           O
ATOM     31  ND2 ASN A   5       5.153 -18.646   6.428  1.00 17.93           N
ATOM     32  C   ASN A   5       4.256 -20.267   2.545  1.00 17.86           C
ATOM     33  O   ASN A   5       4.905 -21.058   1.829  1.00 17.08           O
ATOM     34  N   PRO A   6       3.819 -19.080   2.112  1.00 17.43           N
ATOM     35  CA  PRO A   6       4.175 -18.547   0.790  1.00 18.05           C
ATOM     36  CB  PRO A   6       3.667 -17.106   0.852  1.00 18.49           C
ATOM     37  CG  PRO A   6       2.435 -17.214   1.692  1.00 17.56           C
ATOM     38  CD  PRO A   6       2.865 -18.191   2.799  1.00 17.83           C
ATOM     39  C   PRO A   6       5.672 -18.595   0.449  1.00 18.10           C
ATOM     40  O   PRO A   6       5.994 -18.820  -0.699  1.00 17.59           O
ATOM     41  N   TYR A   7       6.548 -18.426   1.421  1.00 18.60           N
ATOM     42  CA  TYR A   7       7.974 -18.534   1.169  1.00 19.28           C
ATOM     43  CB  TYR A   7       8.783 -18.150   2.406  1.00 19.63           C
ATOM     44  CG  TYR A   7       8.935 -16.649   2.659  1.00 22.93           C
ATOM     45  CD1 TYR A   7       9.805 -15.853   1.886  1.00 23.37           C
ATOM     46  CE1 TYR A   7       9.967 -14.481   2.161  1.00 23.12           C
ATOM     47  CZ  TYR A   7       9.245 -13.908   3.212  1.00 23.76           C
ATOM     48  OH  TYR A   7       9.357 -12.566   3.537  1.00 23.54           O
ATOM     49  CE2 TYR A   7       8.397 -14.676   3.973  1.00 22.81           C
ATOM     50  CD2 TYR A   7       8.254 -16.031   3.718  1.00 21.72           C
```

Fig. 1, continued

```
ATOM    51  C   TYR A   7       8.368 -19.955   0.740  1.00 19.17           C
ATOM    52  O   TYR A   7       9.407 -20.136   0.110  1.00 17.74           O
ATOM    53  N   ASP A   8       7.553 -20.952   1.116  1.00 18.60           N
ATOM    54  CA  ASP A   8       7.809 -22.342   0.758  1.00 18.71           C
ATOM    55  CB  ASP A   8       7.507 -23.275   1.931  1.00 18.61           C
ATOM    56  CG  ASP A   8       8.251 -22.914   3.181  1.00 19.16           C
ATOM    57  OD1 ASP A   8       9.395 -22.409   3.101  1.00 20.91           O
ATOM    58  OD2 ASP A   8       7.765 -23.155   4.305  1.00 19.95           O
ATOM    59  C   ASP A   8       6.995 -22.825  -0.415  1.00 19.13           C
ATOM    60  O   ASP A   8       6.853 -24.039  -0.598  1.00 20.37           O
ATOM    61  N   ASP A   9       6.463 -21.907  -1.210  1.00 18.45           N
ATOM    62  CA  ASP A   9       5.446 -22.253  -2.180  1.00 18.79           C
ATOM    63  CB  ASP A   9       4.100 -21.722  -1.684  1.00 18.15           C
ATOM    64  CG  ASP A   9       2.946 -22.255  -2.463  1.00 19.48           C
ATOM    65  OD1 ASP A   9       3.174 -22.840  -3.557  1.00 18.23           O
ATOM    66  OD2 ASP A   9       1.766 -22.132  -2.053  1.00 19.29           O
ATOM    67  C   ASP A   9       5.777 -21.656  -3.566  1.00 18.22           C
ATOM    68  O   ASP A   9       5.814 -20.436  -3.714  1.00 18.16           O
ATOM    69  N   PRO A  10       6.009 -22.473  -4.580  1.00 18.48           N
ATOM    70  CA  PRO A  10       6.334 -21.909  -5.908  1.00 18.95           C
ATOM    71  CB  PRO A  10       6.633 -23.153  -6.758  1.00 19.28           C
ATOM    72  CG  PRO A  10       5.807 -24.252  -6.099  1.00 19.48           C
ATOM    73  CD  PRO A  10       5.984 -23.951  -4.609  1.00 18.20           C
ATOM    74  C   PRO A  10       5.197 -21.117  -6.543  1.00 19.32           C
ATOM    75  O   PRO A  10       5.433 -20.398  -7.505  1.00 19.29           O
ATOM    76  N   PHE A  11       3.976 -21.244  -6.021  1.00 19.72           N
ATOM    77  CA  PHE A  11       2.858 -20.429  -6.475  1.00 20.00           C
ATOM    78  CB  PHE A  11       1.590 -20.808  -5.705  1.00 20.20           C
ATOM    79  CG  PHE A  11       0.301 -20.560  -6.448  1.00 19.94           C
ATOM    80  CD1 PHE A  11      -0.184 -21.503  -7.376  1.00 21.93           C
ATOM    81  CE1 PHE A  11      -1.379 -21.330  -8.017  1.00 18.93           C
ATOM    82  CZ  PHE A  11      -2.129 -20.186  -7.770  1.00 21.85           C
ATOM    83  CE2 PHE A  11      -1.662 -19.241  -6.849  1.00 20.47           C
ATOM    84  CD2 PHE A  11      -0.459 -19.446  -6.190  1.00 20.72           C
ATOM    85  C   PHE A  11       3.157 -18.942  -6.303  1.00 20.08           C
ATOM    86  O   PHE A  11       2.614 -18.111  -7.049  1.00 21.09           O
ATOM    87  N   TYR A  12       4.028 -18.612  -5.346  1.00 19.33           N
ATOM    88  CA  TYR A  12       4.471 -17.246  -5.110  1.00 19.46           C
ATOM    89  CB  TYR A  12       4.518 -16.930  -3.593  1.00 19.27           C
ATOM    90  CG  TYR A  12       3.158 -16.911  -2.925  1.00 17.20           C
ATOM    91  CD1 TYR A  12       2.571 -18.085  -2.479  1.00 18.84           C
ATOM    92  CE1 TYR A  12       1.292 -18.086  -1.878  1.00 19.29           C
ATOM    93  CZ  TYR A  12       0.620 -16.903  -1.711  1.00 18.45           C
ATOM    94  OH  TYR A  12      -0.613 -16.945  -1.091  1.00 20.99           O
ATOM    95  CE2 TYR A  12       1.197 -15.720  -2.140  1.00 16.84           C
ATOM    96  CD2 TYR A  12       2.462 -15.735  -2.748  1.00 16.02           C
ATOM    97  C   TYR A  12       5.840 -16.965  -5.746  1.00 20.86           C
ATOM    98  O   TYR A  12       6.702 -16.350  -5.120  1.00 21.45           O
ATOM    99  N   THR A  13       6.025 -17.380  -6.997  1.00 21.19           N
ATOM   100  CA  THR A  13       7.235 -17.035  -7.756  1.00 21.89           C
ATOM   101  CB  THR A  13       8.309 -18.210  -7.803  1.00 21.87           C
ATOM   102  OG1 THR A  13       7.725 -19.383  -8.403  1.00 20.75           O
ATOM   103  CG2 THR A  13       8.708 -18.656  -6.402  1.00 21.93           C
ATOM   104  C   THR A  13       6.826 -16.658  -9.153  1.00 22.38           C
```

Fig. 1, continued

```
ATOM    105  O    THR A  13       5.764 -17.057  -9.658  1.00 22.82           O
ATOM    106  N    THR A  14       7.664 -15.842  -9.760  1.00 23.11           N
ATOM    107  CA   THR A  14       7.446 -15.377 -11.111  1.00 23.82           C
ATOM    108  CB   THR A  14       7.974 -13.958 -11.234  1.00 24.49           C
ATOM    109  OG1  THR A  14       7.121 -13.058 -10.485  1.00 23.59           O
ATOM    110  CG2  THR A  14       7.929 -13.463 -12.708  1.00 24.06           C
ATOM    111  C    THR A  14       8.176 -16.330 -12.058  1.00 24.43           C
ATOM    112  O    THR A  14       9.388 -16.562 -11.895  1.00 24.36           O
ATOM    113  N    PRO A  15       7.465 -16.896 -13.023  1.00 25.53           N
ATOM    114  CA   PRO A  15       8.109 -17.804 -13.985  1.00 26.58           C
ATOM    115  CB   PRO A  15       6.939 -18.503 -14.664  1.00 25.70           C
ATOM    116  CG   PRO A  15       5.774 -17.539 -14.533  1.00 26.77           C
ATOM    117  CD   PRO A  15       6.017 -16.753 -13.273  1.00 25.52           C
ATOM    118  C    PRO A  15       9.008 -17.038 -14.975  1.00 28.00           C
ATOM    119  O    PRO A  15       8.813 -15.835 -15.224  1.00 26.69           O
ATOM    120  N    SER A  16      10.048 -17.720 -15.463  1.00 29.39           N
ATOM    121  CA   SER A  16      11.019 -17.106 -16.372  1.00 30.38           C
ATOM    122  CB   SER A  16      12.153 -18.096 -16.706  1.00 30.97           C
ATOM    123  OG   SER A  16      11.608 -19.268 -17.305  1.00 33.22           O
ATOM    124  C    SER A  16      10.357 -16.595 -17.670  1.00 30.31           C
ATOM    125  O    SER A  16      10.857 -15.640 -18.278  1.00 31.76           O
ATOM    126  N    ASN A  17       9.241 -17.193 -18.074  1.00 29.68           N
ATOM    127  CA   ASN A  17       8.487 -16.739 -19.256  1.00 29.87           C
ATOM    128  CB   ASN A  17       7.982 -17.962 -20.052  1.00 30.09           C
ATOM    129  CG   ASN A  17       6.827 -18.662 -19.365  1.00 33.14           C
ATOM    130  OD1  ASN A  17       6.600 -18.461 -18.154  1.00 35.52           O
ATOM    131  ND2  ASN A  17       6.071 -19.467 -20.122  1.00 32.11           N
ATOM    132  C    ASN A  17       7.306 -15.755 -18.965  1.00 29.16           C
ATOM    133  O    ASN A  17       6.373 -15.619 -19.767  1.00 28.47           O
ATOM    134  N    ILE A  18       7.372 -15.050 -17.833  1.00 28.63           N
ATOM    135  CA   ILE A  18       6.343 -14.067 -17.448  1.00 27.68           C
ATOM    136  CB   ILE A  18       6.724 -13.390 -16.093  1.00 27.59           C
ATOM    137  CG1  ILE A  18       5.558 -12.539 -15.546  1.00 25.90           C
ATOM    138  CD1  ILE A  18       4.281 -13.308 -15.337  1.00 24.44           C
ATOM    139  CG2  ILE A  18       8.039 -12.575 -16.210  1.00 28.51           C
ATOM    140  C    ILE A  18       6.026 -12.999 -18.510  1.00 27.69           C
ATOM    141  O    ILE A  18       4.868 -12.576 -18.640  1.00 26.84           O
ATOM    142  N    GLY A  19       7.041 -12.569 -19.259  1.00 28.46           N
ATOM    143  CA   GLY A  19       6.872 -11.572 -20.322  1.00 28.97           C
ATOM    144  C    GLY A  19       5.981 -11.983 -21.491  1.00 29.56           C
ATOM    145  O    GLY A  19       5.529 -11.126 -22.248  1.00 30.57           O
ATOM    146  N    THR A  20       5.694 -13.277 -21.635  1.00 29.45           N
ATOM    147  CA   THR A  20       4.786 -13.741 -22.680  1.00 30.07           C
ATOM    148  CB   THR A  20       5.104 -15.190 -23.081  1.00 30.33           C
ATOM    149  OG1  THR A  20       4.827 -16.074 -21.986  1.00 32.87           O
ATOM    150  CG2  THR A  20       6.609 -15.397 -23.387  1.00 31.40           C
ATOM    151  C    THR A  20       3.308 -13.682 -22.273  1.00 29.28           C
ATOM    152  O    THR A  20       2.451 -13.948 -23.101  1.00 29.75           O
ATOM    153  N    PHE A  21       3.011 -13.343 -21.007  1.00 27.68           N
ATOM    154  CA   PHE A  21       1.623 -13.281 -20.521  1.00 26.11           C
ATOM    155  CB   PHE A  21       1.517 -13.792 -19.054  1.00 26.08           C
ATOM    156  CG   PHE A  21       1.736 -15.281 -18.902  1.00 24.73           C
ATOM    157  CD1  PHE A  21       3.006 -15.792 -18.698  1.00 25.68           C
ATOM    158  CE1  PHE A  21       3.216 -17.162 -18.568  1.00 25.04           C
```

Fig. 1, continued

```
ATOM    159  CZ   PHE A  21       2.141 -18.031 -18.656  1.00 26.17           C
ATOM    160  CE2  PHE A  21       0.873 -17.532 -18.850  1.00 25.03           C
ATOM    161  CD2  PHE A  21       0.676 -16.162 -18.969  1.00 25.94           C
ATOM    162  C    PHE A  21       1.120 -11.866 -20.613  1.00 25.21           C
ATOM    163  O    PHE A  21       1.862 -10.927 -20.363  1.00 25.68           O
ATOM    164  N    ALA A  22      -0.141 -11.703 -20.988  1.00 25.36           N
ATOM    165  CA   ALA A  22      -0.789 -10.395 -20.970  1.00 25.38           C
ATOM    166  CB   ALA A  22      -2.085 -10.442 -21.736  1.00 24.93           C
ATOM    167  C    ALA A  22      -1.081  -9.924 -19.539  1.00 25.73           C
ATOM    168  O    ALA A  22      -1.166 -10.721 -18.603  1.00 25.24           O
ATOM    169  N    LYS A  23      -1.258  -8.616 -19.408  1.00 25.59           N
ATOM    170  CA   LYS A  23      -1.653  -8.020 -18.155  1.00 25.72           C
ATOM    171  CB   LYS A  23      -1.652  -6.500 -18.267  1.00 25.63           C
ATOM    172  CG   LYS A  23      -0.262  -5.902 -18.435  1.00 26.41           C
ATOM    173  CD   LYS A  23      -0.353  -4.435 -18.836  1.00 28.95           C
ATOM    174  CE   LYS A  23       1.001  -3.799 -19.035  1.00 31.63           C
ATOM    175  NZ   LYS A  23       0.853  -2.382 -19.531  1.00 32.78           N
ATOM    176  C    LYS A  23      -3.019  -8.561 -17.733  1.00 25.28           C
ATOM    177  O    LYS A  23      -4.026  -8.411 -18.454  1.00 24.31           O
ATOM    178  N    GLY A  24      -3.033  -9.215 -16.566  1.00 24.12           N
ATOM    179  CA   GLY A  24      -4.256  -9.764 -16.016  1.00 24.03           C
ATOM    180  C    GLY A  24      -4.509 -11.188 -16.428  1.00 24.37           C
ATOM    181  O    GLY A  24      -5.471 -11.817 -15.978  1.00 24.72           O
ATOM    182  N    GLN A  25      -3.620 -11.740 -17.244  1.00 24.80           N
ATOM    183  CA   GLN A  25      -3.803 -13.117 -17.730  1.00 25.06           C
ATOM    184  CB   GLN A  25      -2.890 -13.420 -18.928  1.00 24.58           C
ATOM    185  CG   GLN A  25      -3.081 -14.833 -19.495  1.00 26.13           C
ATOM    186  CD   GLN A  25      -2.380 -15.061 -20.855  1.00 28.90           C
ATOM    187  OE1  GLN A  25      -1.750 -14.152 -21.390  1.00 27.24           O
ATOM    188  NE2  GLN A  25      -2.468 -16.295 -21.379  1.00 27.97           N
ATOM    189  C    GLN A  25      -3.496 -14.120 -16.607  1.00 24.43           C
ATOM    190  O    GLN A  25      -2.522 -13.974 -15.883  1.00 23.58           O
ATOM    191  N    VAL A  26      -4.309 -15.160 -16.519  1.00 24.67           N
ATOM    192  CA   VAL A  26      -4.134 -16.189 -15.494  1.00 25.00           C
ATOM    193  CB   VAL A  26      -5.452 -16.925 -15.258  1.00 25.11           C
ATOM    194  CG1  VAL A  26      -5.300 -18.027 -14.178  1.00 24.52           C
ATOM    195  CG2  VAL A  26      -6.556 -15.920 -14.891  1.00 25.00           C
ATOM    196  C    VAL A  26      -3.081 -17.200 -15.955  1.00 25.84           C
ATOM    197  O    VAL A  26      -3.240 -17.831 -17.005  1.00 26.29           O
ATOM    198  N    ILE A  27      -2.021 -17.341 -15.164  1.00 25.11           N
ATOM    199  CA   ILE A  27      -0.969 -18.311 -15.397  1.00 25.58           C
ATOM    200  CB   ILE A  27       0.337 -17.816 -14.766  1.00 24.83           C
ATOM    201  CG1  ILE A  27       0.711 -16.433 -15.307  1.00 25.49           C
ATOM    202  CD1  ILE A  27       1.595 -15.614 -14.336  1.00 26.18           C
ATOM    203  CG2  ILE A  27       1.481 -18.794 -15.037  1.00 26.17           C
ATOM    204  C    ILE A  27      -1.376 -19.693 -14.846  1.00 25.94           C
ATOM    205  O    ILE A  27      -1.248 -20.706 -15.525  1.00 25.18           O
ATOM    206  N    GLN A  28      -1.820 -19.718 -13.592  1.00 26.82           N
ATOM    207  CA   GLN A  28      -2.453 -20.901 -13.005  1.00 27.20           C
ATOM    208  CB   GLN A  28      -1.397 -21.892 -12.487  1.00 27.83           C
ATOM    209  CG   GLN A  28      -0.302 -21.260 -11.691  1.00 30.73           C
ATOM    210  CD   GLN A  28       0.656 -22.269 -11.082  1.00 32.84           C
ATOM    211  OE1  GLN A  28       0.248 -23.361 -10.668  1.00 34.99           O
ATOM    212  NE2  GLN A  28       1.931 -21.902 -11.020  1.00 35.12           N
```

Fig. 1, continued

```
ATOM    213  C   GLN A  28      -3.462 -20.548 -11.906  1.00 26.29           C
ATOM    214  O   GLN A  28      -3.576 -19.399 -11.479  1.00 25.74           O
ATOM    215  N   SER A  29      -4.242 -21.545 -11.509  1.00 25.45           N
ATOM    216  CA  SER A  29      -5.260 -21.372 -10.489  1.00 24.80           C
ATOM    217  CB  SER A  29      -6.625 -21.123 -11.131  1.00 24.74           C
ATOM    218  OG  SER A  29      -7.016 -22.209 -11.959  1.00 25.00           O
ATOM    219  C   SER A  29      -5.322 -22.606  -9.612  1.00 24.72           C
ATOM    220  O   SER A  29      -4.934 -23.696 -10.036  1.00 24.04           O
ATOM    221  N   ARG A  30      -5.792 -22.422  -8.382  1.00 23.97           N
ATOM    222  CA  ARG A  30      -6.068 -23.539  -7.491  1.00 23.62           C
ATOM    223  CB  ARG A  30      -4.820 -23.933  -6.687  1.00 23.81           C
ATOM    224  CG  ARG A  30      -4.190 -22.780  -5.910  1.00 23.00           C
ATOM    225  CD  ARG A  30      -2.895 -23.175  -5.215  1.00 21.13           C
ATOM    226  NE  ARG A  30      -2.316 -22.072  -4.442  1.00 20.67           N
ATOM    227  CZ  ARG A  30      -1.170 -22.144  -3.807  1.00 21.47           C
ATOM    228  NH1 ARG A  30      -0.438 -23.258  -3.857  1.00 22.82           N
ATOM    229  NH2 ARG A  30      -0.733 -21.100  -3.122  1.00 21.01           N
ATOM    230  C   ARG A  30      -7.244 -23.201  -6.576  1.00 23.37           C
ATOM    231  O   ARG A  30      -7.401 -22.061  -6.113  1.00 23.03           O
ATOM    232  N   LYS A  31      -8.079 -24.198  -6.337  1.00 22.81           N
ATOM    233  CA  LYS A  31      -9.161 -24.092  -5.379  1.00 22.73           C
ATOM    234  CB  LYS A  31     -10.100 -25.317  -5.460  1.00 23.69           C
ATOM    235  CG  LYS A  31     -11.525 -25.088  -4.810  1.00 26.29           C
ATOM    236  CD  LYS A  31     -12.499 -26.204  -5.286  0.65 28.58           C
ATOM    237  CE  LYS A  31     -13.871 -26.218  -4.577  0.65 29.61           C
ATOM    238  NZ  LYS A  31     -13.941 -25.315  -3.414  0.65 28.52           N
ATOM    239  C   LYS A  31      -8.530 -24.014  -3.997  1.00 21.28           C
ATOM    240  O   LYS A  31      -7.611 -24.766  -3.715  1.00 20.75           O
ATOM    241  N   VAL A  32      -8.999 -23.093  -3.154  1.00 20.32           N
ATOM    242  CA  VAL A  32      -8.518 -23.005  -1.766  1.00 19.74           C
ATOM    243  CB  VAL A  32      -7.546 -21.827  -1.582  1.00 20.06           C
ATOM    244  CG1 VAL A  32      -6.327 -21.987  -2.506  1.00 20.48           C
ATOM    245  CG2 VAL A  32      -8.241 -20.492  -1.833  1.00 19.16           C
ATOM    246  C   VAL A  32      -9.685 -22.871  -0.771  1.00 19.50           C
ATOM    247  O   VAL A  32     -10.719 -22.271  -1.097  1.00 19.16           O
ATOM    248  N   PRO A  33      -9.521 -23.430   0.435  1.00 18.78           N
ATOM    249  CA  PRO A  33     -10.501 -23.262   1.508  1.00 18.03           C
ATOM    250  CB  PRO A  33     -10.245 -24.471   2.403  1.00 17.84           C
ATOM    251  CG  PRO A  33      -8.782 -24.785   2.228  1.00 17.56           C
ATOM    252  CD  PRO A  33      -8.378 -24.268   0.865  1.00 18.75           C
ATOM    253  C   PRO A  33     -10.235 -21.962   2.270  1.00 17.90           C
ATOM    254  O   PRO A  33      -9.108 -21.707   2.702  1.00 17.42           O
ATOM    255  N   THR A  34     -11.264 -21.140   2.401  1.00 17.78           N
ATOM    256  CA  THR A  34     -11.175 -19.899   3.161  1.00 18.13           C
ATOM    257  CB  THR A  34     -11.301 -18.670   2.249  1.00 18.25           C
ATOM    258  OG1 THR A  34     -12.504 -18.749   1.491  1.00 17.71           O
ATOM    259  CG2 THR A  34     -10.151 -18.604   1.217  1.00 19.21           C
ATOM    260  C   THR A  34     -12.319 -19.850   4.147  1.00 18.38           C
ATOM    261  O   THR A  34     -13.392 -20.420   3.884  1.00 16.91           O
ATOM    262  N   ASP A  35     -12.083 -19.168   5.273  1.00 19.17           N
ATOM    263  CA  ASP A  35     -13.135 -18.948   6.273  1.00 20.39           C
ATOM    264  CB  ASP A  35     -12.626 -18.096   7.441  1.00 21.89           C
ATOM    265  CG  ASP A  35     -11.617 -18.839   8.307  1.00 25.93           C
ATOM    266  OD1 ASP A  35     -11.687 -20.082   8.446  1.00 33.70           O
```

Fig. 1, continued

```
ATOM    267  OD2 ASP A  35      -10.717 -18.275   8.914  1.00 35.91           O
ATOM    268  C   ASP A  35      -14.346 -18.285   5.664  1.00 20.29           C
ATOM    269  O   ASP A  35      -15.485 -18.678   5.941  1.00 19.64           O
ATOM    270  N   ILE A  36      -14.093 -17.269   4.833  1.00 20.07           N
ATOM    271  CA  ILE A  36      -15.162 -16.492   4.219  1.00 20.14           C
ATOM    272  CB  ILE A  36      -14.594 -15.190   3.580  1.00 20.37           C
ATOM    273  CG1 ILE A  36      -14.215 -14.208   4.690  1.00 21.16           C
ATOM    274  CD1 ILE A  36      -13.263 -13.126   4.222  1.00 22.83           C
ATOM    275  CG2 ILE A  36      -15.618 -14.532   2.660  1.00 20.83           C
ATOM    276  C   ILE A  36      -15.960 -17.338   3.213  1.00 19.53           C
ATOM    277  O   ILE A  36      -17.184 -17.262   3.190  1.00 17.74           O
ATOM    278  N   GLY A  37      -15.261 -18.154   2.423  1.00 19.33           N
ATOM    279  CA  GLY A  37      -15.900 -19.085   1.505  1.00 19.48           C
ATOM    280  C   GLY A  37      -16.799 -20.090   2.216  1.00 20.41           C
ATOM    281  O   GLY A  37      -17.960 -20.297   1.832  1.00 20.67           O
ATOM    282  N   ASN A  38      -16.281 -20.698   3.280  1.00 21.26           N
ATOM    283  CA  ASN A  38      -17.079 -21.617   4.120  1.00 21.47           C
ATOM    284  CB  ASN A  38      -16.218 -22.232   5.227  1.00 20.99           C
ATOM    285  CG  ASN A  38      -15.205 -23.222   4.679  1.00 22.89           C
ATOM    286  OD1 ASN A  38      -15.251 -23.588   3.501  1.00 24.46           O
ATOM    287  ND2 ASN A  38      -14.277 -23.632   5.506  1.00 23.31           N
ATOM    288  C   ASN A  38      -18.298 -20.951   4.738  1.00 21.72           C
ATOM    289  O   ASN A  38      -19.386 -21.530   4.759  1.00 21.00           O
ATOM    290  N   ALA A  39      -18.126 -19.727   5.230  1.00 21.86           N
ATOM    291  CA  ALA A  39      -19.223 -19.033   5.900  1.00 21.54           C
ATOM    292  CB  ALA A  39      -18.682 -17.871   6.699  1.00 22.37           C
ATOM    293  C   ALA A  39      -20.303 -18.559   4.948  1.00 21.69           C
ATOM    294  O   ALA A  39      -21.433 -18.370   5.361  1.00 22.05           O
ATOM    295  N   ASN A  40      -19.978 -18.359   3.673  1.00 21.03           N
ATOM    296  CA  ASN A  40      -20.932 -17.798   2.741  1.00 21.44           C
ATOM    297  CB  ASN A  40      -20.337 -16.522   2.153  1.00 21.99           C
ATOM    298  CG  ASN A  40      -20.241 -15.411   3.177  1.00 21.95           C
ATOM    299  OD1 ASN A  40      -21.226 -14.692   3.423  1.00 19.61           O
ATOM    300  ND2 ASN A  40      -19.056 -15.264   3.791  1.00 16.80           N
ATOM    301  C   ASN A  40      -21.313 -18.725   1.604  1.00 22.49           C
ATOM    302  O   ASN A  40      -21.965 -18.283   0.641  1.00 22.22           O
ATOM    303  N   ASN A  41      -20.900 -19.995   1.706  1.00 22.75           N
ATOM    304  CA  ASN A  41      -21.165 -21.013   0.687  1.00 23.76           C
ATOM    305  CB  ASN A  41      -22.653 -21.437   0.678  1.00 23.65           C
ATOM    306  CG  ASN A  41      -22.929 -22.633  -0.273  1.00 27.83           C
ATOM    307  OD1 ASN A  41      -22.084 -23.550  -0.426  1.00 32.41           O
ATOM    308  ND2 ASN A  41      -24.100 -22.620  -0.921  1.00 28.29           N
ATOM    309  C   ASN A  41      -20.736 -20.520  -0.689  1.00 23.33           C
ATOM    310  O   ASN A  41      -21.481 -20.622  -1.666  1.00 24.35           O
ATOM    311  N   ALA A  42      -19.515 -19.997  -0.751  1.00 23.04           N
ATOM    312  CA  ALA A  42      -18.955 -19.419  -1.959  1.00 22.15           C
ATOM    313  CB  ALA A  42      -18.813 -17.916  -1.802  1.00 21.79           C
ATOM    314  C   ALA A  42      -17.586 -20.064  -2.181  1.00 21.99           C
ATOM    315  O   ALA A  42      -16.715 -20.010  -1.296  1.00 21.99           O
ATOM    316  N   ALA A  43      -17.410 -20.700  -3.339  1.00 20.79           N
ATOM    317  CA  ALA A  43      -16.124 -21.299  -3.701  1.00 19.91           C
ATOM    318  CB  ALA A  43      -16.252 -22.113  -5.014  1.00 20.35           C
ATOM    319  C   ALA A  43      -15.034 -20.220  -3.836  1.00 19.08           C
ATOM    320  O   ALA A  43      -15.278 -19.147  -4.393  1.00 18.72           O
```

Fig. 1, continued

```
ATOM    321  N    SER A  44     -13.848 -20.513  -3.308  1.00 18.56           N
ATOM    322  CA   SER A  44     -12.710 -19.617  -3.405  1.00 18.66           C
ATOM    323  CB   SER A  44     -12.260 -19.111  -2.031  1.00 18.63           C
ATOM    324  OG   SER A  44     -12.353 -20.110  -1.041  1.00 17.75           O
ATOM    325  C    SER A  44     -11.545 -20.279  -4.111  1.00 18.46           C
ATOM    326  O    SER A  44     -11.309 -21.488  -3.978  1.00 18.08           O
ATOM    327  N    PHE A  45     -10.810 -19.443  -4.834  1.00 18.49           N
ATOM    328  CA   PHE A  45      -9.675 -19.849  -5.647  1.00 18.49           C
ATOM    329  CB   PHE A  45     -10.082 -19.981  -7.154  1.00 18.42           C
ATOM    330  CG   PHE A  45     -11.263 -20.882  -7.397  1.00 20.45           C
ATOM    331  CD1  PHE A  45     -11.083 -22.235  -7.702  1.00 21.72           C
ATOM    332  CE1  PHE A  45     -12.163 -23.063  -7.906  1.00 21.56           C
ATOM    333  CZ   PHE A  45     -13.450 -22.567  -7.793  1.00 21.55           C
ATOM    334  CE2  PHE A  45     -13.645 -21.237  -7.481  1.00 22.94           C
ATOM    335  CD2  PHE A  45     -12.558 -20.398  -7.293  1.00 22.45           C
ATOM    336  C    PHE A  45      -8.583 -18.805  -5.521  1.00 17.52           C
ATOM    337  O    PHE A  45      -8.856 -17.630  -5.343  1.00 17.75           O
ATOM    338  N    GLN A  46      -7.341 -19.250  -5.615  1.00 18.43           N
ATOM    339  CA   GLN A  46      -6.192 -18.380  -5.842  1.00 18.20           C
ATOM    340  CB   GLN A  46      -5.017 -18.819  -5.010  1.00 18.17           C
ATOM    341  CG   GLN A  46      -5.172 -18.434  -3.557  1.00 17.96           C
ATOM    342  CD   GLN A  46      -4.034 -18.925  -2.725  1.00 18.16           C
ATOM    343  OE1  GLN A  46      -3.087 -19.504  -3.253  1.00 19.23           O
ATOM    344  NE2  GLN A  46      -4.130 -18.725  -1.413  1.00 19.20           N
ATOM    345  C    GLN A  46      -5.802 -18.416  -7.324  1.00 18.84           C
ATOM    346  O    GLN A  46      -5.794 -19.482  -7.954  1.00 18.01           O
ATOM    347  N    LEU A  47      -5.547 -17.229  -7.866  1.00 18.51           N
ATOM    348  CA   LEU A  47      -5.134 -17.035  -9.253  1.00 17.96           C
ATOM    349  CB   LEU A  47      -6.053 -16.031  -9.948  1.00 17.92           C
ATOM    350  CG   LEU A  47      -7.549 -16.302  -9.895  1.00 17.13           C
ATOM    351  CD1  LEU A  47      -8.275 -15.286 -10.713  1.00 18.91           C
ATOM    352  CD2  LEU A  47      -7.859 -17.733 -10.353  1.00 18.22           C
ATOM    353  C    LEU A  47      -3.749 -16.462  -9.213  1.00 18.23           C
ATOM    354  O    LEU A  47      -3.506 -15.443  -8.540  1.00 18.30           O
ATOM    355  N    GLN A  48      -2.818 -17.150  -9.859  1.00 18.17           N
ATOM    356  CA   GLN A  48      -1.522 -16.597 -10.133  1.00 18.88           C
ATOM    357  CB   GLN A  48      -0.463 -17.687 -10.170  1.00 19.45           C
ATOM    358  CG   GLN A  48       0.936 -17.123 -10.192  1.00 21.19           C
ATOM    359  CD   GLN A  48       1.974 -18.157 -10.647  1.00 25.96           C
ATOM    360  OE1  GLN A  48       1.846 -18.735 -11.723  1.00 29.31           O
ATOM    361  NE2  GLN A  48       2.986 -18.368  -9.840  1.00 26.93           N
ATOM    362  C    GLN A  48      -1.636 -15.955 -11.494  1.00 19.73           C
ATOM    363  O    GLN A  48      -1.993 -16.644 -12.444  1.00 19.42           O
ATOM    364  N    TYR A  49      -1.352 -14.654 -11.579  1.00 19.84           N
ATOM    365  CA   TYR A  49      -1.633 -13.869 -12.782  1.00 20.10           C
ATOM    366  CB   TYR A  49      -2.964 -13.066 -12.649  1.00 19.36           C
ATOM    367  CG   TYR A  49      -2.978 -12.009 -11.550  1.00 19.74           C
ATOM    368  CD1  TYR A  49      -3.226 -12.355 -10.209  1.00 20.04           C
ATOM    369  CE1  TYR A  49      -3.218 -11.390  -9.197  1.00 18.96           C
ATOM    370  CZ   TYR A  49      -2.979 -10.088  -9.501  1.00 18.96           C
ATOM    371  OH   TYR A  49      -3.007  -9.148  -8.498  1.00 18.45           O
ATOM    372  CE2  TYR A  49      -2.735  -9.708 -10.827  1.00 19.66           C
ATOM    373  CD2  TYR A  49      -2.722 -10.670 -11.828  1.00 19.49           C
ATOM    374  C    TYR A  49      -0.474 -12.926 -13.052  1.00 20.70           C
```

Fig. 1, continued

```
ATOM   375  O    TYR A  49       0.318 -12.616 -12.153  1.00 20.17           O
ATOM   376  N    ARG A  50      -0.366 -12.465 -14.292  1.00 20.80           N
ATOM   377  CA   ARG A  50       0.692 -11.531 -14.628  1.00 21.29           C
ATOM   378  CB   ARG A  50       1.163 -11.765 -16.059  1.00 22.46           C
ATOM   379  CG   ARG A  50       2.279 -10.836 -16.498  1.00 23.39           C
ATOM   380  CD   ARG A  50       1.768  -9.708 -17.298  1.00 24.37           C
ATOM   381  NE   ARG A  50       2.500  -8.448 -17.139  1.00 25.70           N
ATOM   382  CZ   ARG A  50       3.027  -7.747 -18.148  1.00 27.53           C
ATOM   383  NH1  ARG A  50       3.598  -6.573 -17.911  1.00 27.59           N
ATOM   384  NH2  ARG A  50       2.988  -8.207 -19.388  1.00 27.50           N
ATOM   385  C    ARG A  50       0.261 -10.086 -14.398  1.00 21.06           C
ATOM   386  O    ARG A  50      -0.878  -9.701 -14.670  1.00 20.26           O
ATOM   387  N    THR A  51       1.178  -9.296 -13.852  1.00 20.62           N
ATOM   388  CA   THR A  51       0.950  -7.876 -13.656  1.00 20.97           C
ATOM   389  CB   THR A  51       0.339  -7.622 -12.214  1.00 21.00           C
ATOM   390  OG1  THR A  51       0.012  -6.227 -12.027  1.00 20.28           O
ATOM   391  CG2  THR A  51       1.340  -7.949 -11.132  1.00 21.43           C
ATOM   392  C    THR A  51       2.262  -7.139 -13.887  1.00 21.05           C
ATOM   393  O    THR A  51       3.172  -7.673 -14.538  1.00 22.32           O
ATOM   394  N    THR A  52       2.393  -5.934 -13.350  1.00 21.14           N
ATOM   395  CA   THR A  52       3.521  -5.087 -13.671  1.00 21.03           C
ATOM   396  CB   THR A  52       3.082  -4.057 -14.740  1.00 21.72           C
ATOM   397  OG1  THR A  52       2.530  -4.717 -15.894  1.00 19.83           O
ATOM   398  CG2  THR A  52       4.279  -3.255 -15.270  1.00 22.04           C
ATOM   399  C    THR A  52       4.039  -4.383 -12.426  1.00 21.47           C
ATOM   400  O    THR A  52       3.263  -3.899 -11.614  1.00 21.00           O
ATOM   401  N    ASN A  53       5.361  -4.328 -12.269  1.00 21.71           N
ATOM   402  CA   ASN A  53       5.943  -3.723 -11.077  1.00 21.81           C
ATOM   403  CB   ASN A  53       7.102  -4.562 -10.509  1.00 21.35           C
ATOM   404  CG   ASN A  53       8.388  -4.497 -11.339  1.00 23.09           C
ATOM   405  OD1  ASN A  53       8.533  -3.666 -12.242  1.00 22.59           O
ATOM   406  ND2  ASN A  53       9.356  -5.373 -10.994  1.00 21.08           N
ATOM   407  C    ASN A  53       6.272  -2.265 -11.341  1.00 22.65           C
ATOM   408  O    ASN A  53       6.011  -1.724 -12.445  1.00 22.41           O
ATOM   409  N    THR A  54       6.758  -1.607 -10.308  1.00 23.39           N
ATOM   410  CA   THR A  54       7.009  -0.177 -10.347  1.00 24.44           C
ATOM   411  CB   THR A  54       7.439   0.315  -8.945  1.00 24.20           C
ATOM   412  OG1  THR A  54       6.360   0.108  -8.023  1.00 23.35           O
ATOM   413  CG2  THR A  54       7.649   1.848  -8.935  1.00 24.97           C
ATOM   414  C    THR A  54       8.061   0.202 -11.391  1.00 25.10           C
ATOM   415  O    THR A  54       8.007   1.302 -11.946  1.00 24.89           O
ATOM   416  N    GLN A  55       9.009  -0.705 -11.642  1.00 26.09           N
ATOM   417  CA   GLN A  55      10.042  -0.515 -12.677  1.00 27.40           C
ATOM   418  CB   GLN A  55      11.323  -1.269 -12.281  1.00 27.59           C
ATOM   419  CG   GLN A  55      11.879  -0.811 -10.916  1.00 29.25           C
ATOM   420  CD   GLN A  55      11.920   0.707 -10.833  1.00 34.15           C
ATOM   421  OE1  GLN A  55      12.415   1.364 -11.774  1.00 35.80           O
ATOM   422  NE2  GLN A  55      11.366   1.284  -9.746  1.00 32.00           N
ATOM   423  C    GLN A  55       9.562  -0.940 -14.079  1.00 27.62           C
ATOM   424  O    GLN A  55      10.364  -1.109 -14.976  1.00 27.19           O
ATOM   425  N    ASN A  56       8.248  -1.093 -14.241  1.00 27.56           N
ATOM   426  CA   ASN A  56       7.615  -1.466 -15.502  1.00 28.41           C
ATOM   427  CB   ASN A  56       7.785  -0.349 -16.567  0.50 28.56           C
ATOM   428  CG   ASN A  56       6.886   0.870 -16.297  0.50 29.41           C
```

Fig. 1, continued

```
ATOM    429  OD1 ASN A  56       7.269   2.013 -16.559  0.50 32.68           O
ATOM    430  ND2 ASN A  56       5.696   0.626 -15.758  0.50 28.23           N
ATOM    431  C   ASN A  56       8.019  -2.844 -16.033  1.00 28.49           C
ATOM    432  O   ASN A  56       7.941  -3.084 -17.226  1.00 28.69           O
ATOM    433  N   GLU A  57       8.393  -3.757 -15.131  1.00 28.18           N
ATOM    434  CA  GLU A  57       8.724  -5.134 -15.487  1.00 28.10           C
ATOM    435  CB  GLU A  57       9.916  -5.645 -14.668  1.00 28.79           C
ATOM    436  CG  GLU A  57      11.194  -4.811 -14.796  1.00 31.53           C
ATOM    437  CD  GLU A  57      12.205  -5.016 -13.661  1.00 37.41           C
ATOM    438  OE1 GLU A  57      11.819  -5.339 -12.498  1.00 38.61           O
ATOM    439  OE2 GLU A  57      13.423  -4.810 -13.922  1.00 41.89           O
ATOM    440  C   GLU A  57       7.521  -6.073 -15.280  1.00 27.43           C
ATOM    441  O   GLU A  57       6.721  -5.894 -14.355  1.00 27.50           O
ATOM    442  N   ALA A  58       7.409  -7.074 -16.148  1.00 25.98           N
ATOM    443  CA  ALA A  58       6.439  -8.141 -16.012  1.00 25.39           C
ATOM    444  CB  ALA A  58       6.390  -8.976 -17.280  1.00 25.41           C
ATOM    445  C   ALA A  58       6.787  -9.018 -14.782  1.00 24.31           C
ATOM    446  O   ALA A  58       7.925  -9.431 -14.599  1.00 23.35           O
ATOM    447  N   VAL A  59       5.797  -9.224 -13.922  1.00 23.11           N
ATOM    448  CA  VAL A  59       5.939 -10.057 -12.719  1.00 22.15           C
ATOM    449  CB  VAL A  59       6.199  -9.219 -11.428  1.00 22.11           C
ATOM    450  CG1 VAL A  59       7.560  -8.567 -11.454  1.00 22.87           C
ATOM    451  CG2 VAL A  59       5.089  -8.162 -11.153  1.00 20.95           C
ATOM    452  C   VAL A  59       4.650 -10.819 -12.541  1.00 21.87           C
ATOM    453  O   VAL A  59       3.635 -10.460 -13.115  1.00 23.11           O
ATOM    454  N   ALA A  60       4.676 -11.879 -11.759  1.00 21.81           N
ATOM    455  CA  ALA A  60       3.444 -12.529 -11.359  1.00 21.70           C
ATOM    456  CB  ALA A  60       3.620 -14.057 -11.305  1.00 22.24           C
ATOM    457  C   ALA A  60       3.007 -11.973  -9.995  1.00 21.72           C
ATOM    458  O   ALA A  60       3.774 -11.273  -9.304  1.00 21.81           O
ATOM    459  N   ASP A  61       1.747 -12.249  -9.665  1.00 21.00           N
ATOM    460  CA  ASP A  61       1.184 -11.997  -8.361  1.00 20.45           C
ATOM    461  CB  ASP A  61       0.638 -10.584  -8.279  1.00 20.21           C
ATOM    462  CG  ASP A  61       0.552 -10.073  -6.842  1.00 20.65           C
ATOM    463  OD1 ASP A  61       0.051  -8.942  -6.645  1.00 20.16           O
ATOM    464  OD2 ASP A  61       0.960 -10.743  -5.850  1.00 19.50           O
ATOM    465  C   ASP A  61       0.081 -13.019  -8.082  1.00 20.37           C
ATOM    466  O   ASP A  61      -0.272 -13.815  -8.962  1.00 19.79           O
ATOM    467  N   VAL A  62      -0.448 -13.007  -6.851  1.00 19.35           N
ATOM    468  CA  VAL A  62      -1.549 -13.876  -6.470  1.00 18.26           C
ATOM    469  CB  VAL A  62      -1.107 -14.832  -5.346  1.00 18.20           C
ATOM    470  CG1 VAL A  62      -2.280 -15.624  -4.786  1.00 19.71           C
ATOM    471  CG2 VAL A  62      -0.030 -15.772  -5.843  1.00 18.58           C
ATOM    472  C   VAL A  62      -2.741 -13.035  -6.020  1.00 17.90           C
ATOM    473  O   VAL A  62      -2.579 -11.980  -5.391  1.00 18.49           O
ATOM    474  N   ALA A  63      -3.926 -13.497  -6.357  1.00 17.25           N
ATOM    475  CA  ALA A  63      -5.193 -12.896  -5.925  1.00 17.95           C
ATOM    476  CB  ALA A  63      -5.832 -12.141  -7.044  1.00 18.21           C
ATOM    477  C   ALA A  63      -6.124 -14.026  -5.498  1.00 17.86           C
ATOM    478  O   ALA A  63      -5.997 -15.154  -5.974  1.00 17.32           O
ATOM    479  N   THR A  64      -7.053 -13.691  -4.614  1.00 17.72           N
ATOM    480  CA  THR A  64      -8.068 -14.590  -4.142  1.00 17.33           C
ATOM    481  CB  THR A  64      -8.136 -14.556  -2.599  1.00 16.57           C
ATOM    482  OG1 THR A  64      -6.861 -14.861  -2.045  1.00 17.35           O
```

Fig. 1, continued

```
ATOM    483  CG2 THR A  64      -9.027 -15.614  -2.085  1.00 17.30           C
ATOM    484  C   THR A  64      -9.394 -14.128  -4.667  1.00 17.88           C
ATOM    485  O   THR A  64      -9.711 -12.932  -4.607  1.00 18.26           O
ATOM    486  N   VAL A  65     -10.206 -15.077  -5.104  1.00 17.26           N
ATOM    487  CA  VAL A  65     -11.526 -14.755  -5.594  1.00 17.82           C
ATOM    488  CB  VAL A  65     -11.628 -14.858  -7.144  1.00 17.59           C
ATOM    489  CG1 VAL A  65     -10.584 -13.967  -7.787  1.00 19.27           C
ATOM    490  CG2 VAL A  65     -11.484 -16.289  -7.630  1.00 16.94           C
ATOM    491  C   VAL A  65     -12.553 -15.658  -4.989  1.00 17.66           C
ATOM    492  O   VAL A  65     -12.284 -16.804  -4.692  1.00 18.39           O
ATOM    493  N   TRP A  66     -13.756 -15.135  -4.870  1.00 18.52           N
ATOM    494  CA  TRP A  66     -14.882 -15.882  -4.362  1.00 18.85           C
ATOM    495  CB  TRP A  66     -15.330 -15.310  -3.031  1.00 18.66           C
ATOM    496  CG  TRP A  66     -14.409 -15.507  -1.833  1.00 18.12           C
ATOM    497  CD1 TRP A  66     -14.520 -16.487  -0.874  1.00 18.35           C
ATOM    498  NE1 TRP A  66     -13.564 -16.306   0.104  1.00 16.91           N
ATOM    499  CE2 TRP A  66     -12.834 -15.183  -0.181  1.00 15.93           C
ATOM    500  CD2 TRP A  66     -13.342 -14.643  -1.392  1.00 16.01           C
ATOM    501  CE3 TRP A  66     -12.762 -13.470  -1.893  1.00 17.73           C
ATOM    502  CZ3 TRP A  66     -11.685 -12.890  -1.186  1.00 17.77           C
ATOM    503  CH2 TRP A  66     -11.203 -13.478   0.005  1.00 16.34           C
ATOM    504  CZ2 TRP A  66     -11.773 -14.602   0.522  1.00 15.33           C
ATOM    505  C   TRP A  66     -16.045 -15.756  -5.320  1.00 19.51           C
ATOM    506  O   TRP A  66     -16.366 -14.665  -5.761  1.00 20.13           O
ATOM    507  N   ILE A  67     -16.713 -16.875  -5.561  1.00 20.32           N
ATOM    508  CA  ILE A  67     -17.776 -16.993  -6.529  1.00 21.63           C
ATOM    509  CB  ILE A  67     -17.494 -18.216  -7.460  1.00 22.11           C
ATOM    510  CG1 ILE A  67     -16.050 -18.231  -7.958  1.00 23.55           C
ATOM    511  CD1 ILE A  67     -15.579 -16.992  -8.684  1.00 24.98           C
ATOM    512  CG2 ILE A  67     -18.474 -18.275  -8.628  1.00 24.15           C
ATOM    513  C   ILE A  67     -19.062 -17.204  -5.745  1.00 21.56           C
ATOM    514  O   ILE A  67     -19.233 -18.215  -5.077  1.00 21.11           O
ATOM    515  N   PRO A  68     -19.982 -16.264  -5.786  1.00 22.73           N
ATOM    516  CA  PRO A  68     -21.220 -16.452  -5.022  1.00 24.46           C
ATOM    517  CB  PRO A  68     -21.945 -15.114  -5.184  1.00 24.18           C
ATOM    518  CG  PRO A  68     -21.327 -14.491  -6.394  1.00 23.73           C
ATOM    519  CD  PRO A  68     -19.961 -15.005  -6.537  1.00 22.64           C
ATOM    520  C   PRO A  68     -22.055 -17.638  -5.557  1.00 25.85           C
ATOM    521  O   PRO A  68     -21.998 -17.923  -6.751  1.00 25.18           O
ATOM    522  N   ALA A  69     -22.818 -18.296  -4.686  1.00 27.95           N
ATOM    523  CA  ALA A  69     -23.665 -19.426  -5.093  1.00 29.72           C
ATOM    524  CB  ALA A  69     -24.397 -20.038  -3.899  1.00 30.10           C
ATOM    525  C   ALA A  69     -24.663 -18.955  -6.122  1.00 30.97           C
ATOM    526  O   ALA A  69     -24.938 -19.657  -7.092  1.00 32.04           O
ATOM    527  N   LYS A  70     -25.138 -17.728  -5.944  1.00 31.45           N
ATOM    528  CA  LYS A  70     -26.171 -17.175  -6.808  1.00 31.79           C
ATOM    529  CB  LYS A  70     -27.512 -17.127  -6.058  1.00 31.92           C
ATOM    530  CG  LYS A  70     -28.700 -16.992  -7.001  1.00 35.01           C
ATOM    531  CD  LYS A  70     -29.917 -17.688  -6.872  0.00 45.92           C
ATOM    532  CE  LYS A  70     -31.056 -16.980  -7.658  0.00 48.09           C
ATOM    533  NZ  LYS A  70     -31.827 -16.006  -6.803  0.00 49.59           N
ATOM    534  C   LYS A  70     -25.762 -15.779  -7.273  1.00 30.51           C
ATOM    535  O   LYS A  70     -26.142 -14.775  -6.682  1.00 29.29           O
ATOM    536  N   PRO A  71     -24.990 -15.705  -8.340  1.00 29.97           N
```

Fig. 1, continued

```
ATOM    537  CA  PRO A  71     -24.475 -14.402  -8.773  1.00 30.06           C
ATOM    538  CB  PRO A  71     -23.562 -14.752  -9.941  1.00 29.67           C
ATOM    539  CG  PRO A  71     -23.315 -16.228  -9.808  1.00 30.43           C
ATOM    540  CD  PRO A  71     -24.532 -16.801  -9.204  1.00 30.23           C
ATOM    541  C   PRO A  71     -25.593 -13.452  -9.201  1.00 29.77           C
ATOM    542  O   PRO A  71     -26.559 -13.886  -9.805  1.00 28.52           O
ATOM    543  N   ALA A  72     -25.457 -12.178  -8.873  1.00 29.59           N
ATOM    544  CA  ALA A  72     -26.305 -11.152  -9.462  1.00 30.01           C
ATOM    545  CB  ALA A  72     -26.100  -9.802  -8.779  1.00 29.69           C
ATOM    546  C   ALA A  72     -26.028 -11.052 -10.972  1.00 30.45           C
ATOM    547  O   ALA A  72     -24.954 -11.432 -11.465  1.00 30.04           O
ATOM    548  N   SER A  73     -27.031 -10.546 -11.678  1.00 31.07           N
ATOM    549  CA  SER A  73     -27.032 -10.382 -13.131  1.00 32.22           C
ATOM    550  CB  SER A  73     -27.988 -11.408 -13.756  1.00 32.53           C
ATOM    551  OG  SER A  73     -27.812 -11.452 -15.158  1.00 36.03           O
ATOM    552  C   SER A  73     -27.543  -8.970 -13.407  1.00 31.84           C
ATOM    553  O   SER A  73     -28.561  -8.582 -12.819  1.00 33.00           O
ATOM    554  N   PRO A  74     -26.856  -8.168 -14.226  1.00 31.37           N
ATOM    555  CA  PRO A  74     -25.574  -8.528 -14.859  1.00 30.52           C
ATOM    556  CB  PRO A  74     -25.307  -7.373 -15.859  1.00 30.91           C
ATOM    557  CG  PRO A  74     -26.549  -6.506 -15.841  1.00 32.46           C
ATOM    558  CD  PRO A  74     -27.283  -6.795 -14.558  1.00 31.58           C
ATOM    559  C   PRO A  74     -24.412  -8.638 -13.844  1.00 28.94           C
ATOM    560  O   PRO A  74     -24.541  -8.167 -12.702  1.00 26.77           O
ATOM    561  N   PRO A  75     -23.321  -9.273 -14.267  1.00 28.03           N
ATOM    562  CA  PRO A  75     -22.180  -9.562 -13.380  1.00 27.53           C
ATOM    563  CB  PRO A  75     -21.193 -10.300 -14.290  1.00 27.69           C
ATOM    564  CG  PRO A  75     -22.073 -10.869 -15.405  1.00 28.44           C
ATOM    565  CD  PRO A  75     -23.111  -9.811 -15.627  1.00 28.28           C
ATOM    566  C   PRO A  75     -21.557  -8.314 -12.741  1.00 26.42           C
ATOM    567  O   PRO A  75     -21.399  -7.274 -13.387  1.00 25.99           O
ATOM    568  N   LYS A  76     -21.304  -8.416 -11.442  1.00 24.74           N
ATOM    569  CA  LYS A  76     -20.787  -7.301 -10.631  1.00 24.32           C
ATOM    570  CB  LYS A  76     -21.873  -6.805  -9.682  1.00 24.70           C
ATOM    571  CG  LYS A  76     -22.986  -6.028 -10.414  1.00 27.51           C
ATOM    572  CD  LYS A  76     -24.219  -5.872  -9.563  1.00 31.40           C
ATOM    573  CE  LYS A  76     -25.334  -5.173 -10.334  1.00 33.95           C
ATOM    574  NZ  LYS A  76     -25.929  -6.062 -11.362  1.00 35.32           N
ATOM    575  C   LYS A  76     -19.573  -7.779  -9.844  1.00 23.28           C
ATOM    576  O   LYS A  76     -19.634  -8.847  -9.205  1.00 23.24           O
ATOM    577  N   ILE A  77     -18.491  -7.003  -9.895  1.00 21.31           N
ATOM    578  CA  ILE A  77     -17.212  -7.380  -9.293  1.00 20.95           C
ATOM    579  CB  ILE A  77     -16.085  -7.404 -10.336  1.00 20.54           C
ATOM    580  CG1 ILE A  77     -16.319  -8.512 -11.347  1.00 21.46           C
ATOM    581  CD1 ILE A  77     -15.614  -8.267 -12.661  1.00 23.01           C
ATOM    582  CG2 ILE A  77     -14.723  -7.656  -9.672  1.00 21.17           C
ATOM    583  C   ILE A  77     -16.851  -6.394  -8.186  1.00 19.99           C
ATOM    584  O   ILE A  77     -16.748  -5.182  -8.425  1.00 19.22           O
ATOM    585  N   PHE A  78     -16.673  -6.924  -6.981  1.00 18.67           N
ATOM    586  CA  PHE A  78     -16.277  -6.131  -5.801  1.00 18.58           C
ATOM    587  CB  PHE A  78     -17.155  -6.546  -4.629  1.00 18.87           C
ATOM    588  CG  PHE A  78     -16.937  -5.769  -3.356  1.00 18.89           C
ATOM    589  CD1 PHE A  78     -16.190  -6.306  -2.324  1.00 19.90           C
ATOM    590  CE1 PHE A  78     -16.039  -5.633  -1.120  1.00 20.76           C
```

Fig. 1, continued

```
ATOM    591  CZ   PHE A  78     -16.645  -4.418  -0.925  1.00 21.25           C
ATOM    592  CE2  PHE A  78     -17.433  -3.883  -1.923  1.00 25.17           C
ATOM    593  CD2  PHE A  78     -17.593  -4.575  -3.133  1.00 24.17           C
ATOM    594  C    PHE A  78     -14.814  -6.456  -5.492  1.00 17.76           C
ATOM    595  O    PHE A  78     -14.492  -7.598  -5.196  1.00 17.63           O
ATOM    596  N    SER A  79     -13.953  -5.452  -5.553  1.00 17.22           N
ATOM    597  CA   SER A  79     -12.523  -5.623  -5.281  1.00 17.11           C
ATOM    598  CB   SER A  79     -11.683  -4.910  -6.329  1.00 16.55           C
ATOM    599  OG   SER A  79     -10.265  -5.195  -6.222  1.00 17.39           O
ATOM    600  C    SER A  79     -12.256  -5.026  -3.903  1.00 16.90           C
ATOM    601  O    SER A  79     -12.421  -3.816  -3.709  1.00 17.01           O
ATOM    602  N    TYR A  80     -11.866  -5.879  -2.957  1.00 15.80           N
ATOM    603  CA   TYR A  80     -11.597  -5.481  -1.574  1.00 15.04           C
ATOM    604  CB   TYR A  80     -12.273  -6.452  -0.599  1.00 15.33           C
ATOM    605  CG   TYR A  80     -11.971  -6.119   0.856  1.00 16.26           C
ATOM    606  CD1  TYR A  80     -12.550  -5.015   1.469  1.00 16.06           C
ATOM    607  CE1  TYR A  80     -12.280  -4.691   2.809  1.00 18.68           C
ATOM    608  CZ   TYR A  80     -11.399  -5.466   3.521  1.00 18.28           C
ATOM    609  OH   TYR A  80     -11.102  -5.175   4.814  1.00 22.44           O
ATOM    610  CE2  TYR A  80     -10.805  -6.558   2.936  1.00 19.69           C
ATOM    611  CD2  TYR A  80     -11.068  -6.874   1.591  1.00 17.69           C
ATOM    612  C    TYR A  80     -10.112  -5.460  -1.323  1.00 14.52           C
ATOM    613  O    TYR A  80      -9.412  -6.462  -1.566  1.00 14.00           O
ATOM    614  N    GLN A  81      -9.632  -4.318  -0.848  1.00 14.24           N
ATOM    615  CA   GLN A  81      -8.241  -4.118  -0.525  1.00 15.97           C
ATOM    616  CB   GLN A  81      -7.771  -2.777  -1.083  1.00 15.96           C
ATOM    617  CG   GLN A  81      -7.562  -2.756  -2.622  1.00 16.32           C
ATOM    618  CD   GLN A  81      -8.871  -3.053  -3.364  1.00 15.67           C
ATOM    619  OE1  GLN A  81      -9.824  -2.255  -3.305  1.00 19.16           O
ATOM    620  NE2  GLN A  81      -8.951  -4.216  -3.970  1.00 12.52           N
ATOM    621  C    GLN A  81      -8.040  -4.157   1.012  1.00 17.06           C
ATOM    622  O    GLN A  81      -8.656  -3.392   1.735  1.00 16.98           O
ATOM    623  N    VAL A  82      -7.156  -5.042   1.478  1.00 19.51           N
ATOM    624  CA   VAL A  82      -6.890  -5.249   2.912  1.00 20.36           C
ATOM    625  CB   VAL A  82      -6.683  -6.776   3.253  0.40 20.68           C
ATOM    626  CG1  VAL A  82      -6.181  -7.544   2.070  0.40 20.65           C
ATOM    627  CG2  VAL A  82      -5.726  -7.018   4.445  0.40 21.15           C
ATOM    628  C    VAL A  82      -5.708  -4.409   3.370  1.00 20.56           C
ATOM    629  O    VAL A  82      -4.806  -4.124   2.598  1.00 20.65           O
ATOM    630  N    TYR A  83      -5.710  -4.014   4.637  1.00 20.35           N
ATOM    631  CA   TYR A  83      -4.574  -3.274   5.214  1.00 20.21           C
ATOM    632  CB   TYR A  83      -5.042  -2.357   6.365  1.00 20.16           C
ATOM    633  CG   TYR A  83      -6.143  -2.958   7.231  1.00 20.76           C
ATOM    634  CD1  TYR A  83      -7.485  -2.663   6.987  1.00 22.87           C
ATOM    635  CE1  TYR A  83      -8.505  -3.219   7.753  1.00 25.63           C
ATOM    636  CZ   TYR A  83      -8.181  -4.080   8.820  1.00 26.13           C
ATOM    637  OH   TYR A  83      -9.180  -4.643   9.573  1.00 25.93           O
ATOM    638  CE2  TYR A  83      -6.855  -4.370   9.099  1.00 23.94           C
ATOM    639  CD2  TYR A  83      -5.840  -3.801   8.296  1.00 22.22           C
ATOM    640  C    TYR A  83      -3.444  -4.228   5.666  1.00 20.67           C
ATOM    641  O    TYR A  83      -3.217  -4.405   6.876  1.00 22.03           O
ATOM    642  N    GLU A  84      -2.695  -4.798   4.719  1.00 20.51           N
ATOM    643  CA   GLU A  84      -1.614  -5.741   5.051  1.00 20.07           C
ATOM    644  CB   GLU A  84      -0.944  -6.307   3.779  1.00 20.53           C
```

Fig. 1, continued

| | | | | | | | | | | |
|---|---|---|---|---|---|---|---|---|---|---|
| ATOM | 645 | CG | GLU | A | 84 | 0.304 | -7.159 | 4.049 | 1.00 18.95 | C |
| ATOM | 646 | CD | GLU | A | 84 | 0.957 | -7.749 | 2.812 | 1.00 23.30 | C |
| ATOM | 647 | OE1 | GLU | A | 84 | 0.424 | -7.578 | 1.681 | 1.00 22.84 | O |
| ATOM | 648 | OE2 | GLU | A | 84 | 2.031 | -8.404 | 2.978 | 1.00 25.55 | O |
| ATOM | 649 | C | GLU | A | 84 | -0.555 | -5.121 | 5.987 | 1.00 20.36 | C |
| ATOM | 650 | O | GLU | A | 84 | -0.156 | -5.748 | 6.964 | 1.00 20.10 | O |
| ATOM | 651 | N | ASP | A | 85 | -0.115 | -3.899 | 5.657 | 1.00 20.58 | N |
| ATOM | 652 | CA | ASP | A | 85 | 0.784 | -3.068 | 6.458 | 1.00 21.01 | C |
| ATOM | 653 | CB | ASP | A | 85 | 0.043 | -2.528 | 7.672 | 1.00 21.53 | C |
| ATOM | 654 | CG | ASP | A | 85 | -1.027 | -1.517 | 7.317 | 1.00 25.21 | C |
| ATOM | 655 | OD1 | ASP | A | 85 | -1.362 | -1.323 | 6.124 | 1.00 25.43 | O |
| ATOM | 656 | OD2 | ASP | A | 85 | -1.624 | -0.884 | 8.222 | 1.00 31.45 | O |
| ATOM | 657 | C | ASP | A | 85 | 2.064 | -3.757 | 6.958 | 1.00 20.40 | C |
| ATOM | 658 | O | ASP | A | 85 | 2.389 | -3.693 | 8.158 | 1.00 19.82 | O |
| ATOM | 659 | N | ALA | A | 86 | 2.764 | -4.410 | 6.043 | 1.00 19.64 | N |
| ATOM | 660 | CA | ALA | A | 86 | 3.955 | -5.181 | 6.378 | 1.00 19.34 | C |
| ATOM | 661 | CB | ALA | A | 86 | 3.530 | -6.497 | 6.981 | 1.00 19.56 | C |
| ATOM | 662 | C | ALA | A | 86 | 4.817 | -5.421 | 5.141 | 1.00 18.99 | C |
| ATOM | 663 | O | ALA | A | 86 | 4.338 | -5.283 | 4.030 | 1.00 19.28 | O |
| ATOM | 664 | N | THR | A | 87 | 6.087 | -5.764 | 5.346 | 1.00 18.85 | N |
| ATOM | 665 | CA | THR | A | 87 | 6.994 | -6.014 | 4.247 | 1.00 18.57 | C |
| ATOM | 666 | CB | THR | A | 87 | 8.084 | -4.892 | 4.099 | 1.00 18.32 | C |
| ATOM | 667 | OG1 | THR | A | 87 | 8.885 | -4.760 | 5.291 | 1.00 20.12 | O |
| ATOM | 668 | CG2 | THR | A | 87 | 7.445 | -3.548 | 3.926 | 1.00 17.37 | C |
| ATOM | 669 | C | THR | A | 87 | 7.625 | -7.389 | 4.362 | 1.00 18.59 | C |
| ATOM | 670 | O | THR | A | 87 | 8.829 | -7.522 | 4.249 | 1.00 18.63 | O |
| ATOM | 671 | N | ALA | A | 88 | 6.799 | -8.399 | 4.600 | 1.00 18.78 | N |
| ATOM | 672 | CA | ALA | A | 88 | 7.236 | -9.800 | 4.497 | 1.00 19.10 | C |
| ATOM | 673 | CB | ALA | A | 88 | 7.376 | -10.418 | 5.870 | 1.00 19.13 | C |
| ATOM | 674 | C | ALA | A | 88 | 6.195 | -10.550 | 3.680 | 1.00 18.66 | C |
| ATOM | 675 | O | ALA | A | 88 | 5.023 | -10.251 | 3.762 | 1.00 18.53 | O |
| ATOM | 676 | N | LEU | A | 89 | 6.634 | -11.530 | 2.908 | 1.00 18.96 | N |
| ATOM | 677 | CA | LEU | A | 89 | 5.783 | -12.166 | 1.912 | 1.00 19.41 | C |
| ATOM | 678 | CB | LEU | A | 89 | 6.584 | -13.174 | 1.082 | 1.00 19.49 | C |
| ATOM | 679 | CG | LEU | A | 89 | 5.789 | -13.920 | -0.008 | 1.00 21.20 | C |
| ATOM | 680 | CD1 | LEU | A | 89 | 5.253 | -12.967 | -1.064 | 1.00 23.23 | C |
| ATOM | 681 | CD2 | LEU | A | 89 | 6.626 | -15.002 | -0.661 | 1.00 22.55 | C |
| ATOM | 682 | C | LEU | A | 89 | 4.594 | -12.868 | 2.558 | 1.00 19.53 | C |
| ATOM | 683 | O | LEU | A | 89 | 3.472 | -12.816 | 2.055 | 1.00 18.43 | O |
| ATOM | 684 | N | ASP | A | 90 | 4.841 | -13.515 | 3.689 | 1.00 19.36 | N |
| ATOM | 685 | CA | ASP | A | 90 | 3.799 | -14.333 | 4.305 | 1.00 19.54 | C |
| ATOM | 686 | CB | ASP | A | 90 | 4.396 | -15.484 | 5.136 | 1.00 19.87 | C |
| ATOM | 687 | CG | ASP | A | 90 | 5.303 | -15.029 | 6.244 | 1.00 20.63 | C |
| ATOM | 688 | OD1 | ASP | A | 90 | 5.468 | -15.866 | 7.189 | 1.00 19.49 | O |
| ATOM | 689 | OD2 | ASP | A | 90 | 5.906 | -13.908 | 6.256 | 1.00 20.42 | O |
| ATOM | 690 | C | ASP | A | 90 | 2.750 | -13.536 | 5.075 | 1.00 19.24 | C |
| ATOM | 691 | O | ASP | A | 90 | 1.857 | -14.109 | 5.671 | 1.00 17.30 | O |
| ATOM | 692 | N | CYS | A | 91 | 2.849 | -12.206 | 4.999 | 1.00 19.08 | N |
| ATOM | 693 | CA | CYS | A | 91 | 1.802 | -11.318 | 5.445 | 1.00 18.97 | C |
| ATOM | 694 | CB | CYS | A | 91 | 2.381 | -9.956 | 5.847 | 1.00 19.57 | C |
| ATOM | 695 | SG | CYS | A | 91 | 3.843 | -10.054 | 6.904 | 1.00 21.52 | S |
| ATOM | 696 | C | CYS | A | 91 | 0.710 | -11.119 | 4.418 | 1.00 18.38 | C |
| ATOM | 697 | O | CYS | A | 91 | -0.294 | -10.487 | 4.731 | 1.00 18.13 | O |
| ATOM | 698 | N | ALA | A | 92 | 0.885 | -11.695 | 3.223 | 1.00 18.73 | N |

Fig. 1, continued

```
ATOM   699  CA   ALA A   92      -0.039  -11.579   2.102  1.00 18.22           C
ATOM   700  CB   ALA A   92       0.387  -12.543   0.992  1.00 18.47           C
ATOM   701  C    ALA A   92      -1.504  -11.843   2.448  1.00 18.22           C
ATOM   702  O    ALA A   92      -1.803  -12.802   3.122  1.00 18.59           O
ATOM   703  N    PRO A   93      -2.432  -11.044   1.927  1.00 18.20           N
ATOM   704  CA   PRO A   93      -3.857  -11.333   2.087  1.00 17.72           C
ATOM   705  CB   PRO A   93      -4.511  -10.319   1.165  1.00 17.91           C
ATOM   706  CG   PRO A   93      -3.532   -9.153   1.190  1.00 18.61           C
ATOM   707  CD   PRO A   93      -2.204   -9.796   1.185  1.00 18.55           C
ATOM   708  C    PRO A   93      -4.246  -12.761   1.728  1.00 17.76           C
ATOM   709  O    PRO A   93      -4.973  -13.403   2.500  1.00 18.20           O
ATOM   710  N    SER A   94      -3.743  -13.268   0.604  1.00 17.65           N
ATOM   711  CA   SER A   94      -4.123  -14.585   0.113  1.00 17.20           C
ATOM   712  CB   SER A   94      -3.369  -14.953  -1.167  1.00 16.45           C
ATOM   713  OG   SER A   94      -1.953  -14.834  -1.031  1.00 16.09           O
ATOM   714  C    SER A   94      -3.904  -15.668   1.173  1.00 17.22           C
ATOM   715  O    SER A   94      -4.772  -16.499   1.395  1.00 16.95           O
ATOM   716  N    TYR A   95      -2.724  -15.661   1.779  1.00 18.14           N
ATOM   717  CA   TYR A   95      -2.370  -16.604   2.836  1.00 17.92           C
ATOM   718  CB   TYR A   95      -0.860  -16.486   3.117  1.00 18.00           C
ATOM   719  CG   TYR A   95      -0.299  -17.506   4.088  1.00 18.13           C
ATOM   720  CD1  TYR A   95       0.438  -17.104   5.199  1.00 16.79           C
ATOM   721  CE1  TYR A   95       0.935  -18.017   6.085  1.00 16.82           C
ATOM   722  CZ   TYR A   95       0.719  -19.363   5.878  1.00 17.86           C
ATOM   723  OH   TYR A   95       1.237  -20.274   6.768  1.00 18.06           O
ATOM   724  CE2  TYR A   95       0.001  -19.793   4.785  1.00 17.11           C
ATOM   725  CD2  TYR A   95      -0.499  -18.865   3.896  1.00 18.37           C
ATOM   726  C    TYR A   95      -3.252  -16.406   4.079  1.00 17.99           C
ATOM   727  O    TYR A   95      -3.804  -17.377   4.656  1.00 17.35           O
ATOM   728  N    SER A   96      -3.453  -15.139   4.432  1.00 17.84           N
ATOM   729  CA   SER A   96      -4.301  -14.749   5.548  1.00 17.76           C
ATOM   730  CB   SER A   96      -4.218  -13.234   5.756  1.00 18.09           C
ATOM   731  OG   SER A   96      -2.856  -12.839   5.927  1.00 20.59           O
ATOM   732  C    SER A   96      -5.778  -15.175   5.434  1.00 17.38           C
ATOM   733  O    SER A   96      -6.417  -15.482   6.462  1.00 17.32           O
ATOM   734  N    TYR A   97      -6.316  -15.233   4.215  1.00 16.66           N
ATOM   735  CA   TYR A   97      -7.728  -15.607   3.999  1.00 15.98           C
ATOM   736  CB   TYR A   97      -8.181  -15.259   2.569  1.00 16.81           C
ATOM   737  CG   TYR A   97      -8.429  -13.786   2.307  1.00 17.37           C
ATOM   738  CD1  TYR A   97      -7.812  -13.137   1.236  1.00 17.95           C
ATOM   739  CE1  TYR A   97      -8.056  -11.799   0.973  1.00 16.76           C
ATOM   740  CZ   TYR A   97      -8.900  -11.100   1.781  1.00 19.77           C
ATOM   741  OH   TYR A   97      -9.115   -9.772   1.541  1.00 18.53           O
ATOM   742  CE2  TYR A   97      -9.505  -11.723   2.888  1.00 18.63           C
ATOM   743  CD2  TYR A   97      -9.281  -13.050   3.114  1.00 16.86           C
ATOM   744  C    TYR A   97      -7.983  -17.113   4.189  1.00 16.01           C
ATOM   745  O    TYR A   97      -9.132  -17.531   4.362  1.00 14.78           O
ATOM   746  N    LEU A   98      -6.936  -17.928   4.076  1.00 15.45           N
ATOM   747  CA   LEU A   98      -7.094  -19.371   4.160  1.00 15.74           C
ATOM   748  CB   LEU A   98      -5.755  -20.102   3.905  1.00 16.19           C
ATOM   749  CG   LEU A   98      -5.017  -19.898   2.590  1.00 16.64           C
ATOM   750  CD1  LEU A   98      -3.617  -20.595   2.670  1.00 17.70           C
ATOM   751  CD2  LEU A   98      -5.844  -20.387   1.412  1.00 15.16           C
ATOM   752  C    LEU A   98      -7.600  -19.804   5.542  1.00 16.24           C
```

Fig. 1, continued

```
ATOM    753  O   LEU A  98      -7.340 -19.162   6.570  1.00 16.13           O
ATOM    754  N   THR A  99      -8.314 -20.910   5.565  1.00 16.75           N
ATOM    755  CA  THR A  99      -8.587 -21.580   6.815  1.00 17.34           C
ATOM    756  CB  THR A  99      -9.390 -22.860   6.592  1.00 17.51           C
ATOM    757  OG1 THR A  99      -8.776 -23.675   5.573  1.00 18.19           O
ATOM    758  CG2 THR A  99     -10.768 -22.541   6.038  1.00 18.43           C
ATOM    759  C   THR A  99      -7.265 -21.942   7.483  1.00 18.12           C
ATOM    760  O   THR A  99      -6.344 -22.430   6.831  1.00 18.19           O
ATOM    761  N   GLY A 100      -7.210 -21.721   8.795  1.00 18.23           N
ATOM    762  CA  GLY A 100      -6.040 -21.955   9.582  1.00 18.98           C
ATOM    763  C   GLY A 100      -5.948 -20.854  10.626  1.00 19.09           C
ATOM    764  O   GLY A 100      -6.660 -19.880  10.544  1.00 20.25           O
ATOM    765  N   LEU A 101      -5.052 -20.998  11.573  1.00 18.42           N
ATOM    766  CA  LEU A 101      -4.959 -20.076  12.701  1.00 20.00           C
ATOM    767  CB  LEU A 101      -5.401 -20.773  14.009  1.00 19.61           C
ATOM    768  CG  LEU A 101      -6.887 -21.010  14.331  1.00 24.02           C
ATOM    769  CD1 LEU A 101      -7.809 -19.807  14.050  1.00 27.46           C
ATOM    770  CD2 LEU A 101      -7.419 -22.218  13.634  1.00 27.56           C
ATOM    771  C   LEU A 101      -3.549 -19.557  12.899  1.00 19.11           C
ATOM    772  O   LEU A 101      -3.361 -18.652  13.688  1.00 21.53           O
ATOM    773  N   ASP A 102      -2.563 -20.108  12.202  1.00 18.66           N
ATOM    774  CA  ASP A 102      -1.160 -19.763  12.449  1.00 18.06           C
ATOM    775  CB  ASP A 102      -0.244 -21.025  12.402  1.00 17.74           C
ATOM    776  CG  ASP A 102      -0.299 -21.767  11.059  1.00 20.10           C
ATOM    777  OD1 ASP A 102       0.630 -22.600  10.748  1.00 18.79           O
ATOM    778  OD2 ASP A 102      -1.248 -21.595  10.259  1.00 19.91           O
ATOM    779  C   ASP A 102      -0.605 -18.698  11.498  1.00 17.51           C
ATOM    780  O   ASP A 102       0.550 -18.362  11.598  1.00 17.54           O
ATOM    781  N   GLN A 103      -1.386 -18.208  10.544  1.00 17.02           N
ATOM    782  CA  GLN A 103      -0.857 -17.213   9.596  1.00 17.48           C
ATOM    783  CB  GLN A 103      -1.855 -16.867   8.496  1.00 16.41           C
ATOM    784  CG  GLN A 103      -2.282 -18.046   7.637  1.00 17.14           C
ATOM    785  CD  GLN A 103      -3.639 -18.590   8.057  1.00 17.97           C
ATOM    786  OE1 GLN A 103      -3.813 -18.982   9.234  1.00 17.05           O
ATOM    787  NE2 GLN A 103      -4.609 -18.598   7.132  1.00 13.26           N
ATOM    788  C   GLN A 103      -0.513 -15.931  10.363  1.00 18.04           C
ATOM    789  O   GLN A 103      -1.332 -15.464  11.164  1.00 17.92           O
ATOM    790  N   PRO A 104       0.673 -15.363  10.122  1.00 18.21           N
ATOM    791  CA  PRO A 104       1.142 -14.228  10.932  1.00 18.52           C
ATOM    792  CB  PRO A 104       2.588 -14.060  10.491  1.00 18.43           C
ATOM    793  CG  PRO A 104       2.654 -14.664   9.104  1.00 19.11           C
ATOM    794  CD  PRO A 104       1.669 -15.775   9.110  1.00 18.58           C
ATOM    795  C   PRO A 104       0.317 -12.942  10.798  1.00 18.27           C
ATOM    796  O   PRO A 104       0.247 -12.163  11.757  1.00 18.98           O
ATOM    797  N   ASN A 105      -0.350 -12.766   9.669  1.00 17.29           N
ATOM    798  CA  ASN A 105      -1.214 -11.612   9.423  1.00 17.71           C
ATOM    799  CB  ASN A 105      -0.797 -10.857   8.121  1.00 17.19           C
ATOM    800  CG  ASN A 105      -0.695  -9.350   8.321  1.00 17.26           C
ATOM    801  OD1 ASN A 105      -0.586  -8.880   9.452  1.00 16.58           O
ATOM    802  ND2 ASN A 105      -0.685  -8.585   7.213  1.00 18.36           N
ATOM    803  C   ASN A 105      -2.683 -11.971   9.367  1.00 17.69           C
ATOM    804  O   ASN A 105      -3.474 -11.213   8.820  1.00 18.07           O
ATOM    805  N   LYS A 106      -3.049 -13.106   9.965  1.00 18.56           N
ATOM    806  CA  LYS A 106      -4.447 -13.578  10.063  1.00 19.10           C
```

Fig. 1, continued

```
ATOM    807  CB   LYS A 106      -4.522 -14.780  11.040  1.00 19.85           C
ATOM    808  CG   LYS A 106      -5.929 -15.423  11.227  1.00 20.65           C
ATOM    809  CD   LYS A 106      -6.385 -16.202  10.024  1.00 21.93           C
ATOM    810  CE   LYS A 106      -7.722 -16.894  10.334  1.00 24.26           C
ATOM    811  NZ   LYS A 106      -8.136 -17.783   9.263  1.00 21.07           N
ATOM    812  C    LYS A 106      -5.427 -12.506  10.526  1.00 18.84           C
ATOM    813  O    LYS A 106      -6.551 -12.411  10.037  1.00 18.38           O
ATOM    814  N    VAL A 107      -5.010 -11.698  11.490  1.00 19.02           N
ATOM    815  CA   VAL A 107      -5.865 -10.660  12.010  1.00 19.27           C
ATOM    816  CB   VAL A 107      -5.157  -9.875  13.171  1.00 20.06           C
ATOM    817  CG1  VAL A 107      -3.950  -9.048  12.668  1.00 20.31           C
ATOM    818  CG2  VAL A 107      -6.162  -9.003  13.910  1.00 21.07           C
ATOM    819  C    VAL A 107      -6.451  -9.722  10.911  1.00 19.20           C
ATOM    820  O    VAL A 107      -7.601  -9.261  11.042  1.00 18.29           O
ATOM    821  N    THR A 108      -5.711  -9.479   9.828  1.00 19.49           N
ATOM    822  CA   THR A 108      -6.202  -8.555   8.767  1.00 20.68           C
ATOM    823  CB   THR A 108      -5.095  -8.113   7.792  1.00 20.42           C
ATOM    824  OG1  THR A 108      -4.539  -9.245   7.121  1.00 20.18           O
ATOM    825  CG2  THR A 108      -3.937  -7.484   8.518  1.00 21.44           C
ATOM    826  C    THR A 108      -7.349  -9.127   7.947  1.00 21.03           C
ATOM    827  O    THR A 108      -8.032  -8.395   7.209  1.00 21.34           O
ATOM    828  N    ALA A 109      -7.573 -10.430   8.088  1.00 21.15           N
ATOM    829  CA   ALA A 109      -8.590 -11.137   7.329  1.00 20.82           C
ATOM    830  CB   ALA A 109      -8.012 -12.437   6.833  1.00 21.32           C
ATOM    831  C    ALA A 109      -9.850 -11.420   8.120  1.00 20.67           C
ATOM    832  O    ALA A 109     -10.803 -11.966   7.568  1.00 21.73           O
ATOM    833  N    VAL A 110      -9.863 -11.095   9.403  1.00 20.21           N
ATOM    834  CA   VAL A 110     -11.003 -11.467  10.264  1.00 20.48           C
ATOM    835  CB   VAL A 110     -10.553 -12.485  11.382  1.00 20.34           C
ATOM    836  CG1  VAL A 110     -10.068 -13.811  10.764  1.00 22.26           C
ATOM    837  CG2  VAL A 110      -9.514 -11.891  12.315  1.00 19.21           C
ATOM    838  C    VAL A 110     -11.378  -9.974  10.631  0.60 20.09           C
ATOM    839  O    VAL A 110     -11.056  -9.008   9.900  0.60 19.65           O
ATOM    840  N    LEU A 111     -12.037  -9.767  11.739  0.60 20.12           N
ATOM    841  CA   LEU A 111     -12.568  -8.443  12.095  1.00 20.23           C
ATOM    842  CB   LEU A 111     -11.535  -7.485  12.680  1.00 20.52           C
ATOM    843  CG   LEU A 111     -10.609  -8.205  13.675  1.00 21.23           C
ATOM    844  CD1  LEU A 111      -9.504  -7.311  14.159  1.00 22.83           C
ATOM    845  CD2  LEU A 111     -11.387  -8.708  14.867  1.00 24.95           C
ATOM    846  C    LEU A 111     -13.600  -7.824  11.120  1.00 19.93           C
ATOM    847  O    LEU A 111     -14.637  -8.444  10.885  1.00 19.97           O
ATOM    848  N    ASP A 112     -13.330  -6.662  10.528  1.00 19.48           N
ATOM    849  CA   ASP A 112     -14.287  -6.087   9.577  1.00 19.26           C
ATOM    850  CB   ASP A 112     -14.222  -4.532   9.492  1.00 19.65           C
ATOM    851  CG   ASP A 112     -12.838  -4.005   9.154  1.00 21.55           C
ATOM    852  OD1  ASP A 112     -12.739  -2.789   8.784  1.00 21.39           O
ATOM    853  OD2  ASP A 112     -11.797  -4.711   9.287  1.00 20.16           O
ATOM    854  C    ASP A 112     -14.226  -6.721   8.184  1.00 17.69           C
ATOM    855  O    ASP A 112     -15.221  -6.769   7.510  1.00 17.04           O
ATOM    856  N    THR A 113     -13.068  -7.215   7.780  1.00 17.35           N
ATOM    857  CA   THR A 113     -12.886  -7.860   6.492  1.00 16.92           C
ATOM    858  CB   THR A 113     -11.449  -8.458   6.395  1.00 17.08           C
ATOM    859  OG1  THR A 113     -10.492  -7.389   6.346  1.00 15.20           O
ATOM    860  CG2  THR A 113     -11.241  -9.182   5.082  1.00 15.97           C
```

Fig. 1, continued

```
ATOM    861  C   THR A 113     -13.964  -8.902   6.118  1.00 17.38           C
ATOM    862  O   THR A 113     -14.542  -8.783   5.051  1.00 17.91           O
ATOM    863  N   PRO A 114     -14.238  -9.916   6.939  1.00 17.62           N
ATOM    864  CA  PRO A 114     -15.252 -10.926   6.573  1.00 17.70           C
ATOM    865  CB  PRO A 114     -15.135 -11.998   7.684  1.00 17.95           C
ATOM    866  CG  PRO A 114     -14.410 -11.355   8.794  1.00 18.62           C
ATOM    867  CD  PRO A 114     -13.591 -10.227   8.218  1.00 18.17           C
ATOM    868  C   PRO A 114     -16.682 -10.375   6.552  1.00 17.81           C
ATOM    869  O   PRO A 114     -17.522 -10.937   5.845  1.00 17.33           O
ATOM    870  N   ILE A 115     -16.960  -9.337   7.339  1.00 17.13           N
ATOM    871  CA  ILE A 115     -18.252  -8.676   7.282  1.00 17.36           C
ATOM    872  CB  ILE A 115     -18.408  -7.652   8.417  1.00 17.04           C
ATOM    873  CG1 ILE A 115     -18.351  -8.361   9.786  1.00 17.42           C
ATOM    874  CD1 ILE A 115     -18.267  -7.399  10.956  1.00 17.73           C
ATOM    875  CG2 ILE A 115     -19.743  -6.859   8.256  1.00 16.99           C
ATOM    876  C   ILE A 115     -18.439  -8.006   5.897  1.00 18.08           C
ATOM    877  O   ILE A 115     -19.510  -8.110   5.291  1.00 18.37           O
ATOM    878  N   ILE A 116     -17.388  -7.353   5.406  1.00 17.63           N
ATOM    879  CA  ILE A 116     -17.458  -6.610   4.155  1.00 17.43           C
ATOM    880  CB  ILE A 116     -16.231  -5.683   4.024  1.00 17.81           C
ATOM    881  CG1 ILE A 116     -16.336  -4.544   5.046  1.00 18.90           C
ATOM    882  CD1 ILE A 116     -15.018  -3.795   5.289  1.00 18.37           C
ATOM    883  CG2 ILE A 116     -16.118  -5.104   2.590  1.00 18.71           C
ATOM    884  C   ILE A 116     -17.567  -7.567   2.974  1.00 17.31           C
ATOM    885  O   ILE A 116     -18.475  -7.461   2.180  1.00 16.15           O
ATOM    886  N   ILE A 117     -16.659  -8.533   2.897  1.00 16.83           N
ATOM    887  CA  ILE A 117     -16.665  -9.504   1.808  1.00 16.71           C
ATOM    888  CB  ILE A 117     -15.369 -10.344   1.821  1.00 16.89           C
ATOM    889  CG1 ILE A 117     -14.160  -9.420   1.581  1.00 15.46           C
ATOM    890  CD1 ILE A 117     -12.797 -10.174   1.595  1.00 19.22           C
ATOM    891  CG2 ILE A 117     -15.460 -11.505   0.845  1.00 15.97           C
ATOM    892  C   ILE A 117     -17.880 -10.389   1.865  1.00 17.59           C
ATOM    893  O   ILE A 117     -18.482 -10.665   0.834  1.00 17.80           O
ATOM    894  N   GLY A 118     -18.239 -10.836   3.071  1.00 17.66           N
ATOM    895  CA  GLY A 118     -19.466 -11.568   3.304  1.00 17.21           C
ATOM    896  C   GLY A 118     -20.699 -10.849   2.772  1.00 17.84           C
ATOM    897  O   GLY A 118     -21.524 -11.434   2.067  1.00 17.70           O
ATOM    898  N   TRP A 119     -20.805  -9.563   3.069  1.00 17.98           N
ATOM    899  CA  TRP A 119     -21.919  -8.764   2.611  1.00 17.83           C
ATOM    900  CB  TRP A 119     -21.820  -7.341   3.168  1.00 18.31           C
ATOM    901  CG  TRP A 119     -22.847  -6.379   2.574  1.00 19.39           C
ATOM    902  CD1 TRP A 119     -24.124  -6.184   3.010  1.00 19.69           C
ATOM    903  NE1 TRP A 119     -24.755  -5.238   2.230  1.00 19.61           N
ATOM    904  CE2 TRP A 119     -23.888  -4.802   1.264  1.00 18.22           C
ATOM    905  CD2 TRP A 119     -22.678  -5.513   1.435  1.00 18.04           C
ATOM    906  CE3 TRP A 119     -21.617  -5.246   0.554  1.00 19.77           C
ATOM    907  CZ3 TRP A 119     -21.801  -4.315  -0.469  1.00 19.28           C
ATOM    908  CH2 TRP A 119     -23.034  -3.637  -0.621  1.00 17.24           C
ATOM    909  CZ2 TRP A 119     -24.080  -3.874   0.231  1.00 19.77           C
ATOM    910  C   TRP A 119     -21.949  -8.712   1.068  1.00 18.21           C
ATOM    911  O   TRP A 119     -23.017  -8.785   0.463  1.00 16.94           O
ATOM    912  N   ALA A 120     -20.780  -8.570   0.449  1.00 18.04           N
ATOM    913  CA  ALA A 120     -20.697  -8.467  -1.010  1.00 18.88           C
ATOM    914  CB  ALA A 120     -19.283  -8.090  -1.456  1.00 18.41           C
```

Fig. 1, continued

```
ATOM    915  C   ALA A 120     -21.156  -9.789  -1.632  1.00 19.52           C
ATOM    916  O   ALA A 120     -21.941  -9.784  -2.583  1.00 19.46           O
ATOM    917  N   LEU A 121     -20.697 -10.915  -1.079  1.00 19.78           N
ATOM    918  CA  LEU A 121     -21.140 -12.228  -1.542  1.00 19.82           C
ATOM    919  CB  LEU A 121     -20.378 -13.348  -0.841  1.00 19.24           C
ATOM    920  CG  LEU A 121     -18.909 -13.430  -1.256  1.00 17.68           C
ATOM    921  CD1 LEU A 121     -18.109 -14.339  -0.334  1.00 17.44           C
ATOM    922  CD2 LEU A 121     -18.773 -13.872  -2.718  1.00 17.51           C
ATOM    923  C   LEU A 121     -22.653 -12.397  -1.390  1.00 20.83           C
ATOM    924  O   LEU A 121     -23.308 -12.918  -2.306  1.00 21.03           O
ATOM    925  N   GLN A 122     -23.230 -11.897  -0.293  1.00 21.80           N
ATOM    926  CA  GLN A 122     -24.682 -11.995  -0.085  1.00 22.36           C
ATOM    927  CB  GLN A 122     -25.077 -11.667   1.360  1.00 22.41           C
ATOM    928  CG  GLN A 122     -24.474 -12.603   2.442  1.00 24.47           C
ATOM    929  CD  GLN A 122     -24.877 -14.063   2.278  1.00 29.82           C
ATOM    930  OE1 GLN A 122     -26.060 -14.349   2.077  1.00 31.45           O
ATOM    931  NE2 GLN A 122     -23.891 -14.999   2.358  1.00 31.09           N
ATOM    932  C   GLN A 122     -25.491 -11.153  -1.067  1.00 23.12           C
ATOM    933  O   GLN A 122     -26.666 -11.434  -1.285  1.00 23.96           O
ATOM    934  N   GLN A 123     -24.882 -10.129  -1.668  1.00 23.34           N
ATOM    935  CA  GLN A 123     -25.525  -9.371  -2.727  1.00 23.32           C
ATOM    936  CB  GLN A 123     -24.872  -7.977  -2.901  1.00 23.46           C
ATOM    937  CG  GLN A 123     -24.742  -7.112  -1.638  1.00 23.19           C
ATOM    938  CD  GLN A 123     -25.955  -7.169  -0.760  1.00 25.33           C
ATOM    939  OE1 GLN A 123     -27.054  -6.778  -1.190  1.00 25.82           O
ATOM    940  NE2 GLN A 123     -25.791  -7.695   0.462  1.00 23.66           N
ATOM    941  C   GLN A 123     -25.426 -10.086  -4.082  1.00 23.47           C
ATOM    942  O   GLN A 123     -25.986  -9.614  -5.050  1.00 22.95           O
ATOM    943  N   GLY A 124     -24.636 -11.158  -4.162  1.00 23.29           N
ATOM    944  CA  GLY A 124     -24.331 -11.826  -5.419  1.00 22.36           C
ATOM    945  C   GLY A 124     -23.155 -11.246  -6.198  1.00 22.24           C
ATOM    946  O   GLY A 124     -23.006 -11.503  -7.403  1.00 21.51           O
ATOM    947  N   TYR A 125     -22.328 -10.433  -5.550  1.00 21.31           N
ATOM    948  CA  TYR A 125     -21.166  -9.883  -6.218  1.00 20.96           C
ATOM    949  CB  TYR A 125     -20.654  -8.606  -5.522  1.00 21.00           C
ATOM    950  CG  TYR A 125     -21.689  -7.506  -5.296  1.00 19.85           C
ATOM    951  CD1 TYR A 125     -22.814  -7.384  -6.105  1.00 20.24           C
ATOM    952  CE1 TYR A 125     -23.760  -6.354  -5.895  1.00 19.30           C
ATOM    953  CZ  TYR A 125     -23.578  -5.458  -4.856  1.00 22.14           C
ATOM    954  OH  TYR A 125     -24.505  -4.457  -4.650  1.00 22.16           O
ATOM    955  CE2 TYR A 125     -22.456  -5.562  -4.033  1.00 20.71           C
ATOM    956  CD2 TYR A 125     -21.522  -6.574  -4.262  1.00 20.20           C
ATOM    957  C   TYR A 125     -20.064 -10.927  -6.206  1.00 20.79           C
ATOM    958  O   TYR A 125     -19.868 -11.619  -5.193  1.00 20.13           O
ATOM    959  N   TYR A 126     -19.369 -11.046  -7.335  1.00 20.14           N
ATOM    960  CA  TYR A 126     -18.071 -11.702  -7.371  1.00 20.71           C
ATOM    961  CB  TYR A 126     -17.538 -11.817  -8.781  1.00 21.12           C
ATOM    962  CG  TYR A 126     -18.338 -12.734  -9.661  1.00 22.96           C
ATOM    963  CD1 TYR A 126     -17.941 -14.066  -9.862  1.00 25.36           C
ATOM    964  CE1 TYR A 126     -18.695 -14.923 -10.684  1.00 26.74           C
ATOM    965  CZ  TYR A 126     -19.831 -14.431 -11.320  1.00 25.35           C
ATOM    966  OH  TYR A 126     -20.587 -15.252 -12.124  1.00 30.13           O
ATOM    967  CE2 TYR A 126     -20.222 -13.119 -11.148  1.00 26.82           C
ATOM    968  CD2 TYR A 126     -19.477 -12.274 -10.322  1.00 24.89           C
```

Fig. 1, continued

```
ATOM    969  C   TYR A 126     -17.129 -10.830  -6.579  1.00 20.21           C
ATOM    970  O   TYR A 126     -17.218  -9.601  -6.675  1.00 19.97           O
ATOM    971  N   VAL A 127     -16.239 -11.451  -5.807  1.00 18.71           N
ATOM    972  CA  VAL A 127     -15.269 -10.708  -5.034  1.00 17.79           C
ATOM    973  CB  VAL A 127     -15.448 -10.931  -3.513  1.00 17.37           C
ATOM    974  CG1 VAL A 127     -14.371 -10.190  -2.744  1.00 15.67           C
ATOM    975  CG2 VAL A 127     -16.857 -10.495  -3.074  1.00 17.50           C
ATOM    976  C   VAL A 127     -13.862 -11.104  -5.390  1.00 17.74           C
ATOM    977  O   VAL A 127     -13.556 -12.285  -5.497  1.00 17.75           O
ATOM    978  N   VAL A 128     -12.998 -10.102  -5.532  1.00 17.13           N
ATOM    979  CA  VAL A 128     -11.574 -10.338  -5.656  1.00 16.91           C
ATOM    980  CB  VAL A 128     -11.037  -9.948  -7.085  1.00 16.56           C
ATOM    981  CG1 VAL A 128     -11.345  -8.509  -7.433  1.00 15.87           C
ATOM    982  CG2 VAL A 128      -9.576 -10.215  -7.197  1.00 18.37           C
ATOM    983  C   VAL A 128     -10.868  -9.530  -4.584  1.00 16.84           C
ATOM    984  O   VAL A 128     -11.254  -8.387  -4.313  1.00 17.04           O
ATOM    985  N   SER A 129      -9.843 -10.118  -3.981  1.00 16.27           N
ATOM    986  CA  SER A 129      -8.888  -9.388  -3.180  1.00 15.93           C
ATOM    987  CB  SER A 129      -9.092  -9.708  -1.675  1.00 17.18           C
ATOM    988  OG  SER A 129      -8.327  -8.860  -0.856  1.00 15.61           O
ATOM    989  C   SER A 129      -7.514  -9.805  -3.646  1.00 17.56           C
ATOM    990  O   SER A 129      -7.143 -10.977  -3.545  1.00 17.26           O
ATOM    991  N   SER A 130      -6.748  -8.858  -4.186  1.00 17.81           N
ATOM    992  CA  SER A 130      -5.428  -9.164  -4.675  1.00 17.80           C
ATOM    993  CB  SER A 130      -5.081  -8.296  -5.903  1.00 18.86           C
ATOM    994  OG  SER A 130      -6.044  -8.448  -6.953  1.00 21.13           O
ATOM    995  C   SER A 130      -4.396  -8.963  -3.587  1.00 17.85           C
ATOM    996  O   SER A 130      -4.607  -8.227  -2.622  1.00 17.31           O
ATOM    997  N   ASP A 131      -3.259  -9.640  -3.748  1.00 17.25           N
ATOM    998  CA  ASP A 131      -2.083  -9.346  -2.967  1.00 17.07           C
ATOM    999  CB  ASP A 131      -1.106 -10.512  -2.962  1.00 16.96           C
ATOM   1000  CG  ASP A 131      -1.653 -11.722  -2.273  1.00 17.79           C
ATOM   1001  OD1 ASP A 131      -0.965 -12.774  -2.350  1.00 17.79           O
ATOM   1002  OD2 ASP A 131      -2.753 -11.720  -1.663  1.00 15.63           O
ATOM   1003  C   ASP A 131      -1.405  -8.104  -3.537  1.00 18.08           C
ATOM   1004  O   ASP A 131      -0.375  -8.174  -4.240  1.00 18.67           O
ATOM   1005  N   HIS A 132      -1.934  -6.955  -3.167  1.00 18.36           N
ATOM   1006  CA  HIS A 132      -1.532  -5.710  -3.800  1.00 19.22           C
ATOM   1007  CB  HIS A 132      -2.467  -4.614  -3.338  1.00 19.67           C
ATOM   1008  CG  HIS A 132      -2.499  -4.446  -1.862  1.00 21.70           C
ATOM   1009  ND1 HIS A 132      -3.598  -4.771  -1.114  1.00 27.08           N
ATOM   1010  CE1 HIS A 132      -3.354  -4.513   0.161  1.00 26.62           C
ATOM   1011  NE2 HIS A 132      -2.122  -4.062   0.269  1.00 24.84           N
ATOM   1012  CD2 HIS A 132      -1.556  -4.037  -0.983  1.00 26.69           C
ATOM   1013  C   HIS A 132      -0.081  -5.254  -3.595  1.00 19.37           C
ATOM   1014  O   HIS A 132       0.400  -4.394  -4.350  1.00 19.25           O
ATOM   1015  N   GLU A 133       0.592  -5.773  -2.570  1.00 18.76           N
ATOM   1016  CA  GLU A 133       2.011  -5.455  -2.331  1.00 18.71           C
ATOM   1017  CB  GLU A 133       2.420  -5.677  -0.869  1.00 18.39           C
ATOM   1018  CG  GLU A 133       1.588  -4.887   0.122  1.00 18.84           C
ATOM   1019  CD  GLU A 133       2.181  -4.901   1.512  1.00 18.27           C
ATOM   1020  OE1 GLU A 133       1.561  -4.271   2.397  1.00 15.80           O
ATOM   1021  OE2 GLU A 133       3.276  -5.506   1.707  1.00 18.17           O
ATOM   1022  C   GLU A 133       2.960  -6.234  -3.217  1.00 19.19           C
```

Fig. 1, continued

```
ATOM   1023  O    GLU A 133       4.149  -5.894  -3.273  1.00 19.06           O
ATOM   1024  N    GLY A 134       2.447  -7.274  -3.892  1.00 19.67           N
ATOM   1025  CA   GLY A 134       3.245  -8.086  -4.801  1.00 19.50           C
ATOM   1026  C    GLY A 134       4.202  -9.016  -4.073  1.00 19.77           C
ATOM   1027  O    GLY A 134       4.266  -9.024  -2.833  1.00 18.32           O
ATOM   1028  N    PHE A 135       4.975  -9.775  -4.847  1.00 19.88           N
ATOM   1029  CA   PHE A 135       5.907 -10.753  -4.279  1.00 20.28           C
ATOM   1030  CB   PHE A 135       6.480 -11.670  -5.354  1.00 20.20           C
ATOM   1031  CG   PHE A 135       5.472 -12.606  -5.975  1.00 19.48           C
ATOM   1032  CD1  PHE A 135       4.247 -12.898  -5.347  1.00 20.81           C
ATOM   1033  CE1  PHE A 135       3.344 -13.788  -5.923  1.00 21.33           C
ATOM   1034  CZ   PHE A 135       3.640 -14.372  -7.189  1.00 19.94           C
ATOM   1035  CE2  PHE A 135       4.853 -14.078  -7.814  1.00 19.38           C
ATOM   1036  CD2  PHE A 135       5.751 -13.196  -7.210  1.00 19.01           C
ATOM   1037  C    PHE A 135       7.054 -10.177  -3.452  1.00 20.99           C
ATOM   1038  O    PHE A 135       7.630 -10.905  -2.666  1.00 20.57           O
ATOM   1039  N    LYS A 136       7.389  -8.894  -3.619  1.00 21.77           N
ATOM   1040  CA   LYS A 136       8.399  -8.247  -2.759  1.00 22.21           C
ATOM   1041  CB   LYS A 136       9.189  -7.170  -3.535  0.50 22.78           C
ATOM   1042  CG   LYS A 136      10.031  -7.698  -4.709  0.50 25.40           C
ATOM   1043  CD   LYS A 136      11.360  -6.942  -4.891  0.50 28.72           C
ATOM   1044  CE   LYS A 136      12.570  -7.704  -4.297  0.50 31.08           C
ATOM   1045  NZ   LYS A 136      13.847  -7.433  -5.030  0.50 32.70           N
ATOM   1046  C    LYS A 136       7.834  -7.635  -1.438  1.00 21.37           C
ATOM   1047  O    LYS A 136       8.582  -7.145  -0.606  1.00 20.19           O
ATOM   1048  N    ALA A 137       6.526  -7.713  -1.239  1.00 20.38           N
ATOM   1049  CA   ALA A 137       5.858  -7.113  -0.087  1.00 20.16           C
ATOM   1050  CB   ALA A 137       6.183  -7.874   1.223  1.00 19.74           C
ATOM   1051  C    ALA A 137       6.177  -5.617   0.048  1.00 19.78           C
ATOM   1052  O    ALA A 137       6.575  -5.140   1.131  1.00 19.76           O
ATOM   1053  N    ALA A 138       5.978  -4.901  -1.053  1.00 18.82           N
ATOM   1054  CA   ALA A 138       6.297  -3.483  -1.175  1.00 19.32           C
ATOM   1055  CB   ALA A 138       6.666  -3.140  -2.617  1.00 19.80           C
ATOM   1056  C    ALA A 138       5.160  -2.607  -0.713  1.00 19.23           C
ATOM   1057  O    ALA A 138       4.516  -1.913  -1.506  1.00 19.12           O
ATOM   1058  N    PHE A 139       4.943  -2.640   0.595  1.00 19.11           N
ATOM   1059  CA   PHE A 139       3.992  -1.813   1.288  1.00 18.31           C
ATOM   1060  CB   PHE A 139       4.215  -1.971   2.804  1.00 18.37           C
ATOM   1061  CG   PHE A 139       3.388  -1.032   3.639  1.00 17.55           C
ATOM   1062  CD1  PHE A 139       3.991  -0.169   4.549  1.00 18.22           C
ATOM   1063  CE1  PHE A 139       3.213   0.709   5.321  1.00 20.68           C
ATOM   1064  CZ   PHE A 139       1.827   0.707   5.178  1.00 18.83           C
ATOM   1065  CE2  PHE A 139       1.241  -0.132   4.256  1.00 18.25           C
ATOM   1066  CD2  PHE A 139       2.015  -0.995   3.496  1.00 18.07           C
ATOM   1067  C    PHE A 139       4.169  -0.338   0.954  1.00 18.79           C
ATOM   1068  O    PHE A 139       5.267   0.210   1.064  1.00 18.92           O
ATOM   1069  N    ILE A 140       3.044   0.281   0.637  1.00 18.83           N
ATOM   1070  CA   ILE A 140       2.893   1.690   0.285  1.00 20.04           C
ATOM   1071  CB   ILE A 140       3.269   2.613   1.486  1.00 20.45           C
ATOM   1072  CG1  ILE A 140       2.157   3.647   1.687  1.00 20.69           C
ATOM   1073  CD1  ILE A 140       0.835   3.034   2.157  1.00 23.74           C
ATOM   1074  CG2  ILE A 140       4.624   3.294   1.319  1.00 20.47           C
ATOM   1075  C    ILE A 140       3.455   2.165  -1.077  1.00 19.71           C
ATOM   1076  O    ILE A 140       3.456   3.365  -1.365  1.00 19.20           O
```

Fig. 1, continued

```
ATOM   1077  N   ALA A 141       3.849   1.207  -1.913  1.00 19.88           N
ATOM   1078  CA  ALA A 141       4.323   1.497  -3.266  1.00 19.73           C
ATOM   1079  CB  ALA A 141       5.332   0.434  -3.755  1.00 19.64           C
ATOM   1080  C   ALA A 141       3.092   1.547  -4.133  1.00 19.73           C
ATOM   1081  O   ALA A 141       2.534   0.520  -4.504  1.00 19.99           O
ATOM   1082  N   GLY A 142       2.634   2.764  -4.400  1.00 19.32           N
ATOM   1083  CA  GLY A 142       1.348   2.991  -5.023  1.00 19.11           C
ATOM   1084  C   GLY A 142       1.175   2.466  -6.434  1.00 19.20           C
ATOM   1085  O   GLY A 142       0.106   1.974  -6.778  1.00 18.24           O
ATOM   1086  N   TYR A 143       2.226   2.558  -7.237  1.00 19.67           N
ATOM   1087  CA  TYR A 143       2.224   2.008  -8.604  1.00 20.14           C
ATOM   1088  CB  TYR A 143       3.474   2.479  -9.376  1.00 19.81           C
ATOM   1089  CG  TYR A 143       3.478   3.987  -9.566  1.00 20.42           C
ATOM   1090  CD1 TYR A 143       2.820   4.601 -10.650  1.00 21.45           C
ATOM   1091  CE1 TYR A 143       2.797   6.017 -10.773  1.00 21.85           C
ATOM   1092  CZ  TYR A 143       3.445   6.782  -9.813  1.00 21.25           C
ATOM   1093  OH  TYR A 143       3.465   8.166  -9.839  1.00 24.17           O
ATOM   1094  CE2 TYR A 143       4.076   6.178  -8.757  1.00 20.37           C
ATOM   1095  CD2 TYR A 143       4.101   4.808  -8.640  1.00 21.30           C
ATOM   1096  C   TYR A 143       2.165   0.481  -8.534  1.00 19.75           C
ATOM   1097  O   TYR A 143       1.411  -0.158  -9.260  1.00 19.66           O
ATOM   1098  N   GLU A 144       2.949  -0.091  -7.624  1.00 20.25           N
ATOM   1099  CA  GLU A 144       2.974  -1.543  -7.415  1.00 20.37           C
ATOM   1100  CB  GLU A 144       3.979  -1.904  -6.333  1.00 19.99           C
ATOM   1101  CG  GLU A 144       4.431  -3.350  -6.357  1.00 21.47           C
ATOM   1102  CD  GLU A 144       5.772  -3.573  -7.062  1.00 22.80           C
ATOM   1103  OE1 GLU A 144       6.204  -4.742  -7.058  1.00 26.36           O
ATOM   1104  OE2 GLU A 144       6.377  -2.624  -7.629  1.00 20.11           O
ATOM   1105  C   GLU A 144       1.551  -2.018  -7.048  1.00 19.66           C
ATOM   1106  O   GLU A 144       1.010  -2.939  -7.670  1.00 19.80           O
ATOM   1107  N   GLU A 145       0.934  -1.296  -6.118  1.00 19.10           N
ATOM   1108  CA  GLU A 145      -0.356  -1.657  -5.571  1.00 19.08           C
ATOM   1109  CB  GLU A 145      -0.670  -0.869  -4.286  1.00 18.67           C
ATOM   1110  CG  GLU A 145       0.165  -1.298  -3.070  1.00 20.74           C
ATOM   1111  CD  GLU A 145      -0.068  -0.460  -1.809  1.00 22.20           C
ATOM   1112  OE1 GLU A 145      -0.803   0.557  -1.852  1.00 24.51           O
ATOM   1113  OE2 GLU A 145       0.488  -0.830  -0.743  1.00 26.44           O
ATOM   1114  C   GLU A 145      -1.446  -1.452  -6.602  1.00 18.88           C
ATOM   1115  O   GLU A 145      -2.248  -2.352  -6.832  1.00 18.73           O
ATOM   1116  N   GLY A 146      -1.492  -0.276  -7.216  1.00 19.03           N
ATOM   1117  CA  GLY A 146      -2.543   0.035  -8.190  1.00 19.01           C
ATOM   1118  C   GLY A 146      -2.600  -0.949  -9.353  1.00 18.81           C
ATOM   1119  O   GLY A 146      -3.668  -1.397  -9.745  1.00 18.79           O
ATOM   1120  N   MET A 147      -1.438  -1.287  -9.894  1.00 19.27           N
ATOM   1121  CA  MET A 147      -1.355  -2.175 -11.052  1.00 19.78           C
ATOM   1122  CB  MET A 147       0.031  -2.091 -11.704  1.00 19.97           C
ATOM   1123  CG  MET A 147       0.257  -0.749 -12.458  1.00 22.37           C
ATOM   1124  SD  MET A 147       1.785  -0.677 -13.415  1.00 23.68           S
ATOM   1125  CE  MET A 147       2.991  -0.514 -12.174  1.00 24.51           C
ATOM   1126  C   MET A 147      -1.704  -3.618 -10.667  1.00 19.36           C
ATOM   1127  O   MET A 147      -2.438  -4.290 -11.395  1.00 18.74           O
ATOM   1128  N   ALA A 148      -1.221  -4.077  -9.507  1.00 18.55           N
ATOM   1129  CA  ALA A 148      -1.583  -5.424  -9.011  1.00 18.00           C
ATOM   1130  CB  ALA A 148      -0.887  -5.726  -7.658  1.00 17.92           C
```

Fig. 1, continued

```
ATOM   1131  C    ALA A 148      -3.095  -5.578  -8.878  1.00 17.53           C
ATOM   1132  O    ALA A 148      -3.673  -6.602  -9.261  1.00 18.66           O
ATOM   1133  N    ILE A 149      -3.740  -4.558  -8.350  1.00 17.01           N
ATOM   1134  CA   ILE A 149      -5.182  -4.602  -8.113  1.00 17.06           C
ATOM   1135  CB   ILE A 149      -5.600  -3.433  -7.233  1.00 16.79           C
ATOM   1136  CG1  ILE A 149      -5.087  -3.656  -5.791  1.00 16.10           C
ATOM   1137  CD1  ILE A 149      -5.061  -2.390  -4.959  1.00 15.93           C
ATOM   1138  CG2  ILE A 149      -7.131  -3.268  -7.247  1.00 16.85           C
ATOM   1139  C    ILE A 149      -5.978  -4.581  -9.424  1.00 17.63           C
ATOM   1140  O    ILE A 149      -6.928  -5.359  -9.604  1.00 17.44           O
ATOM   1141  N    LEU A 150      -5.575  -3.704 -10.340  1.00 17.11           N
ATOM   1142  CA   LEU A 150      -6.274  -3.628 -11.620  1.00 17.88           C
ATOM   1143  CB   LEU A 150      -5.782  -2.435 -12.467  1.00 17.92           C
ATOM   1144  CG   LEU A 150      -6.072  -1.091 -11.797  1.00 18.67           C
ATOM   1145  CD1  LEU A 150      -5.258   0.044 -12.388  1.00 19.43           C
ATOM   1146  CD2  LEU A 150      -7.561  -0.760 -11.830  1.00 21.02           C
ATOM   1147  C    LEU A 150      -6.169  -4.934 -12.346  1.00 16.93           C
ATOM   1148  O    LEU A 150      -7.153  -5.408 -12.864  1.00 17.90           O
ATOM   1149  N    ASP A 151      -4.982  -5.529 -12.364  1.00 17.78           N
ATOM   1150  CA   ASP A 151      -4.759  -6.806 -13.033  1.00 17.79           C
ATOM   1151  CB   ASP A 151      -3.243  -7.049 -13.201  1.00 18.42           C
ATOM   1152  CG   ASP A 151      -2.652  -6.177 -14.296  1.00 20.44           C
ATOM   1153  OD1  ASP A 151      -1.425  -5.863 -14.300  1.00 21.25           O
ATOM   1154  OD2  ASP A 151      -3.398  -5.764 -15.200  1.00 20.75           O
ATOM   1155  C    ASP A 151      -5.435  -7.982 -12.343  1.00 18.25           C
ATOM   1156  O    ASP A 151      -5.792  -8.971 -12.999  1.00 17.56           O
ATOM   1157  N    GLY A 152      -5.639  -7.866 -11.023  1.00 18.69           N
ATOM   1158  CA   GLY A 152      -6.402  -8.856 -10.265  1.00 18.20           C
ATOM   1159  C    GLY A 152      -7.852  -8.886 -10.663  1.00 18.46           C
ATOM   1160  O    GLY A 152      -8.477  -9.960 -10.757  1.00 18.87           O
ATOM   1161  N    ILE A 153      -8.414  -7.706 -10.874  1.00 19.16           N
ATOM   1162  CA   ILE A 153      -9.775  -7.604 -11.398  1.00 20.16           C
ATOM   1163  CB   ILE A 153     -10.251  -6.137 -11.407  1.00 19.93           C
ATOM   1164  CG1  ILE A 153     -10.543  -5.681  -9.982  1.00 20.73           C
ATOM   1165  CD1  ILE A 153     -10.281  -4.242  -9.737  1.00 19.94           C
ATOM   1166  CG2  ILE A 153     -11.503  -5.966 -12.278  1.00 21.13           C
ATOM   1167  C    ILE A 153      -9.836  -8.243 -12.808  1.00 20.39           C
ATOM   1168  O    ILE A 153     -10.703  -9.049 -13.087  1.00 19.65           O
ATOM   1169  N    ARG A 154      -8.894  -7.890 -13.668  1.00 21.45           N
ATOM   1170  CA   ARG A 154      -8.801  -8.509 -15.001  1.00 21.71           C
ATOM   1171  CB   ARG A 154      -7.557  -7.993 -15.732  1.00 21.75           C
ATOM   1172  CG   ARG A 154      -7.675  -6.545 -16.198  1.00 22.29           C
ATOM   1173  CD   ARG A 154      -6.361  -5.999 -16.701  1.00 23.42           C
ATOM   1174  NE   ARG A 154      -6.517  -4.868 -17.606  1.00 23.87           N
ATOM   1175  CZ   ARG A 154      -5.553  -4.003 -17.922  1.00 24.65           C
ATOM   1176  NH1  ARG A 154      -4.328  -4.128 -17.436  1.00 24.67           N
ATOM   1177  NH2  ARG A 154      -5.805  -3.026 -18.796  1.00 26.11           N
ATOM   1178  C    ARG A 154      -8.748 -10.031 -14.887  1.00 22.00           C
ATOM   1179  O    ARG A 154      -9.436 -10.753 -15.615  1.00 22.11           O
ATOM   1180  N    ALA A 155      -7.973 -10.510 -13.923  1.00 22.06           N
ATOM   1181  CA   ALA A 155      -7.738 -11.940 -13.773  1.00 22.45           C
ATOM   1182  CB   ALA A 155      -6.677 -12.200 -12.710  1.00 21.77           C
ATOM   1183  C    ALA A 155      -9.038 -12.654 -13.428  1.00 22.10           C
ATOM   1184  O    ALA A 155      -9.313 -13.744 -13.936  1.00 21.77           O
```

Fig. 1, continued

```
ATOM   1185  N    LEU A 156      -9.825 -12.048 -12.554  1.00 22.32           N
ATOM   1186  CA   LEU A 156     -11.096 -12.647 -12.166  1.00 22.61           C
ATOM   1187  CB   LEU A 156     -11.764 -11.888 -11.026  1.00 22.23           C
ATOM   1188  CG   LEU A 156     -13.254 -12.172 -10.807  1.00 21.51           C
ATOM   1189  CD1  LEU A 156     -13.477 -13.608 -10.397  1.00 20.07           C
ATOM   1190  CD2  LEU A 156     -13.836 -11.234  -9.793  1.00 21.56           C
ATOM   1191  C    LEU A 156     -12.010 -12.683 -13.393  1.00 23.26           C
ATOM   1192  O    LEU A 156     -12.695 -13.668 -13.633  1.00 23.35           O
ATOM   1193  N    LYS A 157     -12.033 -11.597 -14.147  1.00 23.56           N
ATOM   1194  CA   LYS A 157     -12.860 -11.541 -15.350  1.00 24.03           C
ATOM   1195  CB   LYS A 157     -12.766 -10.174 -16.032  1.00 24.21           C
ATOM   1196  CG   LYS A 157     -13.549  -9.092 -15.307  1.00 24.72           C
ATOM   1197  CD   LYS A 157     -13.190  -7.690 -15.813  1.00 25.60           C
ATOM   1198  CE   LYS A 157     -13.647  -7.449 -17.243  1.00 27.23           C
ATOM   1199  NZ   LYS A 157     -12.958  -6.275 -17.887  1.00 29.26           N
ATOM   1200  C    LYS A 157     -12.481 -12.650 -16.311  1.00 23.62           C
ATOM   1201  O    LYS A 157     -13.367 -13.342 -16.797  1.00 23.01           O
ATOM   1202  N    ASN A 158     -11.174 -12.834 -16.532  1.00 23.93           N
ATOM   1203  CA   ASN A 158     -10.635 -13.904 -17.378  1.00 24.56           C
ATOM   1204  CB   ASN A 158      -9.094 -13.764 -17.532  1.00 24.63           C
ATOM   1205  CG   ASN A 158      -8.701 -12.563 -18.398  1.00 26.03           C
ATOM   1206  OD1  ASN A 158      -9.460 -12.178 -19.269  1.00 24.73           O
ATOM   1207  ND2  ASN A 158      -7.536 -11.959 -18.136  1.00 24.73           N
ATOM   1208  C    ASN A 158     -10.981 -15.299 -16.865  1.00 25.42           C
ATOM   1209  O    ASN A 158     -11.396 -16.179 -17.628  1.00 26.64           O
ATOM   1210  N    TYR A 159     -10.834 -15.491 -15.563  1.00 25.31           N
ATOM   1211  CA   TYR A 159     -10.991 -16.793 -14.952  1.00 24.96           C
ATOM   1212  CB   TYR A 159     -10.492 -16.758 -13.500  1.00 25.69           C
ATOM   1213  CG   TYR A 159     -10.641 -18.073 -12.777  1.00 25.36           C
ATOM   1214  CD1  TYR A 159      -9.909 -19.183 -13.167  1.00 27.24           C
ATOM   1215  CE1  TYR A 159     -10.043 -20.387 -12.528  1.00 27.91           C
ATOM   1216  CZ   TYR A 159     -10.934 -20.503 -11.469  1.00 29.12           C
ATOM   1217  OH   TYR A 159     -11.070 -21.707 -10.830  1.00 31.46           O
ATOM   1218  CE2  TYR A 159     -11.678 -19.435 -11.068  1.00 28.34           C
ATOM   1219  CD2  TYR A 159     -11.523 -18.208 -11.726  1.00 27.54           C
ATOM   1220  C    TYR A 159     -12.425 -17.248 -15.019  1.00 24.99           C
ATOM   1221  O    TYR A 159     -12.660 -18.403 -15.306  1.00 25.34           O
ATOM   1222  N    GLN A 160     -13.385 -16.347 -14.795  1.00 24.69           N
ATOM   1223  CA   GLN A 160     -14.802 -16.694 -14.846  1.00 25.53           C
ATOM   1224  CB   GLN A 160     -15.569 -15.997 -13.709  1.00 25.50           C
ATOM   1225  CG   GLN A 160     -15.412 -16.590 -12.339  1.00 27.32           C
ATOM   1226  CD   GLN A 160     -15.961 -17.991 -12.226  1.00 27.08           C
ATOM   1227  OE1  GLN A 160     -15.193 -18.935 -12.142  1.00 30.64           O
ATOM   1228  NE2  GLN A 160     -17.273 -18.133 -12.257  1.00 27.22           N
ATOM   1229  C    GLN A 160     -15.492 -16.314 -16.183  1.00 26.23           C
ATOM   1230  O    GLN A 160     -16.707 -16.389 -16.261  1.00 26.53           O
ATOM   1231  N    ASN A 161     -14.726 -15.896 -17.197  1.00 26.87           N
ATOM   1232  CA   ASN A 161     -15.259 -15.504 -18.510  1.00 27.50           C
ATOM   1233  CB   ASN A 161     -15.646 -16.748 -19.347  0.70 28.09           C
ATOM   1234  CG   ASN A 161     -15.844 -16.431 -20.845  0.70 30.90           C
ATOM   1235  OD1  ASN A 161     -15.153 -15.575 -21.426  0.70 33.63           O
ATOM   1236  ND2  ASN A 161     -16.788 -17.138 -21.474  0.70 31.70           N
ATOM   1237  C    ASN A 161     -16.430 -14.528 -18.371  1.00 27.21           C
ATOM   1238  O    ASN A 161     -17.505 -14.728 -18.942  1.00 27.54           O
```

Fig. 1, continued

```
ATOM   1239  N    LEU A 162     -16.220 -13.485 -17.576  1.00 26.13           N
ATOM   1240  CA   LEU A 162     -17.228 -12.472 -17.359  1.00 25.63           C
ATOM   1241  CB   LEU A 162     -17.013 -11.778 -16.004  1.00 25.91           C
ATOM   1242  CG   LEU A 162     -17.090 -12.689 -14.755  1.00 24.38           C
ATOM   1243  CD1  LEU A 162     -16.816 -11.903 -13.473  1.00 23.93           C
ATOM   1244  CD2  LEU A 162     -18.430 -13.389 -14.690  1.00 23.49           C
ATOM   1245  C    LEU A 162     -17.107 -11.463 -18.494  1.00 25.38           C
ATOM   1246  O    LEU A 162     -16.041 -11.309 -19.083  1.00 24.64           O
ATOM   1247  N    PRO A 163     -18.193 -10.775 -18.797  1.00 25.27           N
ATOM   1248  CA   PRO A 163     -18.160  -9.755 -19.848  1.00 25.78           C
ATOM   1249  CB   PRO A 163     -19.584  -9.211 -19.865  1.00 25.77           C
ATOM   1250  CG   PRO A 163     -20.423 -10.252 -19.170  1.00 25.81           C
ATOM   1251  CD   PRO A 163     -19.529 -10.928 -18.194  1.00 25.34           C
ATOM   1252  C    PRO A 163     -17.155  -8.641 -19.562  1.00 26.86           C
ATOM   1253  O    PRO A 163     -16.856  -8.283 -18.400  1.00 26.65           O
ATOM   1254  N    SER A 164     -16.649  -8.070 -20.646  1.00 27.19           N
ATOM   1255  CA   SER A 164     -15.640  -7.037 -20.565  1.00 27.78           C
ATOM   1256  CB   SER A 164     -15.205  -6.599 -21.978  1.00 28.16           C
ATOM   1257  OG   SER A 164     -13.936  -5.953 -21.921  1.00 31.61           O
ATOM   1258  C    SER A 164     -16.145  -5.835 -19.783  1.00 26.96           C
ATOM   1259  O    SER A 164     -15.369  -5.191 -19.084  1.00 27.33           O
ATOM   1260  N    ASP A 165     -17.443  -5.558 -19.899  1.00 26.28           N
ATOM   1261  CA   ASP A 165     -18.046  -4.378 -19.307  1.00 26.75           C
ATOM   1262  CB   ASP A 165     -19.079  -3.766 -20.278  1.00 27.87           C
ATOM   1263  CG   ASP A 165     -20.333  -4.586 -20.390  1.00 30.29           C
ATOM   1264  OD1  ASP A 165     -20.327  -5.778 -20.010  1.00 33.52           O
ATOM   1265  OD2  ASP A 165     -21.394  -4.117 -20.839  1.00 36.87           O
ATOM   1266  C    ASP A 165     -18.694  -4.654 -17.937  1.00 25.29           C
ATOM   1267  O    ASP A 165     -19.529  -3.880 -17.480  1.00 24.83           O
ATOM   1268  N    SER A 166     -18.304  -5.755 -17.299  1.00 23.73           N
ATOM   1269  CA   SER A 166     -18.807  -6.079 -15.962  1.00 23.11           C
ATOM   1270  CB   SER A 166     -18.086  -7.290 -15.407  1.00 22.78           C
ATOM   1271  OG   SER A 166     -18.521  -8.476 -16.035  1.00 22.23           O
ATOM   1272  C    SER A 166     -18.554  -4.900 -15.055  1.00 22.52           C
ATOM   1273  O    SER A 166     -17.431  -4.385 -14.998  1.00 22.88           O
ATOM   1274  N    LYS A 167     -19.587  -4.460 -14.363  1.00 22.27           N
ATOM   1275  CA   LYS A 167     -19.438  -3.402 -13.380  1.00 22.61           C
ATOM   1276  CB   LYS A 167     -20.779  -3.076 -12.754  1.00 22.88           C
ATOM   1277  CG   LYS A 167     -21.805  -2.635 -13.755  1.00 24.17           C
ATOM   1278  CD   LYS A 167     -23.073  -2.175 -13.063  1.00 26.45           C
ATOM   1279  CE   LYS A 167     -24.103  -1.657 -14.057  1.00 28.78           C
ATOM   1280  NZ   LYS A 167     -25.298  -1.090 -13.311  1.00 30.01           N
ATOM   1281  C    LYS A 167     -18.452  -3.786 -12.280  1.00 21.98           C
ATOM   1282  O    LYS A 167     -18.445  -4.933 -11.803  1.00 22.02           O
ATOM   1283  N    VAL A 168     -17.641  -2.810 -11.886  1.00 20.46           N
ATOM   1284  CA   VAL A 168     -16.590  -3.002 -10.899  1.00 20.34           C
ATOM   1285  CB   VAL A 168     -15.182  -2.921 -11.545  1.00 19.81           C
ATOM   1286  CG1  VAL A 168     -14.091  -2.971 -10.489  1.00 19.67           C
ATOM   1287  CG2  VAL A 168     -15.007  -3.990 -12.578  1.00 19.27           C
ATOM   1288  C    VAL A 168     -16.662  -1.890  -9.875  1.00 20.24           C
ATOM   1289  O    VAL A 168     -16.822  -0.715 -10.227  1.00 19.81           O
ATOM   1290  N    ALA A 169     -16.551  -2.267  -8.610  1.00 19.55           N
ATOM   1291  CA   ALA A 169     -16.458  -1.312  -7.512  1.00 19.79           C
ATOM   1292  CB   ALA A 169     -17.753  -1.215  -6.798  1.00 19.04           C
```

Fig. 1, continued

```
ATOM   1293  C    ALA A 169     -15.348   -1.755   -6.558  1.00 20.01           C
ATOM   1294  O    ALA A 169     -15.086   -2.957   -6.436  1.00 20.33           O
ATOM   1295  N    LEU A 170     -14.704   -0.781   -5.906  1.00 19.29           N
ATOM   1296  CA   LEU A 170     -13.551   -1.036   -5.077  1.00 18.45           C
ATOM   1297  CB   LEU A 170     -12.292   -0.435   -5.717  1.00 18.90           C
ATOM   1298  CG   LEU A 170     -11.905   -0.900   -7.119  1.00 19.66           C
ATOM   1299  CD1  LEU A 170     -12.436    0.045   -8.196  1.00 20.75           C
ATOM   1300  CD2  LEU A 170     -10.410   -0.986   -7.232  1.00 21.93           C
ATOM   1301  C    LEU A 170     -13.737   -0.428   -3.693  1.00 18.22           C
ATOM   1302  O    LEU A 170     -14.300    0.663   -3.550  1.00 18.04           O
ATOM   1303  N    GLU A 171     -13.221   -1.106   -2.675  1.00 17.81           N
ATOM   1304  CA   GLU A 171     -13.392   -0.660   -1.270  1.00 17.24           C
ATOM   1305  CB   GLU A 171     -14.660   -1.281   -0.672  1.00 17.38           C
ATOM   1306  CG   GLU A 171     -15.314   -0.510    0.483  1.00 20.06           C
ATOM   1307  CD   GLU A 171     -14.806   -0.903    1.869  1.00 21.23           C
ATOM   1308  OE1  GLU A 171     -15.153   -0.220    2.865  1.00 22.43           O
ATOM   1309  OE2  GLU A 171     -14.113   -1.922    1.976  1.00 22.33           O
ATOM   1310  C    GLU A 171     -12.189   -1.034   -0.439  1.00 16.65           C
ATOM   1311  O    GLU A 171     -11.611   -2.107   -0.629  1.00 16.34           O
ATOM   1312  N    GLY A 172     -11.854   -0.177    0.530  1.00 16.94           N
ATOM   1313  CA   GLY A 172     -10.847   -0.482    1.533  1.00 16.71           C
ATOM   1314  C    GLY A 172     -10.629    0.622    2.557  1.00 16.76           C
ATOM   1315  O    GLY A 172     -11.059    1.737    2.356  1.00 17.23           O
ATOM   1316  N    TYR A 173      -9.929    0.307    3.647  1.00 16.53           N
ATOM   1317  CA   TYR A 173      -9.625    1.249    4.731  1.00 16.53           C
ATOM   1318  CB   TYR A 173     -10.406    0.862    5.986  1.00 15.98           C
ATOM   1319  CG   TYR A 173     -10.434    1.959    7.044  1.00 16.64           C
ATOM   1320  CD1  TYR A 173     -11.221    3.105    6.866  1.00 16.16           C
ATOM   1321  CE1  TYR A 173     -11.216    4.144    7.786  1.00 16.43           C
ATOM   1322  CZ   TYR A 173     -10.462    4.032    8.929  1.00 16.71           C
ATOM   1323  OH   TYR A 173     -10.480    5.060    9.835  1.00 15.78           O
ATOM   1324  CE2  TYR A 173      -9.658    2.907    9.132  1.00 18.14           C
ATOM   1325  CD2  TYR A 173      -9.659    1.869    8.193  1.00 15.94           C
ATOM   1326  C    TYR A 173      -8.108    1.216    5.052  1.00 17.65           C
ATOM   1327  O    TYR A 173      -7.452    0.178    4.890  1.00 16.91           O
ATOM   1328  N    SER A 174      -7.555    2.352    5.477  1.00 18.52           N
ATOM   1329  CA   SER A 174      -6.176    2.413    6.015  1.00 20.82           C
ATOM   1330  CB   SER A 174      -6.078    1.579    7.329  1.00 21.52           C
ATOM   1331  OG   SER A 174      -5.004    2.030    8.133  1.00 24.05           O
ATOM   1332  C    SER A 174      -5.130    2.045    4.934  1.00 19.94           C
ATOM   1333  O    SER A 174      -5.199    2.615    3.847  1.00 20.91           O
ATOM   1334  N    GLY A 175      -4.193    1.115    5.165  1.00 19.54           N
ATOM   1335  CA   GLY A 175      -3.328    0.646    4.089  1.00 18.75           C
ATOM   1336  C    GLY A 175      -4.103    0.152    2.849  1.00 19.24           C
ATOM   1337  O    GLY A 175      -3.658    0.302    1.714  1.00 18.55           O
ATOM   1338  N    GLY A 176      -5.284   -0.432    3.081  1.00 18.95           N
ATOM   1339  CA   GLY A 176      -6.184   -0.824    2.015  1.00 18.71           C
ATOM   1340  C    GLY A 176      -6.763    0.334    1.211  1.00 18.33           C
ATOM   1341  O    GLY A 176      -7.074    0.164    0.023  1.00 17.16           O
ATOM   1342  N    ALA A 177      -6.939    1.483    1.859  1.00 17.46           N
ATOM   1343  CA   ALA A 177      -7.425    2.702    1.184  1.00 17.47           C
ATOM   1344  CB   ALA A 177      -7.970    3.687    2.167  1.00 17.15           C
ATOM   1345  C    ALA A 177      -6.331    3.359    0.316  1.00 18.06           C
ATOM   1346  O    ALA A 177      -6.634    3.934   -0.731  1.00 18.61           O
```

Fig. 1, continued

```
ATOM   1347  N    HIS A 178      -5.074    3.266    0.743  1.00 17.39           N
ATOM   1348  CA   HIS A 178      -3.964    3.658   -0.113  1.00 17.56           C
ATOM   1349  CB   HIS A 178      -2.639    3.453    0.600  1.00 16.73           C
ATOM   1350  CG   HIS A 178      -1.451    3.818   -0.222  1.00 18.69           C
ATOM   1351  ND1  HIS A 178      -0.692    2.879   -0.895  1.00 18.76           N
ATOM   1352  CE1  HIS A 178       0.300    3.494   -1.522  1.00 18.21           C
ATOM   1353  NE2  HIS A 178       0.211    4.790   -1.280  1.00 17.86           N
ATOM   1354  CD2  HIS A 178      -0.890    5.021   -0.489  1.00 20.15           C
ATOM   1355  C    HIS A 178      -3.958    2.859   -1.400  1.00 17.12           C
ATOM   1356  O    HIS A 178      -3.857    3.399   -2.491  1.00 17.58           O
ATOM   1357  N    ALA A 179      -4.096    1.562   -1.251  1.00 17.12           N
ATOM   1358  CA   ALA A 179      -4.144    0.670   -2.359  1.00 17.01           C
ATOM   1359  CB   ALA A 179      -4.202   -0.777   -1.829  1.00 17.20           C
ATOM   1360  C    ALA A 179      -5.332    0.983   -3.278  1.00 17.47           C
ATOM   1361  O    ALA A 179      -5.181    1.026   -4.493  1.00 17.98           O
ATOM   1362  N    THR A 180      -6.502    1.200   -2.682  1.00 17.20           N
ATOM   1363  CA   THR A 180      -7.696    1.533   -3.413  1.00 17.58           C
ATOM   1364  CB   THR A 180      -8.872    1.622   -2.456  1.00 17.59           C
ATOM   1365  OG1  THR A 180      -9.050    0.359   -1.789  1.00 17.91           O
ATOM   1366  CG2  THR A 180     -10.158    1.854   -3.199  1.00 17.31           C
ATOM   1367  C    THR A 180      -7.543    2.860   -4.186  1.00 18.38           C
ATOM   1368  O    THR A 180      -7.749    2.876   -5.390  1.00 17.41           O
ATOM   1369  N    VAL A 181      -7.148    3.946   -3.509  1.00 18.40           N
ATOM   1370  CA   VAL A 181      -6.978    5.234   -4.187  1.00 18.33           C
ATOM   1371  CB   VAL A 181      -6.634    6.384   -3.215  1.00 18.41           C
ATOM   1372  CG1  VAL A 181      -5.169    6.344   -2.745  1.00 17.82           C
ATOM   1373  CG2  VAL A 181      -6.985    7.731   -3.849  1.00 19.22           C
ATOM   1374  C    VAL A 181      -5.979    5.130   -5.346  1.00 18.60           C
ATOM   1375  O    VAL A 181      -6.203    5.714   -6.413  1.00 19.46           O
ATOM   1376  N    TRP A 182      -4.914    4.341   -5.166  1.00 18.14           N
ATOM   1377  CA   TRP A 182      -3.968    4.131   -6.227  1.00 17.60           C
ATOM   1378  CB   TRP A 182      -2.666    3.526   -5.712  1.00 18.03           C
ATOM   1379  CG   TRP A 182      -1.757    4.594   -5.245  1.00 18.31           C
ATOM   1380  CD1  TRP A 182      -1.643    5.092   -3.973  1.00 19.53           C
ATOM   1381  NE1  TRP A 182      -0.726    6.115   -3.942  1.00 19.79           N
ATOM   1382  CE2  TRP A 182      -0.225    6.294   -5.203  1.00 21.06           C
ATOM   1383  CD2  TRP A 182      -0.875    5.364   -6.053  1.00 19.34           C
ATOM   1384  CE3  TRP A 182      -0.528    5.343   -7.411  1.00 19.55           C
ATOM   1385  CZ3  TRP A 182       0.426    6.261   -7.880  1.00 18.67           C
ATOM   1386  CH2  TRP A 182       1.015    7.182   -7.027  1.00 20.53           C
ATOM   1387  CZ2  TRP A 182       0.721    7.212   -5.680  1.00 22.63           C
ATOM   1388  C    TRP A 182      -4.539    3.344   -7.390  1.00 17.95           C
ATOM   1389  O    TRP A 182      -4.271    3.682   -8.579  1.00 17.51           O
ATOM   1390  N    ALA A 183      -5.290    2.288   -7.097  1.00 17.56           N
ATOM   1391  CA   ALA A 183      -5.973    1.570   -8.168  1.00 18.01           C
ATOM   1392  CB   ALA A 183      -6.722    0.389   -7.638  1.00 18.01           C
ATOM   1393  C    ALA A 183      -6.913    2.517   -8.962  1.00 19.34           C
ATOM   1394  O    ALA A 183      -6.908    2.520  -10.216  1.00 18.59           O
ATOM   1395  N    THR A 184      -7.690    3.343   -8.254  1.00 19.14           N
ATOM   1396  CA   THR A 184      -8.554    4.300   -8.947  1.00 20.30           C
ATOM   1397  CB   THR A 184      -9.542    5.018   -8.016  1.00 19.23           C
ATOM   1398  OG1  THR A 184      -8.842    5.744   -6.998  1.00 20.81           O
ATOM   1399  CG2  THR A 184     -10.450    4.029   -7.314  1.00 18.22           C
ATOM   1400  C    THR A 184      -7.767    5.354   -9.738  1.00 20.69           C
```

Fig. 1, continued

| ATOM | 1401 | O   | THR | A | 184 | -8.227 | 5.774  | -10.784 | 1.00 | 21.92 | O |
|------|------|-----|-----|---|-----|--------|--------|---------|------|-------|---|
| ATOM | 1402 | N   | SER | A | 185 | -6.591 | 5.739  | -9.253  | 1.00 | 20.75 | N |
| ATOM | 1403 | CA  | SER | A | 185 | -5.768 | 6.768  | -9.897  | 1.00 | 21.22 | C |
| ATOM | 1404 | CB  | SER | A | 185 | -4.715 | 7.261  | -8.954  | 0.70 | 20.88 | C |
| ATOM | 1405 | OG  | SER | A | 185 | -5.355 | 7.987  | -7.902  | 0.70 | 19.94 | O |
| ATOM | 1406 | C   | SER | A | 185 | -5.166 | 6.232  | -11.181 | 1.00 | 22.42 | C |
| ATOM | 1407 | O   | SER | A | 185 | -5.001 | 6.980  | -12.142 | 1.00 | 22.85 | O |
| ATOM | 1408 | N   | LEU | A | 186 | -4.804 | 4.950  | -11.181 | 1.00 | 22.61 | N |
| ATOM | 1409 | CA  | LEU | A | 186 | -4.154 | 4.368  | -12.327 | 1.00 | 22.51 | C |
| ATOM | 1410 | CB  | LEU | A | 186 | -3.121 | 3.332  | -11.896 | 1.00 | 22.15 | C |
| ATOM | 1411 | CG  | LEU | A | 186 | -1.965 | 3.905  | -11.091 | 1.00 | 21.68 | C |
| ATOM | 1412 | CD1 | LEU | A | 186 | -0.970 | 2.789  | -10.840 | 1.00 | 23.55 | C |
| ATOM | 1413 | CD2 | LEU | A | 186 | -1.320 | 5.092  | -11.808 | 1.00 | 24.11 | C |
| ATOM | 1414 | C   | LEU | A | 186 | -5.111 | 3.760  | -13.355 | 1.00 | 22.84 | C |
| ATOM | 1415 | O   | LEU | A | 186 | -4.644 | 3.346  | -14.412 | 1.00 | 22.76 | O |
| ATOM | 1416 | N   | ALA | A | 187 | -6.407 | 3.712  | -13.056 | 1.00 | 22.00 | N |
| ATOM | 1417 | CA  | ALA | A | 187 | -7.386 | 3.055  | -13.920 | 1.00 | 22.75 | C |
| ATOM | 1418 | CB  | ALA | A | 187 | -8.777 | 3.147  | -13.312 | 1.00 | 22.12 | C |
| ATOM | 1419 | C   | ALA | A | 187 | -7.372 | 3.662  | -15.345 | 1.00 | 24.08 | C |
| ATOM | 1420 | O   | ALA | A | 187 | -7.281 | 2.943  | -16.308 | 1.00 | 23.65 | O |
| ATOM | 1421 | N   | GLU | A | 188 | -7.410 | 4.992  | -15.418 | 1.00 | 26.10 | N |
| ATOM | 1422 | CA  | GLU | A | 188 | -7.444 | 5.768  | -16.665 | 1.00 | 27.36 | C |
| ATOM | 1423 | CB  | GLU | A | 188 | -7.464 | 7.283  | -16.343 | 1.00 | 28.09 | C |
| ATOM | 1424 | CG  | GLU | A | 188 | -7.472 | 8.188  | -17.571 | 1.00 | 32.06 | C |
| ATOM | 1425 | CD  | GLU | A | 188 | -7.325 | 9.689  | -17.285 | 1.00 | 36.00 | C |
| ATOM | 1426 | OE1 | GLU | A | 188 | -7.436 | 10.429 | -18.291 | 1.00 | 38.66 | O |
| ATOM | 1427 | OE2 | GLU | A | 188 | -7.088 | 10.142 | -16.120 | 1.00 | 35.41 | O |
| ATOM | 1428 | C   | GLU | A | 188 | -6.295 | 5.418  | -17.625 | 1.00 | 27.52 | C |
| ATOM | 1429 | O   | GLU | A | 188 | -6.556 | 5.159  | -18.800 | 1.00 | 27.60 | O |
| ATOM | 1430 | N   | SER | A | 189 | -5.055 | 5.348  | -17.130 | 1.00 | 27.24 | N |
| ATOM | 1431 | CA  | SER | A | 189 | -3.890 | 5.075  | -17.987 | 1.00 | 27.16 | C |
| ATOM | 1432 | CB  | SER | A | 189 | -2.649 | 5.819  | -17.477 | 1.00 | 27.56 | C |
| ATOM | 1433 | OG  | SER | A | 189 | -2.352 | 5.493  | -16.117 | 1.00 | 30.84 | O |
| ATOM | 1434 | C   | SER | A | 189 | -3.546 | 3.589  | -18.128 | 1.00 | 26.81 | C |
| ATOM | 1435 | O   | SER | A | 189 | -3.062 | 3.162  | -19.187 | 1.00 | 25.99 | O |
| ATOM | 1436 | N   | TYR | A | 190 | -3.765 | 2.807  | -17.060 | 1.00 | 24.76 | N |
| ATOM | 1437 | CA  | TYR | A | 190 | -3.362 | 1.407  | -17.022 | 1.00 | 23.80 | C |
| ATOM | 1438 | CB  | TYR | A | 190 | -2.795 | 1.051  | -15.620 | 1.00 | 23.83 | C |
| ATOM | 1439 | CG  | TYR | A | 190 | -2.063 | -0.275 | -15.566 | 1.00 | 21.87 | C |
| ATOM | 1440 | CD1 | TYR | A | 190 | -2.663 | -1.406 | -15.019 | 1.00 | 20.26 | C |
| ATOM | 1441 | CE1 | TYR | A | 190 | -2.000 | -2.638 | -14.977 | 1.00 | 19.66 | C |
| ATOM | 1442 | CZ  | TYR | A | 190 | -0.729 | -2.760 | -15.484 | 1.00 | 21.36 | C |
| ATOM | 1443 | OH  | TYR | A | 190 | -0.053 | -3.988 | -15.435 | 1.00 | 18.57 | O |
| ATOM | 1444 | CE2 | TYR | A | 190 | -0.107 | -1.635 | -16.065 | 1.00 | 22.02 | C |
| ATOM | 1445 | CD2 | TYR | A | 190 | -0.779 | -0.409 | -16.103 | 1.00 | 21.62 | C |
| ATOM | 1446 | C   | TYR | A | 190 | -4.487 | 0.430  | -17.391 | 1.00 | 23.12 | C |
| ATOM | 1447 | O   | TYR | A | 190 | -4.223 | -0.625 | -17.961 | 1.00 | 23.30 | O |
| ATOM | 1448 | N   | ALA | A | 191 | -5.728 | 0.749  | -17.030 | 1.00 | 22.64 | N |
| ATOM | 1449 | CA  | ALA | A | 191 | -6.853 | -0.157 | -17.257 | 1.00 | 22.79 | C |
| ATOM | 1450 | CB  | ALA | A | 191 | -6.981 | -1.162 | -16.077 | 1.00 | 22.71 | C |
| ATOM | 1451 | C   | ALA | A | 191 | -8.184 | 0.577  | -17.506 | 1.00 | 23.43 | C |
| ATOM | 1452 | O   | ALA | A | 191 | -9.171 | 0.376  | -16.769 | 1.00 | 22.09 | O |
| ATOM | 1453 | N   | PRO | A | 192 | -8.228 | 1.397  | -18.573 | 1.00 | 23.95 | N |
| ATOM | 1454 | CA  | PRO | A | 192 | -9.433 | 2.183  | -18.900 | 1.00 | 24.02 | C |

Fig. 1, continued

```
ATOM   1455  CB  PRO A 192      -8.969   3.116 -20.055  1.00 24.39           C
ATOM   1456  CG  PRO A 192      -7.763   2.445 -20.678  1.00 24.60           C
ATOM   1457  CD  PRO A 192      -7.121   1.631 -19.536  1.00 24.39           C
ATOM   1458  C   PRO A 192     -10.661   1.353 -19.289  1.00 24.23           C
ATOM   1459  O   PRO A 192     -11.769   1.856 -19.223  1.00 25.46           O
ATOM   1460  N   GLU A 193     -10.475   0.096 -19.647  1.00 24.32           N
ATOM   1461  CA  GLU A 193     -11.584  -0.779 -20.020  1.00 24.44           C
ATOM   1462  CB  GLU A 193     -11.074  -1.906 -20.932  1.00 24.50           C
ATOM   1463  CG  GLU A 193     -10.579  -3.204 -20.270  1.00 25.90           C
ATOM   1464  CD  GLU A 193      -9.275  -3.105 -19.478  1.00 26.70           C
ATOM   1465  OE1 GLU A 193      -9.004  -4.092 -18.747  1.00 29.13           O
ATOM   1466  OE2 GLU A 193      -8.521  -2.093 -19.559  1.00 25.67           O
ATOM   1467  C   GLU A 193     -12.348  -1.378 -18.838  1.00 24.20           C
ATOM   1468  O   GLU A 193     -13.415  -1.968 -19.037  1.00 23.93           O
ATOM   1469  N   LEU A 194     -11.809  -1.271 -17.615  1.00 23.48           N
ATOM   1470  CA  LEU A 194     -12.574  -1.718 -16.444  1.00 22.67           C
ATOM   1471  CB  LEU A 194     -11.701  -1.850 -15.179  1.00 22.26           C
ATOM   1472  CG  LEU A 194     -10.575  -2.866 -15.314  1.00 22.36           C
ATOM   1473  CD1 LEU A 194      -9.678  -2.885 -14.047  1.00 21.84           C
ATOM   1474  CD2 LEU A 194     -11.127  -4.279 -15.616  1.00 23.36           C
ATOM   1475  C   LEU A 194     -13.722  -0.744 -16.240  1.00 22.14           C
ATOM   1476  O   LEU A 194     -13.529   0.473 -16.111  1.00 23.71           O
ATOM   1477  N   ASN A 195     -14.925  -1.281 -16.226  1.00 21.29           N
ATOM   1478  CA  ASN A 195     -16.116  -0.481 -16.021  1.00 21.12           C
ATOM   1479  CB  ASN A 195     -17.314  -1.203 -16.633  1.00 20.39           C
ATOM   1480  CG  ASN A 195     -18.586  -0.404 -16.533  1.00 20.25           C
ATOM   1481  OD1 ASN A 195     -18.542   0.801 -16.392  1.00 21.97           O
ATOM   1482  ND2 ASN A 195     -19.734  -1.079 -16.595  1.00 21.38           N
ATOM   1483  C   ASN A 195     -16.315  -0.201 -14.514  1.00 21.75           C
ATOM   1484  O   ASN A 195     -17.172  -0.790 -13.854  1.00 20.53           O
ATOM   1485  N   ILE A 196     -15.496   0.708 -13.993  1.00 22.14           N
ATOM   1486  CA  ILE A 196     -15.538   1.053 -12.582  1.00 21.87           C
ATOM   1487  CB  ILE A 196     -14.218   1.656 -12.119  1.00 21.37           C
ATOM   1488  CG1 ILE A 196     -13.077   0.633 -12.304  1.00 24.27           C
ATOM   1489  CD1 ILE A 196     -11.686   1.176 -12.019  1.00 23.11           C
ATOM   1490  CG2 ILE A 196     -14.303   2.055 -10.655  1.00 21.69           C
ATOM   1491  C   ILE A 196     -16.696   2.018 -12.368  1.00 21.55           C
ATOM   1492  O   ILE A 196     -16.671   3.133 -12.829  1.00 21.20           O
ATOM   1493  N   VAL A 197     -17.705   1.559 -11.651  1.00 21.04           N
ATOM   1494  CA  VAL A 197     -18.881   2.351 -11.335  1.00 21.03           C
ATOM   1495  CB  VAL A 197     -20.132   1.479 -11.455  1.00 20.66           C
ATOM   1496  CG1 VAL A 197     -20.231   0.928 -12.870  1.00 22.46           C
ATOM   1497  CG2 VAL A 197     -20.166   0.341 -10.433  1.00 21.65           C
ATOM   1498  C   VAL A 197     -18.852   2.985  -9.943  1.00 20.78           C
ATOM   1499  O   VAL A 197     -19.740   3.763  -9.595  1.00 21.26           O
ATOM   1500  N   GLY A 198     -17.847   2.659  -9.134  1.00 20.74           N
ATOM   1501  CA  GLY A 198     -17.770   3.271  -7.803  1.00 20.91           C
ATOM   1502  C   GLY A 198     -16.565   2.846  -7.016  1.00 20.05           C
ATOM   1503  O   GLY A 198     -16.046   1.779  -7.250  1.00 20.40           O
ATOM   1504  N   ALA A 199     -16.099   3.705  -6.121  1.00 19.59           N
ATOM   1505  CA  ALA A 199     -15.065   3.345  -5.168  1.00 19.06           C
ATOM   1506  CB  ALA A 199     -13.673   3.735  -5.654  1.00 19.09           C
ATOM   1507  C   ALA A 199     -15.365   4.020  -3.850  1.00 18.74           C
ATOM   1508  O   ALA A 199     -15.838   5.149  -3.815  1.00 19.02           O
```

Fig. 1, continued

```
ATOM   1509  N    SER A 200     -15.080   3.306  -2.771  1.00 18.32           N
ATOM   1510  CA   SER A 200     -15.334   3.766  -1.414  1.00 18.14           C
ATOM   1511  CB   SER A 200     -16.571   3.071  -0.872  1.00 18.16           C
ATOM   1512  OG   SER A 200     -16.784   3.436   0.468  1.00 22.31           O
ATOM   1513  C    SER A 200     -14.105   3.443  -0.570  1.00 18.26           C
ATOM   1514  O    SER A 200     -13.684   2.268  -0.507  1.00 18.10           O
ATOM   1515  N    HIS A 201     -13.480   4.475   0.010  1.00 16.76           N
ATOM   1516  CA   HIS A 201     -12.378   4.259   0.897  1.00 16.45           C
ATOM   1517  CB   HIS A 201     -11.066   4.133   0.112  1.00 15.70           C
ATOM   1518  CG   HIS A 201     -10.776   5.276  -0.824  1.00 15.90           C
ATOM   1519  ND1  HIS A 201      -9.944   6.319  -0.485  1.00 14.40           N
ATOM   1520  CE1  HIS A 201      -9.830   7.144  -1.517  1.00 16.27           C
ATOM   1521  NE2  HIS A 201     -10.518   6.645  -2.530  1.00 15.12           N
ATOM   1522  CD2  HIS A 201     -11.119   5.478  -2.125  1.00 16.60           C
ATOM   1523  C    HIS A 201     -12.237   5.273   2.035  1.00 16.46           C
ATOM   1524  O    HIS A 201     -12.662   6.415   1.933  1.00 16.66           O
ATOM   1525  N    GLY A 202     -11.626   4.810   3.121  1.00 16.24           N
ATOM   1526  CA   GLY A 202     -11.524   5.575   4.343  1.00 16.47           C
ATOM   1527  C    GLY A 202     -10.160   5.506   4.976  1.00 16.39           C
ATOM   1528  O    GLY A 202      -9.424   4.558   4.754  1.00 16.21           O
ATOM   1529  N    GLY A 203      -9.817   6.517   5.761  1.00 15.98           N
ATOM   1530  CA   GLY A 203      -8.542   6.544   6.440  1.00 16.24           C
ATOM   1531  C    GLY A 203      -7.370   6.492   5.513  1.00 16.41           C
ATOM   1532  O    GLY A 203      -6.363   5.852   5.825  1.00 16.52           O
ATOM   1533  N    THR A 204      -7.486   7.222   4.401  1.00 16.93           N
ATOM   1534  CA   THR A 204      -6.601   7.089   3.260  1.00 17.06           C
ATOM   1535  CB   THR A 204      -7.331   7.661   2.012  1.00 17.79           C
ATOM   1536  OG1  THR A 204      -8.717   7.236   1.962  1.00 17.25           O
ATOM   1537  CG2  THR A 204      -6.688   7.167   0.728  1.00 15.54           C
ATOM   1538  C    THR A 204      -5.243   7.817   3.384  1.00 18.21           C
ATOM   1539  O    THR A 204      -5.205   9.048   3.449  1.00 17.76           O
ATOM   1540  N    PRO A 205      -4.124   7.074   3.368  1.00 18.56           N
ATOM   1541  CA   PRO A 205      -2.815   7.683   3.131  1.00 18.56           C
ATOM   1542  CB   PRO A 205      -1.823   6.566   3.438  1.00 18.49           C
ATOM   1543  CG   PRO A 205      -2.645   5.394   3.976  1.00 19.40           C
ATOM   1544  CD   PRO A 205      -4.041   5.615   3.548  1.00 19.27           C
ATOM   1545  C    PRO A 205      -2.774   8.076   1.642  1.00 19.33           C
ATOM   1546  O    PRO A 205      -2.992   7.214   0.782  1.00 20.58           O
ATOM   1547  N    VAL A 206      -2.636   9.362   1.351  1.00 18.90           N
ATOM   1548  CA   VAL A 206      -2.589   9.837  -0.046  1.00 19.16           C
ATOM   1549  CB   VAL A 206      -3.595  10.971  -0.309  1.00 18.77           C
ATOM   1550  CG1  VAL A 206      -5.008  10.447  -0.297  1.00 19.18           C
ATOM   1551  CG2  VAL A 206      -3.453  12.097   0.700  1.00 18.17           C
ATOM   1552  C    VAL A 206      -1.156  10.288  -0.440  1.00 19.18           C
ATOM   1553  O    VAL A 206      -0.799  10.297  -1.626  1.00 19.39           O
ATOM   1554  N    SER A 207      -0.354  10.630   0.556  1.00 18.91           N
ATOM   1555  CA   SER A 207       1.022  11.103   0.349  1.00 20.03           C
ATOM   1556  CB   SER A 207       1.115  12.587   0.776  1.00 19.88           C
ATOM   1557  OG   SER A 207       2.446  13.012   1.007  1.00 21.24           O
ATOM   1558  C    SER A 207       1.949  10.245   1.184  1.00 19.41           C
ATOM   1559  O    SER A 207       1.792  10.172   2.403  1.00 20.43           O
ATOM   1560  N    ALA A 208       2.903   9.578   0.553  1.00 19.97           N
ATOM   1561  CA   ALA A 208       3.867   8.775   1.302  1.00 20.47           C
ATOM   1562  CB   ALA A 208       4.820   8.043   0.375  1.00 21.26           C
```

Fig. 1, continued

```
ATOM   1563  C   ALA A 208       4.635   9.635   2.268  1.00 20.72           C
ATOM   1564  O   ALA A 208       4.796   9.260   3.425  1.00 21.23           O
ATOM   1565  N   LYS A 209       5.087  10.800   1.820  1.00 20.87           N
ATOM   1566  CA  LYS A 209       5.870  11.684   2.684  1.00 21.25           C
ATOM   1567  CB  LYS A 209       6.421  12.893   1.909  1.00 21.92           C
ATOM   1568  CG  LYS A 209       7.352  13.822   2.727  1.00 23.22           C
ATOM   1569  CD  LYS A 209       7.856  15.028   1.875  0.65 25.78           C
ATOM   1570  CE  LYS A 209       6.718  16.073   1.604  0.65 26.64           C
ATOM   1571  NZ  LYS A 209       7.102  17.277   0.748  0.65 26.79           N
ATOM   1572  C   LYS A 209       5.066  12.167   3.882  1.00 20.83           C
ATOM   1573  O   LYS A 209       5.551  12.102   5.001  1.00 20.52           O
ATOM   1574  N   ASP A 210       3.849  12.661   3.653  1.00 20.87           N
ATOM   1575  CA  ASP A 210       3.049  13.217   4.736  1.00 20.74           C
ATOM   1576  CB  ASP A 210       1.793  13.962   4.223  1.00 21.02           C
ATOM   1577  CG  ASP A 210       2.144  15.233   3.479  1.00 24.18           C
ATOM   1578  OD1 ASP A 210       1.252  15.790   2.776  1.00 27.41           O
ATOM   1579  OD2 ASP A 210       3.301  15.727   3.524  1.00 25.07           O
ATOM   1580  C   ASP A 210       2.626  12.161   5.712  1.00 20.32           C
ATOM   1581  O   ASP A 210       2.475  12.451   6.890  1.00 20.38           O
ATOM   1582  N   THR A 211       2.419  10.940   5.229  1.00 19.68           N
ATOM   1583  CA  THR A 211       2.129   9.843   6.128  1.00 19.76           C
ATOM   1584  CB  THR A 211       1.624   8.589   5.359  1.00 20.45           C
ATOM   1585  OG1 THR A 211       0.496   8.939   4.537  1.00 19.62           O
ATOM   1586  CG2 THR A 211       1.090   7.561   6.354  1.00 20.71           C
ATOM   1587  C   THR A 211       3.368   9.513   6.949  1.00 19.42           C
ATOM   1588  O   THR A 211       3.280   9.327   8.161  1.00 18.49           O
ATOM   1589  N   PHE A 212       4.527   9.464   6.297  1.00 19.61           N
ATOM   1590  CA  PHE A 212       5.766   9.200   7.013  1.00 19.61           C
ATOM   1591  CB  PHE A 212       6.963   9.174   6.081  1.00 20.41           C
ATOM   1592  CG  PHE A 212       8.281   9.080   6.821  1.00 21.75           C
ATOM   1593  CD1 PHE A 212       8.819   7.846   7.139  1.00 22.58           C
ATOM   1594  CE1 PHE A 212      10.035   7.753   7.818  1.00 23.57           C
ATOM   1595  CZ  PHE A 212      10.728   8.908   8.184  1.00 23.36           C
ATOM   1596  CE2 PHE A 212      10.214  10.131   7.857  1.00 24.28           C
ATOM   1597  CD2 PHE A 212       8.986  10.223   7.163  1.00 22.08           C
ATOM   1598  C   PHE A 212       6.030  10.226   8.131  1.00 19.69           C
ATOM   1599  O   PHE A 212       6.248   9.832   9.268  1.00 18.46           O
ATOM   1600  N   THR A 213       5.970  11.524   7.818  1.00 19.61           N
ATOM   1601  CA  THR A 213       6.282  12.562   8.815  1.00 20.12           C
ATOM   1602  CB  THR A 213       6.443  13.957   8.184  1.00 20.44           C
ATOM   1603  OG1 THR A 213       5.245  14.338   7.505  1.00 18.63           O
ATOM   1604  CG2 THR A 213       7.535  13.973   7.116  1.00 21.51           C
ATOM   1605  C   THR A 213       5.268  12.637   9.953  1.00 20.25           C
ATOM   1606  O   THR A 213       5.596  13.052  11.056  1.00 19.18           O
ATOM   1607  N   PHE A 214       4.033  12.230   9.675  1.00 20.05           N
ATOM   1608  CA  PHE A 214       3.004  12.132  10.699  1.00 19.85           C
ATOM   1609  CB  PHE A 214       1.665  11.886  10.011  1.00 19.86           C
ATOM   1610  CG  PHE A 214       0.478  11.981  10.915  1.00 20.31           C
ATOM   1611  CD1 PHE A 214      -0.068  13.231  11.238  1.00 21.01           C
ATOM   1612  CE1 PHE A 214      -1.179  13.335  12.057  1.00 21.55           C
ATOM   1613  CZ  PHE A 214      -1.788  12.185  12.556  1.00 21.64           C
ATOM   1614  CE2 PHE A 214      -1.278  10.927  12.224  1.00 22.00           C
ATOM   1615  CD2 PHE A 214      -0.137  10.829  11.403  1.00 22.16           C
ATOM   1616  C   PHE A 214       3.316  10.994  11.705  1.00 20.21           C
```

Fig. 1, continued

```
ATOM   1617  O    PHE A 214       3.204  11.167  12.924  1.00 19.94           O
ATOM   1618  N    LEU A 215       3.706   9.844  11.176  1.00 20.17           N
ATOM   1619  CA   LEU A 215       3.954   8.646  11.992  1.00 21.01           C
ATOM   1620  CB   LEU A 215       3.788   7.408  11.121  1.00 20.21           C
ATOM   1621  CG   LEU A 215       2.346   7.179  10.659  1.00 22.27           C
ATOM   1622  CD1  LEU A 215       2.353   6.211   9.468  1.00 23.77           C
ATOM   1623  CD2  LEU A 215       1.494   6.666  11.769  1.00 22.62           C
ATOM   1624  C    LEU A 215       5.317   8.563  12.695  1.00 20.83           C
ATOM   1625  O    LEU A 215       5.430   8.016  13.812  1.00 21.21           O
ATOM   1626  N    ASN A 216       6.344   9.082  12.043  1.00 20.92           N
ATOM   1627  CA   ASN A 216       7.711   8.912  12.536  1.00 21.15           C
ATOM   1628  CB   ASN A 216       8.701   9.613  11.624  1.00 20.08           C
ATOM   1629  CG   ASN A 216      10.139   9.274  11.972  1.00 22.78           C
ATOM   1630  OD1  ASN A 216      10.437   8.133  12.385  1.00 18.94           O
ATOM   1631  ND2  ASN A 216      11.047  10.265  11.812  1.00 22.72           N
ATOM   1632  C    ASN A 216       7.842   9.420  13.978  1.00 21.40           C
ATOM   1633  O    ASN A 216       7.281  10.468  14.317  1.00 21.64           O
ATOM   1634  N    GLY A 217       8.500   8.626  14.826  1.00 21.24           N
ATOM   1635  CA   GLY A 217       8.716   8.961  16.225  1.00 21.27           C
ATOM   1636  C    GLY A 217       7.571   8.741  17.192  1.00 21.45           C
ATOM   1637  O    GLY A 217       7.766   8.838  18.426  1.00 22.11           O
ATOM   1638  N    GLY A 218       6.387   8.423  16.670  1.00 20.91           N
ATOM   1639  CA   GLY A 218       5.203   8.259  17.492  1.00 20.57           C
ATOM   1640  C    GLY A 218       4.898   6.806  17.805  1.00 20.56           C
ATOM   1641  O    GLY A 218       5.676   5.935  17.492  1.00 19.74           O
ATOM   1642  N    PRO A 219       3.754   6.536  18.417  1.00 20.85           N
ATOM   1643  CA   PRO A 219       3.413   5.166  18.840  1.00 21.13           C
ATOM   1644  CB   PRO A 219       2.080   5.333  19.575  1.00 21.72           C
ATOM   1645  CG   PRO A 219       1.676   6.750  19.442  1.00 21.75           C
ATOM   1646  CD   PRO A 219       2.738   7.521  18.782  1.00 20.92           C
ATOM   1647  C    PRO A 219       3.292   4.155  17.681  1.00 21.03           C
ATOM   1648  O    PRO A 219       3.459   2.957  17.904  1.00 20.96           O
ATOM   1649  N    PHE A 220       3.051   4.655  16.465  1.00 20.51           N
ATOM   1650  CA   PHE A 220       2.895   3.836  15.275  1.00 19.85           C
ATOM   1651  CB   PHE A 220       1.529   4.139  14.641  1.00 20.03           C
ATOM   1652  CG   PHE A 220       0.397   3.641  15.450  1.00 19.28           C
ATOM   1653  CD1  PHE A 220      -0.388   4.516  16.193  1.00 20.31           C
ATOM   1654  CE1  PHE A 220      -1.430   4.044  16.973  1.00 19.50           C
ATOM   1655  CZ   PHE A 220      -1.711   2.676  17.016  1.00 20.76           C
ATOM   1656  CE2  PHE A 220      -0.918   1.790  16.291  1.00 21.47           C
ATOM   1657  CD2  PHE A 220       0.118   2.271  15.505  1.00 19.99           C
ATOM   1658  C    PHE A 220       4.019   4.044  14.295  1.00 19.34           C
ATOM   1659  O    PHE A 220       3.863   3.830  13.088  1.00 19.03           O
ATOM   1660  N    ALA A 221       5.187   4.420  14.815  1.00 19.46           N
ATOM   1661  CA   ALA A 221       6.350   4.617  13.971  1.00 19.39           C
ATOM   1662  CB   ALA A 221       7.507   5.125  14.791  1.00 19.46           C
ATOM   1663  C    ALA A 221       6.759   3.375  13.153  1.00 19.16           C
ATOM   1664  O    ALA A 221       7.388   3.493  12.113  1.00 19.76           O
ATOM   1665  N    GLY A 222       6.415   2.183  13.592  1.00 19.86           N
ATOM   1666  CA   GLY A 222       6.677   1.006  12.771  1.00 19.83           C
ATOM   1667  C    GLY A 222       6.149   1.096  11.345  1.00 20.12           C
ATOM   1668  O    GLY A 222       6.746   0.549  10.412  1.00 20.26           O
ATOM   1669  N    PHE A 223       5.023   1.771  11.162  1.00 20.05           N
ATOM   1670  CA   PHE A 223       4.471   1.947   9.828  1.00 20.43           C
```

Fig. 1, continued

| | | | | | | | | | | |
|---|---|---|---|---|---|---|---|---|---|---|
| ATOM | 1671 | CB  | PHE | A | 223 | 3.022  | 2.428  | 9.884  | 1.00 | 21.07 | C |
| ATOM | 1672 | CG  | PHE | A | 223 | 2.071  | 1.439  | 10.485 | 1.00 | 24.53 | C |
| ATOM | 1673 | CD1 | PHE | A | 223 | 1.023  | 1.887  | 11.273 | 1.00 | 30.09 | C |
| ATOM | 1674 | CE1 | PHE | A | 223 | 0.112  | 0.992  | 11.837 | 1.00 | 31.76 | C |
| ATOM | 1675 | CZ  | PHE | A | 223 | 0.255  | -0.359 | 11.603 | 1.00 | 32.47 | C |
| ATOM | 1676 | CE2 | PHE | A | 223 | 1.301  | -0.824 | 10.787 | 1.00 | 30.14 | C |
| ATOM | 1677 | CD2 | PHE | A | 223 | 2.176  | 0.079  | 10.219 | 1.00 | 27.91 | C |
| ATOM | 1678 | C   | PHE | A | 223 | 5.274  | 2.929  | 8.996  | 1.00 | 20.57 | C |
| ATOM | 1679 | O   | PHE | A | 223 | 5.300  | 2.800  | 7.781  | 1.00 | 20.75 | O |
| ATOM | 1680 | N   | ALA | A | 224 | 5.884  | 3.940  | 9.625  | 1.00 | 20.27 | N |
| ATOM | 1681 | CA  | ALA | A | 224 | 6.857  | 4.785  | 8.928  | 1.00 | 20.39 | C |
| ATOM | 1682 | CB  | ALA | A | 224 | 7.342  | 5.936  | 9.849  | 1.00 | 21.10 | C |
| ATOM | 1683 | C   | ALA | A | 224 | 8.044  | 3.948  | 8.455  | 1.00 | 20.23 | C |
| ATOM | 1684 | O   | ALA | A | 224 | 8.477  | 4.067  | 7.313  | 1.00 | 20.55 | O |
| ATOM | 1685 | N   | LEU | A | 225 | 8.558  | 3.081  | 9.307  | 1.00 | 19.68 | N |
| ATOM | 1686 | CA  | LEU | A | 225 | 9.647  | 2.181  | 8.877  | 1.00 | 20.23 | C |
| ATOM | 1687 | CB  | LEU | A | 225 | 10.201 | 1.375  | 10.033 | 1.00 | 20.03 | C |
| ATOM | 1688 | CG  | LEU | A | 225 | 11.319 | 0.372  | 9.702  | 1.00 | 20.81 | C |
| ATOM | 1689 | CD1 | LEU | A | 225 | 12.499 | 1.057  | 9.107  | 1.00 | 21.93 | C |
| ATOM | 1690 | CD2 | LEU | A | 225 | 11.698 | -0.371 | 10.973 | 1.00 | 21.57 | C |
| ATOM | 1691 | C   | LEU | A | 225 | 9.180  | 1.221  | 7.778  | 1.00 | 19.73 | C |
| ATOM | 1692 | O   | LEU | A | 225 | 9.900  | 0.990  | 6.811  | 1.00 | 19.13 | O |
| ATOM | 1693 | N   | ALA | A | 226 | 7.964  | 0.681  | 7.921  | 1.00 | 19.92 | N |
| ATOM | 1694 | CA  | ALA | A | 226 | 7.447  | -0.279 | 6.950  | 1.00 | 19.17 | C |
| ATOM | 1695 | CB  | ALA | A | 226 | 6.116  | -0.839 | 7.396  | 1.00 | 19.18 | C |
| ATOM | 1696 | C   | ALA | A | 226 | 7.326  | 0.378  | 5.569  | 1.00 | 19.23 | C |
| ATOM | 1697 | O   | ALA | A | 226 | 7.585  | -0.266 | 4.556  | 1.00 | 18.88 | O |
| ATOM | 1698 | N   | GLY | A | 227 | 6.970  | 1.657  | 5.537  | 1.00 | 19.37 | N |
| ATOM | 1699 | CA  | GLY | A | 227 | 6.873  | 2.396  | 4.280  | 1.00 | 19.77 | C |
| ATOM | 1700 | C   | GLY | A | 227 | 8.204  | 2.642  | 3.612  | 1.00 | 20.43 | C |
| ATOM | 1701 | O   | GLY | A | 227 | 8.329  | 2.599  | 2.389  | 1.00 | 19.94 | O |
| ATOM | 1702 | N   | VAL | A | 228 | 9.216  | 2.922  | 4.423  | 1.00 | 20.97 | N |
| ATOM | 1703 | CA  | VAL | A | 228 | 10.559 | 3.091  | 3.911  | 1.00 | 21.31 | C |
| ATOM | 1704 | CB  | VAL | A | 228 | 11.531 | 3.544  | 5.044  | 1.00 | 21.90 | C |
| ATOM | 1705 | CG1 | VAL | A | 228 | 12.984 | 3.436  | 4.594  | 1.00 | 22.90 | C |
| ATOM | 1706 | CG2 | VAL | A | 228 | 11.215 | 4.960  | 5.459  | 1.00 | 21.73 | C |
| ATOM | 1707 | C   | VAL | A | 228 | 10.999 | 1.759  | 3.313  | 1.00 | 20.75 | C |
| ATOM | 1708 | O   | VAL | A | 228 | 11.507 | 1.708  | 2.179  | 1.00 | 20.87 | O |
| ATOM | 1709 | N   | SER | A | 229 | 10.772 | 0.681  | 4.070  | 1.00 | 20.35 | N |
| ATOM | 1710 | CA  | SER | A | 229 | 11.084 | -0.672 | 3.611  | 1.00 | 19.49 | C |
| ATOM | 1711 | CB  | SER | A | 229 | 10.655 | -1.703 | 4.661  | 1.00 | 19.90 | C |
| ATOM | 1712 | OG  | SER | A | 229 | 10.892 | -3.029 | 4.204  | 1.00 | 17.53 | O |
| ATOM | 1713 | C   | SER | A | 229 | 10.386 | -0.992 | 2.289  | 1.00 | 19.04 | C |
| ATOM | 1714 | O   | SER | A | 229 | 10.997 | -1.492 | 1.374  | 1.00 | 17.94 | O |
| ATOM | 1715 | N   | GLY | A | 230 | 9.098  | -0.693 | 2.224  | 1.00 | 18.97 | N |
| ATOM | 1716 | CA  | GLY | A | 230 | 8.277  | -1.038 | 1.102  | 1.00 | 19.58 | C |
| ATOM | 1717 | C   | GLY | A | 230 | 8.606  | -0.222 | -0.137 | 1.00 | 20.22 | C |
| ATOM | 1718 | O   | GLY | A | 230 | 8.687  | -0.786 | -1.231 | 1.00 | 19.78 | O |
| ATOM | 1719 | N   | LEU | A | 231 | 8.833  | 1.082  | 0.024  | 1.00 | 20.68 | N |
| ATOM | 1720 | CA  | LEU | A | 231 | 9.217  | 1.917  | -1.130 | 1.00 | 21.59 | C |
| ATOM | 1721 | CB  | LEU | A | 231 | 9.252  | 3.415  | -0.780 | 1.00 | 21.90 | C |
| ATOM | 1722 | CG  | LEU | A | 231 | 7.872  | 4.084  | -0.534 | 1.00 | 21.81 | C |
| ATOM | 1723 | CD1 | LEU | A | 231 | 7.997  | 5.574  | -0.340 | 1.00 | 23.32 | C |
| ATOM | 1724 | CD2 | LEU | A | 231 | 6.928  | 3.827  | -1.622 | 1.00 | 23.62 | C |

Fig. 1, continued

```
ATOM   1725  C    LEU A 231      10.564   1.471  -1.667  1.00 21.97           C
ATOM   1726  O    LEU A 231      10.769   1.418  -2.887  1.00 21.61           O
ATOM   1727  N    SER A 232      11.477   1.138  -0.765  1.00 22.28           N
ATOM   1728  CA   SER A 232      12.812   0.696  -1.169  1.00 23.47           C
ATOM   1729  CB   SER A 232      13.749   0.554   0.036  1.00 22.79           C
ATOM   1730  OG   SER A 232      13.947   1.811   0.674  1.00 23.69           O
ATOM   1731  C    SER A 232      12.728  -0.612  -1.943  1.00 23.84           C
ATOM   1732  O    SER A 232      13.495  -0.825  -2.890  1.00 24.71           O
ATOM   1733  N    LEU A 233      11.768  -1.465  -1.575  1.00 24.54           N
ATOM   1734  CA   LEU A 233      11.559  -2.735  -2.273  1.00 24.35           C
ATOM   1735  CB   LEU A 233      10.642  -3.669  -1.468  1.00 23.89           C
ATOM   1736  CG   LEU A 233      11.297  -4.283  -0.224  1.00 25.69           C
ATOM   1737  CD1  LEU A 233      10.262  -4.676   0.799  1.00 26.23           C
ATOM   1738  CD2  LEU A 233      12.205  -5.493  -0.604  1.00 26.67           C
ATOM   1739  C    LEU A 233      10.988  -2.526  -3.676  1.00 24.62           C
ATOM   1740  O    LEU A 233      11.057  -3.434  -4.491  1.00 26.01           O
ATOM   1741  N    ALA A 234      10.342  -1.395  -3.929  1.00 23.88           N
ATOM   1742  CA   ALA A 234       9.770  -1.120  -5.256  1.00 24.66           C
ATOM   1743  CB   ALA A 234       8.396  -0.487  -5.106  1.00 24.56           C
ATOM   1744  C    ALA A 234      10.678  -0.216  -6.126  1.00 24.56           C
ATOM   1745  O    ALA A 234      10.531  -0.177  -7.351  1.00 24.49           O
ATOM   1746  N    HIS A 235      11.605   0.497  -5.483  1.00 24.18           N
ATOM   1747  CA   HIS A 235      12.500   1.470  -6.148  1.00 23.85           C
ATOM   1748  CB   HIS A 235      12.202   2.873  -5.637  1.00 22.78           C
ATOM   1749  CG   HIS A 235      10.818   3.377  -5.943  1.00 23.42           C
ATOM   1750  ND1  HIS A 235      10.551   4.251  -6.979  1.00 23.44           N
ATOM   1751  CE1  HIS A 235       9.263   4.557  -6.976  1.00 24.49           C
ATOM   1752  NE2  HIS A 235       8.683   3.913  -5.974  1.00 24.18           N
ATOM   1753  CD2  HIS A 235       9.633   3.166  -5.319  1.00 23.19           C
ATOM   1754  C    HIS A 235      13.965   1.130  -5.829  1.00 24.24           C
ATOM   1755  O    HIS A 235      14.481   1.570  -4.817  1.00 23.17           O
ATOM   1756  N    PRO A 236      14.633   0.355  -6.682  1.00 26.07           N
ATOM   1757  CA   PRO A 236      16.036  -0.057  -6.434  1.00 27.33           C
ATOM   1758  CB   PRO A 236      16.416  -0.832  -7.698  1.00 27.12           C
ATOM   1759  CG   PRO A 236      15.114  -1.298  -8.273  1.00 27.78           C
ATOM   1760  CD   PRO A 236      14.113  -0.215  -7.935  1.00 26.15           C
ATOM   1761  C    PRO A 236      17.026   1.080  -6.157  1.00 27.84           C
ATOM   1762  O    PRO A 236      17.904   0.887  -5.331  1.00 28.58           O
ATOM   1763  N    ASP A 237      16.861   2.239  -6.785  1.00 28.65           N
ATOM   1764  CA   ASP A 237      17.729   3.387  -6.498  1.00 29.02           C
ATOM   1765  CB   ASP A 237      17.362   4.607  -7.349  0.65 29.59           C
ATOM   1766  CG   ASP A 237      17.630   4.415  -8.804  0.65 30.71           C
ATOM   1767  OD1  ASP A 237      18.363   3.470  -9.161  0.65 31.84           O
ATOM   1768  OD2  ASP A 237      17.140   5.188  -9.661  0.65 34.33           O
ATOM   1769  C    ASP A 237      17.645   3.830  -5.052  1.00 29.12           C
ATOM   1770  O    ASP A 237      18.650   4.207  -4.458  1.00 29.44           O
ATOM   1771  N    MET A 238      16.435   3.815  -4.504  1.00 29.02           N
ATOM   1772  CA   MET A 238      16.224   4.159  -3.101  1.00 28.44           C
ATOM   1773  CB   MET A 238      14.725   4.315  -2.822  1.00 28.25           C
ATOM   1774  CG   MET A 238      14.375   4.599  -1.369  1.00 29.13           C
ATOM   1775  SD   MET A 238      12.608   5.104  -1.196  1.00 29.83           S
ATOM   1776  CE   MET A 238      12.526   5.041   0.488  1.00 30.21           C
ATOM   1777  C    MET A 238      16.823   3.103  -2.176  1.00 28.05           C
ATOM   1778  O    MET A 238      17.437   3.436  -1.162  1.00 26.86           O
```

Fig. 1, continued

```
ATOM   1779  N    GLU A 239      16.594   1.834  -2.502  1.00 28.53           N
ATOM   1780  CA   GLU A 239      17.206   0.722  -1.779  1.00 29.43           C
ATOM   1781  CB   GLU A 239      16.862  -0.601  -2.482  1.00 29.87           C
ATOM   1782  CG   GLU A 239      17.466  -1.872  -1.890  1.00 30.71           C
ATOM   1783  CD   GLU A 239      16.865  -2.275  -0.541  1.00 34.72           C
ATOM   1784  OE1  GLU A 239      17.431  -3.171   0.118  1.00 38.76           O
ATOM   1785  OE2  GLU A 239      15.845  -1.714  -0.123  1.00 31.69           O
ATOM   1786  C    GLU A 239      18.736   0.904  -1.670  1.00 29.98           C
ATOM   1787  O    GLU A 239      19.295   0.826  -0.578  1.00 29.75           O
ATOM   1788  N    SER A 240      19.406   1.179  -2.780  1.00 30.85           N
ATOM   1789  CA   SER A 240      20.879   1.234  -2.769  1.00 32.36           C
ATOM   1790  CB   SER A 240      21.448   1.119  -4.174  1.00 32.41           C
ATOM   1791  OG   SER A 240      21.204   2.315  -4.862  1.00 37.12           O
ATOM   1792  C    SER A 240      21.369   2.496  -2.076  1.00 32.27           C
ATOM   1793  O    SER A 240      22.352   2.454  -1.374  1.00 32.60           O
ATOM   1794  N    PHE A 241      20.644   3.599  -2.223  1.00 32.95           N
ATOM   1795  CA   PHE A 241      20.947   4.836  -1.493  1.00 33.32           C
ATOM   1796  CB   PHE A 241      19.966   5.939  -1.914  1.00 33.67           C
ATOM   1797  CG   PHE A 241      20.280   7.296  -1.343  1.00 34.48           C
ATOM   1798  CD1  PHE A 241      21.176   8.134  -1.972  1.00 35.96           C
ATOM   1799  CE1  PHE A 241      21.468   9.397  -1.453  1.00 37.63           C
ATOM   1800  CZ   PHE A 241      20.843   9.831  -0.298  1.00 38.09           C
ATOM   1801  CE2  PHE A 241      19.931   9.007   0.342  1.00 38.49           C
ATOM   1802  CD2  PHE A 241      19.643   7.745  -0.195  1.00 37.75           C
ATOM   1803  C    PHE A 241      20.866   4.638   0.027  1.00 33.60           C
ATOM   1804  O    PHE A 241      21.774   5.019   0.785  1.00 33.74           O
ATOM   1805  N    ILE A 242      19.778   4.040   0.477  1.00 33.03           N
ATOM   1806  CA   ILE A 242      19.596   3.780   1.892  1.00 32.85           C
ATOM   1807  CB   ILE A 242      18.139   3.379   2.185  1.00 32.51           C
ATOM   1808  CG1  ILE A 242      17.265   4.630   2.033  1.00 33.45           C
ATOM   1809  CD1  ILE A 242      15.815   4.412   2.234  1.00 34.90           C
ATOM   1810  CG2  ILE A 242      18.016   2.775   3.591  1.00 33.35           C
ATOM   1811  C    ILE A 242      20.594   2.734   2.408  1.00 32.64           C
ATOM   1812  O    ILE A 242      21.124   2.880   3.501  1.00 31.52           O
ATOM   1813  N    GLU A 243      20.836   1.692   1.628  1.00 33.14           N
ATOM   1814  CA   GLU A 243      21.748   0.624   2.041  1.00 34.73           C
ATOM   1815  CB   GLU A 243      21.860  -0.458   0.966  0.40 34.71           C
ATOM   1816  CG   GLU A 243      22.589  -1.714   1.432  0.40 36.12           C
ATOM   1817  CD   GLU A 243      24.102  -1.640   1.261  0.40 36.76           C
ATOM   1818  OE1  GLU A 243      24.820  -2.260   2.077  0.40 37.14           O
ATOM   1819  OE2  GLU A 243      24.572  -0.975   0.308  0.40 37.10           O
ATOM   1820  C    GLU A 243      23.155   1.166   2.412  1.00 34.63           C
ATOM   1821  O    GLU A 243      23.749   0.731   3.395  1.00 34.98           O
ATOM   1822  N    ALA A 244      23.644   2.139   1.653  1.00 34.48           N
ATOM   1823  CA   ALA A 244      24.961   2.751   1.903  1.00 34.94           C
ATOM   1824  CB   ALA A 244      25.457   3.485   0.639  1.00 34.92           C
ATOM   1825  C    ALA A 244      24.989   3.713   3.085  1.00 34.85           C
ATOM   1826  O    ALA A 244      26.078   4.136   3.502  1.00 35.70           O
ATOM   1827  N    ARG A 245      23.813   4.081   3.604  1.00 34.05           N
ATOM   1828  CA   ARG A 245      23.703   5.004   4.732  1.00 33.48           C
ATOM   1829  CB   ARG A 245      22.825   6.186   4.331  1.00 33.99           C
ATOM   1830  CG   ARG A 245      23.557   7.137   3.387  1.00 36.72           C
ATOM   1831  CD   ARG A 245      22.660   7.964   2.525  1.00 39.49           C
ATOM   1832  NE   ARG A 245      23.429   8.779   1.580  1.00 42.41           N
```

Fig. 1, continued

```
ATOM   1833  CZ   ARG A 245      23.933    8.349    0.422  1.00 43.98           C
ATOM   1834  NH1  ARG A 245      24.608    9.198   -0.350  1.00 44.73           N
ATOM   1835  NH2  ARG A 245      23.762    7.090    0.021  1.00 43.09           N
ATOM   1836  C    ARG A 245      23.207    4.391    6.037  1.00 32.44           C
ATOM   1837  O    ARG A 245      23.186    5.057    7.060  1.00 31.78           O
ATOM   1838  N    LEU A 246      22.815    3.124    6.022  1.00 31.94           N
ATOM   1839  CA   LEU A 246      22.401    2.471    7.253  1.00 31.56           C
ATOM   1840  CB   LEU A 246      21.783    1.105    6.965  1.00 31.06           C
ATOM   1841  CG   LEU A 246      20.450    1.075    6.219  1.00 31.07           C
ATOM   1842  CD1  LEU A 246      20.179   -0.359    5.761  1.00 30.68           C
ATOM   1843  CD2  LEU A 246      19.309    1.623    7.064  1.00 30.04           C
ATOM   1844  C    LEU A 246      23.593    2.270    8.188  1.00 31.47           C
ATOM   1845  O    LEU A 246      24.640    1.797    7.779  1.00 31.14           O
ATOM   1846  N    ASN A 247      23.416    2.623    9.448  1.00 31.64           N
ATOM   1847  CA   ASN A 247      24.329    2.189   10.486  1.00 31.87           C
ATOM   1848  CB   ASN A 247      24.306    3.176   11.667  1.00 31.97           C
ATOM   1849  CG   ASN A 247      22.909    3.399   12.247  1.00 31.19           C
ATOM   1850  OD1  ASN A 247      22.135    2.466   12.407  1.00 31.01           O
ATOM   1851  ND2  ASN A 247      22.609    4.642   12.605  1.00 29.83           N
ATOM   1852  C    ASN A 247      23.981    0.750   10.915  1.00 32.53           C
ATOM   1853  O    ASN A 247      23.032    0.140   10.402  1.00 32.20           O
ATOM   1854  N    ALA A 248      24.726    0.214   11.874  1.00 32.82           N
ATOM   1855  CA   ALA A 248      24.553   -1.177   12.274  1.00 32.88           C
ATOM   1856  CB   ALA A 248      25.608   -1.588   13.325  1.00 33.01           C
ATOM   1857  C    ALA A 248      23.122   -1.452   12.771  1.00 32.31           C
ATOM   1858  O    ALA A 248      22.535   -2.465   12.408  1.00 31.29           O
ATOM   1859  N    LYS A 249      22.566   -0.532   13.560  1.00 32.06           N
ATOM   1860  CA   LYS A 249      21.190   -0.643   14.037  1.00 32.25           C
ATOM   1861  CB   LYS A 249      20.849    0.509   14.983  1.00 33.03           C
ATOM   1862  CG   LYS A 249      19.435    0.448   15.608  1.00 34.75           C
ATOM   1863  CD   LYS A 249      19.253    1.563   16.657  1.00 39.61           C
ATOM   1864  CE   LYS A 249      17.771    1.824   17.030  1.00 41.93           C
ATOM   1865  NZ   LYS A 249      17.432    3.310   17.032  1.00 42.79           N
ATOM   1866  C    LYS A 249      20.201   -0.678   12.856  1.00 31.08           C
ATOM   1867  O    LYS A 249      19.281   -1.486   12.838  1.00 30.67           O
ATOM   1868  N    GLY A 250      20.430    0.189   11.882  1.00 29.78           N
ATOM   1869  CA   GLY A 250      19.683    0.233   10.646  1.00 29.14           C
ATOM   1870  C    GLY A 250      19.709   -1.042    9.848  1.00 28.58           C
ATOM   1871  O    GLY A 250      18.676   -1.479    9.378  1.00 27.27           O
ATOM   1872  N    GLN A 251      20.892   -1.631    9.685  1.00 28.32           N
ATOM   1873  CA   GLN A 251      21.062   -2.928    9.017  1.00 28.46           C
ATOM   1874  CB   GLN A 251      22.557   -3.345    8.980  1.00 28.87           C
ATOM   1875  CG   GLN A 251      23.398   -2.418    8.109  1.00 32.13           C
ATOM   1876  CD   GLN A 251      24.901   -2.738    8.121  1.00 37.39           C
ATOM   1877  OE1  GLN A 251      25.432   -3.327    9.087  1.00 38.31           O
ATOM   1878  NE2  GLN A 251      25.584   -2.367    7.025  1.00 37.57           N
ATOM   1879  C    GLN A 251      20.235   -4.015    9.696  1.00 27.44           C
ATOM   1880  O    GLN A 251      19.482   -4.703    9.034  1.00 26.40           O
ATOM   1881  N    ARG A 252      20.343   -4.142   11.016  1.00 27.13           N
ATOM   1882  CA   ARG A 252      19.604   -5.166   11.741  1.00 28.00           C
ATOM   1883  CB   ARG A 252      20.029   -5.230   13.218  1.00 28.73           C
ATOM   1884  CG   ARG A 252      21.467   -5.676   13.476  1.00 32.98           C
ATOM   1885  CD   ARG A 252      21.727   -5.980   14.970  1.00 37.55           C
ATOM   1886  NE   ARG A 252      21.471   -4.819   15.832  1.00 41.11           N
```

Fig. 1, continued

```
ATOM   1887  CZ   ARG A 252      22.336   -3.811   16.028  1.00 42.74           C
ATOM   1888  NH1  ARG A 252      23.528   -3.826   15.430  1.00 43.52           N
ATOM   1889  NH2  ARG A 252      22.012   -2.784   16.825  1.00 41.21           N
ATOM   1890  C    ARG A 252      18.074   -4.910   11.676  1.00 27.37           C
ATOM   1891  O    ARG A 252      17.280   -5.836   11.567  1.00 26.47           O
ATOM   1892  N    THR A 253      17.692   -3.646   11.741  1.00 26.21           N
ATOM   1893  CA   THR A 253      16.297   -3.281   11.768  1.00 25.98           C
ATOM   1894  CB   THR A 253      16.175   -1.815   12.190  1.00 25.70           C
ATOM   1895  OG1  THR A 253      16.727   -1.670   13.499  1.00 25.51           O
ATOM   1896  CG2  THR A 253      14.715   -1.398   12.369  1.00 26.42           C
ATOM   1897  C    THR A 253      15.617   -3.546   10.418  1.00 25.74           C
ATOM   1898  O    THR A 253      14.516   -4.069   10.371  1.00 24.92           O
ATOM   1899  N    LEU A 254      16.279   -3.214    9.320  1.00 26.41           N
ATOM   1900  CA   LEU A 254      15.660   -3.359    8.012  1.00 27.64           C
ATOM   1901  CB   LEU A 254      16.525   -2.727    6.920  1.00 28.18           C
ATOM   1902  CG   LEU A 254      15.889   -1.892    5.820  1.00 29.66           C
ATOM   1903  CD1  LEU A 254      16.677   -2.068    4.521  1.00 32.01           C
ATOM   1904  CD2  LEU A 254      14.377   -2.120    5.611  1.00 29.04           C
ATOM   1905  C    LEU A 254      15.453   -4.851    7.722  1.00 28.25           C
ATOM   1906  O    LEU A 254      14.430   -5.254    7.169  1.00 28.10           O
ATOM   1907  N    LYS A 255      16.448   -5.650    8.100  1.00 28.14           N
ATOM   1908  CA   LYS A 255      16.370   -7.105    8.018  1.00 28.40           C
ATOM   1909  CB   LYS A 255      17.641   -7.733    8.601  1.00 29.12           C
ATOM   1910  CG   LYS A 255      18.565   -8.331    7.598  1.00 35.58           C
ATOM   1911  CD   LYS A 255      19.675   -7.392    7.166  1.00 40.47           C
ATOM   1912  CE   LYS A 255      21.082   -8.026    7.334  1.00 43.61           C
ATOM   1913  NZ   LYS A 255      22.150   -6.998    7.066  1.00 43.82           N
ATOM   1914  C    LYS A 255      15.200   -7.677    8.804  1.00 26.47           C
ATOM   1915  O    LYS A 255      14.480   -8.528    8.319  1.00 25.47           O
ATOM   1916  N    GLN A 256      15.076   -7.234   10.052  1.00 25.10           N
ATOM   1917  CA   GLN A 256      14.018   -7.669   10.930  1.00 23.94           C
ATOM   1918  CB   GLN A 256      14.128   -6.927   12.256  1.00 24.22           C
ATOM   1919  CG   GLN A 256      13.113   -7.375   13.260  1.00 22.31           C
ATOM   1920  CD   GLN A 256      13.251   -6.702   14.618  1.00 24.27           C
ATOM   1921  OE1  GLN A 256      13.068   -7.352   15.652  1.00 27.91           O
ATOM   1922  NE2  GLN A 256      13.492   -5.411   14.623  1.00 21.24           N
ATOM   1923  C    GLN A 256      12.634   -7.433   10.318  1.00 22.88           C
ATOM   1924  O    GLN A 256      11.810   -8.335   10.276  1.00 22.60           O
ATOM   1925  N    ILE A 257      12.374   -6.223    9.834  1.00 22.33           N
ATOM   1926  CA   ILE A 257      11.025   -5.879    9.335  1.00 21.34           C
ATOM   1927  CB   ILE A 257      10.848   -4.335    9.244  1.00 20.77           C
ATOM   1928  CG1  ILE A 257       9.354   -3.999    9.167  1.00 21.03           C
ATOM   1929  CD1  ILE A 257       8.991   -2.564    9.448  1.00 22.54           C
ATOM   1930  CG2  ILE A 257      11.613   -3.760    8.036  1.00 20.66           C
ATOM   1931  C    ILE A 257      10.702   -6.586    7.987  1.00 20.55           C
ATOM   1932  O    ILE A 257       9.534   -6.655    7.552  1.00 19.97           O
ATOM   1933  N    ARG A 258      11.739   -7.115    7.347  1.00 19.93           N
ATOM   1934  CA   ARG A 258      11.574   -7.927    6.133  1.00 20.43           C
ATOM   1935  CB   ARG A 258      12.589   -7.534    5.076  1.00 20.43           C
ATOM   1936  CG   ARG A 258      12.356   -6.141    4.500  1.00 22.50           C
ATOM   1937  CD   ARG A 258      13.556   -5.618    3.721  1.00 21.73           C
ATOM   1938  NE   ARG A 258      13.292   -4.314    3.125  1.00 23.53           N
ATOM   1939  CZ   ARG A 258      14.134   -3.698    2.297  1.00 23.90           C
ATOM   1940  NH1  ARG A 258      15.304   -4.261    2.000  1.00 23.14           N
```

Fig. 1, continued

```
ATOM   1941  NH2  ARG A 258      13.814   -2.516   1.782  1.00 20.62           N
ATOM   1942  C    ARG A 258      11.679   -9.435   6.405  1.00 20.25           C
ATOM   1943  O    ARG A 258      11.643  -10.230   5.485  1.00 19.80           O
ATOM   1944  N    GLY A 259      11.765   -9.827   7.670  1.00 19.67           N
ATOM   1945  CA   GLY A 259      11.892  -11.238   8.008  1.00 19.06           C
ATOM   1946  C    GLY A 259      10.566  -11.962   7.949  1.00 18.93           C
ATOM   1947  O    GLY A 259       9.482  -11.403   8.206  1.00 19.16           O
ATOM   1948  N    ARG A 260      10.658  -13.231   7.612  1.00 18.71           N
ATOM   1949  CA   ARG A 260       9.525  -14.127   7.558  1.00 19.12           C
ATOM   1950  CB   ARG A 260      10.069  -15.541   7.368  1.00 19.46           C
ATOM   1951  CG   ARG A 260       9.057  -16.643   7.354  1.00 20.36           C
ATOM   1952  CD   ARG A 260       9.658  -17.929   6.786  1.00 22.53           C
ATOM   1953  NE   ARG A 260       8.726  -19.044   6.910  1.00 23.86           N
ATOM   1954  CZ   ARG A 260       8.776  -20.137   6.162  1.00 22.13           C
ATOM   1955  NH1  ARG A 260       7.908  -21.093   6.370  1.00 23.83           N
ATOM   1956  NH2  ARG A 260       9.691  -20.275   5.225  1.00 22.85           N
ATOM   1957  C    ARG A 260       8.748  -14.063   8.849  1.00 19.65           C
ATOM   1958  O    ARG A 260       9.340  -14.183   9.919  1.00 19.49           O
ATOM   1959  N    GLY A 261       7.436  -13.858   8.741  1.00 19.12           N
ATOM   1960  CA   GLY A 261       6.542  -13.853   9.878  1.00 20.54           C
ATOM   1961  C    GLY A 261       6.376  -12.485  10.550  1.00 20.59           C
ATOM   1962  O    GLY A 261       5.609  -12.361  11.481  1.00 21.76           O
ATOM   1963  N    PHE A 262       7.095  -11.476  10.078  1.00 20.18           N
ATOM   1964  CA   PHE A 262       7.061  -10.141  10.668  1.00 19.03           C
ATOM   1965  CB   PHE A 262       8.433   -9.470  10.569  1.00 19.34           C
ATOM   1966  CG   PHE A 262       8.650   -8.415  11.590  1.00 19.98           C
ATOM   1967  CD1  PHE A 262       8.123   -7.135  11.400  1.00 20.35           C
ATOM   1968  CE1  PHE A 262       8.297   -6.154  12.361  1.00 20.22           C
ATOM   1969  CZ   PHE A 262       8.999   -6.445  13.524  1.00 22.45           C
ATOM   1970  CE2  PHE A 262       9.525   -7.729  13.733  1.00 20.89           C
ATOM   1971  CD2  PHE A 262       9.342   -8.700  12.768  1.00 22.74           C
ATOM   1972  C    PHE A 262       5.979   -9.323   9.973  1.00 18.98           C
ATOM   1973  O    PHE A 262       6.184   -8.711   8.900  1.00 18.79           O
ATOM   1974  N    CYS A 263       4.807   -9.344  10.585  1.00 18.71           N
ATOM   1975  CA   CYS A 263       3.615   -8.781   9.986  1.00 19.19           C
ATOM   1976  CB   CYS A 263       2.624   -9.922   9.739  1.00 20.01           C
ATOM   1977  SG   CYS A 263       3.315  -11.123   8.567  1.00 21.00           S
ATOM   1978  C    CYS A 263       3.046   -7.621  10.787  1.00 18.60           C
ATOM   1979  O    CYS A 263       3.761   -7.007  11.590  1.00 18.14           O
ATOM   1980  N    LEU A 264       1.787   -7.262  10.544  1.00 18.39           N
ATOM   1981  CA   LEU A 264       1.245   -6.045  11.099  1.00 18.53           C
ATOM   1982  CB   LEU A 264      -0.199   -5.828  10.640  1.00 18.74           C
ATOM   1983  CG   LEU A 264      -0.879   -4.477  10.889  1.00 20.81           C
ATOM   1984  CD1  LEU A 264      -2.239   -4.456  10.141  1.00 22.12           C
ATOM   1985  CD2  LEU A 264      -1.140   -4.225  12.347  1.00 25.24           C
ATOM   1986  C    LEU A 264       1.404   -6.004  12.643  1.00 18.96           C
ATOM   1987  O    LEU A 264       1.872   -4.988  13.176  1.00 18.09           O
ATOM   1988  N    PRO A 265       1.016   -7.054  13.371  1.00 20.02           N
ATOM   1989  CA   PRO A 265       1.155   -7.001  14.848  1.00 20.38           C
ATOM   1990  CB   PRO A 265       0.620   -8.367  15.318  1.00 20.48           C
ATOM   1991  CG   PRO A 265      -0.305   -8.830  14.159  1.00 20.93           C
ATOM   1992  CD   PRO A 265       0.421   -8.332  12.925  1.00 19.91           C
ATOM   1993  C    PRO A 265       2.584   -6.784  15.278  1.00 20.25           C
ATOM   1994  O    PRO A 265       2.822   -6.019  16.219  1.00 22.03           O
```

Fig. 1, continued

```
ATOM   1995  N    GLN A 266       3.527  -7.400  14.588  1.00 20.31           N
ATOM   1996  CA   GLN A 266       4.938  -7.251  14.943  1.00 20.71           C
ATOM   1997  CB   GLN A 266       5.796  -8.309  14.258  1.00 21.26           C
ATOM   1998  CG   GLN A 266       5.591  -9.755  14.779  1.00 21.52           C
ATOM   1999  CD   GLN A 266       4.262 -10.355  14.345  1.00 22.49           C
ATOM   2000  OE1  GLN A 266       3.743 -10.039  13.249  1.00 19.94           O
ATOM   2001  NE2  GLN A 266       3.682 -11.197  15.208  1.00 21.10           N
ATOM   2002  C    GLN A 266       5.444  -5.824  14.649  1.00 20.82           C
ATOM   2003  O    GLN A 266       6.191  -5.256  15.450  1.00 20.00           O
ATOM   2004  N    VAL A 267       5.001  -5.241  13.528  1.00 20.57           N
ATOM   2005  CA   VAL A 267       5.355  -3.864  13.173  1.00 20.83           C
ATOM   2006  CB   VAL A 267       4.751  -3.454  11.801  1.00 20.84           C
ATOM   2007  CG1  VAL A 267       4.918  -1.941  11.549  1.00 22.16           C
ATOM   2008  CG2  VAL A 267       5.403  -4.244  10.683  1.00 19.95           C
ATOM   2009  C    VAL A 267       4.904  -2.896  14.263  1.00 21.54           C
ATOM   2010  O    VAL A 267       5.665  -2.008  14.665  1.00 22.45           O
ATOM   2011  N    VAL A 268       3.688  -3.084  14.750  1.00 22.21           N
ATOM   2012  CA   VAL A 268       3.097  -2.220  15.753  1.00 23.53           C
ATOM   2013  CB   VAL A 268       1.591  -2.539  15.949  1.00 23.70           C
ATOM   2014  CG1  VAL A 268       1.049  -1.869  17.200  1.00 25.83           C
ATOM   2015  CG2  VAL A 268       0.783  -2.101  14.729  1.00 25.11           C
ATOM   2016  C    VAL A 268       3.810  -2.367  17.112  1.00 23.89           C
ATOM   2017  O    VAL A 268       4.129  -1.362  17.768  1.00 24.12           O
ATOM   2018  N    LEU A 269       4.078  -3.608  17.518  1.00 24.17           N
ATOM   2019  CA   LEU A 269       4.626  -3.887  18.864  1.00 24.38           C
ATOM   2020  CB   LEU A 269       4.333  -5.336  19.297  1.00 24.85           C
ATOM   2021  CG   LEU A 269       2.859  -5.656  19.557  1.00 28.33           C
ATOM   2022  CD1  LEU A 269       2.661  -7.167  19.773  1.00 31.14           C
ATOM   2023  CD2  LEU A 269       2.250  -4.860  20.763  1.00 32.16           C
ATOM   2024  C    LEU A 269       6.114  -3.616  18.997  1.00 23.41           C
ATOM   2025  O    LEU A 269       6.595  -3.299  20.085  1.00 23.41           O
ATOM   2026  N    THR A 270       6.854  -3.725  17.900  1.00 22.72           N
ATOM   2027  CA   THR A 270       8.309  -3.727  17.979  1.00 21.98           C
ATOM   2028  CB   THR A 270       8.873  -4.600  16.838  1.00 21.93           C
ATOM   2029  OG1  THR A 270       8.290  -5.918  16.921  1.00 21.02           O
ATOM   2030  CG2  THR A 270      10.382  -4.831  16.982  1.00 22.55           C
ATOM   2031  C    THR A 270       8.859  -2.298  17.935  1.00 22.07           C
ATOM   2032  O    THR A 270       9.898  -2.006  18.538  1.00 22.01           O
ATOM   2033  N    TYR A 271       8.151  -1.390  17.253  1.00 21.81           N
ATOM   2034  CA   TYR A 271       8.745  -0.111  16.884  1.00 21.69           C
ATOM   2035  CB   TYR A 271       8.809  -0.018  15.354  1.00 21.10           C
ATOM   2036  CG   TYR A 271       9.616  -1.118  14.702  1.00 21.83           C
ATOM   2037  CD1  TYR A 271       9.041  -1.945  13.733  1.00 20.37           C
ATOM   2038  CE1  TYR A 271       9.767  -2.958  13.122  1.00 20.34           C
ATOM   2039  CZ   TYR A 271      11.090  -3.157  13.461  1.00 20.04           C
ATOM   2040  OH   TYR A 271      11.764  -4.167  12.830  1.00 21.73           O
ATOM   2041  CE2  TYR A 271      11.710  -2.349  14.419  1.00 21.95           C
ATOM   2042  CD2  TYR A 271      10.970  -1.323  15.032  1.00 23.26           C
ATOM   2043  C    TYR A 271       8.131   1.195  17.455  1.00 21.36           C
ATOM   2044  O    TYR A 271       8.422   2.247  16.922  1.00 21.36           O
ATOM   2045  N    PRO A 272       7.329   1.176  18.510  1.00 21.75           N
ATOM   2046  CA   PRO A 272       6.762   2.448  18.998  1.00 22.22           C
ATOM   2047  CB   PRO A 272       5.947   2.054  20.249  1.00 22.58           C
ATOM   2048  CG   PRO A 272       6.322   0.655  20.586  1.00 23.51           C
```

Fig. 1, continued

```
ATOM   2049  CD   PRO A 272       6.959   0.039  19.369  1.00 22.42           C
ATOM   2050  C    PRO A 272       7.889   3.422  19.345  1.00 22.14           C
ATOM   2051  O    PRO A 272       8.903   2.989  19.897  1.00 21.32           O
ATOM   2052  N    PHE A 273       7.757   4.691  18.933  1.00 22.28           N
ATOM   2053  CA   PHE A 273       8.710   5.766  19.272  1.00 22.18           C
ATOM   2054  CB   PHE A 273       8.852   5.920  20.814  1.00 22.15           C
ATOM   2055  CG   PHE A 273       7.520   5.915  21.519  1.00 20.75           C
ATOM   2056  CD1  PHE A 273       6.551   6.878  21.192  1.00 20.53           C
ATOM   2057  CE1  PHE A 273       5.307   6.868  21.769  1.00 18.78           C
ATOM   2058  CZ   PHE A 273       4.975   5.859  22.702  1.00 19.61           C
ATOM   2059  CE2  PHE A 273       5.927   4.893  23.033  1.00 19.67           C
ATOM   2060  CD2  PHE A 273       7.188   4.917  22.422  1.00 21.84           C
ATOM   2061  C    PHE A 273      10.052   5.658  18.557  1.00 23.45           C
ATOM   2062  O    PHE A 273      10.933   6.471  18.767  1.00 24.38           O
ATOM   2063  N    LEU A 274      10.205   4.697  17.657  1.00 24.31           N
ATOM   2064  CA   LEU A 274      11.342   4.707  16.749  1.00 24.81           C
ATOM   2065  CB   LEU A 274      11.301   3.500  15.805  1.00 24.63           C
ATOM   2066  CG   LEU A 274      12.336   3.503  14.685  1.00 26.53           C
ATOM   2067  CD1  LEU A 274      13.744   3.322  15.268  1.00 28.45           C
ATOM   2068  CD2  LEU A 274      12.054   2.417  13.657  1.00 25.69           C
ATOM   2069  C    LEU A 274      11.344   5.997  15.928  1.00 24.33           C
ATOM   2070  O    LEU A 274      10.338   6.360  15.338  1.00 24.52           O
ATOM   2071  N    ASN A 275      12.485   6.676  15.901  1.00 24.15           N
ATOM   2072  CA   ASN A 275      12.774   7.711  14.913  1.00 24.19           C
ATOM   2073  CB   ASN A 275      13.591   8.868  15.543  1.00 23.75           C
ATOM   2074  CG   ASN A 275      14.009   9.924  14.531  1.00 23.64           C
ATOM   2075  OD1  ASN A 275      13.746   9.805  13.327  1.00 23.12           O
ATOM   2076  ND2  ASN A 275      14.719  10.950  15.007  1.00 25.11           N
ATOM   2077  C    ASN A 275      13.554   7.023  13.824  1.00 24.36           C
ATOM   2078  O    ASN A 275      14.698   6.614  14.044  1.00 24.30           O
ATOM   2079  N    VAL A 276      12.960   6.900  12.642  1.00 24.49           N
ATOM   2080  CA   VAL A 276      13.598   6.190  11.528  1.00 25.16           C
ATOM   2081  CB   VAL A 276      12.616   6.048  10.320  1.00 24.87           C
ATOM   2082  CG1  VAL A 276      13.293   5.454   9.122  1.00 25.09           C
ATOM   2083  CG2  VAL A 276      11.411   5.178  10.706  1.00 24.05           C
ATOM   2084  C    VAL A 276      14.969   6.795  11.102  1.00 26.41           C
ATOM   2085  O    VAL A 276      15.828   6.096  10.551  1.00 25.72           O
ATOM   2086  N    PHE A 277      15.183   8.081  11.383  1.00 28.02           N
ATOM   2087  CA   PHE A 277      16.449   8.732  11.043  1.00 28.99           C
ATOM   2088  CB   PHE A 277      16.318  10.246  11.155  1.00 29.81           C
ATOM   2089  CG   PHE A 277      15.328  10.844  10.196  1.00 30.82           C
ATOM   2090  CD1  PHE A 277      14.324  11.684  10.652  1.00 33.52           C
ATOM   2091  CE1  PHE A 277      13.414  12.249   9.767  1.00 34.57           C
ATOM   2092  CZ   PHE A 277      13.479  11.955   8.422  1.00 33.22           C
ATOM   2093  CE2  PHE A 277      14.476  11.129   7.948  1.00 34.98           C
ATOM   2094  CD2  PHE A 277      15.404  10.571   8.845  1.00 34.49           C
ATOM   2095  C    PHE A 277      17.642   8.254  11.889  1.00 30.01           C
ATOM   2096  O    PHE A 277      18.790   8.373  11.447  1.00 30.13           O
ATOM   2097  N    SER A 278      17.366   7.720  13.083  1.00 30.09           N
ATOM   2098  CA   SER A 278      18.371   7.069  13.911  1.00 30.89           C
ATOM   2099  CB   SER A 278      17.792   6.671  15.276  1.00 30.66           C
ATOM   2100  OG   SER A 278      17.010   5.477  15.181  1.00 30.79           O
ATOM   2101  C    SER A 278      18.994   5.852  13.234  1.00 31.53           C
ATOM   2102  O    SER A 278      20.069   5.411  13.633  1.00 31.47           O
```

Fig. 1, continued

```
ATOM   2103  N    LEU A 279      18.347   5.326  12.193  1.00 32.03           N
ATOM   2104  CA   LEU A 279      18.874   4.167  11.467  1.00 32.31           C
ATOM   2105  CB   LEU A 279      17.724   3.372  10.822  1.00 32.13           C
ATOM   2106  CG   LEU A 279      16.592   2.957  11.772  1.00 31.36           C
ATOM   2107  CD1  LEU A 279      15.581   2.108  11.011  1.00 31.45           C
ATOM   2108  CD2  LEU A 279      17.136   2.206  12.982  1.00 31.30           C
ATOM   2109  C    LEU A 279      19.891   4.531  10.391  1.00 33.30           C
ATOM   2110  O    LEU A 279      20.561   3.655   9.867  1.00 31.05           O
ATOM   2111  N    VAL A 280      19.970   5.812  10.035  1.00 35.28           N
ATOM   2112  CA   VAL A 280      20.894   6.274   9.003  1.00 37.40           C
ATOM   2113  CB   VAL A 280      20.144   6.752   7.720  1.00 37.20           C
ATOM   2114  CG1  VAL A 280      19.464   5.589   7.052  1.00 36.37           C
ATOM   2115  CG2  VAL A 280      19.156   7.895   8.033  1.00 35.61           C
ATOM   2116  C    VAL A 280      21.842   7.369   9.509  1.00 40.45           C
ATOM   2117  O    VAL A 280      21.800   7.790  10.672  1.00 40.07           O
ATOM   2118  N    ASN A 281      22.705   7.816   8.612  1.00 44.73           N
ATOM   2119  CA   ASN A 281      23.806   8.722   8.956  1.00 48.30           C
ATOM   2120  CB   ASN A 281      25.071   8.307   8.163  1.00 48.77           C
ATOM   2121  CG   ASN A 281      25.107   8.861   6.730  1.00 51.32           C
ATOM   2122  OD1  ASN A 281      26.195   9.127   6.180  1.00 55.46           O
ATOM   2123  ND2  ASN A 281      23.932   9.035   6.116  1.00 53.72           N
ATOM   2124  C    ASN A 281      23.467  10.216   8.749  1.00 50.36           C
ATOM   2125  O    ASN A 281      24.362  11.070   8.811  1.00 51.01           O
ATOM   2126  N    ASP A 282      22.175  10.512   8.542  1.00 52.63           N
ATOM   2127  CA   ASP A 282      21.733  11.775   7.958  1.00 53.93           C
ATOM   2128  CB   ASP A 282      22.079  11.779   6.460  1.00 54.59           C
ATOM   2129  CG   ASP A 282      21.804  13.128   5.772  1.00 56.80           C
ATOM   2130  OD1  ASP A 282      21.800  14.178   6.457  1.00 59.26           O
ATOM   2131  OD2  ASP A 282      21.601  13.231   4.536  1.00 60.00           O
ATOM   2132  C    ASP A 282      20.224  12.016   8.142  1.00 54.69           C
ATOM   2133  O    ASP A 282      19.376  11.324   7.564  1.00 54.92           O
ATOM   2134  N    THR A 283      19.906  13.037   8.924  1.00 55.14           N
ATOM   2135  CA   THR A 283      18.526  13.489   9.128  1.00 55.47           C
ATOM   2136  CB   THR A 283      18.507  14.458  10.334  1.00 55.94           C
ATOM   2137  OG1  THR A 283      19.442  15.532  10.120  1.00 56.07           O
ATOM   2138  CG2  THR A 283      19.024  13.751  11.610  1.00 56.96           C
ATOM   2139  C    THR A 283      17.869  14.181   7.904  1.00 55.09           C
ATOM   2140  O    THR A 283      16.655  14.419   7.883  1.00 55.10           O
ATOM   2141  N    ASN A 284      18.672  14.519   6.903  1.00 54.56           N
ATOM   2142  CA   ASN A 284      18.199  15.263   5.734  1.00 53.89           C
ATOM   2143  CB   ASN A 284      19.294  16.251   5.280  1.00 54.03           C
ATOM   2144  CG   ASN A 284      18.748  17.406   4.434  1.00 55.55           C
ATOM   2145  OD1  ASN A 284      17.903  18.193   4.891  1.00 55.89           O
ATOM   2146  ND2  ASN A 284      19.232  17.509   3.190  1.00 56.29           N
ATOM   2147  C    ASN A 284      17.807  14.330   4.585  1.00 52.67           C
ATOM   2148  O    ASN A 284      17.758  14.757   3.431  1.00 52.66           O
ATOM   2149  N    LEU A 285      17.493  13.071   4.895  1.00 51.11           N
ATOM   2150  CA   LEU A 285      17.303  12.056   3.849  1.00 50.21           C
ATOM   2151  CB   LEU A 285      17.191  10.657   4.465  1.00 50.68           C
ATOM   2152  CG   LEU A 285      18.272   9.685   4.007  1.00 51.71           C
ATOM   2153  CD1  LEU A 285      19.644  10.086   4.534  1.00 53.21           C
ATOM   2154  CD2  LEU A 285      17.917   8.276   4.451  1.00 52.98           C
ATOM   2155  C    LEU A 285      16.115  12.297   2.911  1.00 48.62           C
ATOM   2156  O    LEU A 285      16.205  12.004   1.716  1.00 47.51           O
```

Fig. 1, continued

```
ATOM   2157  N    LEU A 286      15.011  12.813   3.451  1.00 47.17           N
ATOM   2158  CA   LEU A 286      13.825  13.140   2.648  1.00 46.45           C
ATOM   2159  CB   LEU A 286      12.697  13.712   3.518  1.00 46.47           C
ATOM   2160  CG   LEU A 286      12.123  12.862   4.647  1.00 46.38           C
ATOM   2161  CD1  LEU A 286      11.164  13.693   5.469  1.00 46.60           C
ATOM   2162  CD2  LEU A 286      11.429  11.640   4.119  1.00 46.87           C
ATOM   2163  C    LEU A 286      14.119  14.147   1.540  1.00 45.74           C
ATOM   2164  O    LEU A 286      13.507  14.087   0.468  1.00 45.32           O
ATOM   2165  N    ASN A 287      15.047  15.068   1.803  1.00 45.06           N
ATOM   2166  CA   ASN A 287      15.427  16.096   0.828  1.00 45.15           C
ATOM   2167  CB   ASN A 287      15.864  17.370   1.556  1.00 45.70           C
ATOM   2168  CG   ASN A 287      14.806  17.884   2.499  1.00 46.56           C
ATOM   2169  OD1  ASN A 287      13.661  18.074   2.100  1.00 48.78           O
ATOM   2170  ND2  ASN A 287      15.173  18.086   3.758  1.00 47.24           N
ATOM   2171  C    ASN A 287      16.520  15.703  -0.161  1.00 44.45           C
ATOM   2172  O    ASN A 287      16.858  16.493  -1.035  1.00 44.52           O
ATOM   2173  N    GLU A 288      17.067  14.499  -0.030  1.00 43.97           N
ATOM   2174  CA   GLU A 288      18.135  14.020  -0.918  1.00 43.90           C
ATOM   2175  CB   GLU A 288      19.036  13.052  -0.177  1.00 44.13           C
ATOM   2176  CG   GLU A 288      19.556  13.575   1.142  1.00 47.48           C
ATOM   2177  CD   GLU A 288      21.017  13.906   1.072  1.00 51.81           C
ATOM   2178  OE1  GLU A 288      21.828  13.046   1.478  1.00 55.30           O
ATOM   2179  OE2  GLU A 288      21.341  15.017   0.590  1.00 54.63           O
ATOM   2180  C    GLU A 288      17.605  13.285  -2.129  1.00 43.05           C
ATOM   2181  O    GLU A 288      16.540  12.673  -2.067  1.00 42.61           O
ATOM   2182  N    ALA A 289      18.375  13.303  -3.214  1.00 42.37           N
ATOM   2183  CA   ALA A 289      18.112  12.436  -4.372  1.00 41.54           C
ATOM   2184  CB   ALA A 289      18.769  12.989  -5.616  1.00 41.65           C
ATOM   2185  C    ALA A 289      18.645  11.042  -4.071  1.00 40.48           C
ATOM   2186  O    ALA A 289      19.673  10.927  -3.421  1.00 41.60           O
ATOM   2187  N    PRO A 290      17.953   9.980  -4.493  1.00 38.68           N
ATOM   2188  CA   PRO A 290      16.731  10.046  -5.302  1.00 36.92           C
ATOM   2189  CB   PRO A 290      16.840   8.781  -6.143  1.00 37.32           C
ATOM   2190  CG   PRO A 290      17.457   7.757  -5.147  1.00 38.54           C
ATOM   2191  CD   PRO A 290      18.303   8.583  -4.171  1.00 38.67           C
ATOM   2192  C    PRO A 290      15.430   9.990  -4.471  1.00 35.02           C
ATOM   2193  O    PRO A 290      14.373   9.844  -5.070  1.00 33.65           O
ATOM   2194  N    ILE A 291      15.499  10.128  -3.146  1.00 33.50           N
ATOM   2195  CA   ILE A 291      14.304  10.010  -2.312  1.00 32.63           C
ATOM   2196  CB   ILE A 291      14.683   9.900  -0.829  1.00 32.77           C
ATOM   2197  CG1  ILE A 291      15.400   8.564  -0.578  1.00 33.25           C
ATOM   2198  CD1  ILE A 291      15.934   8.421   0.831  1.00 35.56           C
ATOM   2199  CG2  ILE A 291      13.416  10.009   0.060  1.00 32.87           C
ATOM   2200  C    ILE A 291      13.277  11.131  -2.535  1.00 31.62           C
ATOM   2201  O    ILE A 291      12.095  10.866  -2.672  1.00 30.05           O
ATOM   2202  N    ALA A 292      13.731  12.381  -2.579  1.00 30.96           N
ATOM   2203  CA   ALA A 292      12.820  13.515  -2.759  1.00 30.68           C
ATOM   2204  CB   ALA A 292      13.601  14.850  -2.783  1.00 30.89           C
ATOM   2205  C    ALA A 292      12.021  13.343  -4.044  1.00 29.64           C
ATOM   2206  O    ALA A 292      10.814  13.599  -4.101  1.00 29.42           O
ATOM   2207  N    SER A 293      12.705  12.871  -5.065  1.00 28.56           N
ATOM   2208  CA   SER A 293      12.099  12.691  -6.372  1.00 28.39           C
ATOM   2209  CB   SER A 293      13.195  12.416  -7.396  1.00 28.23           C
ATOM   2210  OG   SER A 293      12.600  12.131  -8.647  1.00 33.02           O
```

Fig. 1, continued

```
ATOM   2211  C   SER A 293      11.061  11.541  -6.352  1.00 27.13           C
ATOM   2212  O   SER A 293       9.967  11.649  -6.927  1.00 26.86           O
ATOM   2213  N   ILE A 294      11.407  10.456  -5.670  1.00 25.19           N
ATOM   2214  CA  ILE A 294      10.511   9.326  -5.551  1.00 24.66           C
ATOM   2215  CB  ILE A 294      11.251   8.117  -4.888  1.00 24.91           C
ATOM   2216  CG1 ILE A 294      12.299   7.564  -5.863  1.00 25.54           C
ATOM   2217  CD1 ILE A 294      13.356   6.692  -5.213  1.00 26.58           C
ATOM   2218  CG2 ILE A 294      10.256   7.014  -4.469  1.00 24.68           C
ATOM   2219  C   ILE A 294       9.246   9.718  -4.769  1.00 23.70           C
ATOM   2220  O   ILE A 294       8.163   9.307  -5.117  1.00 22.42           O
ATOM   2221  N   LEU A 295       9.390  10.524  -3.727  1.00 24.12           N
ATOM   2222  CA  LEU A 295       8.249  10.927  -2.911  1.00 24.72           C
ATOM   2223  CB  LEU A 295       8.721  11.646  -1.654  1.00 24.80           C
ATOM   2224  CG  LEU A 295       9.396  10.702  -0.648  1.00 26.25           C
ATOM   2225  CD1 LEU A 295       9.963  11.447   0.572  1.00 28.33           C
ATOM   2226  CD2 LEU A 295       8.461   9.586  -0.188  1.00 26.48           C
ATOM   2227  C   LEU A 295       7.230  11.762  -3.679  1.00 24.94           C
ATOM   2228  O   LEU A 295       6.007  11.675  -3.414  1.00 24.79           O
ATOM   2229  N   LYS A 296       7.725  12.534  -4.654  1.00 24.74           N
ATOM   2230  CA  LYS A 296       6.881  13.311  -5.564  1.00 24.48           C
ATOM   2231  CB  LYS A 296       7.717  14.385  -6.275  1.00 24.80           C
ATOM   2232  CG  LYS A 296       8.246  15.468  -5.365  1.00 27.78           C
ATOM   2233  CD  LYS A 296       8.911  16.616  -6.161  1.00 33.10           C
ATOM   2234  CE  LYS A 296       9.591  17.644  -5.231  1.00 37.18           C
ATOM   2235  NZ  LYS A 296      10.364  18.714  -6.028  1.00 40.74           N
ATOM   2236  C   LYS A 296       6.152  12.462  -6.604  1.00 23.56           C
ATOM   2237  O   LYS A 296       5.176  12.902  -7.193  1.00 23.24           O
ATOM   2238  N   GLN A 297       6.658  11.268  -6.857  1.00 23.49           N
ATOM   2239  CA  GLN A 297       5.950  10.242  -7.619  1.00 23.95           C
ATOM   2240  CB  GLN A 297       6.954   9.276  -8.258  1.00 24.77           C
ATOM   2241  CG  GLN A 297       7.912  10.018  -9.185  1.00 29.61           C
ATOM   2242  CD  GLN A 297       8.948   9.155  -9.881  1.00 33.66           C
ATOM   2243  OE1 GLN A 297       9.324   9.476 -10.999  1.00 42.22           O
ATOM   2244  NE2 GLN A 297       9.411   8.105  -9.247  1.00 34.66           N
ATOM   2245  C   GLN A 297       4.956   9.453  -6.744  1.00 23.03           C
ATOM   2246  O   GLN A 297       3.927   9.029  -7.242  1.00 23.07           O
ATOM   2247  N   GLU A 298       5.265   9.289  -5.449  1.00 21.77           N
ATOM   2248  CA  GLU A 298       4.501   8.399  -4.557  1.00 21.72           C
ATOM   2249  CB  GLU A 298       5.462   7.599  -3.673  1.00 20.67           C
ATOM   2250  CG  GLU A 298       6.244   6.541  -4.445  1.00 20.98           C
ATOM   2251  CD  GLU A 298       5.453   5.265  -4.784  1.00 22.06           C
ATOM   2252  OE1 GLU A 298       4.238   5.190  -4.475  1.00 20.49           O
ATOM   2253  OE2 GLU A 298       6.056   4.319  -5.373  1.00 23.05           O
ATOM   2254  C   GLU A 298       3.453   9.191  -3.749  1.00 20.88           C
ATOM   2255  O   GLU A 298       3.338   9.104  -2.525  1.00 21.60           O
ATOM   2256  N   THR A 299       2.709  10.001  -4.474  1.00 20.90           N
ATOM   2257  CA  THR A 299       1.629  10.787  -3.923  1.00 20.98           C
ATOM   2258  CB  THR A 299       2.186  12.138  -3.364  1.00 21.34           C
ATOM   2259  OG1 THR A 299       1.126  12.929  -2.783  1.00 21.22           O
ATOM   2260  CG2 THR A 299       2.777  13.016  -4.517  1.00 21.88           C
ATOM   2261  C   THR A 299       0.580  10.993  -4.998  1.00 21.57           C
ATOM   2262  O   THR A 299       0.893  11.043  -6.206  1.00 22.29           O
ATOM   2263  N   VAL A 300      -0.677  11.104  -4.570  1.00 22.33           N
ATOM   2264  CA  VAL A 300      -1.768  11.531  -5.438  1.00 22.15           C
```

Fig. 1, continued

```
ATOM   2265  CB   VAL A 300      -2.963  10.510  -5.431  1.00 22.32           C
ATOM   2266  CG1  VAL A 300      -2.546   9.206  -6.008  1.00 22.29           C
ATOM   2267  CG2  VAL A 300      -3.500  10.300  -4.031  1.00 21.60           C
ATOM   2268  C    VAL A 300      -2.279  12.948  -5.088  1.00 22.51           C
ATOM   2269  O    VAL A 300      -3.288  13.397  -5.641  1.00 23.33           O
ATOM   2270  N    VAL A 301      -1.594  13.641  -4.179  1.00 23.23           N
ATOM   2271  CA   VAL A 301      -1.860  15.054  -3.873  1.00 23.06           C
ATOM   2272  CB   VAL A 301      -1.331  15.437  -2.494  1.00 22.95           C
ATOM   2273  CG1  VAL A 301      -1.566  16.952  -2.187  1.00 23.04           C
ATOM   2274  CG2  VAL A 301      -1.980  14.578  -1.421  1.00 24.43           C
ATOM   2275  C    VAL A 301      -1.145  15.905  -4.942  1.00 23.26           C
ATOM   2276  O    VAL A 301       0.077  15.882  -5.020  1.00 22.55           O
ATOM   2277  N    GLN A 302      -1.910  16.599  -5.776  1.00 23.96           N
ATOM   2278  CA   GLN A 302      -1.374  17.318  -6.952  1.00 24.66           C
ATOM   2279  CB   GLN A 302      -2.498  17.786  -7.891  1.00 25.15           C
ATOM   2280  CG   GLN A 302      -2.030  18.428  -9.253  1.00 24.20           C
ATOM   2281  CD   GLN A 302      -1.296  17.454 -10.147  1.00 24.79           C
ATOM   2282  OE1  GLN A 302      -1.922  16.788 -10.959  1.00 26.48           O
ATOM   2283  NE2  GLN A 302       0.038  17.393 -10.026  1.00 23.36           N
ATOM   2284  C    GLN A 302      -0.435  18.478  -6.585  1.00 25.05           C
ATOM   2285  O    GLN A 302       0.536  18.691  -7.278  1.00 25.61           O
ATOM   2286  N    ALA A 303      -0.658  19.149  -5.460  1.00 25.53           N
ATOM   2287  CA   ALA A 303       0.236  20.223  -5.041  1.00 25.96           C
ATOM   2288  CB   ALA A 303      -0.305  20.938  -3.802  1.00 25.95           C
ATOM   2289  C    ALA A 303       1.650  19.688  -4.793  1.00 26.24           C
ATOM   2290  O    ALA A 303       2.631  20.430  -4.915  1.00 26.29           O
ATOM   2291  N    GLU A 304       1.750  18.395  -4.455  1.00 25.79           N
ATOM   2292  CA   GLU A 304       3.019  17.751  -4.139  1.00 25.41           C
ATOM   2293  CB   GLU A 304       2.806  16.747  -2.978  1.00 25.70           C
ATOM   2294  CG   GLU A 304       4.092  16.131  -2.454  1.00 25.88           C
ATOM   2295  CD   GLU A 304       3.905  14.977  -1.457  1.00 26.20           C
ATOM   2296  OE1  GLU A 304       2.751  14.602  -1.080  1.00 22.74           O
ATOM   2297  OE2  GLU A 304       4.954  14.425  -1.089  1.00 24.86           O
ATOM   2298  C    GLU A 304       3.624  17.007  -5.329  1.00 25.26           C
ATOM   2299  O    GLU A 304       4.848  16.879  -5.427  1.00 25.45           O
ATOM   2300  N    ALA A 305       2.773  16.473  -6.196  1.00 24.86           N
ATOM   2301  CA   ALA A 305       3.205  15.536  -7.236  1.00 25.33           C
ATOM   2302  CB   ALA A 305       2.007  14.826  -7.830  1.00 25.38           C
ATOM   2303  C    ALA A 305       4.006  16.181  -8.363  1.00 26.01           C
ATOM   2304  O    ALA A 305       3.779  17.339  -8.716  1.00 25.55           O
ATOM   2305  N    SER A 306       4.903  15.386  -8.950  1.00 26.68           N
ATOM   2306  CA   SER A 306       5.768  15.830 -10.039  1.00 27.13           C
ATOM   2307  CB   SER A 306       7.184  15.261  -9.849  1.00 27.31           C
ATOM   2308  OG   SER A 306       7.175  13.834  -9.821  1.00 27.83           O
ATOM   2309  C    SER A 306       5.179  15.404 -11.388  1.00 27.38           C
ATOM   2310  O    SER A 306       5.861  15.498 -12.412  1.00 28.39           O
ATOM   2311  N    TYR A 307       3.927  14.917 -11.376  1.00 26.23           N
ATOM   2312  CA   TYR A 307       3.232  14.429 -12.581  1.00 25.48           C
ATOM   2313  CB   TYR A 307       3.329  12.886 -12.741  1.00 25.58           C
ATOM   2314  CG   TYR A 307       2.565  12.141 -11.645  1.00 24.84           C
ATOM   2315  CD1  TYR A 307       3.045  12.104 -10.346  1.00 24.62           C
ATOM   2316  CE1  TYR A 307       2.327  11.476  -9.330  1.00 24.64           C
ATOM   2317  CZ   TYR A 307       1.125  10.874  -9.621  1.00 24.51           C
ATOM   2318  OH   TYR A 307       0.405  10.273  -8.622  1.00 24.83           O
```

Fig. 1, continued

```
ATOM   2319  CE2 TYR A 307       0.631  10.888 -10.912  1.00 25.01           C
ATOM   2320  CD2 TYR A 307       1.339  11.534 -11.906  1.00 26.47           C
ATOM   2321  C   TYR A 307       1.776  14.886 -12.463  1.00 25.06           C
ATOM   2322  O   TYR A 307       1.365  15.410 -11.426  1.00 24.91           O
ATOM   2323  N   THR A 308       1.027  14.722 -13.540  1.00 24.57           N
ATOM   2324  CA  THR A 308      -0.381  15.070 -13.580  1.00 25.51           C
ATOM   2325  CB  THR A 308      -0.812  15.463 -15.019  1.00 26.03           C
ATOM   2326  OG1 THR A 308      -0.078  16.632 -15.412  1.00 26.17           O
ATOM   2327  CG2 THR A 308      -2.297  15.919 -15.042  1.00 27.12           C
ATOM   2328  C   THR A 308      -1.218  13.903 -13.075  1.00 24.67           C
ATOM   2329  O   THR A 308      -1.286  12.865 -13.706  1.00 24.23           O
ATOM   2330  N   VAL A 309      -1.853  14.107 -11.926  1.00 23.99           N
ATOM   2331  CA  VAL A 309      -2.606  13.067 -11.236  1.00 23.38           C
ATOM   2332  CB  VAL A 309      -2.809  13.451  -9.723  1.00 22.92           C
ATOM   2333  CG1 VAL A 309      -3.551  12.352  -8.990  1.00 23.97           C
ATOM   2334  CG2 VAL A 309      -1.475  13.751  -9.049  1.00 22.40           C
ATOM   2335  C   VAL A 309      -3.973  12.914 -11.899  1.00 22.73           C
ATOM   2336  O   VAL A 309      -4.679  13.890 -12.094  1.00 23.35           O
ATOM   2337  N   SER A 310      -4.361  11.685 -12.190  1.00 21.79           N
ATOM   2338  CA  SER A 310      -5.691  11.391 -12.684  1.00 21.76           C
ATOM   2339  CB  SER A 310      -5.831   9.893 -12.918  1.00 22.10           C
ATOM   2340  OG  SER A 310      -7.119   9.555 -13.371  1.00 23.46           O
ATOM   2341  C   SER A 310      -6.795  11.860 -11.739  1.00 21.55           C
ATOM   2342  O   SER A 310      -6.627  11.889 -10.511  1.00 20.23           O
ATOM   2343  N   VAL A 311      -7.916  12.244 -12.340  1.00 21.49           N
ATOM   2344  CA  VAL A 311      -9.123  12.648 -11.623  1.00 22.12           C
ATOM   2345  CB  VAL A 311      -9.505  14.107 -11.910  1.00 21.99           C
ATOM   2346  CG1 VAL A 311     -10.714  14.514 -11.114  1.00 23.07           C
ATOM   2347  CG2 VAL A 311      -8.346  15.024 -11.551  1.00 23.86           C
ATOM   2348  C   VAL A 311     -10.251  11.725 -12.046  1.00 22.27           C
ATOM   2349  O   VAL A 311     -11.001  12.031 -12.957  1.00 22.09           O
ATOM   2350  N   PRO A 312     -10.368  10.571 -11.390  1.00 22.51           N
ATOM   2351  CA  PRO A 312     -11.463   9.642 -11.683  1.00 22.11           C
ATOM   2352  CB  PRO A 312     -11.329   8.569 -10.587  1.00 22.65           C
ATOM   2353  CG  PRO A 312      -9.969   8.714 -10.045  1.00 22.74           C
ATOM   2354  CD  PRO A 312      -9.450  10.063 -10.356  1.00 21.88           C
ATOM   2355  C   PRO A 312     -12.808  10.353 -11.593  1.00 21.59           C
ATOM   2356  O   PRO A 312     -12.989  11.172 -10.705  1.00 22.74           O
ATOM   2357  N   LYS A 313     -13.746  10.010 -12.466  1.00 21.79           N
ATOM   2358  CA  LYS A 313     -15.012  10.745 -12.610  1.00 21.53           C
ATOM   2359  CB  LYS A 313     -15.226  11.161 -14.096  1.00 21.97           C
ATOM   2360  CG  LYS A 313     -14.114  12.075 -14.664  1.00 23.17           C
ATOM   2361  CD  LYS A 313     -14.076  13.401 -13.961  1.00 24.55           C
ATOM   2362  CE  LYS A 313     -13.157  14.426 -14.676  1.00 24.92           C
ATOM   2363  NZ  LYS A 313     -11.800  13.922 -14.803  1.00 26.19           N
ATOM   2364  C   LYS A 313     -16.235   9.991 -12.134  1.00 20.43           C
ATOM   2365  O   LYS A 313     -17.296  10.590 -11.938  1.00 21.06           O
ATOM   2366  N   PHE A 314     -16.101   8.687 -11.974  1.00 19.52           N
ATOM   2367  CA  PHE A 314     -17.173   7.857 -11.441  1.00 20.02           C
ATOM   2368  CB  PHE A 314     -16.829   6.375 -11.640  1.00 20.17           C
ATOM   2369  CG  PHE A 314     -15.489   5.971 -11.063  1.00 20.88           C
ATOM   2370  CD1 PHE A 314     -14.396   5.779 -11.888  1.00 19.49           C
ATOM   2371  CE1 PHE A 314     -13.169   5.395 -11.370  1.00 19.98           C
ATOM   2372  CZ  PHE A 314     -13.009   5.214  -9.981  1.00 19.06           C
```

Fig. 1, continued

| | | | | | | | | | | |
|---|---|---|---|---|---|---|---|---|---|---|
| ATOM | 2373 | CE2 | PHE | A | 314 | -14.066 | 5.396 | -9.153 | 1.00 20.31 | C |
| ATOM | 2374 | CD2 | PHE | A | 314 | -15.327 | 5.782 | -9.682 | 1.00 21.66 | C |
| ATOM | 2375 | C | PHE | A | 314 | -17.466 | 8.190 | -9.956 | 1.00 19.85 | C |
| ATOM | 2376 | O | PHE | A | 314 | -16.610 | 8.775 | -9.274 | 1.00 19.87 | O |
| ATOM | 2377 | N | PRO | A | 315 | -18.672 | 7.867 | -9.477 | 1.00 20.23 | N |
| ATOM | 2378 | CA | PRO | A | 315 | -19.052 | 8.174 | -8.087 | 1.00 20.39 | C |
| ATOM | 2379 | CB | PRO | A | 315 | -20.451 | 7.559 | -7.937 | 1.00 20.37 | C |
| ATOM | 2380 | CG | PRO | A | 315 | -20.999 | 7.485 | -9.404 | 1.00 20.58 | C |
| ATOM | 2381 | CD | PRO | A | 315 | -19.758 | 7.169 | -10.208 | 1.00 20.97 | C |
| ATOM | 2382 | C | PRO | A | 315 | -18.064 | 7.584 | -7.061 | 1.00 19.49 | C |
| ATOM | 2383 | O | PRO | A | 315 | -17.639 | 6.431 | -7.184 | 1.00 19.66 | O |
| ATOM | 2384 | N | ARG | A | 316 | -17.707 | 8.396 | -6.080 | 1.00 18.61 | N |
| ATOM | 2385 | CA | ARG | A | 316 | -16.861 | 7.970 | -4.998 | 1.00 18.56 | C |
| ATOM | 2386 | CB | ARG | A | 316 | -15.445 | 8.479 | -5.197 | 1.00 18.76 | C |
| ATOM | 2387 | CG | ARG | A | 316 | -14.715 | 7.796 | -6.338 | 1.00 20.03 | C |
| ATOM | 2388 | CD | ARG | A | 316 | -13.269 | 8.208 | -6.445 | 1.00 21.92 | C |
| ATOM | 2389 | NE | ARG | A | 316 | -13.099 | 9.503 | -7.100 | 1.00 21.83 | N |
| ATOM | 2390 | CZ | ARG | A | 316 | -11.958 | 10.202 | -7.093 | 1.00 23.41 | C |
| ATOM | 2391 | NH1 | ARG | A | 316 | -10.890 | 9.777 | -6.417 | 1.00 20.92 | N |
| ATOM | 2392 | NH2 | ARG | A | 316 | -11.876 | 11.346 | -7.779 | 1.00 22.76 | N |
| ATOM | 2393 | C | ARG | A | 316 | -17.401 | 8.421 | -3.643 | 1.00 18.45 | C |
| ATOM | 2394 | O | ARG | A | 316 | -18.106 | 9.413 | -3.533 | 1.00 17.80 | O |
| ATOM | 2395 | N | PHE | A | 317 | -17.089 | 7.622 | -2.631 | 1.00 18.17 | N |
| ATOM | 2396 | CA | PHE | A | 317 | -17.351 | 7.933 | -1.233 | 1.00 17.99 | C |
| ATOM | 2397 | CB | PHE | A | 317 | -18.374 | 6.964 | -0.671 | 1.00 17.54 | C |
| ATOM | 2398 | CG | PHE | A | 317 | -18.642 | 7.167 | 0.791 | 1.00 18.51 | C |
| ATOM | 2399 | CD1 | PHE | A | 317 | -18.094 | 6.299 | 1.739 | 1.00 16.77 | C |
| ATOM | 2400 | CE1 | PHE | A | 317 | -18.324 | 6.499 | 3.094 | 1.00 16.51 | C |
| ATOM | 2401 | CZ | PHE | A | 317 | -19.138 | 7.541 | 3.515 | 1.00 16.95 | C |
| ATOM | 2402 | CE2 | PHE | A | 317 | -19.675 | 8.431 | 2.580 | 1.00 17.79 | C |
| ATOM | 2403 | CD2 | PHE | A | 317 | -19.448 | 8.230 | 1.230 | 1.00 17.50 | C |
| ATOM | 2404 | C | PHE | A | 317 | -16.039 | 7.814 | -0.463 | 1.00 17.45 | C |
| ATOM | 2405 | O | PHE | A | 317 | -15.413 | 6.761 | -0.482 | 1.00 17.38 | O |
| ATOM | 2406 | N | ILE | A | 318 | -15.610 | 8.894 | 0.171 | 1.00 17.10 | N |
| ATOM | 2407 | CA | ILE | A | 318 | -14.349 | 8.930 | 0.906 | 1.00 16.69 | C |
| ATOM | 2408 | CB | ILE | A | 318 | -13.291 | 9.803 | 0.170 | 1.00 16.99 | C |
| ATOM | 2409 | CG1 | ILE | A | 318 | -12.989 | 9.229 | -1.217 | 1.00 16.46 | C |
| ATOM | 2410 | CD1 | ILE | A | 318 | -12.039 | 10.090 | -2.094 | 1.00 18.19 | C |
| ATOM | 2411 | CG2 | ILE | A | 318 | -11.999 | 9.914 | 1.010 | 1.00 16.93 | C |
| ATOM | 2412 | C | ILE | A | 318 | -14.611 | 9.416 | 2.337 | 1.00 16.83 | C |
| ATOM | 2413 | O | ILE | A | 318 | -15.210 | 10.485 | 2.559 | 1.00 17.56 | O |
| ATOM | 2414 | N | TRP | A | 319 | -14.192 | 8.624 | 3.317 | 1.00 16.20 | N |
| ATOM | 2415 | CA | TRP | A | 319 | -14.371 | 8.994 | 4.720 | 1.00 16.17 | C |
| ATOM | 2416 | CB | TRP | A | 319 | -15.427 | 8.110 | 5.415 | 1.00 16.17 | C |
| ATOM | 2417 | CG | TRP | A | 319 | -15.036 | 6.746 | 5.907 | 1.00 15.43 | C |
| ATOM | 2418 | CD1 | TRP | A | 319 | -14.762 | 6.397 | 7.210 | 1.00 15.40 | C |
| ATOM | 2419 | NE1 | TRP | A | 319 | -14.532 | 5.049 | 7.302 | 1.00 14.82 | N |
| ATOM | 2420 | CE2 | TRP | A | 319 | -14.678 | 4.484 | 6.061 | 1.00 14.01 | C |
| ATOM | 2421 | CD2 | TRP | A | 319 | -14.987 | 5.523 | 5.156 | 1.00 14.13 | C |
| ATOM | 2422 | CE3 | TRP | A | 319 | -15.206 | 5.190 | 3.820 | 1.00 14.37 | C |
| ATOM | 2423 | CZ3 | TRP | A | 319 | -15.053 | 3.859 | 3.417 | 1.00 15.28 | C |
| ATOM | 2424 | CH2 | TRP | A | 319 | -14.719 | 2.859 | 4.338 | 1.00 15.32 | C |
| ATOM | 2425 | CZ2 | TRP | A | 319 | -14.537 | 3.150 | 5.661 | 1.00 14.53 | C |
| ATOM | 2426 | C | TRP | A | 319 | -13.085 | 9.037 | 5.489 | 1.00 16.17 | C |

Fig. 1, continued

```
ATOM   2427  O    TRP A 319     -12.076   8.517   5.059  1.00 16.63           O
ATOM   2428  N    HIS A 320     -13.113   9.709   6.628  1.00 17.29           N
ATOM   2429  CA   HIS A 320     -11.906   9.876   7.415  1.00 17.01           C
ATOM   2430  CB   HIS A 320     -10.942  10.716   6.600  1.00 17.67           C
ATOM   2431  CG   HIS A 320      -9.490  10.426   6.854  1.00 18.97           C
ATOM   2432  ND1  HIS A 320      -8.548  10.541   5.884  1.00 18.20           N
ATOM   2433  CE1  HIS A 320      -7.350  10.319   6.380  1.00 20.65           C
ATOM   2434  NE2  HIS A 320      -7.491   9.977   7.632  1.00 20.18           N
ATOM   2435  CD2  HIS A 320      -8.832   9.968   7.936  1.00 23.20           C
ATOM   2436  C    HIS A 320     -12.226  10.529   8.762  1.00 17.34           C
ATOM   2437  O    HIS A 320     -13.093  11.401   8.852  1.00 17.11           O
ATOM   2438  N    ALA A 321     -11.562  10.079   9.825  1.00 16.69           N
ATOM   2439  CA   ALA A 321     -11.624  10.779  11.110  1.00 16.93           C
ATOM   2440  CB   ALA A 321     -11.033   9.928  12.195  1.00 16.71           C
ATOM   2441  C    ALA A 321     -10.844  12.082  11.012  1.00 17.10           C
ATOM   2442  O    ALA A 321      -9.656  12.077  10.667  1.00 16.28           O
ATOM   2443  N    ILE A 322     -11.482  13.208  11.300  1.00 17.47           N
ATOM   2444  CA   ILE A 322     -10.707  14.454  11.371  1.00 17.83           C
ATOM   2445  CB   ILE A 322     -11.606  15.688  11.582  1.00 18.61           C
ATOM   2446  CG1  ILE A 322     -12.530  15.882  10.357  1.00 19.70           C
ATOM   2447  CD1  ILE A 322     -13.722  16.962  10.531  1.00 19.95           C
ATOM   2448  CG2  ILE A 322     -10.750  16.954  11.760  1.00 19.67           C
ATOM   2449  C    ILE A 322      -9.548  14.319  12.397  1.00 17.57           C
ATOM   2450  O    ILE A 322      -8.356  14.600  12.048  1.00 16.86           O
ATOM   2451  N    PRO A 323      -9.852  13.825  13.604  1.00 16.94           N
ATOM   2452  CA   PRO A 323      -8.829  13.606  14.636  1.00 16.77           C
ATOM   2453  CB   PRO A 323      -9.645  13.595  15.939  1.00 16.64           C
ATOM   2454  CG   PRO A 323     -11.024  14.048  15.547  1.00 17.19           C
ATOM   2455  CD   PRO A 323     -11.189  13.529  14.136  1.00 17.13           C
ATOM   2456  C    PRO A 323      -8.018  12.308  14.496  1.00 17.08           C
ATOM   2457  O    PRO A 323      -7.527  11.781  15.504  1.00 16.47           O
ATOM   2458  N    ASP A 324      -7.876  11.797  13.281  1.00 16.39           N
ATOM   2459  CA   ASP A 324      -7.137  10.545  13.063  1.00 17.07           C
ATOM   2460  CB   ASP A 324      -7.119  10.231  11.567  1.00 16.53           C
ATOM   2461  CG   ASP A 324      -6.819   8.758  11.244  1.00 19.18           C
ATOM   2462  OD1  ASP A 324      -5.877   8.168  11.825  1.00 18.18           O
ATOM   2463  OD2  ASP A 324      -7.458   8.143  10.342  1.00 20.26           O
ATOM   2464  C    ASP A 324      -5.698  10.703  13.592  1.00 16.97           C
ATOM   2465  O    ASP A 324      -5.041  11.711  13.314  1.00 16.57           O
ATOM   2466  N    GLU A 325      -5.246   9.684  14.319  1.00 17.49           N
ATOM   2467  CA   GLU A 325      -3.977   9.643  15.043  1.00 17.53           C
ATOM   2468  CB   GLU A 325      -4.264   9.307  16.519  1.00 17.94           C
ATOM   2469  CG   GLU A 325      -4.471   7.830  16.892  1.00 18.30           C
ATOM   2470  CD   GLU A 325      -5.849   7.245  16.582  1.00 19.99           C
ATOM   2471  OE1  GLU A 325      -6.537   7.683  15.628  1.00 19.57           O
ATOM   2472  OE2  GLU A 325      -6.247   6.295  17.288  1.00 21.72           O
ATOM   2473  C    GLU A 325      -2.963   8.662  14.416  1.00 18.35           C
ATOM   2474  O    GLU A 325      -1.843   8.465  14.926  1.00 17.85           O
ATOM   2475  N    ILE A 326      -3.352   8.109  13.261  1.00 18.90           N
ATOM   2476  CA   ILE A 326      -2.567   7.154  12.518  1.00 18.69           C
ATOM   2477  CB   ILE A 326      -3.264   5.780  12.581  1.00 18.93           C
ATOM   2478  CG1  ILE A 326      -3.484   5.385  14.047  1.00 19.16           C
ATOM   2479  CD1  ILE A 326      -3.915   3.961  14.271  1.00 19.57           C
ATOM   2480  CG2  ILE A 326      -2.440   4.751  11.884  1.00 20.31           C
```

Fig. 1, continued

```
ATOM   2481  C    ILE A 326      -2.353   7.614  11.071  1.00 18.82           C
ATOM   2482  O    ILE A 326      -1.212   7.588  10.544  1.00 19.40           O
ATOM   2483  N    VAL A 327      -3.416   8.031  10.407  1.00 17.95           N
ATOM   2484  CA   VAL A 327      -3.292   8.508   9.028  1.00 18.14           C
ATOM   2485  CB   VAL A 327      -4.090   7.622   8.032  1.00 17.71           C
ATOM   2486  CG1  VAL A 327      -4.004   8.178   6.607  1.00 17.69           C
ATOM   2487  CG2  VAL A 327      -3.594   6.185   8.076  1.00 18.63           C
ATOM   2488  C    VAL A 327      -3.803   9.948   9.005  1.00 17.96           C
ATOM   2489  O    VAL A 327      -4.967  10.204   9.318  1.00 18.31           O
ATOM   2490  N    PRO A 328      -2.951  10.885   8.620  1.00 18.22           N
ATOM   2491  CA   PRO A 328      -3.283  12.305   8.766  1.00 18.48           C
ATOM   2492  CB   PRO A 328      -2.041  13.006   8.219  1.00 17.93           C
ATOM   2493  CG   PRO A 328      -1.398  12.010   7.322  1.00 18.91           C
ATOM   2494  CD   PRO A 328      -1.638  10.690   7.978  1.00 18.59           C
ATOM   2495  C    PRO A 328      -4.528  12.717   7.965  1.00 18.20           C
ATOM   2496  O    PRO A 328      -4.622  12.341   6.819  1.00 18.83           O
ATOM   2497  N    TYR A 329      -5.437  13.484   8.561  1.00 18.31           N
ATOM   2498  CA   TYR A 329      -6.643  13.907   7.860  1.00 18.60           C
ATOM   2499  CB   TYR A 329      -7.657  14.481   8.868  1.00 18.68           C
ATOM   2500  CG   TYR A 329      -8.818  15.185   8.222  1.00 18.85           C
ATOM   2501  CD1  TYR A 329      -9.836  14.450   7.633  1.00 19.56           C
ATOM   2502  CE1  TYR A 329     -10.899  15.058   7.020  1.00 21.17           C
ATOM   2503  CZ   TYR A 329     -10.978  16.446   6.968  1.00 21.29           C
ATOM   2504  OH   TYR A 329     -12.072  17.009   6.342  1.00 23.55           O
ATOM   2505  CE2  TYR A 329      -9.975  17.230   7.552  1.00 20.37           C
ATOM   2506  CD2  TYR A 329      -8.893  16.592   8.177  1.00 19.31           C
ATOM   2507  C    TYR A 329      -6.363  14.924   6.711  1.00 18.45           C
ATOM   2508  O    TYR A 329      -6.943  14.804   5.635  1.00 19.27           O
ATOM   2509  N    GLN A 330      -5.500  15.917   6.918  1.00 18.57           N
ATOM   2510  CA   GLN A 330      -5.471  17.059   6.000  1.00 18.82           C
ATOM   2511  CB   GLN A 330      -4.706  18.285   6.541  1.00 19.05           C
ATOM   2512  CG   GLN A 330      -5.461  19.061   7.649  1.00 22.73           C
ATOM   2513  CD   GLN A 330      -6.825  19.657   7.251  1.00 25.20           C
ATOM   2514  OE1  GLN A 330      -7.091  19.888   6.068  1.00 29.84           O
ATOM   2515  NE2  GLN A 330      -7.681  19.904   8.243  1.00 25.03           N
ATOM   2516  C    GLN A 330      -5.038  16.724   4.596  1.00 18.78           C
ATOM   2517  O    GLN A 330      -5.608  17.255   3.674  1.00 16.77           O
ATOM   2518  N    PRO A 331      -4.039  15.850   4.405  1.00 19.48           N
ATOM   2519  CA   PRO A 331      -3.687  15.451   3.055  1.00 19.39           C
ATOM   2520  CB   PRO A 331      -2.544  14.450   3.275  1.00 19.40           C
ATOM   2521  CG   PRO A 331      -1.957  14.883   4.541  1.00 19.78           C
ATOM   2522  CD   PRO A 331      -3.159  15.209   5.397  1.00 19.47           C
ATOM   2523  C    PRO A 331      -4.851  14.818   2.306  1.00 19.60           C
ATOM   2524  O    PRO A 331      -4.971  15.039   1.085  1.00 18.45           O
ATOM   2525  N    ALA A 332      -5.654  13.999   2.993  1.00 20.00           N
ATOM   2526  CA   ALA A 332      -6.830  13.411   2.349  1.00 20.17           C
ATOM   2527  CB   ALA A 332      -7.458  12.327   3.213  1.00 20.99           C
ATOM   2528  C    ALA A 332      -7.869  14.503   2.012  1.00 20.10           C
ATOM   2529  O    ALA A 332      -8.448  14.487   0.938  1.00 19.48           O
ATOM   2530  N    ALA A 333      -8.095  15.431   2.927  1.00 19.86           N
ATOM   2531  CA   ALA A 333      -8.979  16.563   2.655  1.00 20.51           C
ATOM   2532  CB   ALA A 333      -9.108  17.450   3.852  1.00 20.16           C
ATOM   2533  C    ALA A 333      -8.491  17.392   1.454  1.00 21.34           C
ATOM   2534  O    ALA A 333      -9.315  17.847   0.649  1.00 20.38           O
```

Fig. 1, continued

```
ATOM   2535  N    THR A 334      -7.170  17.567   1.305  1.00 21.65           N
ATOM   2536  CA   THR A 334      -6.708  18.335   0.151  1.00 21.66           C
ATOM   2537  CB   THR A 334      -5.395  19.178   0.355  1.00 22.72           C
ATOM   2538  OG1  THR A 334      -4.399  18.897  -0.634  1.00 27.06           O
ATOM   2539  CG2  THR A 334      -4.784  19.048   1.632  1.00 19.30           C
ATOM   2540  C    THR A 334      -6.790  17.551  -1.144  1.00 21.84           C
ATOM   2541  O    THR A 334      -7.197  18.118  -2.156  1.00 21.78           O
ATOM   2542  N    TYR A 335      -6.529  16.237  -1.111  1.00 21.11           N
ATOM   2543  CA   TYR A 335      -6.819  15.400  -2.262  1.00 20.81           C
ATOM   2544  CB   TYR A 335      -6.589  13.920  -1.919  1.00 20.80           C
ATOM   2545  CG   TYR A 335      -6.975  12.983  -3.012  1.00 18.77           C
ATOM   2546  CD1  TYR A 335      -8.135  12.223  -2.920  1.00 18.78           C
ATOM   2547  CE1  TYR A 335      -8.501  11.354  -3.933  1.00 18.34           C
ATOM   2548  CZ   TYR A 335      -7.729  11.291  -5.077  1.00 18.42           C
ATOM   2549  OH   TYR A 335      -8.096  10.454  -6.068  1.00 18.37           O
ATOM   2550  CE2  TYR A 335      -6.578  12.061  -5.209  1.00 18.06           C
ATOM   2551  CD2  TYR A 335      -6.213  12.896  -4.176  1.00 20.16           C
ATOM   2552  C    TYR A 335      -8.266  15.595  -2.730  1.00 21.04           C
ATOM   2553  O    TYR A 335      -8.541  15.795  -3.931  1.00 21.37           O
ATOM   2554  N    VAL A 336      -9.207  15.492  -1.805  1.00 20.43           N
ATOM   2555  CA   VAL A 336     -10.624  15.635  -2.180  1.00 21.10           C
ATOM   2556  CB   VAL A 336     -11.575  15.382  -0.978  1.00 20.73           C
ATOM   2557  CG1  VAL A 336     -12.989  15.805  -1.306  1.00 20.99           C
ATOM   2558  CG2  VAL A 336     -11.545  13.894  -0.575  1.00 20.91           C
ATOM   2559  C    VAL A 336     -10.889  17.025  -2.803  1.00 21.63           C
ATOM   2560  O    VAL A 336     -11.595  17.129  -3.810  1.00 21.79           O
ATOM   2561  N    LYS A 337     -10.328  18.067  -2.206  1.00 22.56           N
ATOM   2562  CA   LYS A 337     -10.544  19.445  -2.687  1.00 24.34           C
ATOM   2563  CB   LYS A 337      -9.858  20.437  -1.761  1.00 25.01           C
ATOM   2564  CG   LYS A 337     -10.031  21.892  -2.148  1.00 29.76           C
ATOM   2565  CD   LYS A 337      -9.531  22.832  -1.026  1.00 34.88           C
ATOM   2566  CE   LYS A 337      -9.585  24.308  -1.463  1.00 38.70           C
ATOM   2567  NZ   LYS A 337      -8.546  25.131  -0.737  1.00 43.01           N
ATOM   2568  C    LYS A 337     -10.056  19.631  -4.117  1.00 24.07           C
ATOM   2569  O    LYS A 337     -10.764  20.192  -4.947  1.00 23.75           O
ATOM   2570  N    GLU A 338      -8.856  19.109  -4.396  1.00 24.14           N
ATOM   2571  CA   GLU A 338      -8.242  19.161  -5.709  1.00 23.64           C
ATOM   2572  CB   GLU A 338      -6.835  18.538  -5.679  1.00 23.73           C
ATOM   2573  CG   GLU A 338      -5.823  19.242  -4.801  1.00 23.29           C
ATOM   2574  CD   GLU A 338      -4.471  18.516  -4.738  1.00 24.91           C
ATOM   2575  OE1  GLU A 338      -3.457  19.208  -4.465  1.00 23.66           O
ATOM   2576  OE2  GLU A 338      -4.404  17.266  -4.940  1.00 22.05           O
ATOM   2577  C    GLU A 338      -9.060  18.414  -6.721  1.00 23.93           C
ATOM   2578  O    GLU A 338      -9.263  18.879  -7.858  1.00 24.21           O
ATOM   2579  N    GLN A 339      -9.486  17.209  -6.346  1.00 23.70           N
ATOM   2580  CA   GLN A 339     -10.232  16.361  -7.257  1.00 22.84           C
ATOM   2581  CB   GLN A 339     -10.456  14.966  -6.662  1.00 22.82           C
ATOM   2582  CG   GLN A 339      -9.158  14.185  -6.452  1.00 21.51           C
ATOM   2583  CD   GLN A 339      -8.670  13.504  -7.727  1.00 19.99           C
ATOM   2584  OE1  GLN A 339      -9.401  12.761  -8.375  1.00 19.00           O
ATOM   2585  NE2  GLN A 339      -7.433  13.726  -8.051  1.00 18.92           N
ATOM   2586  C    GLN A 339     -11.565  16.999  -7.598  1.00 23.49           C
ATOM   2587  O    GLN A 339     -11.984  16.986  -8.756  1.00 23.44           O
ATOM   2588  N    CYS A 340     -12.234  17.556  -6.603  1.00 24.27           N
```

Fig. 1, continued

```
ATOM   2589  CA   CYS A 340     -13.537  18.196  -6.827  1.00 25.67           C
ATOM   2590  CB   CYS A 340     -14.186  18.558  -5.501  1.00 26.28           C
ATOM   2591  SG   CYS A 340     -14.804  17.075  -4.637  1.00 30.72           S
ATOM   2592  C    CYS A 340     -13.445  19.436  -7.753  1.00 25.83           C
ATOM   2593  O    CYS A 340     -14.340  19.666  -8.573  1.00 25.31           O
ATOM   2594  N    ALA A 341     -12.347  20.181  -7.648  1.00 26.10           N
ATOM   2595  CA   ALA A 341     -12.138  21.372  -8.493  1.00 27.02           C
ATOM   2596  CB   ALA A 341     -11.026  22.249  -7.924  1.00 26.84           C
ATOM   2597  C    ALA A 341     -11.837  20.970  -9.945  1.00 27.34           C
ATOM   2598  O    ALA A 341     -11.935  21.789 -10.846  1.00 27.67           O
ATOM   2599  N    LYS A 342     -11.499  19.698 -10.168  1.00 27.30           N
ATOM   2600  CA   LYS A 342     -11.268  19.190 -11.510  1.00 27.50           C
ATOM   2601  CB   LYS A 342      -9.912  18.511 -11.569  1.00 28.24           C
ATOM   2602  CG   LYS A 342      -8.740  19.466 -11.370  1.00 31.04           C
ATOM   2603  CD   LYS A 342      -7.760  19.401 -12.555  1.00 37.32           C
ATOM   2604  CE   LYS A 342      -6.546  18.528 -12.295  1.00 39.41           C
ATOM   2605  NZ   LYS A 342      -5.613  18.346 -13.509  1.00 39.19           N
ATOM   2606  C    LYS A 342     -12.369  18.271 -12.022  1.00 26.61           C
ATOM   2607  O    LYS A 342     -12.157  17.527 -12.966  1.00 26.57           O
ATOM   2608  N    GLY A 343     -13.563  18.358 -11.442  1.00 25.91           N
ATOM   2609  CA   GLY A 343     -14.706  17.609 -11.945  1.00 25.82           C
ATOM   2610  C    GLY A 343     -15.001  16.242 -11.335  1.00 25.12           C
ATOM   2611  O    GLY A 343     -15.850  15.499 -11.849  1.00 25.02           O
ATOM   2612  N    ALA A 344     -14.369  15.917 -10.211  1.00 24.51           N
ATOM   2613  CA   ALA A 344     -14.650  14.636  -9.529  1.00 24.15           C
ATOM   2614  CB   ALA A 344     -13.648  14.386  -8.404  1.00 23.82           C
ATOM   2615  C    ALA A 344     -16.084  14.593  -8.983  1.00 23.68           C
ATOM   2616  O    ALA A 344     -16.746  15.634  -8.860  1.00 23.32           O
ATOM   2617  N    ASN A 345     -16.562  13.384  -8.693  1.00 22.87           N
ATOM   2618  CA   ASN A 345     -17.847  13.189  -8.021  1.00 22.42           C
ATOM   2619  CB   ASN A 345     -18.803  12.406  -8.925  1.00 22.40           C
ATOM   2620  CG   ASN A 345     -20.137  12.114  -8.255  1.00 21.21           C
ATOM   2621  OD1  ASN A 345     -20.404  12.605  -7.173  1.00 21.53           O
ATOM   2622  ND2  ASN A 345     -20.953  11.282  -8.880  1.00 20.57           N
ATOM   2623  C    ASN A 345     -17.636  12.459  -6.691  1.00 22.25           C
ATOM   2624  O    ASN A 345     -17.765  11.228  -6.603  1.00 21.90           O
ATOM   2625  N    ILE A 346     -17.323  13.214  -5.651  1.00 21.97           N
ATOM   2626  CA   ILE A 346     -16.983  12.627  -4.352  1.00 21.38           C
ATOM   2627  CB   ILE A 346     -15.567  13.043  -3.931  1.00 21.25           C
ATOM   2628  CG1  ILE A 346     -14.538  12.557  -4.948  1.00 21.84           C
ATOM   2629  CD1  ILE A 346     -13.172  13.196  -4.785  1.00 22.76           C
ATOM   2630  CG2  ILE A 346     -15.242  12.477  -2.499  1.00 22.57           C
ATOM   2631  C    ILE A 346     -17.943  13.041  -3.258  1.00 20.53           C
ATOM   2632  O    ILE A 346     -18.133  14.221  -3.008  1.00 20.68           O
ATOM   2633  N    ASN A 347     -18.537  12.065  -2.587  1.00 19.78           N
ATOM   2634  CA   ASN A 347     -19.253  12.302  -1.347  1.00 19.81           C
ATOM   2635  CB   ASN A 347     -20.459  11.349  -1.241  1.00 20.67           C
ATOM   2636  CG   ASN A 347     -21.214  11.487   0.070  1.00 21.47           C
ATOM   2637  OD1  ASN A 347     -20.770  12.182   0.963  1.00 25.41           O
ATOM   2638  ND2  ASN A 347     -22.362  10.793   0.194  1.00 20.98           N
ATOM   2639  C    ASN A 347     -18.248  12.119  -0.204  1.00 19.30           C
ATOM   2640  O    ASN A 347     -17.792  10.999   0.062  1.00 19.31           O
ATOM   2641  N    PHE A 348     -17.888  13.224   0.439  1.00 18.35           N
ATOM   2642  CA   PHE A 348     -16.818  13.280   1.442  1.00 18.49           C
```

Fig. 1, continued

```
ATOM   2643  CB   PHE A 348     -16.020  14.572   1.254  1.00 18.01           C
ATOM   2644  CG   PHE A 348     -14.785  14.684   2.095  1.00 20.02           C
ATOM   2645  CD1  PHE A 348     -13.963  13.600   2.327  1.00 21.35           C
ATOM   2646  CE1  PHE A 348     -12.829  13.732   3.060  1.00 21.76           C
ATOM   2647  CZ   PHE A 348     -12.465  14.981   3.560  1.00 23.97           C
ATOM   2648  CE2  PHE A 348     -13.249  16.079   3.328  1.00 21.30           C
ATOM   2649  CD2  PHE A 348     -14.401  15.936   2.605  1.00 22.15           C
ATOM   2650  C    PHE A 348     -17.419  13.239   2.824  1.00 18.40           C
ATOM   2651  O    PHE A 348     -18.307  14.046   3.128  1.00 18.50           O
ATOM   2652  N    SER A 349     -16.951  12.306   3.656  1.00 18.04           N
ATOM   2653  CA   SER A 349     -17.470  12.118   5.007  1.00 17.89           C
ATOM   2654  CB   SER A 349     -18.250  10.794   5.115  1.00 18.09           C
ATOM   2655  OG   SER A 349     -18.481  10.444   6.481  1.00 16.36           O
ATOM   2656  C    SER A 349     -16.380  12.175   6.094  1.00 19.27           C
ATOM   2657  O    SER A 349     -15.947  11.132   6.629  1.00 19.32           O
ATOM   2658  N    PRO A 350     -15.975  13.389   6.466  1.00 20.34           N
ATOM   2659  CA   PRO A 350     -15.074  13.587   7.601  1.00 21.22           C
ATOM   2660  CB   PRO A 350     -14.528  15.005   7.380  1.00 21.73           C
ATOM   2661  CG   PRO A 350     -15.467  15.682   6.469  1.00 21.83           C
ATOM   2662  CD   PRO A 350     -16.339  14.660   5.822  1.00 20.86           C
ATOM   2663  C    PRO A 350     -15.805  13.491   8.928  1.00 21.18           C
ATOM   2664  O    PRO A 350     -16.846  14.135   9.060  1.00 23.46           O
ATOM   2665  N    TYR A 351     -15.321  12.687   9.871  1.00 19.76           N
ATOM   2666  CA   TYR A 351     -15.986  12.529  11.175  1.00 19.39           C
ATOM   2667  CB   TYR A 351     -15.979  11.054  11.640  1.00 19.38           C
ATOM   2668  CG   TYR A 351     -16.844  10.153  10.779  1.00 18.58           C
ATOM   2669  CD1  TYR A 351     -16.297   9.397   9.762  1.00 16.07           C
ATOM   2670  CE1  TYR A 351     -17.085   8.579   8.976  1.00 17.63           C
ATOM   2671  CZ   TYR A 351     -18.457   8.550   9.188  1.00 16.52           C
ATOM   2672  OH   TYR A 351     -19.239   7.739   8.420  1.00 16.61           O
ATOM   2673  CE2  TYR A 351     -19.021   9.298  10.185  1.00 16.68           C
ATOM   2674  CD2  TYR A 351     -18.227  10.092  10.975  1.00 17.58           C
ATOM   2675  C    TYR A 351     -15.264  13.425  12.162  1.00 19.24           C
ATOM   2676  O    TYR A 351     -14.058  13.280  12.347  1.00 19.29           O
ATOM   2677  N    PRO A 352     -15.949  14.422  12.726  1.00 19.77           N
ATOM   2678  CA   PRO A 352     -15.263  15.376  13.616  1.00 19.90           C
ATOM   2679  CB   PRO A 352     -16.241  16.561  13.690  1.00 19.85           C
ATOM   2680  CG   PRO A 352     -17.582  15.950  13.466  1.00 21.29           C
ATOM   2681  CD   PRO A 352     -17.360  14.795  12.509  1.00 19.93           C
ATOM   2682  C    PRO A 352     -14.946  14.820  14.995  1.00 18.89           C
ATOM   2683  O    PRO A 352     -14.007  15.299  15.590  1.00 19.68           O
ATOM   2684  N    ILE A 353     -15.689  13.836  15.475  1.00 18.41           N
ATOM   2685  CA   ILE A 353     -15.407  13.145  16.737  1.00 19.04           C
ATOM   2686  CB   ILE A 353     -16.553  13.376  17.752  1.00 19.74           C
ATOM   2687  CG1  ILE A 353     -16.854  14.886  17.896  1.00 22.78           C
ATOM   2688  CD1  ILE A 353     -18.048  15.175  18.745  1.00 27.83           C
ATOM   2689  CG2  ILE A 353     -16.204  12.729  19.128  1.00 21.20           C
ATOM   2690  C    ILE A 353     -15.220  11.639  16.450  1.00 19.10           C
ATOM   2691  O    ILE A 353     -16.193  10.865  16.349  1.00 20.43           O
ATOM   2692  N    ALA A 354     -13.965  11.249  16.308  1.00 18.34           N
ATOM   2693  CA   ALA A 354     -13.575   9.929  15.856  1.00 18.17           C
ATOM   2694  CB   ALA A 354     -13.985   9.705  14.383  1.00 18.66           C
ATOM   2695  C    ALA A 354     -12.054   9.804  15.966  1.00 18.37           C
ATOM   2696  O    ALA A 354     -11.334  10.799  16.137  1.00 18.21           O
```

Fig. 1, continued

| | | | | | | | | | | |
|---|---|---|---|---|---|---|---|---|---|---|
| ATOM | 2697 | N   | GLU | A | 355 | -11.596 |  8.569 | 15.852 | 1.00 17.83 | N |
| ATOM | 2698 | CA  | GLU | A | 355 | -10.175 |  8.228 | 15.714 | 1.00 18.53 | C |
| ATOM | 2699 | CB  | GLU | A | 355 |  -9.668 |  7.632 | 17.026 | 1.00 18.65 | C |
| ATOM | 2700 | CG  | GLU | A | 355 |  -9.702 |  8.614 | 18.186 | 1.00 23.45 | C |
| ATOM | 2701 | CD  | GLU | A | 355 |  -9.595 |  7.919 | 19.541 | 1.00 29.00 | C |
| ATOM | 2702 | OE1 | GLU | A | 355 | -10.618 |  7.311 | 19.992 | 1.00 30.21 | O |
| ATOM | 2703 | OE2 | GLU | A | 355 |  -8.474 |  7.972 | 20.118 | 1.00 29.06 | O |
| ATOM | 2704 | C   | GLU | A | 355 | -10.088 |  7.200 | 14.587 | 1.00 17.28 | C |
| ATOM | 2705 | O   | GLU | A | 355 | -11.110 |  6.826 | 14.026 | 1.00 17.42 | O |
| ATOM | 2706 | N   | HIS | A | 356 |  -8.897 |  6.721 | 14.257 | 1.00 16.96 | N |
| ATOM | 2707 | CA  | HIS | A | 356 |  -8.737 |  5.831 | 13.114 | 1.00 16.91 | C |
| ATOM | 2708 | CB  | HIS | A | 356 |  -7.296 |  5.396 | 12.995 | 1.00 17.28 | C |
| ATOM | 2709 | CG  | HIS | A | 356 |  -6.943 |  4.779 | 11.688 | 1.00 16.92 | C |
| ATOM | 2710 | ND1 | HIS | A | 356 |  -6.802 |  5.519 | 10.536 | 1.00 18.65 | N |
| ATOM | 2711 | CE1 | HIS | A | 356 |  -6.414 |  4.718 |  9.553 | 1.00 19.63 | C |
| ATOM | 2712 | NE2 | HIS | A | 356 |  -6.319 |  3.487 | 10.027 | 1.00 17.35 | N |
| ATOM | 2713 | CD2 | HIS | A | 356 |  -6.669 |  3.494 | 11.351 | 1.00 17.01 | C |
| ATOM | 2714 | C   | HIS | A | 356 |  -9.587 |  4.571 | 13.174 | 1.00 17.20 | C |
| ATOM | 2715 | O   | HIS | A | 356 | -10.202 |  4.183 | 12.167 | 1.00 15.70 | O |
| ATOM | 2716 | N   | LEU | A | 357 |  -9.591 |  3.910 | 14.335 | 1.00 17.11 | N |
| ATOM | 2717 | CA  | LEU | A | 357 | -10.304 |  2.638 | 14.470 | 1.00 18.17 | C |
| ATOM | 2718 | CB  | LEU | A | 357 |  -9.710 |  1.756 | 15.584 | 1.00 18.57 | C |
| ATOM | 2719 | CG  | LEU | A | 357 |  -8.452 |  0.937 | 15.233 | 1.00 21.01 | C |
| ATOM | 2720 | CD1 | LEU | A | 357 |  -8.667 |  0.054 | 14.012 | 1.00 22.91 | C |
| ATOM | 2721 | CD2 | LEU | A | 357 |  -7.269 |  1.821 | 15.016 | 1.00 21.20 | C |
| ATOM | 2722 | C   | LEU | A | 357 | -11.826 |  2.853 | 14.701 | 1.00 17.91 | C |
| ATOM | 2723 | O   | LEU | A | 357 | -12.616 |  2.008 | 14.309 | 1.00 19.06 | O |
| ATOM | 2724 | N   | THR | A | 358 | -12.249 |  3.961 | 15.287 | 1.00 17.31 | N |
| ATOM | 2725 | CA  | THR | A | 358 | -13.696 |  4.199 | 15.399 | 1.00 17.10 | C |
| ATOM | 2726 | CB  | THR | A | 358 | -14.059 |  5.126 | 16.545 | 1.00 17.39 | C |
| ATOM | 2727 | OG1 | THR | A | 358 | -13.365 |  6.367 | 16.440 | 1.00 15.93 | O |
| ATOM | 2728 | CG2 | THR | A | 358 | -13.618 |  4.509 | 17.943 | 1.00 17.62 | C |
| ATOM | 2729 | C   | THR | A | 358 | -14.308 |  4.663 | 14.069 | 1.00 17.53 | C |
| ATOM | 2730 | O   | THR | A | 358 | -15.408 |  4.233 | 13.721 | 1.00 17.12 | O |
| ATOM | 2731 | N   | ALA | A | 359 | -13.597 |  5.495 | 13.307 | 1.00 16.58 | N |
| ATOM | 2732 | CA  | ALA | A | 359 | -14.053 |  5.836 | 11.950 | 1.00 16.90 | C |
| ATOM | 2733 | CB  | ALA | A | 359 | -13.189 |  6.930 | 11.354 | 1.00 16.26 | C |
| ATOM | 2734 | C   | ALA | A | 359 | -14.124 |  4.623 | 10.993 | 1.00 17.25 | C |
| ATOM | 2735 | O   | ALA | A | 359 | -14.956 |  4.608 | 10.081 | 1.00 17.06 | O |
| ATOM | 2736 | N   | GLU | A | 360 | -13.244 |  3.632 | 11.193 | 1.00 17.23 | N |
| ATOM | 2737 | CA  | GLU | A | 360 | -13.280 |  2.382 | 10.436 | 1.00 17.22 | C |
| ATOM | 2738 | CB  | GLU | A | 360 | -12.245 |  1.369 | 10.975 | 1.00 17.42 | C |
| ATOM | 2739 | CG  | GLU | A | 360 | -12.190 |  0.043 | 10.200 | 1.00 16.64 | C |
| ATOM | 2740 | CD  | GLU | A | 360 | -10.856 | -0.701 | 10.351 | 1.00 18.61 | C |
| ATOM | 2741 | OE1 | GLU | A | 360 | -10.702 | -1.796 |  9.762 | 1.00 22.02 | O |
| ATOM | 2742 | OE2 | GLU | A | 360 |  -9.956 | -0.201 | 11.054 | 1.00 18.54 | O |
| ATOM | 2743 | C   | GLU | A | 360 | -14.672 |  1.751 | 10.458 | 1.00 17.56 | C |
| ATOM | 2744 | O   | GLU | A | 360 | -15.144 |  1.237 |  9.443 | 1.00 18.48 | O |
| ATOM | 2745 | N   | ILE | A | 361 | -15.319 |  1.800 | 11.614 | 1.00 17.06 | N |
| ATOM | 2746 | CA  | ILE | A | 361 | -16.683 |  1.294 | 11.762 | 1.00 17.14 | C |
| ATOM | 2747 | CB  | ILE | A | 361 | -16.907 |  0.810 | 13.202 | 1.00 16.98 | C |
| ATOM | 2748 | CG1 | ILE | A | 361 | -15.834 | -0.218 | 13.612 | 1.00 19.28 | C |
| ATOM | 2749 | CD1 | ILE | A | 361 | -15.786 | -1.435 | 12.768 | 1.00 20.33 | C |
| ATOM | 2750 | CG2 | ILE | A | 361 | -18.294 |  0.253 | 13.370 | 1.00 17.55 | C |

Fig. 1, continued

```
ATOM   2751  C    ILE A 361     -17.763   2.311  11.376  1.00 16.67           C
ATOM   2752  O    ILE A 361     -18.744   1.942  10.750  1.00 16.82           O
ATOM   2753  N    PHE A 362     -17.607   3.572  11.763  1.00 16.61           N
ATOM   2754  CA   PHE A 362     -18.629   4.598  11.488  1.00 17.35           C
ATOM   2755  CB   PHE A 362     -18.163   6.006  11.918  1.00 17.49           C
ATOM   2756  CG   PHE A 362     -17.960   6.202  13.421  1.00 17.81           C
ATOM   2757  CD1  PHE A 362     -18.612   5.429  14.361  1.00 17.54           C
ATOM   2758  CE1  PHE A 362     -18.431   5.659  15.720  1.00 20.22           C
ATOM   2759  CZ   PHE A 362     -17.595   6.688  16.162  1.00 19.53           C
ATOM   2760  CE2  PHE A 362     -16.962   7.491  15.223  1.00 20.42           C
ATOM   2761  CD2  PHE A 362     -17.145   7.240  13.861  1.00 17.56           C
ATOM   2762  C    PHE A 362     -18.920   4.685   9.993  1.00 16.99           C
ATOM   2763  O    PHE A 362     -20.053   4.891   9.591  1.00 17.10           O
ATOM   2764  N    GLY A 363     -17.865   4.589   9.190  1.00 16.12           N
ATOM   2765  CA   GLY A 363     -17.951   4.695   7.740  1.00 16.15           C
ATOM   2766  C    GLY A 363     -18.382   3.432   7.022  1.00 16.54           C
ATOM   2767  O    GLY A 363     -18.699   3.483   5.818  1.00 16.01           O
ATOM   2768  N    LEU A 364     -18.475   2.304   7.739  1.00 17.33           N
ATOM   2769  CA   LEU A 364     -18.677   1.008   7.074  1.00 18.12           C
ATOM   2770  CB   LEU A 364     -18.357  -0.149   8.035  1.00 18.55           C
ATOM   2771  CG   LEU A 364     -18.259  -1.590   7.465  1.00 19.74           C
ATOM   2772  CD1  LEU A 364     -17.357  -2.466   8.296  1.00 21.28           C
ATOM   2773  CD2  LEU A 364     -19.618  -2.281   7.386  1.00 21.89           C
ATOM   2774  C    LEU A 364     -20.072   0.842   6.415  1.00 18.11           C
ATOM   2775  O    LEU A 364     -20.174   0.481   5.254  1.00 17.39           O
ATOM   2776  N    VAL A 365     -21.143   1.118   7.150  1.00 18.78           N
ATOM   2777  CA   VAL A 365     -22.487   0.975   6.588  1.00 17.85           C
ATOM   2778  CB   VAL A 365     -23.556   1.049   7.680  1.00 17.96           C
ATOM   2779  CG1  VAL A 365     -24.980   1.243   7.100  1.00 18.75           C
ATOM   2780  CG2  VAL A 365     -23.482  -0.216   8.550  1.00 17.06           C
ATOM   2781  C    VAL A 365     -22.660   1.963   5.419  1.00 17.99           C
ATOM   2782  O    VAL A 365     -23.036   1.554   4.333  1.00 17.35           O
ATOM   2783  N    PRO A 366     -22.312   3.234   5.594  1.00 18.40           N
ATOM   2784  CA   PRO A 366     -22.315   4.170   4.464  1.00 17.74           C
ATOM   2785  CB   PRO A 366     -21.756   5.458   5.081  1.00 17.40           C
ATOM   2786  CG   PRO A 366     -22.162   5.378   6.482  1.00 19.24           C
ATOM   2787  CD   PRO A 366     -21.963   3.908   6.856  1.00 18.13           C
ATOM   2788  C    PRO A 366     -21.502   3.719   3.257  1.00 17.98           C
ATOM   2789  O    PRO A 366     -21.951   3.842   2.105  1.00 18.60           O
ATOM   2790  N    SER A 367     -20.318   3.182   3.505  1.00 17.31           N
ATOM   2791  CA   SER A 367     -19.478   2.656   2.452  1.00 17.59           C
ATOM   2792  CB   SER A 367     -18.189   2.108   3.056  1.00 17.83           C
ATOM   2793  OG   SER A 367     -17.418   1.462   2.085  1.00 18.72           O
ATOM   2794  C    SER A 367     -20.175   1.571   1.632  1.00 17.98           C
ATOM   2795  O    SER A 367     -20.194   1.624   0.389  1.00 17.27           O
ATOM   2796  N    LEU A 368     -20.725   0.571   2.313  1.00 18.09           N
ATOM   2797  CA   LEU A 368     -21.378  -0.528   1.615  1.00 18.36           C
ATOM   2798  CB   LEU A 368     -21.508  -1.747   2.518  1.00 18.28           C
ATOM   2799  CG   LEU A 368     -20.180  -2.256   3.115  1.00 18.76           C
ATOM   2800  CD1  LEU A 368     -20.381  -3.599   3.770  1.00 20.96           C
ATOM   2801  CD2  LEU A 368     -19.101  -2.348   2.065  1.00 19.44           C
ATOM   2802  C    LEU A 368     -22.714  -0.121   0.986  1.00 18.80           C
ATOM   2803  O    LEU A 368     -23.033  -0.547  -0.129  1.00 18.67           O
ATOM   2804  N    TRP A 369     -23.475   0.740   1.657  1.00 18.68           N
```

Fig. 1, continued

| | | | | | | | | | |
|---|---|---|---|---|---|---|---|---|---|
| ATOM | 2805 | CA | TRP | A | 369 | -24.699 | 1.269 | 1.051 | 1.00 18.30 | C |
| ATOM | 2806 | CB | TRP | A | 369 | -25.439 | 2.173 | 2.026 | 1.00 18.58 | C |
| ATOM | 2807 | CG | TRP | A | 369 | -26.713 | 2.750 | 1.490 | 1.00 20.67 | C |
| ATOM | 2808 | CD1 | TRP | A | 369 | -26.993 | 4.071 | 1.312 | 1.00 22.20 | C |
| ATOM | 2809 | NE1 | TRP | A | 369 | -28.254 | 4.219 | 0.787 | 1.00 23.98 | N |
| ATOM | 2810 | CE2 | TRP | A | 369 | -28.806 | 2.985 | 0.584 | 1.00 24.37 | C |
| ATOM | 2811 | CD2 | TRP | A | 369 | -27.859 | 2.029 | 1.023 | 1.00 22.29 | C |
| ATOM | 2812 | CE3 | TRP | A | 369 | -28.182 | 0.671 | 0.919 | 1.00 25.77 | C |
| ATOM | 2813 | CZ3 | TRP | A | 369 | -29.468 | 0.306 | 0.399 | 1.00 27.65 | C |
| ATOM | 2814 | CH2 | TRP | A | 369 | -30.382 | 1.287 | -0.014 | 1.00 29.02 | C |
| ATOM | 2815 | CZ2 | TRP | A | 369 | -30.073 | 2.634 | 0.070 | 1.00 28.84 | C |
| ATOM | 2816 | C | TRP | A | 369 | -24.345 | 2.006 | -0.240 | 1.00 18.36 | C |
| ATOM | 2817 | O | TRP | A | 369 | -25.003 | 1.821 | -1.250 | 1.00 17.80 | O |
| ATOM | 2818 | N | PHE | A | 370 | -23.264 | 2.791 | -0.211 | 1.00 18.41 | N |
| ATOM | 2819 | CA | PHE | A | 370 | -22.776 | 3.487 | -1.383 | 1.00 19.10 | C |
| ATOM | 2820 | CB | PHE | A | 370 | -21.611 | 4.394 | -1.058 | 1.00 19.04 | C |
| ATOM | 2821 | CG | PHE | A | 370 | -21.075 | 5.104 | -2.247 | 1.00 19.82 | C |
| ATOM | 2822 | CD1 | PHE | A | 370 | -20.017 | 4.566 | -2.974 | 1.00 21.74 | C |
| ATOM | 2823 | CE1 | PHE | A | 370 | -19.536 | 5.206 | -4.094 | 1.00 22.65 | C |
| ATOM | 2824 | CZ | PHE | A | 370 | -20.082 | 6.410 | -4.476 | 1.00 22.21 | C |
| ATOM | 2825 | CE2 | PHE | A | 370 | -21.123 | 6.953 | -3.773 | 1.00 22.02 | C |
| ATOM | 2826 | CD2 | PHE | A | 370 | -21.623 | 6.302 | -2.650 | 1.00 19.90 | C |
| ATOM | 2827 | C | PHE | A | 370 | -22.388 | 2.546 | -2.528 | 1.00 19.70 | C |
| ATOM | 2828 | O | PHE | A | 370 | -22.734 | 2.805 | -3.679 | 1.00 18.16 | O |
| ATOM | 2829 | N | ILE | A | 371 | -21.692 | 1.461 | -2.204 | 1.00 20.49 | N |
| ATOM | 2830 | CA | ILE | A | 371 | -21.270 | 0.482 | -3.206 | 1.00 21.18 | C |
| ATOM | 2831 | CB | ILE | A | 371 | -20.394 | -0.627 | -2.578 | 1.00 21.08 | C |
| ATOM | 2832 | CG1 | ILE | A | 371 | -19.047 | -0.047 | -2.102 | 1.00 22.33 | C |
| ATOM | 2833 | CD1 | ILE | A | 371 | -18.048 | 0.198 | -3.149 | 1.00 23.17 | C |
| ATOM | 2834 | CG2 | ILE | A | 371 | -20.217 | -1.810 | -3.545 | 1.00 21.64 | C |
| ATOM | 2835 | C | ILE | A | 371 | -22.507 | -0.140 | -3.844 | 1.00 21.12 | C |
| ATOM | 2836 | O | ILE | A | 371 | -22.569 | -0.285 | -5.041 | 1.00 20.88 | O |
| ATOM | 2837 | N | LYS | A | 372 | -23.482 | -0.503 | -3.031 | 1.00 22.07 | N |
| ATOM | 2838 | CA | LYS | A | 372 | -24.773 | -0.986 | -3.540 | 1.00 22.76 | C |
| ATOM | 2839 | CB | LYS | A | 372 | -25.736 | -1.297 | -2.409 | 1.00 23.28 | C |
| ATOM | 2840 | CG | LYS | A | 372 | -27.134 | -1.694 | -2.900 | 1.00 26.62 | C |
| ATOM | 2841 | CD | LYS | A | 372 | -27.716 | -2.853 | -2.168 | 1.00 31.28 | C |
| ATOM | 2842 | CE | LYS | A | 372 | -29.230 | -2.957 | -2.454 | 1.00 35.39 | C |
| ATOM | 2843 | NZ | LYS | A | 372 | -29.515 | -3.285 | -3.913 | 1.00 37.10 | N |
| ATOM | 2844 | C | LYS | A | 372 | -25.415 | 0.016 | -4.511 | 1.00 22.91 | C |
| ATOM | 2845 | O | LYS | A | 372 | -25.842 | -0.360 | -5.617 | 1.00 22.95 | O |
| ATOM | 2846 | N | GLN | A | 373 | -25.466 | 1.281 | -4.118 | 1.00 22.52 | N |
| ATOM | 2847 | CA | GLN | A | 373 | -26.003 | 2.321 | -4.992 | 1.00 22.83 | C |
| ATOM | 2848 | CB | GLN | A | 373 | -26.091 | 3.663 | -4.276 | 1.00 22.49 | C |
| ATOM | 2849 | CG | GLN | A | 373 | -27.123 | 3.707 | -3.178 | 1.00 22.63 | C |
| ATOM | 2850 | CD | GLN | A | 373 | -27.028 | 4.992 | -2.387 | 1.00 23.65 | C |
| ATOM | 2851 | OE1 | GLN | A | 373 | -25.941 | 5.357 | -1.894 | 1.00 25.06 | O |
| ATOM | 2852 | NE2 | GLN | A | 373 | -28.149 | 5.684 | -2.250 | 1.00 21.25 | N |
| ATOM | 2853 | C | GLN | A | 373 | -25.178 | 2.471 | -6.261 | 1.00 23.30 | C |
| ATOM | 2854 | O | GLN | A | 373 | -25.723 | 2.698 | -7.333 | 1.00 23.12 | O |
| ATOM | 2855 | N | ALA | A | 374 | -23.858 | 2.345 | -6.144 | 1.00 22.89 | N |
| ATOM | 2856 | CA | ALA | A | 374 | -22.995 | 2.462 | -7.304 | 1.00 23.25 | C |
| ATOM | 2857 | CB | ALA | A | 374 | -21.535 | 2.418 | -6.880 | 1.00 23.72 | C |
| ATOM | 2858 | C | ALA | A | 374 | -23.301 | 1.349 | -8.325 | 1.00 23.94 | C |

Fig. 1, continued

```
ATOM   2859  O    ALA A 374     -23.345   1.602  -9.529  1.00 23.48           O
ATOM   2860  N    PHE A 375     -23.494   0.115  -7.848  1.00 24.09           N
ATOM   2861  CA   PHE A 375     -23.793  -1.005  -8.739  1.00 24.18           C
ATOM   2862  CB   PHE A 375     -23.676  -2.353  -8.009  1.00 23.65           C
ATOM   2863  CG   PHE A 375     -22.255  -2.890  -7.868  1.00 22.86           C
ATOM   2864  CD1  PHE A 375     -21.766  -3.260  -6.618  1.00 22.79           C
ATOM   2865  CE1  PHE A 375     -20.463  -3.812  -6.470  1.00 21.70           C
ATOM   2866  CZ   PHE A 375     -19.655  -3.979  -7.595  1.00 23.34           C
ATOM   2867  CE2  PHE A 375     -20.148  -3.618  -8.856  1.00 21.75           C
ATOM   2868  CD2  PHE A 375     -21.439  -3.084  -8.980  1.00 21.89           C
ATOM   2869  C    PHE A 375     -25.201  -0.881  -9.353  1.00 25.62           C
ATOM   2870  O    PHE A 375     -25.417  -1.332 -10.484  1.00 25.91           O
ATOM   2871  N    ASP A 376     -26.154  -0.323  -8.598  1.00 26.43           N
ATOM   2872  CA   ASP A 376     -27.533  -0.114  -9.080  1.00 27.17           C
ATOM   2873  CB   ASP A 376     -28.514  -0.015  -7.917  1.00 27.10           C
ATOM   2874  CG   ASP A 376     -28.598  -1.286  -7.091  1.00 28.33           C
ATOM   2875  OD1  ASP A 376     -28.091  -2.345  -7.524  1.00 28.54           O
ATOM   2876  OD2  ASP A 376     -29.144  -1.300  -5.967  1.00 29.42           O
ATOM   2877  C    ASP A 376     -27.731   1.155  -9.930  1.00 28.11           C
ATOM   2878  O    ASP A 376     -28.790   1.316 -10.535  1.00 28.60           O
ATOM   2879  N    GLY A 377     -26.740   2.050  -9.956  1.00 28.32           N
ATOM   2880  CA   GLY A 377     -26.851   3.329 -10.638  1.00 28.64           C
ATOM   2881  C    GLY A 377     -27.708   4.360  -9.936  1.00 29.04           C
ATOM   2882  O    GLY A 377     -28.297   5.215 -10.595  1.00 29.79           O
ATOM   2883  N    THR A 378     -27.774   4.298  -8.607  1.00 28.49           N
ATOM   2884  CA   THR A 378     -28.616   5.187  -7.813  1.00 28.47           C
ATOM   2885  CB   THR A 378     -29.670   4.358  -7.017  1.00 28.64           C
ATOM   2886  OG1  THR A 378     -29.003   3.315  -6.292  1.00 27.21           O
ATOM   2887  CG2  THR A 378     -30.640   3.611  -7.967  1.00 29.76           C
ATOM   2888  C    THR A 378     -27.844   6.043  -6.814  1.00 27.95           C
ATOM   2889  O    THR A 378     -28.426   6.512  -5.870  1.00 27.63           O
ATOM   2890  N    THR A 379     -26.547   6.248  -6.983  1.00 28.31           N
ATOM   2891  CA   THR A 379     -25.857   7.162  -6.059  1.00 28.40           C
ATOM   2892  CB   THR A 379     -24.335   7.271  -6.319  1.00 27.94           C
ATOM   2893  OG1  THR A 379     -24.091   7.723  -7.653  1.00 26.61           O
ATOM   2894  CG2  THR A 379     -23.650   5.913  -6.207  1.00 27.17           C
ATOM   2895  C    THR A 379     -26.496   8.558  -6.127  1.00 29.58           C
ATOM   2896  O    THR A 379     -26.877   9.029  -7.202  1.00 29.08           O
ATOM   2897  N    PRO A 380     -26.637   9.205  -4.985  1.00 31.22           N
ATOM   2898  CA   PRO A 380     -27.269  10.531  -4.952  1.00 32.57           C
ATOM   2899  CB   PRO A 380     -27.455  10.810  -3.459  1.00 32.61           C
ATOM   2900  CG   PRO A 380     -26.507   9.883  -2.742  1.00 32.18           C
ATOM   2901  CD   PRO A 380     -26.216   8.742  -3.651  1.00 31.17           C
ATOM   2902  C    PRO A 380     -26.393  11.596  -5.606  1.00 33.55           C
ATOM   2903  O    PRO A 380     -25.161  11.469  -5.566  1.00 32.89           O
ATOM   2904  N    LYS A 381     -27.028  12.590  -6.238  1.00 34.14           N
ATOM   2905  CA   LYS A 381     -26.320  13.734  -6.787  1.00 34.61           C
ATOM   2906  CB   LYS A 381     -27.188  14.539  -7.757  1.00 35.76           C
ATOM   2907  CG   LYS A 381     -27.668  13.769  -8.996  1.00 39.32           C
ATOM   2908  CD   LYS A 381     -26.516  13.386  -9.952  1.00 44.68           C
ATOM   2909  CE   LYS A 381     -27.037  12.624 -11.208  1.00 46.91           C
ATOM   2910  NZ   LYS A 381     -26.787  13.367 -12.508  1.00 47.33           N
ATOM   2911  C    LYS A 381     -25.924  14.599  -5.623  1.00 33.51           C
ATOM   2912  O    LYS A 381     -26.765  14.991  -4.840  1.00 33.73           O
```

Fig. 1, continued

```
ATOM   2913  N    VAL A 382     -24.629  14.873  -5.491  1.00 31.73           N
ATOM   2914  CA   VAL A 382     -24.129  15.685  -4.386  1.00 30.63           C
ATOM   2915  CB   VAL A 382     -23.360  14.822  -3.327  1.00 30.45           C
ATOM   2916  CG1  VAL A 382     -24.214  13.654  -2.847  1.00 32.12           C
ATOM   2917  CG2  VAL A 382     -22.039  14.285  -3.872  1.00 30.84           C
ATOM   2918  C    VAL A 382     -23.215  16.767  -4.943  1.00 29.19           C
ATOM   2919  O    VAL A 382     -22.640  16.616  -6.019  1.00 28.14           O
ATOM   2920  N    ILE A 383     -23.053  17.842  -4.193  1.00 28.20           N
ATOM   2921  CA   ILE A 383     -22.001  18.810  -4.490  1.00 28.34           C
ATOM   2922  CB   ILE A 383     -22.319  20.161  -3.841  1.00 28.68           C
ATOM   2923  CG1  ILE A 383     -23.633  20.707  -4.419  1.00 31.77           C
ATOM   2924  CD1  ILE A 383     -24.178  21.861  -3.639  1.00 34.81           C
ATOM   2925  CG2  ILE A 383     -21.165  21.173  -4.048  1.00 28.65           C
ATOM   2926  C    ILE A 383     -20.660  18.227  -4.015  1.00 27.49           C
ATOM   2927  O    ILE A 383     -20.467  17.974  -2.832  1.00 27.88           O
ATOM   2928  N    CYS A 384     -19.763  18.003  -4.961  1.00 26.31           N
ATOM   2929  CA   CYS A 384     -18.508  17.296  -4.728  1.00 26.08           C
ATOM   2930  CB   CYS A 384     -17.638  17.381  -5.976  1.00 26.07           C
ATOM   2931  SG   CYS A 384     -16.173  16.308  -5.978  1.00 27.49           S
ATOM   2932  C    CYS A 384     -17.740  17.843  -3.526  1.00 24.89           C
ATOM   2933  O    CYS A 384     -17.483  19.034  -3.461  1.00 25.18           O
ATOM   2934  N    GLY A 385     -17.423  16.979  -2.564  1.00 23.34           N
ATOM   2935  CA   GLY A 385     -16.505  17.321  -1.483  1.00 22.42           C
ATOM   2936  C    GLY A 385     -17.110  18.038  -0.294  1.00 22.22           C
ATOM   2937  O    GLY A 385     -16.402  18.410   0.628  1.00 22.36           O
ATOM   2938  N    THR A 386     -18.423  18.222  -0.284  1.00 22.16           N
ATOM   2939  CA   THR A 386     -19.080  18.873   0.845  1.00 22.63           C
ATOM   2940  CB   THR A 386     -20.610  19.025   0.524  1.00 22.97           C
ATOM   2941  OG1  THR A 386     -20.782  19.805  -0.676  1.00 24.56           O
ATOM   2942  CG2  THR A 386     -21.302  19.819   1.573  1.00 23.62           C
ATOM   2943  C    THR A 386     -18.864  18.004   2.091  1.00 22.23           C
ATOM   2944  O    THR A 386     -19.195  16.828   2.059  1.00 21.42           O
ATOM   2945  N    PRO A 387     -18.244  18.532   3.150  1.00 22.83           N
ATOM   2946  CA   PRO A 387     -17.920  17.703   4.319  1.00 22.48           C
ATOM   2947  CB   PRO A 387     -16.962  18.591   5.132  1.00 23.28           C
ATOM   2948  CG   PRO A 387     -17.302  20.017   4.737  1.00 22.70           C
ATOM   2949  CD   PRO A 387     -17.726  19.915   3.290  1.00 22.95           C
ATOM   2950  C    PRO A 387     -19.138  17.310   5.159  1.00 22.63           C
ATOM   2951  O    PRO A 387     -19.608  18.108   5.946  1.00 23.14           O
ATOM   2952  N    ILE A 388     -19.634  16.092   4.976  1.00 22.52           N
ATOM   2953  CA   ILE A 388     -20.822  15.603   5.670  1.00 22.05           C
ATOM   2954  CB   ILE A 388     -22.012  15.447   4.665  1.00 23.53           C
ATOM   2955  CG1  ILE A 388     -22.379  16.802   4.031  1.00 24.92           C
ATOM   2956  CD1  ILE A 388     -23.208  16.678   2.787  1.00 27.24           C
ATOM   2957  CG2  ILE A 388     -23.239  14.857   5.374  1.00 23.73           C
ATOM   2958  C    ILE A 388     -20.555  14.255   6.362  1.00 20.72           C
ATOM   2959  O    ILE A 388     -20.343  13.229   5.701  1.00 19.84           O
ATOM   2960  N    PRO A 389     -20.583  14.238   7.685  1.00 19.41           N
ATOM   2961  CA   PRO A 389     -20.468  12.965   8.397  1.00 19.22           C
ATOM   2962  CB   PRO A 389     -20.523  13.360   9.879  1.00 19.95           C
ATOM   2963  CG   PRO A 389     -20.308  14.898   9.930  1.00 21.12           C
ATOM   2964  CD   PRO A 389     -20.706  15.413   8.576  1.00 19.86           C
ATOM   2965  C    PRO A 389     -21.600  11.962   8.009  1.00 19.47           C
ATOM   2966  O    PRO A 389     -22.786  12.263   8.199  1.00 18.20           O
```

Fig. 1, continued

```
ATOM   2967  N    ALA A 390     -21.234  10.809   7.442  1.00 18.48           N
ATOM   2968  CA   ALA A 390     -22.227   9.797   7.051  1.00 18.90           C
ATOM   2969  CB   ALA A 390     -21.729   8.983   5.882  1.00 18.08           C
ATOM   2970  C    ALA A 390     -22.559   8.893   8.256  1.00 20.26           C
ATOM   2971  O    ALA A 390     -21.651   8.269   8.839  1.00 20.18           O
ATOM   2972  N    ILE A 391     -23.839   8.870   8.649  1.00 20.42           N
ATOM   2973  CA   ILE A 391     -24.306   8.174   9.847  1.00 22.00           C
ATOM   2974  CB   ILE A 391     -24.931   9.173  10.884  1.00 22.73           C
ATOM   2975  CG1  ILE A 391     -24.065  10.420  11.113  1.00 23.95           C
ATOM   2976  CD1  ILE A 391     -22.843  10.206  11.833  1.00 25.88           C
ATOM   2977  CG2  ILE A 391     -25.274   8.462  12.205  1.00 22.84           C
ATOM   2978  C    ILE A 391     -25.413   7.158   9.462  1.00 22.02           C
ATOM   2979  O    ILE A 391     -26.458   7.525   8.898  1.00 21.18           O
ATOM   2980  N    ALA A 392     -25.161   5.899   9.777  1.00 21.78           N
ATOM   2981  CA   ALA A 392     -26.096   4.814   9.524  1.00 21.75           C
ATOM   2982  CB   ALA A 392     -25.535   3.538  10.065  1.00 21.59           C
ATOM   2983  C    ALA A 392     -27.414   5.117  10.212  1.00 21.47           C
ATOM   2984  O    ALA A 392     -27.430   5.480  11.368  1.00 20.96           O
ATOM   2985  N    GLY A 393     -28.495   4.986   9.472  1.00 22.59           N
ATOM   2986  CA   GLY A 393     -29.835   5.274   9.955  1.00 23.14           C
ATOM   2987  C    GLY A 393     -30.288   6.694   9.723  1.00 23.74           C
ATOM   2988  O    GLY A 393     -31.461   6.964   9.841  1.00 24.14           O
ATOM   2989  N    ILE A 394     -29.365   7.610   9.433  1.00 23.83           N
ATOM   2990  CA   ILE A 394     -29.712   9.008   9.159  1.00 24.07           C
ATOM   2991  CB   ILE A 394     -28.910   9.952  10.048  1.00 24.36           C
ATOM   2992  CG1  ILE A 394     -29.235   9.660  11.513  1.00 26.85           C
ATOM   2993  CD1  ILE A 394     -28.381  10.425  12.477  1.00 29.96           C
ATOM   2994  CG2  ILE A 394     -29.256  11.413   9.727  1.00 25.23           C
ATOM   2995  C    ILE A 394     -29.496   9.350   7.693  1.00 23.12           C
ATOM   2996  O    ILE A 394     -30.443   9.712   7.012  1.00 22.82           O
ATOM   2997  N    THR A 395     -28.251   9.238   7.219  1.00 22.00           N
ATOM   2998  CA   THR A 395     -27.931   9.484   5.820  1.00 20.93           C
ATOM   2999  CB   THR A 395     -26.561  10.180   5.683  1.00 21.81           C
ATOM   3000  OG1  THR A 395     -25.501   9.339   6.196  1.00 20.44           O
ATOM   3001  CG2  THR A 395     -26.506  11.446   6.497  1.00 21.70           C
ATOM   3002  C    THR A 395     -27.950   8.226   4.985  1.00 20.59           C
ATOM   3003  O    THR A 395     -27.730   8.273   3.765  1.00 20.10           O
ATOM   3004  N    THR A 396     -28.176   7.091   5.638  1.00 20.18           N
ATOM   3005  CA   THR A 396     -28.376   5.822   4.953  1.00 20.41           C
ATOM   3006  CB   THR A 396     -27.099   4.913   5.037  1.00 20.05           C
ATOM   3007  OG1  THR A 396     -26.981   4.344   6.357  1.00 20.29           O
ATOM   3008  CG2  THR A 396     -25.820   5.694   4.808  1.00 20.70           C
ATOM   3009  C    THR A 396     -29.515   5.088   5.634  1.00 20.61           C
ATOM   3010  O    THR A 396     -29.919   5.472   6.716  1.00 21.82           O
ATOM   3011  N    PRO A 397     -29.976   3.980   5.079  1.00 21.69           N
ATOM   3012  CA   PRO A 397     -30.822   3.080   5.871  1.00 22.41           C
ATOM   3013  CB   PRO A 397     -31.188   1.964   4.877  1.00 22.36           C
ATOM   3014  CG   PRO A 397     -31.052   2.616   3.546  1.00 22.97           C
ATOM   3015  CD   PRO A 397     -29.796   3.489   3.698  1.00 21.75           C
ATOM   3016  C    PRO A 397     -30.061   2.527   7.088  1.00 23.16           C
ATOM   3017  O    PRO A 397     -28.813   2.634   7.174  1.00 23.00           O
ATOM   3018  N    SER A 398     -30.800   1.923   8.011  1.00 23.03           N
ATOM   3019  CA   SER A 398     -30.201   1.357   9.209  1.00 23.12           C
ATOM   3020  CB   SER A 398     -31.283   0.798  10.136  1.00 22.95           C
```

Fig. 1, continued

```
ATOM   3021  OG   SER A 398     -31.714   -0.456    9.649  1.00 24.30           O
ATOM   3022  C    SER A 398     -29.208    0.241    8.857  1.00 22.77           C
ATOM   3023  O    SER A 398     -29.228   -0.309    7.745  1.00 21.47           O
ATOM   3024  N    ALA A 399     -28.335   -0.062    9.806  1.00 23.01           N
ATOM   3025  CA   ALA A 399     -27.367   -1.144    9.652  1.00 23.75           C
ATOM   3026  CB   ALA A 399     -26.518   -1.275   10.914  1.00 23.61           C
ATOM   3027  C    ALA A 399     -28.049   -2.485    9.300  1.00 24.08           C
ATOM   3028  O    ALA A 399     -27.561   -3.221    8.431  1.00 24.12           O
ATOM   3029  N    ASP A 400     -29.184   -2.774    9.934  1.00 24.17           N
ATOM   3030  CA   ASP A 400     -29.949   -4.003    9.666  1.00 24.96           C
ATOM   3031  CB   ASP A 400     -31.185   -4.135   10.586  1.00 25.53           C
ATOM   3032  CG   ASP A 400     -30.846   -4.584   11.993  1.00 28.76           C
ATOM   3033  OD1  ASP A 400     -29.684   -4.900   12.295  1.00 28.78           O
ATOM   3034  OD2  ASP A 400     -31.723   -4.643   12.889  1.00 36.21           O
ATOM   3035  C    ASP A 400     -30.471   -4.031    8.250  1.00 25.08           C
ATOM   3036  O    ASP A 400     -30.465   -5.075    7.624  1.00 25.51           O
ATOM   3037  N    GLN A 401     -30.982   -2.905    7.767  1.00 25.31           N
ATOM   3038  CA   GLN A 401     -31.506   -2.825    6.402  1.00 25.87           C
ATOM   3039  CB   GLN A 401     -32.298   -1.525    6.182  1.00 26.63           C
ATOM   3040  CG   GLN A 401     -33.556   -1.362    7.074  1.00 30.14           C
ATOM   3041  CD   GLN A 401     -34.258    0.022    6.906  1.00 36.20           C
ATOM   3042  OE1  GLN A 401     -33.654    1.098    7.148  1.00 36.97           O
ATOM   3043  NE2  GLN A 401     -35.535   -0.015    6.498  1.00 38.04           N
ATOM   3044  C    GLN A 401     -30.382   -2.925    5.375  1.00 25.12           C
ATOM   3045  O    GLN A 401     -30.546   -3.555    4.343  1.00 25.05           O
ATOM   3046  N    VAL A 402     -29.233   -2.303    5.649  1.00 23.60           N
ATOM   3047  CA   VAL A 402     -28.148   -2.319    4.686  1.00 22.44           C
ATOM   3048  CB   VAL A 402     -27.081   -1.238    4.974  1.00 22.00           C
ATOM   3049  CG1  VAL A 402     -25.842   -1.453    4.096  1.00 19.92           C
ATOM   3050  CG2  VAL A 402     -27.668    0.125    4.742  1.00 22.30           C
ATOM   3051  C    VAL A 402     -27.468   -3.675    4.676  1.00 22.04           C
ATOM   3052  O    VAL A 402     -27.215   -4.206    3.637  1.00 22.00           O
ATOM   3053  N    LEU A 403     -27.141   -4.194    5.851  1.00 22.57           N
ATOM   3054  CA   LEU A 403     -26.348   -5.404    5.976  1.00 23.07           C
ATOM   3055  CB   LEU A 403     -25.413   -5.286    7.185  1.00 22.45           C
ATOM   3056  CG   LEU A 403     -24.521   -4.057    7.264  1.00 23.92           C
ATOM   3057  CD1  LEU A 403     -23.792   -4.094    8.612  1.00 23.88           C
ATOM   3058  CD2  LEU A 403     -23.545   -4.053    6.110  1.00 24.28           C
ATOM   3059  C    LEU A 403     -27.144   -6.705    6.145  1.00 23.40           C
ATOM   3060  O    LEU A 403     -26.582   -7.781    5.973  1.00 23.40           O
ATOM   3061  N    GLY A 404     -28.427   -6.607    6.500  1.00 24.30           N
ATOM   3062  CA   GLY A 404     -29.163   -7.732    7.078  1.00 25.22           C
ATOM   3063  C    GLY A 404     -28.783   -7.885    8.563  1.00 26.41           C
ATOM   3064  O    GLY A 404     -27.674   -7.489    8.970  1.00 26.28           O
ATOM   3065  N    SER A 405     -29.675   -8.477    9.361  1.00 26.97           N
ATOM   3066  CA   SER A 405     -29.491   -8.625   10.823  1.00 28.40           C
ATOM   3067  CB   SER A 405     -30.657   -9.410   11.469  1.00 28.82           C
ATOM   3068  OG   SER A 405     -31.883   -8.874   11.059  1.00 34.02           O
ATOM   3069  C    SER A 405     -28.249   -9.367   11.246  1.00 27.19           C
ATOM   3070  O    SER A 405     -27.653   -9.023   12.241  1.00 27.66           O
ATOM   3071  N    ASP A 406     -27.946  -10.458   10.559  1.00 26.47           N
ATOM   3072  CA   ASP A 406     -26.831  -11.327   10.930  1.00 25.86           C
ATOM   3073  CB   ASP A 406     -26.807  -12.521    9.959  0.50 26.51           C
ATOM   3074  CG   ASP A 406     -25.869  -13.644   10.385  0.50 27.69           C
```

Fig. 1, continued

```
ATOM   3075  OD1 ASP A 406     -24.846 -13.392  11.051  0.50 29.76           O
ATOM   3076  OD2 ASP A 406     -26.087 -14.842  10.074  0.50 31.26           O
ATOM   3077  C   ASP A 406     -25.494 -10.554  10.842  1.00 24.81           C
ATOM   3078  O   ASP A 406     -24.691 -10.588  11.761  1.00 24.93           O
ATOM   3079  N   LEU A 407     -25.260  -9.872   9.728  1.00 23.25           N
ATOM   3080  CA  LEU A 407     -24.010  -9.136   9.538  1.00 22.19           C
ATOM   3081  CB  LEU A 407     -23.777  -8.816   8.054  1.00 22.13           C
ATOM   3082  CG  LEU A 407     -23.311 -10.017   7.220  1.00 21.94           C
ATOM   3083  CD1 LEU A 407     -23.487  -9.785   5.738  1.00 22.08           C
ATOM   3084  CD2 LEU A 407     -21.889 -10.364   7.502  1.00 22.28           C
ATOM   3085  C   LEU A 407     -23.957  -7.873  10.400  1.00 21.15           C
ATOM   3086  O   LEU A 407     -22.888  -7.475  10.842  1.00 20.03           O
ATOM   3087  N   ALA A 408     -25.105  -7.248  10.627  1.00 20.68           N
ATOM   3088  CA  ALA A 408     -25.199  -6.101  11.513  1.00 21.08           C
ATOM   3089  CB  ALA A 408     -26.608  -5.438  11.424  1.00 21.41           C
ATOM   3090  C   ALA A 408     -24.886  -6.504  12.952  1.00 21.40           C
ATOM   3091  O   ALA A 408     -24.220  -5.766  13.674  1.00 21.40           O
ATOM   3092  N   ASN A 409     -25.333  -7.687  13.365  1.00 22.07           N
ATOM   3093  CA  ASN A 409     -24.996  -8.191  14.688  1.00 22.29           C
ATOM   3094  CB  ASN A 409     -25.855  -9.416  15.061  1.00 23.84           C
ATOM   3095  CG  ASN A 409     -27.289  -9.030  15.454  1.00 26.03           C
ATOM   3096  OD1 ASN A 409     -27.541  -7.929  15.953  1.00 30.25           O
ATOM   3097  ND2 ASN A 409     -28.223  -9.920  15.199  1.00 29.18           N
ATOM   3098  C   ASN A 409     -23.512  -8.519  14.760  1.00 21.82           C
ATOM   3099  O   ASN A 409     -22.900  -8.296  15.796  1.00 21.60           O
ATOM   3100  N   GLN A 410     -22.899  -8.983  13.667  1.00 21.36           N
ATOM   3101  CA  GLN A 410     -21.446  -9.212  13.700  1.00 22.08           C
ATOM   3102  CB  GLN A 410     -20.949 -10.000  12.502  1.00 22.89           C
ATOM   3103  CG  GLN A 410     -21.420 -11.431  12.490  1.00 27.18           C
ATOM   3104  CD  GLN A 410     -21.133 -12.102  11.167  1.00 31.79           C
ATOM   3105  OE1 GLN A 410     -20.022 -11.987  10.640  1.00 33.06           O
ATOM   3106  NE2 GLN A 410     -22.139 -12.788  10.614  1.00 33.90           N
ATOM   3107  C   GLN A 410     -20.680  -7.902  13.829  1.00 21.01           C
ATOM   3108  O   GLN A 410     -19.678  -7.835  14.551  1.00 20.76           O
ATOM   3109  N   LEU A 411     -21.161  -6.869  13.153  1.00 20.63           N
ATOM   3110  CA  LEU A 411     -20.545  -5.535  13.227  1.00 20.74           C
ATOM   3111  CB  LEU A 411     -21.178  -4.587  12.209  1.00 20.91           C
ATOM   3112  CG  LEU A 411     -20.540  -3.205  12.119  1.00 20.24           C
ATOM   3113  CD1 LEU A 411     -19.065  -3.343  11.870  1.00 20.72           C
ATOM   3114  CD2 LEU A 411     -21.220  -2.378  11.002  1.00 20.71           C
ATOM   3115  C   LEU A 411     -20.663  -4.944  14.632  1.00 21.23           C
ATOM   3116  O   LEU A 411     -19.691  -4.415  15.187  1.00 20.65           O
ATOM   3117  N   ARG A 412     -21.851  -5.052  15.212  1.00 21.55           N
ATOM   3118  CA  ARG A 412     -22.034  -4.679  16.617  1.00 22.71           C
ATOM   3119  CB  ARG A 412     -23.464  -4.952  17.054  1.00 22.93           C
ATOM   3120  CG  ARG A 412     -24.452  -3.973  16.517  1.00 24.29           C
ATOM   3121  CD  ARG A 412     -25.911  -4.301  16.891  1.00 27.52           C
ATOM   3122  NE  ARG A 412     -26.779  -3.501  16.030  1.00 31.14           N
ATOM   3123  CZ  ARG A 412     -27.560  -3.967  15.069  1.00 30.64           C
ATOM   3124  NH1 ARG A 412     -27.696  -5.266  14.839  1.00 31.09           N
ATOM   3125  NH2 ARG A 412     -28.242  -3.097  14.353  1.00 34.20           N
ATOM   3126  C   ARG A 412     -21.088  -5.389  17.590  1.00 22.25           C
ATOM   3127  O   ARG A 412     -20.622  -4.781  18.554  1.00 21.95           O
ATOM   3128  N   SER A 413     -20.790  -6.666  17.334  1.00 22.94           N
```

Fig. 1, continued

```
ATOM   3129  CA   SER A 413     -19.904   -7.422   18.232  1.00 23.17           C
ATOM   3130  CB   SER A 413     -20.000   -8.940   17.988  0.65 23.45           C
ATOM   3131  OG   SER A 413     -19.474   -9.312   16.722  0.65 24.53           O
ATOM   3132  C    SER A 413     -18.437   -6.952   18.164  1.00 23.08           C
ATOM   3133  O    SER A 413     -17.656   -7.296   19.035  1.00 22.78           O
ATOM   3134  N    LEU A 414     -18.063   -6.142   17.167  1.00 22.79           N
ATOM   3135  CA   LEU A 414     -16.710   -5.549   17.147  1.00 22.82           C
ATOM   3136  CB   LEU A 414     -16.367   -4.999   15.760  1.00 22.69           C
ATOM   3137  CG   LEU A 414     -16.310   -6.041   14.642  1.00 24.38           C
ATOM   3138  CD1  LEU A 414     -15.886   -5.387   13.334  1.00 23.31           C
ATOM   3139  CD2  LEU A 414     -15.347   -7.153   15.057  1.00 25.08           C
ATOM   3140  C    LEU A 414     -16.511   -4.427   18.156  1.00 22.61           C
ATOM   3141  O    LEU A 414     -15.386   -4.062   18.442  1.00 22.47           O
ATOM   3142  N    ASP A 415     -17.599   -3.862   18.649  1.00 22.35           N
ATOM   3143  CA   ASP A 415     -17.541   -2.732   19.549  1.00 23.50           C
ATOM   3144  CB   ASP A 415     -18.960   -2.245   19.874  1.00 23.21           C
ATOM   3145  CG   ASP A 415     -18.970   -0.965   20.684  1.00 23.17           C
ATOM   3146  OD1  ASP A 415     -20.063   -0.533   21.113  1.00 25.06           O
ATOM   3147  OD2  ASP A 415     -17.946   -0.300   20.913  1.00 22.44           O
ATOM   3148  C    ASP A 415     -16.807   -3.127   20.839  1.00 24.26           C
ATOM   3149  O    ASP A 415     -17.209   -4.033   21.518  1.00 23.82           O
ATOM   3150  N    GLY A 416     -15.710   -2.442   21.135  1.00 25.50           N
ATOM   3151  CA   GLY A 416     -14.866   -2.776   22.271  1.00 26.47           C
ATOM   3152  C    GLY A 416     -13.826   -3.865   22.003  1.00 27.16           C
ATOM   3153  O    GLY A 416     -13.018   -4.111   22.870  1.00 27.34           O
ATOM   3154  N    LYS A 417     -13.855   -4.554   20.859  1.00 27.32           N
ATOM   3155  CA   LYS A 417     -12.831   -5.577   20.582  1.00 27.91           C
ATOM   3156  CB   LYS A 417     -13.297   -6.614   19.556  1.00 28.86           C
ATOM   3157  CG   LYS A 417     -14.613   -7.285   19.847  1.00 34.49           C
ATOM   3158  CD   LYS A 417     -14.476   -8.480   20.758  1.00 40.96           C
ATOM   3159  CE   LYS A 417     -15.844   -8.974   21.251  1.00 43.76           C
ATOM   3160  NZ   LYS A 417     -15.781   -9.188   22.735  1.00 48.33           N
ATOM   3161  C    LYS A 417     -11.551   -4.941   20.052  1.00 26.99           C
ATOM   3162  O    LYS A 417     -11.607   -3.924   19.361  1.00 26.53           O
ATOM   3163  N    GLN A 418     -10.407   -5.557   20.350  1.00 26.79           N
ATOM   3164  CA   GLN A 418      -9.111   -5.088   19.865  1.00 27.20           C
ATOM   3165  CB   GLN A 418      -7.947   -5.786   20.596  0.65 27.76           C
ATOM   3166  CG   GLN A 418      -7.661   -5.203   22.004  0.65 30.87           C
ATOM   3167  CD   GLN A 418      -7.390   -3.681   22.017  0.65 34.53           C
ATOM   3168  OE1  GLN A 418      -7.773   -2.982   22.972  0.65 36.04           O
ATOM   3169  NE2  GLN A 418      -6.727   -3.176   20.968  0.65 34.09           N
ATOM   3170  C    GLN A 418      -8.980   -5.245   18.355  1.00 25.80           C
ATOM   3171  O    GLN A 418      -9.298   -6.281   17.804  1.00 25.73           O
ATOM   3172  N    SER A 419      -8.473   -4.211   17.706  1.00 24.27           N
ATOM   3173  CA   SER A 419      -8.187   -4.256   16.282  1.00 23.53           C
ATOM   3174  CB   SER A 419      -8.260   -2.847   15.681  1.00 23.29           C
ATOM   3175  OG   SER A 419      -7.194   -2.040   16.181  1.00 22.14           O
ATOM   3176  C    SER A 419      -6.769   -4.792   16.094  1.00 23.48           C
ATOM   3177  O    SER A 419      -6.055   -5.029   17.053  1.00 22.42           O
ATOM   3178  N    ALA A 420      -6.361   -4.905   14.841  1.00 24.25           N
ATOM   3179  CA   ALA A 420      -4.985   -5.267   14.483  1.00 25.40           C
ATOM   3180  CB   ALA A 420      -4.885   -5.423   12.950  1.00 25.46           C
ATOM   3181  C    ALA A 420      -3.988   -4.235   14.974  1.00 25.41           C
ATOM   3182  O    ALA A 420      -2.828   -4.541   15.209  1.00 27.29           O
```

Fig. 1, continued

```
ATOM   3183  N    PHE A 421      -4.433  -3.009  15.153  1.00 25.58           N
ATOM   3184  CA   PHE A 421      -3.562  -1.932  15.601  1.00 25.99           C
ATOM   3185  CB   PHE A 421      -4.057  -0.594  15.037  1.00 26.21           C
ATOM   3186  CG   PHE A 421      -4.083  -0.540  13.559  1.00 27.81           C
ATOM   3187  CD1  PHE A 421      -3.018  -0.020  12.861  1.00 31.19           C
ATOM   3188  CE1  PHE A 421      -3.040   0.032  11.448  1.00 33.17           C
ATOM   3189  CZ   PHE A 421      -4.114  -0.446  10.767  1.00 31.30           C
ATOM   3190  CE2  PHE A 421      -5.192  -0.975  11.460  1.00 33.82           C
ATOM   3191  CD2  PHE A 421      -5.175  -1.026  12.850  1.00 32.15           C
ATOM   3192  C    PHE A 421      -3.484  -1.813  17.126  1.00 26.11           C
ATOM   3193  O    PHE A 421      -2.870  -0.884  17.632  1.00 26.69           O
ATOM   3194  N    GLY A 422      -4.123  -2.706  17.864  1.00 26.66           N
ATOM   3195  CA   GLY A 422      -4.038  -2.662  19.322  1.00 27.34           C
ATOM   3196  C    GLY A 422      -4.918  -1.587  19.961  1.00 28.33           C
ATOM   3197  O    GLY A 422      -4.740  -1.272  21.147  1.00 31.32           O
ATOM   3198  N    LYS A 423      -5.802  -0.971  19.185  1.00 26.86           N
ATOM   3199  CA   LYS A 423      -6.795  -0.047  19.705  1.00 26.62           C
ATOM   3200  CB   LYS A 423      -6.636   1.320  19.064  1.00 26.92           C
ATOM   3201  CG   LYS A 423      -5.426   2.126  19.545  1.00 28.63           C
ATOM   3202  CD   LYS A 423      -5.559   3.541  19.064  1.00 30.07           C
ATOM   3203  CE   LYS A 423      -4.753   4.541  19.810  1.00 30.29           C
ATOM   3204  NZ   LYS A 423      -5.407   5.878  19.754  1.00 27.46           N
ATOM   3205  C    LYS A 423      -8.170  -0.622  19.374  1.00 26.10           C
ATOM   3206  O    LYS A 423      -8.333  -1.301  18.359  1.00 25.25           O
ATOM   3207  N    PRO A 424      -9.149  -0.398  20.241  1.00 25.97           N
ATOM   3208  CA   PRO A 424     -10.476  -1.000  20.056  1.00 25.45           C
ATOM   3209  CB   PRO A 424     -11.117  -0.869  21.454  1.00 25.67           C
ATOM   3210  CG   PRO A 424     -10.518   0.360  22.022  1.00 27.01           C
ATOM   3211  CD   PRO A 424      -9.068   0.380  21.502  1.00 26.86           C
ATOM   3212  C    PRO A 424     -11.351  -0.355  18.993  1.00 23.92           C
ATOM   3213  O    PRO A 424     -11.305   0.827  18.776  1.00 23.84           O
ATOM   3214  N    PHE A 425     -12.156  -1.164  18.327  1.00 23.02           N
ATOM   3215  CA   PHE A 425     -13.263  -0.661  17.549  1.00 22.49           C
ATOM   3216  CB   PHE A 425     -13.903  -1.785  16.743  1.00 22.42           C
ATOM   3217  CG   PHE A 425     -12.978  -2.435  15.758  1.00 22.00           C
ATOM   3218  CD1  PHE A 425     -12.563  -3.749  15.938  1.00 22.39           C
ATOM   3219  CE1  PHE A 425     -11.700  -4.363  15.011  1.00 22.16           C
ATOM   3220  CZ   PHE A 425     -11.268  -3.653  13.893  1.00 21.91           C
ATOM   3221  CE2  PHE A 425     -11.666  -2.343  13.717  1.00 22.19           C
ATOM   3222  CD2  PHE A 425     -12.529  -1.738  14.645  1.00 22.24           C
ATOM   3223  C    PHE A 425     -14.319  -0.059  18.477  1.00 22.24           C
ATOM   3224  O    PHE A 425     -14.380  -0.378  19.684  1.00 22.05           O
ATOM   3225  N    GLY A 426     -15.171   0.781  17.905  1.00 21.25           N
ATOM   3226  CA   GLY A 426     -16.297   1.351  18.611  1.00 20.33           C
ATOM   3227  C    GLY A 426     -17.644   0.928  18.029  1.00 19.87           C
ATOM   3228  O    GLY A 426     -17.757  -0.071  17.320  1.00 19.66           O
ATOM   3229  N    PRO A 427     -18.675   1.711  18.316  1.00 19.05           N
ATOM   3230  CA   PRO A 427     -20.027   1.425  17.828  1.00 19.31           C
ATOM   3231  CB   PRO A 427     -20.914   2.244  18.779  1.00 19.31           C
ATOM   3232  CG   PRO A 427     -20.079   3.395  19.210  1.00 19.38           C
ATOM   3233  CD   PRO A 427     -18.620   2.940  19.118  1.00 19.45           C
ATOM   3234  C    PRO A 427     -20.236   1.854  16.357  1.00 19.72           C
ATOM   3235  O    PRO A 427     -19.380   2.509  15.747  1.00 18.20           O
ATOM   3236  N    ILE A 428     -21.387   1.478  15.816  1.00 20.45           N
```

Fig. 1, continued

```
ATOM   3237  CA   ILE A 428     -21.748    1.767   14.423  1.00 21.79           C
ATOM   3238  CB   ILE A 428     -22.978    0.914   14.033  1.00 21.74           C
ATOM   3239  CG1  ILE A 428     -22.551   -0.544   13.931  1.00 21.64           C
ATOM   3240  CD1  ILE A 428     -23.714   -1.520   13.897  1.00 22.58           C
ATOM   3241  CG2  ILE A 428     -23.614    1.413   12.709  1.00 21.03           C
ATOM   3242  C    ILE A 428     -21.970    3.289   14.133  1.00 22.67           C
ATOM   3243  O    ILE A 428     -21.656    3.780   13.040  1.00 21.73           O
ATOM   3244  N    THR A 429     -22.477    4.020   15.117  1.00 23.75           N
ATOM   3245  CA   THR A 429     -22.669    5.471   14.996  1.00 25.11           C
ATOM   3246  CB   THR A 429     -24.168    5.848   15.010  1.00 24.85           C
ATOM   3247  OG1  THR A 429     -24.796    5.293   16.164  1.00 24.15           O
ATOM   3248  CG2  THR A 429     -24.897    5.220   13.852  1.00 25.72           C
ATOM   3249  C    THR A 429     -21.979    6.208   16.139  1.00 26.74           C
ATOM   3250  O    THR A 429     -21.874    5.685   17.231  1.00 25.18           O
ATOM   3251  N    PRO A 430     -21.480    7.408   15.882  1.00 29.68           N
ATOM   3252  CA   PRO A 430     -20.854    8.203   16.943  1.00 32.70           C
ATOM   3253  CB   PRO A 430     -20.466    9.490   16.238  1.00 32.22           C
ATOM   3254  CG   PRO A 430     -20.309    9.092   14.810  1.00 31.28           C
ATOM   3255  CD   PRO A 430     -21.389    8.067   14.572  1.00 30.40           C
ATOM   3256  C    PRO A 430     -21.817    8.453   18.124  1.00 35.74           C
ATOM   3257  O    PRO A 430     -22.968    8.793   17.883  1.00 35.50           O
ATOM   3258  N    PRO A 431     -21.384    8.165   19.355  1.00 39.00           N
ATOM   3259  CA   PRO A 431     -22.204    8.447   20.545  1.00 41.17           C
ATOM   3260  CB   PRO A 431     -21.233    8.225   21.720  1.00 41.30           C
ATOM   3261  CG   PRO A 431     -20.131    7.304   21.175  1.00 40.41           C
ATOM   3262  CD   PRO A 431     -20.107    7.497   19.695  1.00 38.73           C
ATOM   3263  C    PRO A 431     -22.752    9.886   20.567  1.00 42.89           C
ATOM   3264  O    PRO A 431     -22.062   10.839   20.135  1.00 44.56           O
ATOM   3265  OXT  PRO A 431     -23.901   10.088   21.000  1.00 43.72           O
ATOM   3266  O1   MYR D 471      -2.485    1.762    8.151  1.00 45.83           O
ATOM   3267  C1   MYR D 471      -1.474    2.308    7.326  1.00 46.46           C
ATOM   3268  O2   MYR D 471      -1.389    1.952    6.068  1.00 49.79           O
ATOM   3269  C2   MYR D 471      -0.479    3.295    7.853  1.00 45.74           C
ATOM   3270  C3   MYR D 471       0.154    4.056    6.690  1.00 43.98           C
ATOM   3271  C4   MYR D 471       1.656    3.953    6.790  1.00 42.98           C
ATOM   3272  C5   MYR D 471       2.324    4.475    5.537  1.00 42.81           C
ATOM   3273  C6   MYR D 471       3.738    4.943    5.839  1.00 41.11           C
ATOM   3274  C7   MYR D 471       4.317    5.590    4.593  1.00 41.91           C
ATOM   3275  C8   MYR D 471       5.768    5.946    4.825  1.00 41.38           C
ATOM   3276  C9   MYR D 471       6.461    6.300    3.517  1.00 42.57           C
ATOM   3277  C10  MYR D 471       7.964    6.344    3.726  1.00 43.67           C
ATOM   3278  C11  MYR D 471       8.684    7.510    3.051  1.00 45.72           C
ATOM   3279  C12  MYR D 471      10.164    7.322    3.396  1.00 47.13           C
ATOM   3280  C13  MYR D 471      11.111    8.451    3.053  1.00 47.97           C
ATOM   3281  C14  MYR D 471      12.427    8.350    3.840  1.00 48.54           C
ATOM   3282  O    HOH W 501     -28.349    1.588   12.399  1.00 28.37           O
ATOM   3283  O    HOH W 502       0.197   -8.238   -1.012  1.00 16.70           O
ATOM   3284  O    HOH W 506     -15.041   10.937   -8.948  1.00 18.06           O
ATOM   3285  O    HOH W 507      -0.868   -2.943    2.692  1.00 19.13           O
ATOM   3286  O    HOH W 508     -19.852   -1.879   16.461  1.00 18.83           O
ATOM   3287  O    HOH W 509       3.500   15.763    8.934  1.00 18.58           O
ATOM   3288  O    HOH W 511      -9.925    7.852    9.335  1.00 13.03           O
ATOM   3289  O    HOH W 515     -22.487  -10.783  -10.101  1.00 21.53           O
ATOM   3290  O    HOH W 518      -2.406  -12.104   12.902  1.00 21.34           O
```

Fig. 1, continued

```
ATOM   3291  O   HOH W 520     -13.588  -0.793   4.886  1.00 20.72           O
ATOM   3292  O   HOH W 521       5.219   2.075  -6.441  1.00 20.16           O
ATOM   3293  O   HOH W 523     -11.199   1.871 -15.861  1.00 19.38           O
ATOM   3294  O   HOH W 524      -1.524 -19.182   0.197  1.00 14.68           O
ATOM   3295  O   HOH W 528      -8.042  -6.705  -7.274  1.00 18.24           O
ATOM   3296  O   HOH W 530      -5.831  -6.480  -0.969  1.00 18.91           O
ATOM   3297  O   HOH W 532     -21.235  11.876   3.623  1.00 19.46           O
ATOM   3298  O   HOH W 534     -20.517  10.394  -5.161  1.00 18.83           O
ATOM   3299  O   HOH W 535      -8.309   4.618  16.860  1.00 19.12           O
ATOM   3300  O   HOH W 536     -10.573   7.193  -5.196  1.00 20.32           O
ATOM   3301  O   HOH W 538      -9.781 -21.059  10.087  1.00 23.88           O
ATOM   3302  O   HOH W 539      14.650  -2.719  -4.664  1.00 25.62           O
ATOM   3303  O   HOH W 541     -26.840 -10.205   7.148  1.00 24.88           O
ATOM   3304  O   HOH W 542      -0.989  -0.284   1.455  1.00 21.35           O
ATOM   3305  O   HOH W 546     -19.937  10.304 -11.645  1.00 23.13           O
ATOM   3306  O   HOH W 547      -5.754  13.742  11.626  1.00 14.43           O
ATOM   3307  O   HOH W 548       9.779  15.109  -2.032  1.00 22.88           O
ATOM   3308  O   HOH W 550     -24.247   8.658   3.546  1.00 21.94           O
ATOM   3309  O   HOH W 553     -18.270 -13.589   5.954  1.00 21.98           O
ATOM   3310  O   HOH W 556     -21.317   2.003  10.047  1.00 18.58           O
ATOM   3311  O   HOH W 559      11.753 -22.111   1.503  1.00 29.18           O
ATOM   3312  O   HOH W 560      -5.207  15.339  -6.701  1.00 19.52           O
ATOM   3313  O   HOH W 561      -6.366  10.247  -8.194  1.00 21.99           O
ATOM   3314  O   HOH W 562     -17.961  12.151  14.423  1.00 20.33           O
ATOM   3315  O   HOH W 566     -24.606   7.311  -0.615  1.00 24.02           O
ATOM   3316  O   HOH W 570       8.701 -11.444  -8.979  1.00 27.59           O
ATOM   3317  O   HOH W 572       2.242 -10.147  -1.384  1.00 15.71           O
ATOM   3318  O   HOH W 573       2.473 -22.504   8.845  1.00 21.54           O
ATOM   3319  O   HOH W 574     -13.333   7.592  18.897  1.00 34.30           O
ATOM   3320  O   HOH W 575     -29.839 -11.526   7.920  1.00 36.34           O
ATOM   3321  O   HOH W 576       4.728  -9.265  -7.678  1.00 17.96           O
ATOM   3322  O   HOH W 577      -1.154  10.944   3.561  1.00 18.41           O
ATOM   3323  O   HOH W 579      -5.959  -9.830 -19.229  1.00 25.29           O
ATOM   3324  O   HOH W 580      -8.159   6.920 -13.153  1.00 18.81           O
ATOM   3325  O   HOH W 582     -11.148 -14.689   6.998  1.00 20.51           O
ATOM   3326  O   HOH W 583       9.602 -23.925  -4.181  1.00 30.46           O
ATOM   3327  O   HOH W 585       9.864 -12.700  12.062  1.00 32.83           O
ATOM   3328  O   HOH W 587     -24.521  14.027   9.439  1.00 20.48           O
ATOM   3329  O   HOH W 590       5.470  15.782   5.128  1.00 25.65           O
ATOM   3330  O   HOH W 591     -26.490  -4.252  -6.390  1.00 31.69           O
ATOM   3331  O   HOH W 592     -24.093   1.094 -12.138  1.00 32.78           O
ATOM   3332  O   HOH W 593     -20.242  15.468  -6.878  1.00 30.83           O
ATOM   3333  O   HOH W 595       3.063   7.318  15.295  1.00 19.29           O
ATOM   3334  O   HOH W 597       4.881  11.595  -0.961  1.00 18.82           O
ATOM   3335  O   HOH W 598       0.818 -20.767   0.155  1.00 18.27           O
ATOM   3336  O   HOH W 599      -9.905   9.234   3.489  1.00 18.72           O
ATOM   3337  O   HOH W 600     -23.094   9.958  -4.480  1.00 21.50           O
ATOM   3338  O   HOH W 601     -13.103  18.153  15.208  1.00 29.33           O
ATOM   3339  O   HOH W 602     -21.329 -22.246  -3.972  1.00 33.79           O
ATOM   3340  O   HOH W 603      -6.993  -6.054  -3.721  1.00 18.62           O
ATOM   3341  O   HOH W 604       9.684  13.142  -9.113  1.00 26.22           O
ATOM   3342  O   HOH W 608     -12.005  19.688   6.123  1.00 29.34           O
ATOM   3343  O   HOH W 610       3.367 -20.033   8.445  1.00 32.65           O
ATOM   3344  O   HOH W 611       2.059 -25.451  -4.225  1.00 23.12           O
```

Fig. 1, continued

| | | | | | | | | | | |
|---|---|---|---|---|---|---|---|---|---|---|
| ATOM | 3345 | O | HOH | W | 613 | -23.503 | 10.416 | -8.229 | 1.00 | 24.14 | O |
| ATOM | 3346 | O | HOH | W | 616 | -21.293 | 20.309 | 5.239 | 1.00 | 27.04 | O |
| ATOM | 3347 | O | HOH | W | 622 | -12.791 | 8.378 | -14.698 | 1.00 | 28.29 | O |
| ATOM | 3348 | O | HOH | W | 624 | -8.915 | -16.084 | 7.321 | 1.00 | 25.66 | O |
| ATOM | 3349 | O | HOH | W | 625 | -5.805 | 17.006 | -8.881 | 1.00 | 22.54 | O |
| ATOM | 3350 | O | HOH | W | 626 | -1.123 | -28.036 | -2.105 | 1.00 | 26.02 | O |
| ATOM | 3351 | O | HOH | W | 627 | 10.731 | -8.407 | 0.227 | 1.00 | 30.49 | O |
| ATOM | 3352 | O | HOH | W | 629 | 7.900 | -18.004 | -2.768 | 1.00 | 30.97 | O |
| ATOM | 3353 | O | HOH | W | 630 | 2.808 | 5.861 | -2.187 | 1.00 | 18.67 | O |
| ATOM | 3354 | O | HOH | W | 631 | 4.968 | 1.023 | 15.989 | 1.00 | 21.56 | O |
| ATOM | 3355 | O | HOH | W | 633 | -13.236 | -23.356 | -2.260 | 1.00 | 22.13 | O |
| ATOM | 3356 | O | HOH | W | 635 | -0.805 | 16.596 | 7.615 | 1.00 | 32.90 | O |
| ATOM | 3357 | O | HOH | W | 637 | 8.884 | -6.979 | -8.376 | 1.00 | 29.01 | O |
| ATOM | 3358 | O | HOH | W | 639 | 9.779 | -2.631 | -8.635 | 1.00 | 29.46 | O |
| ATOM | 3359 | O | HOH | W | 640 | -16.031 | -10.396 | 12.196 | 1.00 | 26.20 | O |
| ATOM | 3360 | O | HOH | W | 642 | -7.325 | -26.864 | -7.516 | 1.00 | 31.98 | O |
| ATOM | 3361 | O | HOH | W | 643 | 13.371 | -14.221 | 7.010 | 1.00 | 35.95 | O |
| ATOM | 3362 | O | HOH | W | 646 | -12.771 | 21.793 | -4.401 | 1.00 | 29.40 | O |
| ATOM | 3363 | O | HOH | W | 647 | -25.056 | -16.430 | -3.322 | 1.00 | 40.53 | O |
| ATOM | 3364 | O | HOH | W | 651 | -3.828 | -23.937 | -13.177 | 1.00 | 28.06 | O |
| ATOM | 3365 | O | HOH | W | 654 | 1.646 | 1.595 | 20.034 | 1.00 | 43.07 | O |
| ATOM | 3366 | O | HOH | W | 655 | -22.202 | -1.327 | 17.879 | 1.00 | 30.44 | O |
| ATOM | 3367 | O | HOH | W | 657 | -20.271 | 19.219 | -7.689 | 1.00 | 30.75 | O |
| ATOM | 3368 | O | HOH | W | 658 | -10.522 | -8.152 | 21.841 | 1.00 | 39.72 | O |
| ATOM | 3369 | O | HOH | W | 659 | -13.445 | -15.009 | 8.685 | 1.00 | 29.56 | O |
| ATOM | 3370 | O | HOH | W | 660 | -3.534 | 16.197 | 9.258 | 1.00 | 19.32 | O |
| ATOM | 3371 | O | HOH | W | 661 | -7.842 | 12.544 | -15.295 | 1.00 | 27.76 | O |
| ATOM | 3372 | O | HOH | W | 663 | 6.997 | -19.229 | 9.383 | 1.00 | 25.74 | O |
| ATOM | 3373 | O | HOH | W | 664 | 11.334 | -18.358 | -0.545 | 1.00 | 31.34 | O |
| ATOM | 3374 | O | HOH | W | 665 | -22.630 | -17.198 | -1.837 | 1.00 | 31.25 | O |
| ATOM | 3375 | O | HOH | W | 666 | 18.795 | -3.323 | 17.051 | 1.00 | 45.50 | O |
| ATOM | 3376 | O | HOH | W | 667 | 1.155 | 16.254 | 0.198 | 1.00 | 33.71 | O |
| ATOM | 3377 | O | HOH | W | 668 | 9.924 | 12.688 | 10.926 | 1.00 | 35.35 | O |
| ATOM | 3378 | O | HOH | W | 669 | 10.102 | 9.383 | 19.954 | 1.00 | 38.55 | O |
| ATOM | 3379 | O | HOH | W | 670 | 24.192 | 1.433 | 15.174 | 1.00 | 39.72 | O |
| ATOM | 3380 | O | HOH | W | 671 | -14.227 | 1.236 | 21.973 | 1.00 | 38.79 | O |
| ATOM | 3381 | O | HOH | W | 672 | -14.805 | 3.997 | -14.859 | 1.00 | 29.68 | O |
| ATOM | 3382 | O | HOH | W | 674 | -13.994 | -22.492 | 8.089 | 1.00 | 29.16 | O |
| ATOM | 3383 | O | HOH | W | 675 | 12.076 | -18.773 | 4.356 | 1.00 | 27.01 | O |
| ATOM | 3384 | O | HOH | W | 676 | 14.738 | 5.971 | 17.942 | 1.00 | 28.68 | O |
| ATOM | 3385 | O | HOH | W | 677 | 0.988 | 9.026 | 14.732 | 1.00 | 18.07 | O |
| ATOM | 3386 | O | HOH | W | 685 | -10.366 | 16.480 | -14.865 | 1.00 | 39.39 | O |
| ATOM | 3387 | O | HOH | W | 686 | -30.045 | 1.108 | -4.725 | 1.00 | 42.53 | O |
| ATOM | 3388 | O | HOH | W | 687 | 10.035 | -14.922 | -8.262 | 1.00 | 38.27 | O |
| ATOM | 3389 | O | HOH | W | 688 | 5.030 | -14.184 | 13.269 | 1.00 | 25.48 | O |
| ATOM | 3390 | O | HOH | W | 690 | -1.554 | -6.303 | 17.237 | 1.00 | 42.30 | O |
| ATOM | 3391 | O | HOH | W | 691 | -23.004 | 13.425 | -7.426 | 1.00 | 33.24 | O |
| ATOM | 3392 | O | HOH | W | 692 | -11.753 | 18.838 | 1.393 | 1.00 | 29.23 | O |
| ATOM | 3393 | O | HOH | W | 693 | -32.107 | -9.386 | 7.767 | 1.00 | 40.24 | O |
| ATOM | 3394 | O | HOH | W | 695 | -2.936 | -9.389 | 4.709 | 1.00 | 26.73 | O |
| ATOM | 3395 | O | HOH | W | 696 | -17.570 | 13.470 | -12.150 | 1.00 | 36.38 | O |
| ATOM | 3396 | O | HOH | W | 699 | 2.386 | 13.767 | -16.166 | 1.00 | 37.25 | O |
| ATOM | 3397 | O | HOH | W | 709 | -34.164 | -1.234 | 10.792 | 1.00 | 39.70 | O |
| ATOM | 3398 | O | HOH | W | 712 | 13.598 | -23.098 | 2.546 | 1.00 | 36.48 | O |

Fig. 1, continued

```
ATOM   3399  O    HOH W 714     -21.654  17.359  12.106  1.00 32.18           O
ATOM   3400  O    HOH W 715      -4.197   6.990 -14.569  1.00 23.58           O
ATOM   3401  O    HOH W 718      -9.667   3.435  18.959  1.00 36.74           O
ATOM   3402  O    HOH W 719     -15.730 -22.299  -0.317  1.00 46.65           O
ATOM   3403  O    HOH W 720     -28.242   7.591   0.130  1.00 30.49           O
ATOM   3404  O    HOH W 722     -24.232   2.621  17.474  1.00 33.28           O
ATOM   3405  O    HOH W 725     -19.470 -16.710 -16.639  1.00 49.26           O
ATOM   3406  O    HOH W 728     -11.948   4.219 -14.719  1.00 39.02           O
ATOM   3407  O    HOH W 729       2.585  -4.775  -9.055  1.00 22.46           O
ATOM   3408  O    HOH W 731     -20.517  12.695  18.085  1.00 51.54           O
ATOM   3409  O    HOH W 735       2.774 -17.920 -22.578  1.00 51.09           O
ATOM   3410  O    HOH W 738       4.512   9.192 -12.330  1.00 48.15           O
ATOM   3411  O    HOH W 740     -16.632   2.842  15.987  1.00 16.31           O
ATOM   3412  O    HOH W 744     -11.331 -16.059   4.575  1.00 14.21           O
ATOM   3413  O    HOH W 746      -9.294  -2.475   4.206  1.00 17.94           O
ATOM   3414  O    HOH W 748      -6.528 -17.375  -0.582  1.00 14.64           O
ATOM   3415  O    HOH W 749       0.623 -22.840   6.608  1.00 17.26           O
ATOM   3416  O    HOH W 755      -3.759  11.212   4.382  1.00 16.88           O
ATOM   3417  O    HOH W 758       1.596 -12.237  -3.181  1.00 20.26           O
ATOM   3418  O    HOH W 763       6.982  -6.421   7.952  1.00 13.54           O
ATOM   3419  O    HOH W 764      -5.382 -12.324  -2.126  1.00 18.79           O
ATOM   3420  O    HOH W 765      -0.544 -13.965   6.962  1.00 18.19           O
ATOM   3421  O    HOH W 769      -7.295  11.638  18.187  1.00 17.46           O
ATOM   3422  O    HOH W 770       4.444  10.579  15.336  1.00 25.74           O
ATOM   3423  O    HOH W 771       6.324  -6.455  -4.996  1.00 19.29           O
ATOM   3424  O    HOH W 773      -2.335   6.557  19.629  1.00 27.47           O
ATOM   3425  O    HOH W 780       5.481 -17.217   9.508  1.00 25.85           O
ATOM   3426  O    HOH W 783     -16.595  18.319  -9.029  1.00 25.99           O
ATOM   3427  O    HOH W 784     -13.745 -22.504   1.440  1.00 26.72           O
ATOM   3428  O    HOH W 785     -25.776   7.686   1.635  1.00 27.47           O
ATOM   3429  O    HOH W 786       1.269 -12.512  14.246  1.00 23.95           O
ATOM   3430  O    HOH W 788       1.184 -26.782  -1.833  1.00 22.86           O
ATOM   3431  O    HOH W 789     -22.374   5.113  10.797  1.00 22.90           O
ATOM   3432  O    HOH W 790       7.342  15.732  -1.686  1.00 28.55           O
ATOM   3433  O    HOH W 791       0.677   7.766  -1.883  1.00 22.06           O
ATOM   3434  O    HOH W 792      -8.161  -4.126  12.421  1.00 30.40           O
ATOM   3435  O    HOH W 793      -0.108 -26.102  -5.413  1.00 32.84           O
ATOM   3436  O    HOH W 796      -3.738  21.611  -3.329  1.00 26.96           O
ATOM   3437  O    HOH W 797     -10.500  -6.338 -18.708  1.00 27.32           O
ATOM   3438  O    HOH W 798      -4.567  16.508 -11.350  1.00 27.32           O
ATOM   3439  O    HOH W 800       3.018  -9.798   1.164  1.00 21.23           O
ATOM   3440  O    HOH W 801     -15.149  -4.131 -16.516  1.00 23.00           O
ATOM   3441  O    HOH W 803     -22.126  -5.810 -15.345  1.00 30.38           O
ATOM   3442  O    HOH W 804     -13.790  19.185   0.067  1.00 30.17           O
ATOM   3443  O    HOH W 808     -24.516   5.828  -9.523  1.00 28.24           O
ATOM   3444  O    HOH W 811      12.147 -10.594  11.669  1.00 28.55           O
ATOM   3445  O    HOH W 815     -30.009  -1.319  12.522  1.00 30.33           O
ATOM   3446  O    HOH W 819      -8.102  -2.256  11.172  1.00 48.39           O
ATOM   3447  O    HOH W 821       7.503  -9.207  -7.922  1.00 22.87           O
ATOM   3448  O    HOH W 824     -14.405  -0.711   7.541  1.00 24.08           O
ATOM   3449  O    HOH W 827     -11.915  -2.552   5.927  1.00 29.17           O
ATOM   3450  O    HOH W 828      -1.372   8.326  -9.409  1.00 22.78           O
ATOM   3451  O    HOH W 829      -2.504   9.308 -11.739  1.00 23.60           O
ATOM   3452  O    HOH W 833     -23.781  11.228   3.171  1.00 24.67           O
```

Fig. 1, continued

```
ATOM   3453  O   HOH W 836    -23.323    9.531   -1.773  1.00 34.83           O
ATOM   3454  O   HOH W 837      1.201   14.905    7.640  1.00 27.49           O
ATOM   3455  O   HOH W 838    -27.753    0.473   14.478  1.00 42.69           O
ATOM   3456  O   HOH W 839    -22.763    4.181  -10.180  1.00 29.15           O
ATOM   3457  O   HOH W 845      9.628  -20.408   -3.459  1.00 37.99           O
ATOM   3458  O   HOH W 847      4.252   -6.656   -8.003  1.00 26.77           O
ATOM   3459  O   HOH W 851     -1.037   -6.755  -21.788  1.00 36.35           O
ATOM   3460  O   HOH W 856      9.199   -7.235  -18.369  1.00 29.72           O
ATOM   3461  O   HOH W 857      9.860  -13.224  -19.539  1.00 37.28           O
ATOM   3462  O   HOH W 860      8.836  -14.490   -4.931  1.00 32.31           O
ATOM   3463  O   HOH W 862      7.109   12.689   13.134  1.00 33.76           O
ATOM   3464  O   HOH W 866    -20.321   15.014    0.433  1.00 27.34           O
ATOM   3465  O   HOH W 869     -1.987  -16.229   13.647  1.00 26.06           O
ATOM   3466  O   HOH W 873    -11.150  -20.285  -16.201  1.00 36.72           O
ATOM   3467  O   HOH W 874    -17.687   -9.867   14.474  1.00 39.47           O
ATOM   3468  O   HOH W 875    -11.921   12.537   19.082  1.00 36.02           O
ATOM   3469  O   HOH W 878    -15.772    7.962   19.643  1.00 43.01           O
ATOM   3470  O   HOH W 883    -16.693   -9.542  -23.227  1.00 36.71           O
ATOM   3471  O   HOH W 886     -5.311   19.647   -8.846  1.00 31.11           O
ATOM   3472  O   HOH W 887     -0.170  -21.100  -17.985  1.00 36.95           O
ATOM   3473  O   HOH W 888     10.089  -20.559  -14.543  1.00 42.42           O
ATOM   3474  O   HOH W 889    -15.774  -20.088    8.248  1.00 33.92           O
ATOM   3475  O   HOH W 890    -12.648  -16.725   10.934  1.00 45.03           O
ATOM   3476  O   HOH W 891     24.339    0.774   -1.977  1.00 39.43           O
ATOM   3477  O   HOH W 892    -19.664  -20.866   -5.434  1.00 29.61           O
ATOM   3478  O   HOH W 893     -6.454  -15.739  -18.578  1.00 29.86           O
ATOM   3479  O   HOH W 895     -6.377   20.609    3.633  1.00 38.43           O
ATOM   3480  O   HOH W 897     -7.966   -5.616    5.997  1.00 46.04           O
ATOM   3481  O   HOH W 900    -15.441  -21.677  -11.070  1.00 42.69           O
ATOM   3482  O   HOH W 902     -7.585   20.903   -8.475  1.00 33.18           O
ATOM   3483  O   HOH W 907     17.843   -8.435   12.278  1.00 32.90           O
ATOM   3484  O   HOH W 908      5.251    2.886  -13.468  1.00 54.00           O
ATOM   3485  O   HOH W 910    -23.981    0.172   17.346  1.00 33.56           O
ATOM   3486  O   HOH W 913    -14.658    1.422  -19.340  1.00 41.43           O
ATOM   3487  O   HOH W 914    -23.244    4.915   19.586  1.00 33.21           O
ATOM   3488  O   HOH W 915    -22.376   18.465    8.596  1.00 35.10           O
ATOM   3489  O   HOH W 920     -7.353    6.583   21.946  1.00 46.57           O
ATOM   3490  O   HOH W 921     12.744    4.417   -8.731  1.00 34.53           O
ATOM   3491  O   HOH W 922     -6.596    9.455   19.630  1.00 30.39           O
ATOM   3492  O   HOH W 928    -10.727    6.682  -14.180  1.00 28.67           O
ATOM   3493  O   HOH W 929      2.718    2.782   22.387  1.00 49.72           O
ATOM   3494  O   HOH W 930     -2.123   -1.764  -18.911  1.00 39.59           O
ATOM   3495  O   HOH W 933     16.992   -6.390    3.461  1.00 38.57           O
ATOM   3496  O   HOH W 936     -6.827  -14.413  -20.937  1.00 38.14           O
ATOM   3497  O   HOH W 939    -14.282  -11.952   12.764  0.50 31.32           O
ATOM   3498  O   HOH W 941    -29.357   -5.893    0.146  1.00 44.33           O
ATOM   3499  O   HOH W 943     27.194    1.619   12.837  1.00 38.03           O
ATOM   3500  O   HOH W 945     24.913    6.770   12.057  1.00 39.69           O
ATOM   3501  O   HOH W 946    -29.517  -10.139   -9.940  1.00 36.26           O
ATOM   3502  O   HOH W 947    -22.073   -6.824  -17.983  1.00 42.54           O
ATOM   3503  O   HOH W 948    -20.172   16.153   -9.561  1.00 37.72           O
ATOM   3504  O   HOH W 950    -19.428   10.650   19.862  1.00 48.18           O
ATOM   3505  O   HOH W 952      9.534  -11.373   -0.819  1.00 34.68           O
ATOM   3506  O   HOH W 955     -2.470   22.389   -1.283  1.00 33.04           O
```

Fig. 1, continued

```
ATOM   3507  O    HOH W 956      -7.479  -1.410 -21.940  1.00 36.54           O
ATOM   3508  O    HOH W 957     -27.053  -3.235 -12.454  1.00 47.52           O
ATOM   3509  O    HOH W 958     -12.892 -25.144  -0.483  1.00 38.24           O
ATOM   3510  O    HOH W 960      -8.974 -23.787 -10.673  1.00 43.97           O
ATOM   3511  O    HOH W 961      10.690 -11.194 -10.757  1.00 43.18           O
ATOM   3512  O    HOH W 962     -14.898  21.990  -6.146  1.00 45.51           O
ATOM   3513  O    HOH W 966       6.522  18.068  -3.777  1.00 45.25           O
ATOM   3514  O    HOH W 969      -5.522 -26.667   0.587  1.00 36.31           O
ATOM   3515  O    HOH W 970      -9.495  20.927   5.377  1.00 42.99           O
ATOM   3516  O    HOH W 971      15.231 -10.121   6.378  1.00 38.68           O
ATOM   3517  O    HOH W 974     -19.782 -23.781   2.936  1.00 43.09           O
ATOM   3518  O    HOH W 977     -14.623  -2.948 -21.308  1.00 35.49           O
ATOM   3519  O    HOH W 979      15.812  13.271  13.605  1.00 45.03           O
ATOM   3520  O    HOH W 982      -1.032 -20.903  15.912  1.00 29.47           O
ATOM   3521  O    HOH W 983     -17.708 -23.966  -1.021  1.00 47.69           O
ATOM   3522  O    HOH W 984      10.996  15.079   0.241  1.00 37.58           O
ATOM   3523  O    HOH W 985     -17.565   9.595  18.332  1.00 44.48           O
ATOM   3524  O    HOH W 986       6.332   5.038 -12.408  1.00 50.05           O
ATOM   3525  O    HOH W 988     -30.816   3.227  12.635  1.00 32.66           O
ATOM   3526  O    HOH W 989     -10.433 -26.422  -0.983  1.00 40.31           O
ATOM   3527  O    HOH W 990     -20.390  13.085  15.755  1.00 39.05           O
ATOM   3528  O    HOH W 995     -10.065 -28.226   1.069  1.00 39.96           O
ATOM   3529  O    HOH W 998     -17.552  21.293  -5.155  1.00 38.25           O
ATOM   3530  O    HOH W 999      14.440  -4.054  16.744  1.00 42.91           O
ATOM   3531  O    HOH W1003     -10.192  -8.925 -18.345  1.00 42.47           O
ATOM   3532  O    HOH W1004      19.141  -5.370   4.034  1.00 53.22           O
ATOM   3533  O    HOH W1005      10.001 -10.604   1.518  1.00 46.35           O
ATOM   3534  O    HOH W1006     -19.944 -14.019   7.953  1.00 44.37           O
ATOM   3535  O    HOH W1009     -11.583  -6.919 -21.080  1.00 46.74           O
ATOM   3536  O    HOH W1012     -28.830   6.289  13.636  1.00 40.57           O
ATOM   3537  O    HOH W1014     -24.489 -13.050 -13.525  1.00 35.37           O
ATOM   3538  O    HOH W1016     -12.038   4.593 -18.721  1.00 52.97           O
ATOM   3539  O    HOH W1019     -15.273   6.982 -15.284  1.00 43.17           O
ATOM   3540  O    HOH W1020     -11.758  12.207 -17.332  1.00 40.11           O
ATOM   3541  O    HOH W1021     -16.825   1.429  22.628  1.00 36.98           O
ATOM   3542  O    HOH W1022     -26.389  -0.683  16.386  1.00 36.83           O
ATOM   3543  O    HOH W1025      11.435 -18.879 -20.389  1.00 52.55           O
ATOM   3544  O    HOH W1026     -22.343   0.108 -16.930  1.00 49.60           O
ATOM   3545  O    HOH W1027       2.690 -14.792  14.383  1.00 42.30           O
ATOM   3546  O    HOH W1028       4.183 -19.812 -12.848  1.00 45.23           O
ATOM   3547  O    HOH W1030      -3.963   9.559 -16.372  1.00 51.22           O
ATOM   3548  O    HOH W1031     -21.644 -13.657   5.912  1.00 44.81           O
ATOM   3549  O    HOH W1032     -21.329 -12.005  16.301  1.00 46.29           O
ATOM   3550  O    HOH W1033     -20.395   2.624 -16.201  1.00 40.93           O
ATOM   3551  O    HOH W1035      -8.052  23.194 -10.331  1.00 44.61           O
ATOM   3552  O    HOH W1037      -4.284  -6.777 -20.909  1.00 41.53           O
ATOM   3553  O    HOH W1038      10.162 -16.751  -1.884  1.00 40.81           O
ATOM   3554  O    HOH W1039     -18.860 -21.941  -7.865  1.00 44.11           O
ATOM   3555  O    HOH W1043       3.680  18.050   2.412  1.00 52.25           O
ATOM   3556  O    HOH W1044      14.773  14.411   6.083  1.00 38.04           O
ATOM   3557  O    HOH W1045      10.227 -22.353  -2.523  1.00 42.55           O
ATOM   3558  O    HOH W1047      15.583  13.230  -5.613  1.00 38.05           O
ATOM   3559  O    HOH W1048     -25.727  12.816   2.670  1.00 41.02           O
ATOM   3560  O    HOH W1051      27.006   8.619   3.902  1.00 49.61           O
```

Fig. 1, continued

```
ATOM   3561  O    HOH W1052    -29.028   -7.053    2.282  1.00 42.95           O
ATOM   3562  O    HOH W1053     -1.608   -5.003   19.611  1.00 52.03           O
ATOM   3563  O    HOH W1054     19.874   -3.886   -0.173  1.00 47.42           O
ATOM   3564  O    HOH W1055    -24.448   10.543  -10.620  1.00 56.72           O
ATOM   3565  O    HOH W1057     -2.004   18.625    2.851  1.00 47.08           O
ATOM   3566  O    HOH W1058    -18.290   -6.247  -22.670  1.00 45.95           O
ATOM   3567  O    HOH W1059      8.943   -4.636   -7.168  1.00 40.91           O
ATOM   3568  O    HOH W1061    -13.386  -10.168  -19.754  1.00 46.83           O
ATOM   3569  O    HOH W1062      3.476  -21.177   13.370  1.00 33.92           O
ATOM   3570  O    HOH W1066    -11.721  -23.002    9.926  1.00 42.61           O
ATOM   3571  O    HOH W1068      4.856  -11.715   17.572  1.00 40.00           O
ATOM   3572  O    HOH W1069     -6.156   14.581  -14.833  1.00 41.43           O
ATOM   3573  O    HOH W1070    -15.834  -15.626    7.856  1.00 34.72           O
ATOM   3574  O    HOH W1072      4.958  -22.209    8.680  1.00 48.56           O
ATOM   3575  O    HOH W1074     -2.837  -14.178   14.494  1.00 41.00           O
ATOM   3576  O    HOH W1076    -10.592   20.772    8.366  1.00 44.01           O
ATOM   3577  O    HOH W1079     -6.658   -6.276  -20.965  1.00 51.65           O
ATOM   3578  O    HOH W1080      9.645  -12.840   -6.763  1.00 45.35           O
ATOM   3579  O    HOH W1081    -22.297  -14.403  -13.848  1.00 46.89           O
ATOM   3580  O    HOH W1082      0.285  -17.223  -23.147  1.00 44.60           O
ATOM   3581  O    HOH W1083     12.362  -10.468   14.893  1.00 41.47           O
ATOM   3582  O    HOH W1084      8.649  -12.492   14.203  1.00 51.65           O
ATOM   3583  O    HOH W1088     17.039   -5.085   15.937  1.00 48.59           O
ATOM   3584  O    HOH W1093    -27.838   -5.627   -3.892  1.00 41.53           O
ATOM   3585  O    HOH W1095    -25.004  -16.513   -1.187  1.00 45.00           O
ATOM   3586  O    HOH W1098    -32.143    1.220   -3.727  1.00 53.84           O
ATOM   3587  O    HOH W1100      2.673   -9.511  -23.528  1.00 47.29           O
ATOM   3588  O    HOH W1102      9.134   -8.409   17.428  1.00 44.76           O
ATOM   3589  O    HOH W1103    -28.030   -7.814   -5.259  1.00 39.52           O
ATOM   3590  O    HOH W1104    -17.716    8.061  -15.054  1.00 46.69           O
ATOM   3591  O    HOH W1105     24.265   -5.719    5.717  1.00 46.43           O
ATOM   3592  O    HOH W1107     11.932  -11.599    3.133  1.00 48.74           O
ATOM   3593  O    HOH W1108    -23.526   -3.820  -17.194  1.00 48.25           O
ATOM   3594  O    HOH W1109    -22.396   -2.538   19.890  1.00 42.81           O
ATOM   3595  O    HOH W1110      3.117   -0.821   20.548  1.00 50.73           O
ATOM   3596  O    HOH W1112      5.341   -2.734   22.442  1.00 44.50           O
ATOM   3597  O    HOH W1119      2.598   22.999   -5.190  1.00 41.74           O
ATOM   3598  O    HOH W1123     -7.244   22.864   -6.238  1.00 42.05           O
ATOM   3599  O    HOH W1124    -24.774  -18.102    2.954  1.00 45.33           O
ATOM   3600  O    HOH W1125    -28.477   -3.605   -9.741  1.00 50.15           O
ATOM   3601  O    HOH W1127    -21.047   23.555    1.673  1.00 37.86           O
ATOM   3602  O    HOH W1129    -21.951  -19.775   -8.986  1.00 43.69           O
ATOM   3603  O    HOH W1131     -3.114   21.261   -7.298  1.00 45.64           O
ATOM   3604  O    HOH W1132    -22.355   22.323   -0.450  1.00 52.17           O
ATOM   3605  O    HOH W1134     10.077   -9.693  -16.170  1.00 44.33           O
ATOM   3606  O    HOH W1137      6.134  -19.773  -11.055  1.00 46.78           O
ATOM   3607  O    HOH W1138     12.816  -16.580    4.647  1.00 43.19           O
ATOM   3608  O    HOH W1140     -0.868   18.304    5.373  1.00 44.59           O
ATOM   3609  O    HOH W1142    -26.324   -7.231   18.809  1.00 48.14           O
ATOM   3610  O    HOH W1143     -3.677  -18.088  -19.618  1.00 43.40           O
ATOM   3611  O    HOH W1146     -5.752  -25.798   -1.940  1.00 40.45           O
ATOM   3612  O    HOH W1147     17.136   -3.426   -5.084  1.00 46.39           O
ATOM   3613  O    HOH W1148     -5.180  -17.270   15.251  1.00 49.18           O
ATOM   3614  O    HOH W1149     12.934  -14.234    5.050  1.00 38.13           O
```

Fig. 1, continued

```
ATOM   3615  O    HOH W1151      10.425  15.398   9.787  1.00 47.13           O
ATOM   3616  O    HOH W1153      -2.310 -24.704  -9.681  1.00 46.45           O
ATOM   3617  O    HOH W1154      24.848  -5.430  13.210  1.00 51.89           O
ATOM   3618  O    HOH W1155      21.135   5.202  -5.353  1.00 49.38           O
ATOM   3619  O    HOH W1157     -13.391   3.262  21.528  1.00 44.78           O
ATOM   3620  O    HOH W1159     -16.516  16.266 -14.439  1.00 46.23           O
ATOM   3621  O    HOH W1160      -9.932  -8.926  18.548  1.00 43.92           O
ATOM   3622  O    HOH W1162     -30.369   6.493   0.732  1.00 52.27           O
ATOM   3623  O    HOH W1163       4.505  -5.592 -20.625  1.00 53.23           O
ATOM   3624  O    HOH W1165      19.655   1.168  -8.908  0.65 48.28           O
ATOM   3625  O    HOH W1169      -8.436 -17.670 -18.143  0.50 31.27           O
ATOM   3626  O    HOH W1173      -0.763 -11.849  16.442  1.00 51.57           O
ATOM   3627  O    HOH W1179     -23.924  -8.401  18.579  1.00 45.88           O
ATOM   3628  O    HOH W1180      19.336  -1.851  -5.098  1.00 48.03           O
ATOM   3629  O    HOH W1181     -32.430   7.073   4.755  1.00 53.44           O
ATOM   3630  O    HOH W1184     -12.882 -12.393 -20.486  1.00 46.51           O
ATOM   3631  O    HOH W1185      -3.310  -8.227  16.438  1.00 36.68           O
ATOM   3632  O    HOH W1186       7.042  12.193 -12.160  1.00 43.57           O
ATOM   3633  O    HOH W1187       3.214  -0.962 -18.220  1.00 45.18           O
ATOM   3634  O    HOH W1192      -1.129   0.668  20.278  1.00 56.19           O
ATOM   3635  O    HOH W1195     -12.382   9.506 -17.317  1.00 51.17           O
ATOM   3636  O    HOH W1198       9.694 -21.748  -9.285  1.00 44.48           O
ATOM   3637  O    HOH W1199     -14.320  21.009  -1.992  1.00 42.80           O
ATOM   3638  O    HOH W1201      13.239  -6.846  18.293  1.00 49.62           O
ATOM   3639  O    HOH W1202      20.622  10.343  12.202  1.00 54.10           O
ATOM   3640  O    HOH W1203      -0.684  20.259   0.596  1.00 59.70           O
ATOM   3641  O    HOH W1205     -22.169  16.475  -0.782  1.00 47.93           O
ATOM   3642  O    HOH W1206     -24.802 -12.656  13.818  1.00 52.70           O
ATOM   3643  O    HOH W1207     -20.624   1.899  22.685  1.00 41.58           O
ATOM   3644  O    HOH W1208     -26.665   8.529  -9.812  1.00 48.72           O
ATOM   3645  O    HOH W1209      -7.845  21.556   1.854  1.00 53.29           O
END
```

Fig. 2. Alignment of polypeptide sequences

```
CAND_A:    AALPNPYDDPFYTTPSNIGTFAKGQVIQSRKVPTDIGNAN-----NAASFQ
ADY62089   LTVKSPLVDDFYTAPDGYESAKLGEILKLRKTPSKLSSMFF-EIDIKNSWQ
ADY62090   ILPTKPSNDPFYNAPAGFEKAAVGDILQSRKTPKPITGVFV-PVKIQNSWQ
ABJ25493   DALVRPLEDPFYSAPKGFESTVPGTILRWRNPPNPISAFGFAPINLAASYQ
ADZ72148   AALPNPYDDPFYTTPSNIGTFAKGQVIQSRKVPTDIGNAN-----NAASFQ
Q8NIN8     LAPKKPSQDDFYTPPQGYEAQPLGSILKTRNVPNPLTNVFT-PVKVQNAWQ
Q8NJ51     IAPVKPSQDNFYTPPDGYENSKVGTILKFRNTPFPLSGIIN-TVNVQNSWQ

CAND_A:    LQYRTTNTQNEAVADVATVWIPAKPASPPKIFSYQVYEDATALDCAPSYS
ADY62089   LLVRSEDSFGNATAIVTTVIEPYN-ADPSKVLSYQTFEDSANIECSPSYG
ADY62090   LLVRSEDSFGNPNVIVTTVMEPFN-ADPSKLASYQVFEDSAKADCAPSYA
ABJ25493   LLYRSTDSFGEPIAAASTILVPHN-ADNTKLLSFQAAEDAANPNCAPSYA
ADZ72148   LQYRTTNTQNEAVADVATVWIPAKPASPPKIFSYQVYEDATALDCAPSYS
Q8NIN8     LLVRSEDTFGNPNAIVTTIIQPFN-AKKDKLVSYQTFEDSGKLDCAPSYA
Q8NJ51     LLVRSEDTFGNPNAIVTTVIQPFN-ATSDKVVSYQTWEDAANLDFSPSYG

CAND_A:    YLTGLDQPNKVTAVLD--TPIIIGWALQQGYYVVSSDHEGFKAAFIAGYEEG
ADY62089   MQYGAPWSTVATQI----DMALMVPMLKQGYYVVSPDYEGPKSTFTVGRQSG
ADY62090   LQFGSDVTTIATQV----ETYLLAPLLDQGYYVVSPDYEGPKSTFTVGKQSG
ABJ25493   FQLDSATDDELGLIMPQAELVLIIAALDKGWVVTVPDHLGPNATFLANNLSG
ADZ72148   YLTGLDQPNKVTAVLD--TPIIIGWALQQGYYVVSSDHEGFKAAFIAGYEEG
Q8NIN8     IQYGSDISTLTTQG----EMYYISALLDQGYYVVTPDYEGPKSTFTVGLQSG
Q8NJ51     IQYGADLTTLISSF----EMYFMSALLDQGYYVVTPDYEGPKSTFTVGLQSG

CAND_A:    MAILDGIRALKNY---QNLPSDSKVALEGYSGGAHATVWATSLAESYAPE
ADY62089   KATLDSIRAILKSNKFTGIKSDAKVAMWGYSGGSLASGWAAALQPKYAPE
ADY62090   QAVLNSIRAALKSGKITNLAENAKVVMWGYSGGSLASGWAAALQPNYAPE
ABJ25493   HVVLDNIRALRSSAF-SGISPKATITLWGYSGGSLASGLAAELRASYAPE
ADZ72148   MAILDGIRALKNY---QNLPSDSKVALEGYSGGAHATVWATSLAESYAPE
Q8NIN8     RATLNSLRATLKSGNLTGVSSDAETLLWGYSGGSLASGWAAAIQKEYAPE
Q8NJ51     KATLNSIRAALGSGNLTGIDSNAEVMMWGYSGGTIASGWAAAIQSEYAPE

CAND_A:    L--NIVGASHGGTPVSAKDTFTFLNGGPFAGFALAGVSGLSLAHPDMESF
ADY62089   LKKNLIGAALGGFVTNITATAEATDGTLFAGLVPNALSGLANEYPEFKEI
ADY62090   LGGNLLGAALGGFVTNITATAEATDGTVFAGIMANALGGVANEYPEFKQI
ABJ25493   L--NIAGAALGGTVPKIMPVFNTVNKGIYAGLLPAGMQGLSNEYPAIEKI
ADZ72148   L--NIVGASHGGTPVSAKDTFTFLNGGPFAGFALAGVSGLSLAHPDMESF
Q8NIN8     LSKNLLGAALGGFVTNITATAEAVDSGPFAGIISNALAGIGNEYPDFKNY
Q8NJ51     LTDNLIGAALGGFVTNITATAEATDGGLFAGLIANALGGLGNEYSNLTTF

CAND_A:    IEARLNAKGQRTLKQIRGRGFCLPQVVLTYPFLNVFSLVND-----TNLL
ADY62089   LYQKVSKAATDNLRQ--GTEHCIGGAILYFAEDQYFTGDDRAFPGGYGLL
ADY62090   LQNDTDKQSVFDQF----DNHCLADGVINYIGKHFLSGTNKIFKSGWNIL
ABJ25493   LYDHLVPAKKADFVK--TKNLCIVEDLLTYSFQDFYRYITD-----ANML
ADZ72148   IEARLNAKGQQTLKQIRGRGFCLPQVVLTYPFLNVFSLVND-----TNLL
Q8NIN8     LLKKVSPLLSITYRL--GNTHCLLDGGIAYFGKSFFSRIIRYFPDGWDLV
Q8NJ51     MQESVSSEQQPAFER--RDDHCLVDSILGNIGSQFFSGEDRWFPDGWKIF
```

Fig. 2, continued

```
CAND_A:    NEAPIASILKQETVVQAEASYTVSVPKFPRFIWHAIPDEIVPYQPAATYV
ADY62089   KEEVVNKTISENNLM---QMDKDYLPDIPIFVYHGALDSIVPISNVHVTY
ADY62090   KNPTISKIVEDNGLV----YQKQLVPKIPILIYHGAIDQIVPIVNVKKTY
ABJ25493   KDPEVTRVLGENAMG-------QHVPDIPLFVYKSTNDDVSPVGDTDALV
ADZ72148   NEAPIAGILKQETVVQAEASYTVSVPKFPRFIWHAIPDEIVPYQPAATYV
Q8NIN8     NQEPIKTILQDNGLV---YQPKDLTPQIPLFIYHGTLDAIVPIVNSRKTF
Q8NJ51     DEEPVDSIVKNNGLV---YQPKKYLPQIPIFVYQGTQDNIVPIKSAKTTF

CAND_A:    KEQCAKGA-NINFSPYPIAEHLTAEIFGLVPSLWFIKQAFDGTTPKVICG
ADY62089   KNWCDWGINSFEFSEDLLNGHITETIVGAPAAITWLEARFDGEPVVKGCK
ADY62090   QNWCDAGIASLEFSEDATNGHITETIVGAPVALTWIINRFNGKQTVSGCQ
ABJ25493   SGYCAAGG-KVEYYRDELSNHATMAVIGVPNALLWLKDRMNGVPARAGCK
ADZ72148   KEQCAKGA-NINFSPYPIAEHLTAEIFGLVPSLWFTKQAFDGTTPKVICG
Q8NIN8     QQWCDWGLKSGEYNEDLTNGHITESIVGAPAALTWIINRFNGQPPVDGCQ
Q8NJ51     KQWCEWGLESGEFAEDEATGHITEVFVGAPAALTWIINRFNGVEPVQGCN

CAND_A:    TPIPAIAGITTPSADQVLGSDLANQLRSLDGKQSAFGKPFGPITPP
ADY62089   KTSRITNF-SYPNISDSTSSIFEGILNSVTGSELGPVTSDNITLDGLTGFLGNFIDLK
ADY62090   HVKRTSNF-EYPNIPPSILNYFKAALNILIQKGLGPDIQKDQVNPDGLKKISILV
ABJ25493   TQTALTGLLDPRT-LAVLGIDLIKVLLALLSAPVGTFVIG
ADZ72148   TPIPAIAGITTPSADQVLGSDLANQLRSLDGKQSAFGKPFGPITPP
Q8NIN8     HNVRASNL-EYPGTPQSIKNYFEAALHAILGFDLGPDVKRDKVTLGGLLKLERFAF
Q8NJ51     HTSRASNF-DYPGISQSYVEYFTAALNVVLGINMGPLTKREVNSIQDLNNLEYVKV
```

LIPOLYTIC ENZYME VARIANTS

CROSS-REFERENCE TO RELATED APPLICATIONS

This application is a 35 U.S.C. 371 national application of PCT/EP2007/060473 filed Oct. 2, 2007, which claims priority or the benefit under 35 U.S.C. 119 of European application no. 06121678.4 filed Oct. 3, 2006 and U.S. provisional application no. 60/849,072 filed Oct. 3, 2006, the contents of which are fully incorporated herein by reference.

FIELD OF THE INVENTION

The present invention relates to a polypeptide with lipolytic enzyme activity and to a method of preparing it.

BACKGROUND OF THE INVENTION

WO2004064537 discloses a method for the in-situ production of an emulsifier in a foodstuff, wherein a lipid acyl transferase is added to the foodstuff. WO2005066347 discloses a method of producing a variant glycolipid acyl transferase enzyme.

V Neugnot et al., European Journal of Biochemistry, Vol. 269 (6) pp. 1734-1745 (2002) March, describes a lipase/acyl transferase from *Candida parapsilosis*.

WO8802775A1 describes *Candida antarctica* lipase A. WO9401541A1 discloses variants of *C. antarctica* lipase A.

SUMMARY OF THE INVENTION

The inventors have found that variants with increased acyl transferase activity can be designed on the basis of a three-dimensional model by making amino acid alterations near the active Ser of lipolytic enzymes such as *C. antarctica* lipase A or the lipase/acyl transferase from *C. parapsilosis*.

Accordingly, the invention provides a method of preparing a polypeptide, comprising:

a) providing a three dimensional model of a parent polypeptide having lipolytic enzyme activity and an amino acid sequence with an active Ser having at least 80% identity to any of SEQ ID NOS: 1-5, b) selecting an amino acid residue in the parent polypeptide which has a non-hydrogen atom within 10 Å of the a non-hydrogen atom in the active Ser in the model, c) providing an altered amino acid sequence which is at least 80% identical to any of SEQ ID NOS: 1-5, and wherein the difference from the parent polypeptide comprises substitution or deletion of the selected residue or insertion of at least one residue adjacent to the selected residue, d) preparing an altered polypeptide having the altered amino acid sequence, e) determining the acyl transferase activity of the altered polypeptide, and f) selecting an altered polypeptide which has an increased acyl transferase activity compared to the parent polypeptide.

The invention also provides a polypeptide which:

has lipolytic enzyme activity, and has an amino acid sequence which has at least 80% identity to SEQ ID NO: 1 and has a different residue at a position or has an insertion adjacent to a position corresponding to any of residues 82-87, 108, 132-133, 138, 140-142, 145, 172-179, 182, 202-216, 220-232, 235, 238, 241-242, 257, 264, 267- 268, 275-277, 280, 282-288, 290-296, 298-299, 304, 320, 324-328, 356-357, 360 and 420-421 of SEQ ID NO: 1.

BRIEF DESCRIPTION OF THE DRAWINGS

FIG. 1 shows a three-dimensional model of *Candida antarctica* lipase A (CALA, SEQ ID NO: 1) with a substrate analog (myristic acid).

FIG. 2 shows an alignment based on the three-dimensional structure of the following sequences in full-length or truncated form:

SEQ ID NO: 1 (CAND_A)
SEQ ID NO: 5 (CaLIP1, ADY62089)
SEQ ID NO: 6 (ADY62090, CaLIP2)
SEQ ID NO: 7 (ABJ25493, *A. fumigatus* lipase)
SEQ ID NO: 2 (*Pseudozyma* lipase, ADZ72148)
SEQ ID NO: 4 (CpLIP2, Q8NIN8)
SEQ ID NO: 3 (CpLIP1, Q8NJ51)

DETAILED DESCRIPTION OF THE INVENTION

Parent Polypeptide

The invention uses a parent polypeptide with lipolytic enzyme activity. It may be *Candida antarctica* lipase A (CALA, SEQ ID NO: 1), *Pseudozyma* sp. lipase (SEQ ID NO: 2) described in WO2005040334, *C. parapsilosis* lipase CpLIP1 (SEQ ID NO: 3) or CpLIP2 (SEQ ID NO: 4), any of CaLIP1-10 from *Candida albicans*, e.g. CaLIP1 or CaLIP2 shown as SEQ ID NOS: 5-6, or *Aspergillus fumigatus* lipase (SEQ ID NO: 7).

Three-Dimensional Model

The invention uses a 3D model of the parent polypeptide. FIG. 1 gives the coordinates for a 3D model of CALA with myristic acid as a substrate analogue. The active Ser is in position 174.

Selection of Amino Acid Residue

An amino acid residue is selected in the 3D model having a non-hydrogen atom within 10 Å of a non-H atom of the active Ser.

In the model in FIG. 1, the following residues have a non-H atom within 10 Å of a non-H atom of the active Ser (position 174 of SEQ ID NO: 1): 80-85, 108, 112, 116, 132-133, 139-140, 145, 171-182, 200-207, 211, 215, 220, 223, 264, 268, 318-321, 324-328, 332, 355-357, 359-361, 419-421, 425.

Altered Amino Acid Sequence

The selected residue may be substituted with a different residue, particularly with a more efficient pi electron donor residue. Amino acid residues are ranked as follows from least efficient to most efficient pi donors (an equal sign indicates residues with practically indistinguishable efficiency). Other residues are not considered to be pi electron donors:

T<N<H<F<Y<W

The substitution may particularly be conservative, i.e. substitution with another residue of the same type (negative, positive, hydrophobic or hydrophilic). The negative residues are D,E, the positive residues are K,R, the hydrophobic residues are A,C,F,G,I,L,M,P,V,W,Y, and the hydrophilic residues are H,N,Q,S,T.

Alternatively, an amino acid insertion may be made at the N- or C-terminal side of the selected residue, particularly an insertion of 1-2 residues.

CpLIP1 or CpLIP2 (SEQ ID NO: 3 or 4) may be used as a template for the amino acid alteration by referring to an alignment as shown in FIG. 3 for SEQ ID NOS: 1-5. Thus, the selected residue may be substituted with the residue found in the corresponding position for SEQ ID NO: 3 or 4. The selected residue may be deleted if SEQ ID NO: 3 or 4 has a gap at that position. An insertion may be made adjacent to the selected residue if SEQ ID NO: 3 or 4 has an additional residue at that position; the insertion may in particular be the same residue found in SEQ ID NO: 3 or 4.

Particular Substitutions

The variant may particularly comprise one or more of the following substitutions: Y83W, V103T and/or H132Y. More particularly, it may comprise the combination F223A F421V Y83W.

Nomenclature for Amino Acid Alterations

In this specification, an amino acid substitution is described by use of one-letter codes, e.g. P205W. Multiple substitutions are concatenated, e.g. P205F T211W to indicate a variant with two substitutions. P205W, Y, F is used to indicate alternatives, i.e. substitution of P205 with W, Y or F.

Assay for Acyl Transferase Activity

In general, the activity may be determined by incubating the polypeptide with an acyl ester as acyl donor and an alcohol as acyl acceptor in an aqueous system and analyzing the mixture after the incubation to determine the transfer of the acyl group. This may be done, e.g. as described in WO2004064537.

Use of Lipolytic Enzyme Variant

The variants of the invention have increased acyl transferase activity. They may be used in various processes where they are mixed with an acyl donor and an acyl acceptor in an aqueous system to effect acyl transfer, e.g. as described in the indicated publications:

In-situ production of an emulsifier in a foodstuff, such as baked goods made from dough, e.g. as described in WO2004064537.

Production of a carbohydrate ester, a protein ester or a hydroxyl acid ester, WO2004064987.

Reducing or removing diglyceride from edible oil, WO2005066351.

Enzymatic degumming of edible oil, WO2005066351.

The invention claimed is:

1. A polypeptide which:
    a) has lipolytic enzyme activity, and
    b) has an amino acid sequence which has at least 80% identity to SEQ ID NO: 1 and comprises an amino acid difference compared to SEQ ID NO: 1 at a position corresponding to any one of positions 83, 103, 112, 116, 132, 215, 223, 355, 357 and/or 425 in SEQ ID NO: 1.

2. The polypeptide of claim 1, which comprises a substitution at a position corresponding to position 83.

3. The polypeptide of claim 1, which comprises a substitution at a position corresponding to position 103.

4. The polypeptide of claim 1, which comprises a substitution at a position corresponding to position 112.

5. The polypeptide of claim 1, which comprises a substitution at a position corresponding to position 116.

6. The polypeptide of claim 1, which comprises a substitution at a position corresponding to position 132.

7. The polypeptide of claim 1, which comprises a substitution at a position corresponding to position 215.

8. The polypeptide of claim 1, which comprises a substitution at a position corresponding to position 223.

9. The polypeptide of claim 1, which comprises a substitution at a position corresponding to position 355.

10. The polypeptide of claim 1, which comprises a substitution at a position corresponding to position 357.

11. The polypeptide of claim 1, which comprises a substitution at a position corresponding to position 425.

12. The polypeptide of claim 1, which comprises at least one of the substitutions: Y83W, V103T and/or H132Y.

13. The polypeptide of claim 1, which further comprises 1-10 amino acid differences compared to SEQ ID NO: 1 at a position corresponding to any of positions 80-82, 84-85, 108, 133, 139-140, 145, 171-182, 200-207, 211, 220, 264, 268, 318-321, 324-328, 332, 356, 359-361 or 419-421 of SEQ ID NO: 1.

14. The polypeptide of claim 1, which comprises the substitutions F223A and F421V and Y83W.

15. A method of producing an emulsifier in a foodstuff, comprising adding the polypeptide of claim 1 to a dough.

\* \* \* \* \*

SEQUENCE LISTING

```
<160> NUMBER OF SEQ ID NOS: 7

<210> SEQ ID NO 1
<211> LENGTH: 431
<212> TYPE: PRT
<213> ORGANISM: Candida antarctica

<400> SEQUENCE: 1

Ala Ala Leu Pro Asn Pro Tyr Asp Asp Pro Phe Tyr Thr Thr Pro Ser
1               5                   10                  15

Asn Ile Gly Thr Phe Ala Lys Gly Gln Val Ile Gln Ser Arg Lys Val
            20                  25                  30

Pro Thr Asp Ile Gly Asn Ala Asn Asn Ala Ala Ser Phe Gln Leu Gln
        35                  40                  45

Tyr Arg Thr Thr Asn Thr Gln Asn Glu Ala Val Ala Asp Val Ala Thr
    50                  55                  60

Val Trp Ile Pro Ala Lys Pro Ala Ser Pro Pro Lys Ile Phe Ser Tyr
65                  70                  75                  80

Gln Val Tyr Glu Asp Ala Thr Ala Leu Asp Cys Ala Pro Ser Tyr Ser
                85                  90                  95

Tyr Leu Thr Gly Leu Asp Gln Pro Asn Lys Val Thr Ala Val Leu Asp
            100                 105                 110

Thr Pro Ile Ile Ile Gly Trp Ala Leu Gln Gln Gly Tyr Tyr Val Val
        115                 120                 125

Ser Ser Asp His Glu Gly Phe Lys Ala Ala Phe Ile Ala Gly Tyr Glu
    130                 135                 140

Glu Gly Met Ala Ile Leu Asp Gly Ile Arg Ala Leu Lys Asn Tyr Gln
145                 150                 155                 160

Asn Leu Pro Ser Asp Ser Lys Val Ala Leu Glu Gly Tyr Ser Gly Gly
                165                 170                 175

Ala His Ala Thr Val Trp Ala Thr Ser Leu Ala Glu Ser Tyr Ala Pro
            180                 185                 190

Glu Leu Asn Ile Val Gly Ala Ser His Gly Gly Thr Pro Val Ser Ala
        195                 200                 205
```

-continued

```
Lys Asp Thr Phe Thr Phe Leu Asn Gly Gly Pro Phe Ala Gly Phe Ala
210                 215                 220
Leu Ala Gly Val Ser Gly Leu Ser Leu Ala His Pro Asp Met Glu Ser
225                 230                 235                 240
Phe Ile Glu Ala Arg Leu Asn Ala Lys Gly Gln Arg Thr Leu Lys Gln
                245                 250                 255
Ile Arg Gly Arg Gly Phe Cys Leu Pro Gln Val Val Leu Thr Tyr Pro
            260                 265                 270
Phe Leu Asn Val Phe Ser Leu Val Asn Asp Thr Asn Leu Leu Asn Glu
        275                 280                 285
Ala Pro Ile Ala Ser Ile Leu Lys Gln Glu Thr Val Val Gln Ala Glu
    290                 295                 300
Ala Ser Tyr Thr Val Ser Val Pro Lys Phe Pro Arg Phe Ile Trp His
305                 310                 315                 320
Ala Ile Pro Asp Glu Ile Val Pro Tyr Gln Pro Ala Ala Thr Tyr Val
                325                 330                 335
Lys Glu Gln Cys Ala Lys Gly Ala Asn Ile Asn Phe Ser Pro Tyr Pro
            340                 345                 350
Ile Ala Glu His Leu Thr Ala Glu Ile Phe Gly Leu Val Pro Ser Leu
        355                 360                 365
Trp Phe Ile Lys Gln Ala Phe Asp Gly Thr Thr Pro Lys Val Ile Cys
    370                 375                 380
Gly Thr Pro Ile Pro Ala Ile Ala Gly Ile Thr Thr Pro Ser Ala Asp
385                 390                 395                 400
Gln Val Leu Gly Ser Asp Leu Ala Asn Gln Leu Arg Ser Leu Asp Gly
                405                 410                 415
Lys Gln Ser Ala Phe Gly Lys Pro Phe Gly Pro Ile Thr Pro Pro
            420                 425                 430

<210> SEQ ID NO 2
<211> LENGTH: 431
<212> TYPE: PRT
<213> ORGANISM: Pseudozyma species.

<400> SEQUENCE: 2

Ala Ala Leu Pro Asn Pro Tyr Asp Asp Pro Phe Tyr Thr Thr Pro Ser
1               5                   10                  15
Asn Ile Gly Thr Phe Ala Lys Gly Gln Val Ile Gln Ser Arg Lys Val
                20                  25                  30
Pro Thr Asp Ile Gly Asn Ala Asn Asn Ala Ala Ser Phe Gln Leu Gln
            35                  40                  45
Tyr Arg Thr Thr Asn Thr Gln Asn Glu Ala Val Ala Asp Val Ala Thr
        50                  55                  60
Val Trp Ile Pro Ala Lys Pro Ala Ser Pro Pro Lys Ile Phe Ser Tyr
65                  70                  75                  80
Gln Val Tyr Glu Asp Ala Thr Ala Leu Asp Cys Ala Pro Ser Tyr Ser
                85                  90                  95
Tyr Leu Thr Gly Leu Asp Gln Pro Asn Lys Val Thr Ala Val Leu Asp
            100                 105                 110
Thr Pro Ile Ile Ile Gly Trp Ala Leu Gln Gln Gly Tyr Tyr Val Val
        115                 120                 125
Ser Ser Asp His Glu Gly Phe Lys Ala Ala Phe Ile Ala Gly Tyr Glu
    130                 135                 140
Glu Gly Met Ala Ile Leu Asp Gly Ile Arg Ala Leu Lys Asn Tyr Gln
145                 150                 155                 160
```

```
Asn Leu Pro Ser Asp Ser Lys Val Ala Leu Glu Gly Tyr Ser Gly Gly
                165                 170                 175

Ala His Ala Thr Val Trp Ala Thr Ser Leu Ala Glu Ser Tyr Ala Pro
            180                 185                 190

Glu Leu Asn Ile Val Gly Ala Ser His Gly Gly Thr Pro Val Ser Ala
        195                 200                 205

Lys Asp Thr Phe Thr Phe Leu Asn Gly Gly Pro Phe Ala Gly Phe Ala
    210                 215                 220

Leu Ala Gly Val Ser Gly Leu Ser Leu Ala His Pro Asp Met Glu Ser
225                 230                 235                 240

Phe Ile Glu Ala Arg Leu Asn Ala Lys Gly Gln Gln Thr Leu Lys Gln
                245                 250                 255

Ile Arg Gly Arg Gly Phe Cys Leu Pro Gln Val Val Leu Thr Tyr Pro
            260                 265                 270

Phe Leu Asn Val Phe Ser Leu Val Asn Asp Thr Asn Leu Leu Asn Glu
        275                 280                 285

Ala Pro Ile Ala Gly Ile Leu Lys Gln Glu Thr Val Val Gln Ala Glu
    290                 295                 300

Ala Ser Tyr Thr Val Ser Val Pro Lys Phe Pro Arg Phe Ile Trp His
305                 310                 315                 320

Ala Ile Pro Asp Glu Ile Val Pro Tyr Gln Pro Ala Ala Thr Tyr Val
                325                 330                 335

Lys Glu Gln Cys Ala Lys Gly Ala Asn Ile Asn Phe Ser Pro Tyr Pro
            340                 345                 350

Ile Ala Glu His Leu Thr Ala Glu Ile Phe Gly Leu Val Pro Ser Leu
        355                 360                 365

Trp Phe Thr Lys Gln Ala Phe Asp Gly Thr Thr Pro Lys Val Ile Cys
    370                 375                 380

Gly Thr Pro Ile Pro Ala Ile Ala Gly Ile Thr Thr Pro Ser Ala Asp
385                 390                 395                 400

Gln Val Leu Gly Ser Asp Leu Ala Asn Gln Leu Arg Ser Leu Asp Gly
                405                 410                 415

Lys Gln Ser Ala Phe Gly Lys Pro Phe Gly Pro Ile Thr Pro Pro
            420                 425                 430

<210> SEQ ID NO 3
<211> LENGTH: 449
<212> TYPE: PRT
<213> ORGANISM: Candida parapsilosis

<400> SEQUENCE: 3

Ala Val Ile Ala Pro Val Lys Pro Ser Gln Asp Asn Phe Tyr Thr Pro
1               5                   10                  15

Pro Asp Gly Tyr Glu Asn Ser Lys Val Gly Thr Ile Leu Lys Phe Arg
            20                  25                  30

Asn Thr Pro Phe Pro Leu Ser Gly Ile Ile Asn Thr Val Asn Val Gln
        35                  40                  45

Asn Ser Trp Gln Leu Leu Val Arg Ser Glu Asp Thr Phe Gly Asn Pro
    50                  55                  60

Asn Ala Ile Val Thr Thr Val Ile Gln Pro Phe Asn Ala Thr Ser Asp
65                  70                  75                  80

Lys Val Val Ser Tyr Gln Thr Trp Glu Asp Ala Ala Asn Leu Asp Phe
                85                  90                  95

Ser Pro Ser Tyr Gly Ile Gln Tyr Gly Ala Asp Leu Thr Thr Leu Ile
```

```
            100                 105                 110
Ser Ser Phe Glu Met Tyr Phe Met Ser Ala Leu Leu Asp Gln Gly Tyr
        115                 120                 125

Tyr Val Val Thr Pro Asp Tyr Glu Gly Pro Lys Ser Thr Phe Thr Val
130                 135                 140

Gly Leu Gln Ser Gly Lys Ala Thr Leu Asn Ser Ile Arg Ala Ala Leu
145                 150                 155                 160

Gly Ser Gly Asn Leu Thr Gly Ile Asp Ser Asn Ala Glu Val Met Met
                165                 170                 175

Trp Gly Tyr Ser Gly Thr Ile Ala Ser Gly Trp Ala Ala Ile
                180                 185                 190

Gln Ser Glu Tyr Ala Pro Glu Leu Thr Asp Asn Leu Ile Gly Ala Ala
        195                 200                 205

Leu Gly Gly Phe Val Thr Asn Ile Thr Ala Thr Ala Glu Ala Thr Asp
210                 215                 220

Gly Gly Leu Phe Ala Gly Leu Ile Ala Asn Ala Leu Gly Gly Leu Gly
225                 230                 235                 240

Asn Glu Tyr Ser Asn Leu Thr Thr Phe Met Gln Glu Ser Val Ser Ser
                245                 250                 255

Glu Gln Gln Pro Ala Phe Glu Arg Arg Asp Asp His Cys Leu Val Asp
        260                 265                 270

Ser Ile Leu Gly Asn Ile Gly Ser Gln Phe Phe Ser Gly Glu Asp Arg
        275                 280                 285

Trp Phe Pro Asp Gly Trp Lys Ile Phe Asp Glu Pro Val Asp Ser
290                 295                 300

Ile Val Lys Asn Asn Gly Leu Val Tyr Gln Pro Lys Lys Tyr Leu Pro
305                 310                 315                 320

Gln Ile Pro Ile Phe Val Tyr Gln Gly Thr Gln Asp Asn Ile Val Pro
                325                 330                 335

Ile Lys Ser Ala Lys Thr Thr Phe Lys Gln Trp Cys Glu Trp Gly Leu
                340                 345                 350

Glu Ser Gly Glu Phe Ala Glu Asp Glu Ala Thr Gly His Ile Thr Glu
        355                 360                 365

Val Phe Val Gly Ala Pro Ala Ala Leu Thr Trp Ile Ile Asn Arg Phe
370                 375                 380

Asn Gly Val Glu Pro Val Gln Gly Cys Asn His Thr Ser Arg Ala Ser
385                 390                 395                 400

Asn Phe Asp Tyr Pro Gly Ile Ser Gln Ser Tyr Val Glu Tyr Phe Thr
                405                 410                 415

Ala Ala Leu Asn Val Val Leu Gly Ile Asn Met Gly Pro Leu Thr Lys
        420                 425                 430

Arg Glu Val Asn Ser Ile Gln Asp Leu Asn Asn Leu Glu Tyr Val Lys
        435                 440                 445
Val

<210> SEQ ID NO 4
<211> LENGTH: 449
<212> TYPE: PRT
<213> ORGANISM: Candida parapsilosis

<400> SEQUENCE: 4

Phe Val Leu Ala Pro Lys Lys Pro Ser Gln Asp Asp Phe Tyr Thr Pro
1               5                   10                  15

Pro Gln Gly Tyr Glu Ala Gln Pro Leu Gly Ser Ile Leu Lys Thr Arg
```

-continued

```
                    20                  25                  30
Asn Val Pro Asn Pro Leu Thr Asn Val Phe Thr Pro Val Lys Val Gln
                35                  40                  45
Asn Ala Trp Gln Leu Leu Val Arg Ser Glu Asp Thr Phe Gly Asn Pro
            50                  55                  60
Asn Ala Ile Val Thr Thr Ile Ile Gln Pro Phe Asn Ala Lys Lys Asp
 65                  70                  75                  80
Lys Leu Val Ser Tyr Gln Thr Phe Glu Asp Ser Gly Lys Leu Asp Cys
                85                  90                  95
Ala Pro Ser Tyr Ala Ile Gln Tyr Gly Ser Asp Ile Ser Thr Leu Thr
            100                 105                 110
Thr Gln Gly Glu Met Tyr Tyr Ile Ser Ala Leu Leu Asp Gln Gly Tyr
            115                 120                 125
Tyr Val Val Thr Pro Asp Tyr Glu Gly Pro Lys Ser Thr Phe Thr Val
            130                 135                 140
Gly Leu Gln Ser Gly Arg Ala Thr Leu Asn Ser Leu Arg Ala Thr Leu
145                 150                 155                 160
Lys Ser Gly Asn Leu Thr Gly Val Ser Ser Asp Ala Glu Thr Leu Leu
                165                 170                 175
Trp Gly Tyr Ser Gly Gly Ser Leu Ala Ser Gly Trp Ala Ala Ala Ile
            180                 185                 190
Gln Lys Glu Tyr Ala Pro Glu Leu Ser Lys Asn Leu Leu Gly Ala Ala
            195                 200                 205
Leu Gly Gly Phe Val Thr Asn Ile Thr Ala Thr Ala Glu Ala Val Asp
            210                 215                 220
Ser Gly Pro Phe Ala Gly Ile Ile Ser Asn Ala Leu Ala Gly Ile Gly
225                 230                 235                 240
Asn Glu Tyr Pro Asp Phe Lys Asn Tyr Leu Leu Lys Val Ser Pro
                245                 250                 255
Leu Leu Ser Ile Thr Tyr Arg Leu Gly Asn Thr His Cys Leu Leu Asp
                260                 265                 270
Gly Gly Ile Ala Tyr Phe Gly Lys Ser Phe Phe Ser Arg Ile Ile Arg
            275                 280                 285
Tyr Phe Pro Asp Gly Trp Asp Leu Val Asn Gln Glu Pro Ile Lys Thr
290                 295                 300
Ile Leu Gln Asp Asn Gly Leu Val Tyr Gln Pro Lys Asp Leu Thr Pro
305                 310                 315                 320
Gln Ile Pro Leu Phe Ile Tyr His Gly Thr Leu Asp Ala Ile Val Pro
                325                 330                 335
Ile Val Asn Ser Arg Lys Thr Phe Gln Gln Trp Cys Asp Trp Gly Leu
                340                 345                 350
Lys Ser Gly Glu Tyr Asn Glu Asp Leu Thr Asn Gly His Ile Thr Glu
                355                 360                 365
Ser Ile Val Gly Ala Pro Ala Ala Leu Thr Trp Ile Ile Asn Arg Phe
            370                 375                 380
Asn Gly Gln Pro Pro Val Asp Gly Cys Gln His Asn Val Arg Ala Ser
385                 390                 395                 400
Asn Leu Glu Tyr Pro Gly Thr Pro Gln Ser Ile Lys Asn Tyr Phe Glu
                405                 410                 415
Ala Ala Leu His Ala Ile Leu Gly Phe Asp Leu Gly Pro Asp Val Lys
                420                 425                 430
Arg Asp Lys Val Thr Leu Gly Gly Leu Leu Lys Leu Glu Arg Phe Ala
            435                 440                 445
```

Phe

<210> SEQ ID NO 5
<211> LENGTH: 451
<212> TYPE: PRT
<213> ORGANISM: Candida albicans

<400> SEQUENCE: 5

```
Pro Leu Thr Val Lys Ser Pro Leu Val Asp Phe Tyr Thr Ala Pro
1               5                   10                  15

Asp Gly Tyr Glu Ser Ala Lys Leu Gly Glu Ile Leu Lys Leu Arg Lys
            20                  25                  30

Thr Pro Ser Lys Leu Ser Ser Met Phe Phe Glu Ile Asp Ile Lys Asn
            35                  40                  45

Ser Trp Gln Leu Leu Val Arg Ser Glu Asp Ser Phe Gly Asn Ala Thr
50                  55                  60

Ala Ile Val Thr Thr Val Ile Glu Pro Tyr Asn Ala Asp Pro Ser Lys
65                  70                  75                  80

Val Leu Ser Tyr Gln Thr Phe Glu Asp Ser Ala Asn Ile Glu Cys Ser
                85                  90                  95

Pro Ser Tyr Gly Met Gln Tyr Gly Ala Pro Trp Ser Thr Val Ala Thr
            100                 105                 110

Gln Ile Asp Met Ala Leu Met Val Pro Met Leu Lys Gln Gly Tyr Tyr
            115                 120                 125

Val Val Ser Pro Asp Tyr Glu Gly Pro Lys Ser Thr Phe Thr Val Gly
            130                 135                 140

Arg Gln Ser Gly Lys Ala Thr Leu Asp Ser Ile Arg Ala Ile Leu Lys
145                 150                 155                 160

Ser Asn Lys Phe Thr Gly Ile Lys Ser Asp Ala Lys Val Ala Met Trp
                165                 170                 175

Gly Tyr Ser Gly Gly Ser Leu Ala Ser Gly Trp Ala Ala Ala Leu Gln
            180                 185                 190

Pro Lys Tyr Ala Pro Glu Leu Lys Lys Asn Leu Ile Gly Ala Ala Leu
        195                 200                 205

Gly Gly Phe Val Thr Asn Ile Thr Ala Thr Ala Glu Ala Thr Asp Gly
    210                 215                 220

Thr Leu Phe Ala Gly Leu Val Pro Asn Ala Leu Ser Gly Leu Ala Asn
225                 230                 235                 240

Glu Tyr Pro Glu Phe Lys Glu Ile Leu Tyr Gln Lys Val Ser Lys Ala
                245                 250                 255

Ala Thr Asp Asn Leu Arg Gln Gly Thr Glu His Cys Ile Gly Gly Ala
            260                 265                 270

Ile Leu Tyr Phe Ala Glu Asp Gln Tyr Phe Thr Gly Asp Asp Arg Ala
        275                 280                 285

Phe Pro Gly Gly Tyr Gly Leu Leu Lys Glu Glu Val Val Asn Lys Thr
    290                 295                 300

Ile Ser Glu Asn Asn Leu Met Gln Met Asp Lys Asp Tyr Leu Pro Asp
305                 310                 315                 320

Ile Pro Ile Phe Val Tyr His Gly Ala Leu Asp Ser Ile Val Pro Ile
                325                 330                 335

Ser Asn Val His Val Thr Tyr Lys Asn Trp Cys Asp Trp Gly Ile Asn
            340                 345                 350

Ser Phe Glu Phe Ser Glu Asp Leu Leu Asn Gly His Ile Thr Glu Thr
        355                 360                 365
```

```
Ile Val Gly Ala Pro Ala Ala Ile Thr Trp Leu Glu Ala Arg Phe Asp
            370                 375                 380

Gly Glu Pro Val Val Lys Gly Cys Lys Lys Thr Ser Arg Ile Thr Asn
385                 390                 395                 400

Phe Ser Tyr Pro Asn Ile Ser Asp Ser Thr Ser Ser Ile Phe Glu Gly
                405                 410                 415

Ile Leu Asn Ser Val Thr Gly Ser Glu Leu Gly Pro Gly Val Thr Ser
            420                 425                 430

Asp Asn Ile Thr Leu Asp Gly Leu Thr Gly Phe Leu Gly Asn Phe Ile
            435                 440                 445

Asp Leu Lys
        450

<210> SEQ ID NO 6
<211> LENGTH: 443
<212> TYPE: PRT
<213> ORGANISM: Candida albicans

<400> SEQUENCE: 6

Ile Leu Pro Thr Lys Pro Ser Asn Asp Pro Phe Tyr Asn Ala Pro Ala
1               5                   10                  15

Gly Phe Glu Lys Ala Ala Val Gly Asp Ile Leu Gln Ser Arg Lys Thr
            20                  25                  30

Pro Lys Pro Ile Thr Gly Val Phe Val Pro Val Lys Ile Gln Asn Ser
        35                  40                  45

Trp Gln Leu Leu Val Arg Ser Glu Asp Ser Phe Gly Asn Pro Asn Val
    50                  55                  60

Ile Val Thr Thr Val Met Glu Pro Phe Asn Ala Asp Pro Ser Lys Leu
65                  70                  75                  80

Ala Ser Tyr Gln Val Phe Glu Asp Ser Ala Lys Ala Asp Cys Ala Pro
                85                  90                  95

Ser Tyr Ala Leu Gln Phe Gly Ser Asp Val Thr Thr Ile Ala Thr Gln
            100                 105                 110

Val Glu Thr Tyr Leu Leu Ala Pro Leu Leu Asp Gln Gly Tyr Tyr Val
            115                 120                 125

Val Ser Pro Asp Tyr Glu Gly Pro Lys Ser Thr Phe Thr Val Gly Lys
130                 135                 140

Gln Ser Gly Gln Ala Val Leu Asn Ser Ile Arg Ala Ala Leu Lys Ser
145                 150                 155                 160

Gly Lys Ile Thr Asn Leu Ala Glu Asn Ala Lys Val Val Met Trp Gly
                165                 170                 175

Tyr Ser Gly Gly Ser Leu Ala Ser Gly Trp Ala Ala Ala Leu Gln Pro
            180                 185                 190

Asn Tyr Ala Pro Glu Leu Gly Gly Asn Leu Leu Gly Ala Ala Leu Gly
        195                 200                 205

Gly Phe Val Thr Asn Ile Thr Ala Thr Ala Glu Ala Thr Asp Gly Thr
    210                 215                 220

Val Phe Ala Gly Ile Met Ala Asn Ala Leu Gly Gly Val Ala Asn Glu
225                 230                 235                 240

Tyr Pro Glu Phe Lys Gln Ile Leu Gln Asn Asp Thr Asp Lys Gln Ser
                245                 250                 255

Val Phe Asp Gln Phe Asp Asn His Cys Leu Ala Asp Gly Val Ile Asn
            260                 265                 270

Tyr Ile Gly Lys His Phe Leu Ser Gly Thr Asn Lys Ile Phe Lys Ser
```

```
                    275                 280                 285
Gly Trp Asn Ile Leu Lys Asn Pro Thr Ile Ser Lys Ile Val Glu Asp
    290                 295                 300

Asn Gly Leu Val Tyr Gln Lys Gln Leu Val Pro Lys Ile Pro Ile Leu
305                 310                 315                 320

Ile Tyr His Gly Ala Ile Asp Gln Ile Val Pro Ile Asn Val Lys
                325                 330                 335

Lys Thr Tyr Gln Asn Trp Cys Asp Ala Gly Ile Ala Ser Leu Glu Phe
                340                 345                 350

Ser Glu Asp Ala Thr Asn Gly His Ile Thr Glu Thr Ile Val Gly Ala
            355                 360                 365

Pro Val Ala Leu Thr Trp Ile Ile Asn Arg Phe Asn Gly Lys Gln Thr
    370                 375                 380

Val Ser Gly Cys Gln His Val Lys Arg Thr Ser Asn Phe Glu Tyr Pro
385                 390                 395                 400

Asn Ile Pro Pro Ser Ile Leu Asn Tyr Phe Lys Ala Ala Leu Asn Ile
                405                 410                 415

Leu Ile Gln Lys Gly Leu Gly Pro Asp Ile Gln Lys Asp Gln Val Asn
            420                 425                 430

Pro Asp Gly Leu Lys Lys Ile Ser Ile Leu Val
            435                 440

<210> SEQ ID NO 7
<211> LENGTH: 423
<212> TYPE: PRT
<213> ORGANISM: Aspergillus fumigatus

<400> SEQUENCE: 7

Asp Ala Leu Val Arg Pro Leu Glu Asp Pro Phe Tyr Ser Ala Pro Lys
1               5                   10                  15

Gly Phe Glu Ser Thr Val Pro Gly Thr Ile Leu Arg Trp Arg Asn Pro
                20                  25                  30

Pro Asn Pro Ile Ser Ala Phe Gly Phe Ala Pro Ile Asn Leu Ala Ala
            35                  40                  45

Ser Tyr Gln Leu Leu Tyr Arg Ser Thr Asp Ser Phe Gly Glu Pro Ile
    50                  55                  60

Ala Ala Ala Ser Thr Ile Leu Val Pro His Asn Ala Asp Asn Thr Lys
65                  70                  75                  80

Leu Leu Ser Phe Gln Ala Ala Glu Asp Ala Ala Asn Pro Asn Cys Ala
                85                  90                  95

Pro Ser Tyr Ala Phe Gln Leu Asp Ser Ala Thr Asp Glu Leu Gly
            100                 105                 110

Leu Ile Met Pro Gln Ala Glu Leu Val Leu Ile Ile Ala Ala Leu Asp
    115                 120                 125

Lys Gly Trp Val Thr Val Pro Asp His Leu Gly Pro Asn Ala Thr
            130                 135                 140

Phe Leu Ala Asn Asn Leu Ser Gly His Val Val Leu Asp Asn Ile Arg
145                 150                 155                 160

Ala Leu Arg Ser Ser Ala Phe Ser Gly Ile Ser Pro Lys Ala Thr Ile
                165                 170                 175

Thr Leu Trp Gly Tyr Ser Gly Gly Ser Leu Ala Ser Gly Leu Ala Ala
            180                 185                 190

Glu Leu Arg Ala Ser Tyr Ala Pro Glu Leu Asn Ile Ala Gly Ala Ala
    195                 200                 205
```

-continued

```
Leu Gly Gly Thr Val Pro Lys Ile Met Pro Val Phe Asn Thr Val Asn
    210             215             220
Lys Gly Ile Tyr Ala Gly Leu Leu Pro Ala Gly Met Gln Gly Leu Ser
225             230             235             240
Asn Glu Tyr Pro Ala Ile Glu Lys Ile Leu Tyr Asp His Leu Val Pro
                245             250             255
Ala Lys Lys Ala Asp Phe Val Lys Thr Lys Asn Leu Cys Ile Val Glu
            260             265             270
Asp Leu Leu Thr Tyr Ser Phe Gln Asp Phe Tyr Arg Tyr Ile Thr Asp
        275             280             285
Ala Asn Met Leu Lys Asp Pro Glu Val Thr Arg Val Leu Gly Glu Asn
    290             295             300
Ala Met Gly Gln His Val Pro Asp Ile Pro Leu Phe Val Tyr Lys Ser
305             310             315             320
Thr Asn Asp Asp Val Ser Pro Val Gly Asp Thr Asp Ala Leu Val Ser
                325             330             335
Gly Tyr Cys Ala Ala Gly Gly Lys Val Glu Tyr Tyr Arg Asp Glu Leu
            340             345             350
Ser Asn His Ala Thr Met Ala Val Ile Gly Val Pro Asn Ala Leu Leu
        355             360             365
Trp Leu Lys Asp Arg Met Asn Gly Val Pro Ala Arg Ala Gly Cys Lys
    370             375             380
Thr Gln Thr Ala Leu Thr Gly Leu Leu Asp Pro Arg Thr Leu Ala Val
385             390             395             400
Leu Gly Ile Asp Leu Ile Lys Val Leu Leu Ala Leu Leu Ser Ala Pro
                405             410             415
Val Gly Thr Phe Val Ile Gly
            420
```